US007572606B1

(12) United States Patent
Lam et al.

(10) Patent No.: US 7,572,606 B1
(45) Date of Patent: Aug. 11, 2009

(54) BIOSYNTHESES OF SALINOSPORAMIDE A AND ITS ANALOGS AND RELATED METHODS OF MAKING SALINOSPORAMIDE A AND ITS ANALOGS

(75) Inventors: Kin Sing Lam, San Diego, CA (US); Michael Palladino, Olivenhain, CA (US); Ginger Tsueng, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 312 days.

(21) Appl. No.: 11/517,899

(22) Filed: Sep. 8, 2006

Related U.S. Application Data

(60) Provisional application No. 60/715,404, filed on Sep. 9, 2005, provisional application No. 60/816,771, filed on Jun. 26, 2006, provisional application No. 60/816,753, filed on Jun. 26, 2006.

(51) Int. Cl.

| | |
|---|---|
| *C12P 17/18* | (2006.01) |
| *A61K 31/047* | (2006.01) |
| *C07D 491/044* | (2006.01) |
| *C12P 41/00* | (2006.01) |

(52) U.S. Cl. ......................... 435/119; 514/64; 514/412; 514/210.06; 514/421; 530/347; 548/453; 549/302; 435/280

(58) Field of Classification Search ....................... None
See application file for complete search history.

(56) References Cited

U.S. PATENT DOCUMENTS

| | | | | |
|---|---|---|---|---|
| 7,144,723 | B2 | 12/2006 | Fenical et al. | |
| 7,176,232 | B2 * | 2/2007 | Fenical et al. | 514/421 |
| 7,176,233 | B2 * | 2/2007 | Fenical et al. | 514/421 |
| 7,179,834 | B2 * | 2/2007 | Fenical et al. | 514/421 |
| 7,276,530 | B2 * | 10/2007 | Potts et al. | 514/421 |
| 2004/0266701 | A1 * | 12/2004 | Fenical et al. | 514/28 |
| 2005/0049294 | A1 * | 3/2005 | Palladino et al. | 514/412 |
| 2006/0264495 | A1 * | 11/2006 | Palladino et al. | 514/412 |
| 2007/0004676 | A1 * | 1/2007 | Palladino et al. | 514/64 |
| 2008/0070273 | A1 | 3/2008 | Fenical et al. | |
| 2008/0070969 | A1 | 3/2008 | Potts et al. | |

FOREIGN PATENT DOCUMENTS

| | | |
|---|---|---|
| WO | WO 2005/002572 A | 1/2005 |
| WO | WO 2006/124902 A | 11/2006 |

OTHER PUBLICATIONS

Beer and Moore, "Biosynthetic Convergence of Salinosporamides A and B in the Marine Actinomycete *Salinispora tropica*". *Org Lett* (2007) 9(5):845-848.

Eustáquio and Moore, "Mutasynthesis of Fluorosalinosporamide, a Potent and Reversible Inhibitor of the Proteasome". *Angew Chem Int Ed Engl* (2008) 47(21):3936-3938.

Feling, et al. "Salinosporamide A: A Highly Cytotoxic Proteasome Inhibitor from a Novel Microbial Source, a Marine Bacterium of the New Genus *Salinospora*", *Angew. Chem. Int. Ed.*, (2003) 42(3):355-357.

Fenical, et al., "Marine Microorganisms as a Biomedical Source: Are they unculturable or Uncultured?", PowerPoint Presentation, Center for Marine Biotechnology and Biomedicine (Feb. 24, 2002).

Fenical, et al., "*Salinospora*, a Major New Marine Actinomycete Taxon for Drug Discovery", Powerpoint Presentation, Center for Marine Biotechnology and Biomedicine (Jun. 24, 2001).

Lam, et al., "Effect of Halogens on the Production of Salinosporamides by the Obligate Marine Actinomycete *Salinispora tropica*". *J Antibiotic* (2007) 60(1):13-19.

Liu. et al., "Precursor Supply for Polyketide Biosynthesis: The Role of Crotonyl-CoA Reductase", *Metab Eng*, (2001) 3:40-48.

Macherla, et al., "Structure-Activity Relationship Studies of Salinosporamide A (NPI-0052), a Novel Marine Derived Proteasome Inhibitor", *J. Med. Chem.*, (2005) 48(11):3684-7.

Moore, B.S., "Biosynthesis of Marine Natural Products: Microorganisms and Macroalgae", *Nat Prod Rep*. (1999) 16(6):653-674.

Reed et al., "Salinosporamides D-J from the Marine Actinomycete *Salinispora tropica*, Bromosalinosporamide, and Thioester Derivatives are Potent Inhibitors of the 20S Proteasome". *J Nat Prod* (2007) 70(2):269-276.

Tsueng, et al., "Unique Butyric Acid Incorporation Patterns for Salinosporamides A and B Reveal Distinct Biosynthetic Origins". *Appl Microbiol Biotechnol* (2007) 75(5):999-1005.

Williams et al., "New Cytotoxic Salinosporamides from the Marine Actinomycete *Salinispora tropica*", *J. of Organic Chemistry*, (2005) 70(16):6196-6203.

International Search Report and Written Opinion issued in PCT Application No. PCT/US2006/034930, dated Feb. 20, 2007.

* cited by examiner

*Primary Examiner*—Herbert J. Lilling
(74) *Attorney, Agent, or Firm*—Knobbe, Martens, Olson & Bear LLP

(57) ABSTRACT

Disclosed are methods of modulating biosynthesis of Salinosporamide A and its analogs, which are useful in treating cancer, inflammatory conditions, and/or infectious disease. The methods involve, for example, genetic manipulation, selection of reagents in the fermentation feedstock, and selection of fermentation conditions.

18 Claims, 52 Drawing Sheets

II-20

II-24C

II-19

II-2

II-3

II-4

II-5A

II-5B

IV-3C

IV-3C

II-13C

II-8C

II-25

II-21

II-22

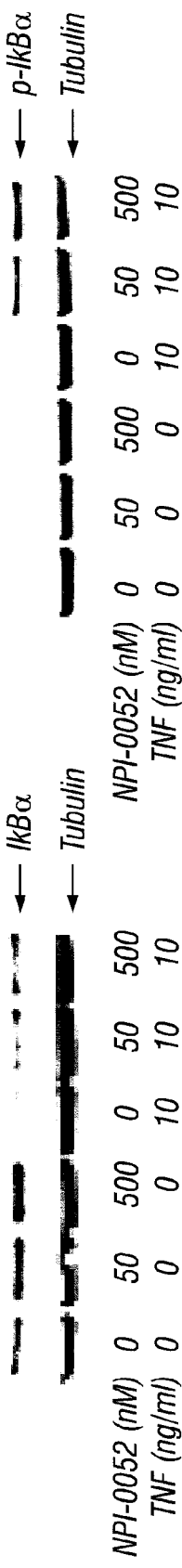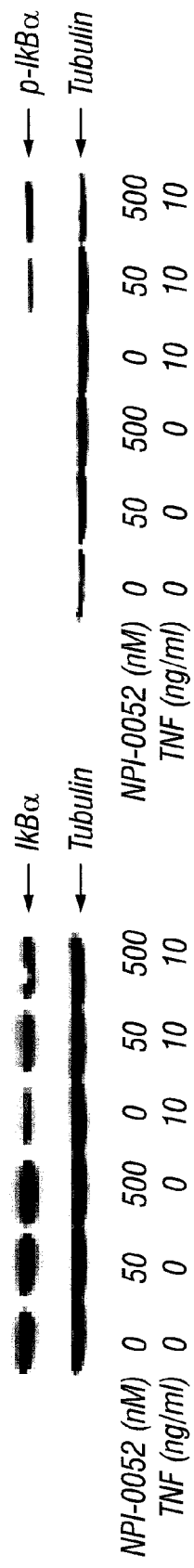
Reduction of IkBα degradation and retention of Phosphorylated IkBα by II-16 in HEK293 Cells (A) and the HEK293 NF-kB/Luciferase Reporter Clone (B)
FIG. 32A
FIG. 32B

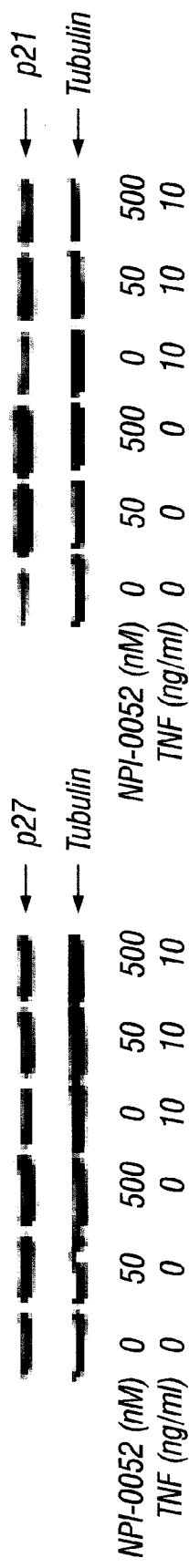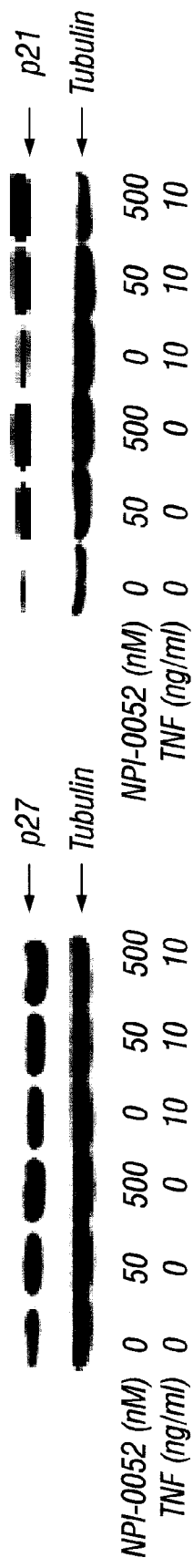
FIG. 33A
FIG. 33B
Accumulation of Cell Cycle Regulatory Proteins, p21 and p27 by II-16 Treatment of HEK293 Cells (A) and the HEK293 NF-kB/Luciferase Reporter Clone (B).

II-17

II-18

II-26

II-27

II-28

II-29

II-30

II-44

I-7

II-47

II-38

II-50

BIOSYNTHESES OF SALINOSPORAMIDE A AND ITS ANALOGS AND RELATED METHODS OF MAKING SALINOSPORAMIDE A AND ITS ANALOGS

RELATED APPLICATIONS

This application claims the benefit of U.S. Provisional Application No. 60/715,404, filed Sep. 9, 2005 and U.S. Provisional Application No. 60/816,771, filed Jun. 26, 2006, both of which are incorporated herein by reference in their entirety. This application also claims the benefit of U.S. Provisional Application No. 60/816,753, filed Jun. 26, 2006.

BACKGROUND OF THE INVENTION

1. Field of the Invention

The present invention relates to method of making, including biosynthetic and related methods of making, certain compounds and to the use of such compounds in the fields of chemistry and medicine. Embodiments of the invention disclosed herein relate to methods of making and using heterocyclic compounds. In some embodiments, the compounds are made by controlled biosynthesis, and may be used as proteasome inhibitors. In other embodiments, the compounds are made by controlled biosynthesis, and may be used to treat inflammation, cancer, and infectious diseases.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria, fungi and protozoa are becoming increasingly difficult to treat and cure. For example, more and more bacteria, fungi and protozoa are developing resistance to current antibiotics and chemotherapeutic agents. Examples of such microbes include *Bacillus, Leishmania, Plasmodium* and *Trypanosoma*.

Furthermore, a growing number of diseases and medical conditions are classified as inflammatory diseases. Such diseases include conditions such as asthma to cardiovascular diseases. These diseases continue to affect larger and larger numbers of people worldwide despite new therapies and medical advances.

Therefore, a need exists for additional chemotherapeutics, anti-microbial agents, and anti-inflammatory agents to treat cancer, inflammatory diseases and infectious disease. A continuing effort is being made by individual investigators, academia and companies to identify new, potentially useful chemotherapeutic and anti-microbial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S. 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY OF THE INVENTION

The embodiments disclosed herein generally relate to chemical compounds, including heterocyclic compounds and analogs thereof. Some embodiments are directed to the use of compounds as proteasome inhibitors.

In other embodiments, the compounds are used to treat neoplastic diseases, for example, to inhibit the growth of tumors, cancers and other neoplastic tissues. The methods of treatment disclosed herein can be employed with any patient suspected of carrying tumorous growths, cancers, or other neoplastic growths, either benign or malignant ("tumor" or "tumors" as used herein encompasses tumors, cancers, disseminated neoplastic cells and localized neoplastic growths). Examples of such growths include but are not limited to breast cancers; osteosarcomas, angiosarcomas, fibrosarcomas and other sarcomas; leukemias; sinus tumors; ovarian, uretal, bladder, prostate and other genitourinary cancers; colon, esophageal and stomach cancers and other gastrointestinal cancers; lung cancers; lymphomas; myelomas; pancreatic cancers; liver cancers; kidney cancers; endocrine cancers; skin cancers; melanomas; angiomas; and brain or central nervous system (CNS; glioma) cancers. In general, the tumor or growth to be treated can be any tumor or cancer, primary or secondary. Certain embodiments relate to methods of treating neoplastic diseases in animals. The method can include, for example, administering an effective amount of a compound to a patient in need thereof. Other embodiments relate to the use of compounds in the manufacture of a pharmaceutical or medicament for the treatment of a neoplastic disease.

The compounds can be administered or used in combination with treatments such as chemotherapy, radiation, and biologic therapies. In some embodiments the compounds can be administered or used with a chemotherapeutic agent. Examples of such chemotherapeutics include Alkaloids, alkylating agents, antibiotics, antimetabolites, enzymes, hormones, platinum compounds, immunotherapeutics (antibodies, T-cells, epitopes), BRMs, and the like. Examples include, Vincristine, Vinblastine, Vindesine, Paclitaxel (Taxol), Docetaxel, topoisomerase inhibitors epipodophyllotoxins (Etoposide (VP-16), Teniposide (VM-26)), Camptothecin, nitrogen mustards (cyclophosphamide), Nitrosoureas, Carmustine, lomustine, dacarbazine, hydroxymethylmelamine, thiotepa and mitocycin C, Dactinomycin (Actinomycin D), anthracycline antibiotics (Daunorubicin, Daunomycin, Cerubidine), Doxorubicin (Adriamycin), Idarubicin (Idamycin), Anthracenediones (Mitoxantrone), Bleomycin (Blenoxane), Plicamycin (Mithramycin, Antifolates (Methotrexate (Folex, Mexate)), purine antimetabolites (6-mercaptopurine (6-MP, Purinethol) and 6-thioguanine (6-TG). The two major anticancer drugs in this category are 6-mercaptopurine and 6-thioguanine, Chlorodeoxyadenosine and Pentostatin, Pentostatin (2'-deoxycoformycin), pyrimidine antagonists, fluoropyrimidines (5-fluorouracil (Adrucil), 5-fluorodeoxyuridine (FdUrd) (Floxuridine)), Cytosine Arabinoside (Cytosar, ara-C), Fludarabine, L-ASPARAGINASE, Hydroxyurea, glucocorticoids, antiestrogens, tamoxifen, nonsteroidal antiandrogens, flutamide, aromatase inhibitors Anastrozole (Arimidex), Cisplatin, 6-Mercaptopurine and Thioguanine, Methotrexate, Cytoxan, Cytarabine, L-Asparaginase, Steroids: Prednisone and Dexamethasone. Also, proteasome inhibitors such as bortezomib can be used in combination with the instant compounds, for example. Examples of biologics can include agents such as TRAIL antibodies to TRAIL, integrins such as alpha-V-beta-3 (αVβ3) and/or other cytokine/growth factors that are involved in angiogenesis, VEGF, EGF, FGF and PDGF. In some aspects, the compounds can be conjugated to or delivered with an antibody. The above-described combination methods can be used to treat a variety of conditions, including cancer and neoplastic diseases, inflammation, and microbial infections.

In still other embodiments, the compounds are used to treat inflammatory conditions. Certain embodiments relate to methods of treating inflammatory conditions in animals. The method can include, for example, administering an effective amount of a compound to a patient in need thereof. Other embodiments relate to the use of compounds in the manufacture of a pharmaceutical or medicament for the treatment of inflammation.

In certain embodiments, the compounds are used to treat infectious diseases. The infectious agent can be a microbe, for example, bacteria, fungi, protozoans, and microscopic algae, or viruses. Further, the infectious agent can be *B. anthracis* (anthrax). In some embodiments the infectious agent is a parasite. For example, the infectious agent can be *Plasmodium, Leishmania*, and *Trypanosoma*. Certain embodiments relate to methods of treating infectious agents in animals. The method can include, for example, administering an effective amount of a compound to a patient in need thereof. Other embodiments relate to the use of compounds in the manufacture of a pharmaceutical or medicament for the treatment of infectious agents.

Some embodiments relate to uses of a compound having the structure of Formula I, and pharmaceutically acceptable salts and pro-drug esters thereof:

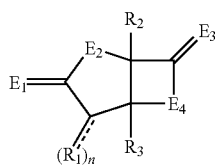

Formula I wherein the dashed lines represent a single or a double bond, wherein R1 can be separately selected from the group consisting of a hydrogen, a halogen, mono-substituted, poly- substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, where n is equal to 1 or 2, and if n is equal to 2, then $R_1$ can be the same or different;

wherein $R_2$, can be selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl (including, for example, cyclohexylcarbinol), alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl; and wherein each of $E_1$, $E_2$, $E_3$ and $E_4$ is a substituted or unsubstituted heteroatom; in the treatment of cancer, inflammation, and infectious disease.

In some embodiments, preferably R1 is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

Other embodiments relate to methods of treating a neoplastic disease in an animal. The methods can include, for example, administering to the animal, a therapeutically effective amount of a compound of a formula selected from Formulae I-VI, and pharmaceutically acceptable salts and pro-drug esters thereof.

Further embodiments relate to pharmaceutical compositions which include a compound of a formula selected from Formulae I-VI. The pharmaceutical compositions can further include an anti-microbial agent.

Still further embodiments relate to methods of inhibiting the growth of a cancer cell. The methods can include, for example, contacting a cancer cell with a compound of a formula selected from Formulae I-VI, and pharmaceutically acceptable salts and pro-drug esters thereof.

Other embodiments relate to methods of inhibiting proteasome activity that include the step contacting a cell with a compound of a formula selected from Formulae I-VI, and pharmaceutically acceptable salts and pro-drug esters thereof.

Other embodiments relate to methods of inhibiting nuclear factor-kappa B (NF-?B) activation including the step contacting a cell with a compound of a formula selected from Formulae I-VI, and pharmaceutically acceptable salts and pro-drug esters thereof.

Some embodiments relate to methods for treating an inflammatory condition, including administering an effective amount of a compound of a formula selected from Formulae I-VI to a patient in need thereof.

Further embodiments relate to methods for treating a microbial illness including administering an effective amount of a compound of a formula selected from Formulae I-VI to a patient in need thereof.

Further embodiments relate to biosynthetic methods of making a compound, and methods for modulation of biosynthesis of a compound of a formula selected from Formulae I-VI, salinosporamide A, and analogs thereof. In vivo, in vitro, in sito and enzyme-directed methods, for example, of making the compounds, in addition to synthetic and semi-synthetic methods, are disclosed.

In some embodiments, biosynthetic methods include fermenting a strain of *Salinospora* and selecting one or more fermentation condition, feedstock, or strain genetic make-up such that the relative yield of the compound in comparison to that of at least one other compound of Formula I is substantially different than the naturally occurring relative yield. In some embodiments, a feedstock is selected that is deficient in one or more of butyrate, propionate, and valerate. In some embodiments, a feedstock is selected that has an excess of one or more of butyrate, propionate, and valerate.

BRIEF DESCRIPTION OF THE DRAWINGS

The accompanying drawings, which are incorporated in and form part of the specification, merely illustrate certain preferred embodiments of the present invention. Together with the remainder of the specification, they are meant to serve to explain preferred modes of making certain compounds of the invention to those of skilled in the art. In the drawings:

FIG. 32 shows reduction of IκBα degradation and retention of phosphorylated IκBα by II-16 in HEK293 cells (A) and the HEK293 NF-κB/Luciferase reporter clone (B).

FIG. 33 shows accumulation of cell cycle regulatory proteins, p21 and p27, by II-16 treatment of HEK293 cells (A) and the HEK293 NF-κB/Luciferase reporter clone (B).

DETAILED DESCRIPTION OF THE PREFERRED EMBODIMENT

Figure 1:
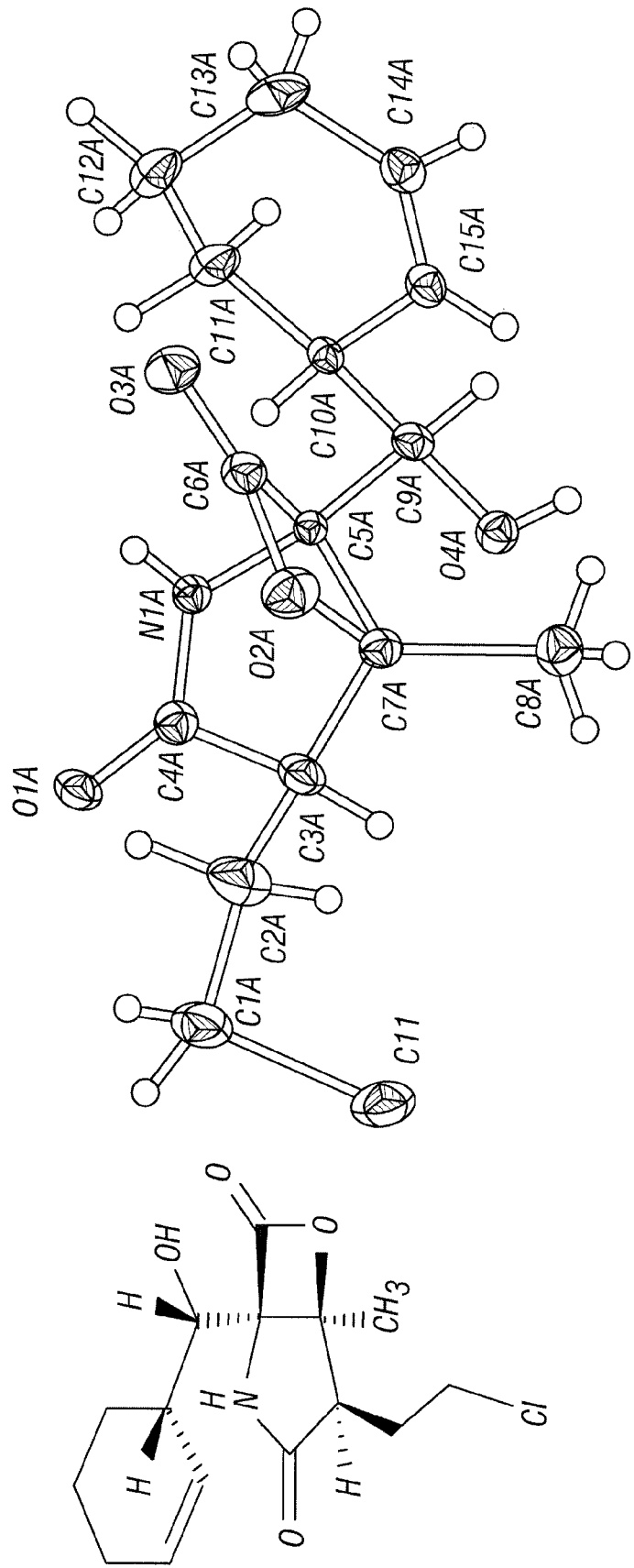
FIG. 1 shows the chemical structure of Salinosporamide A.
Figure 2:
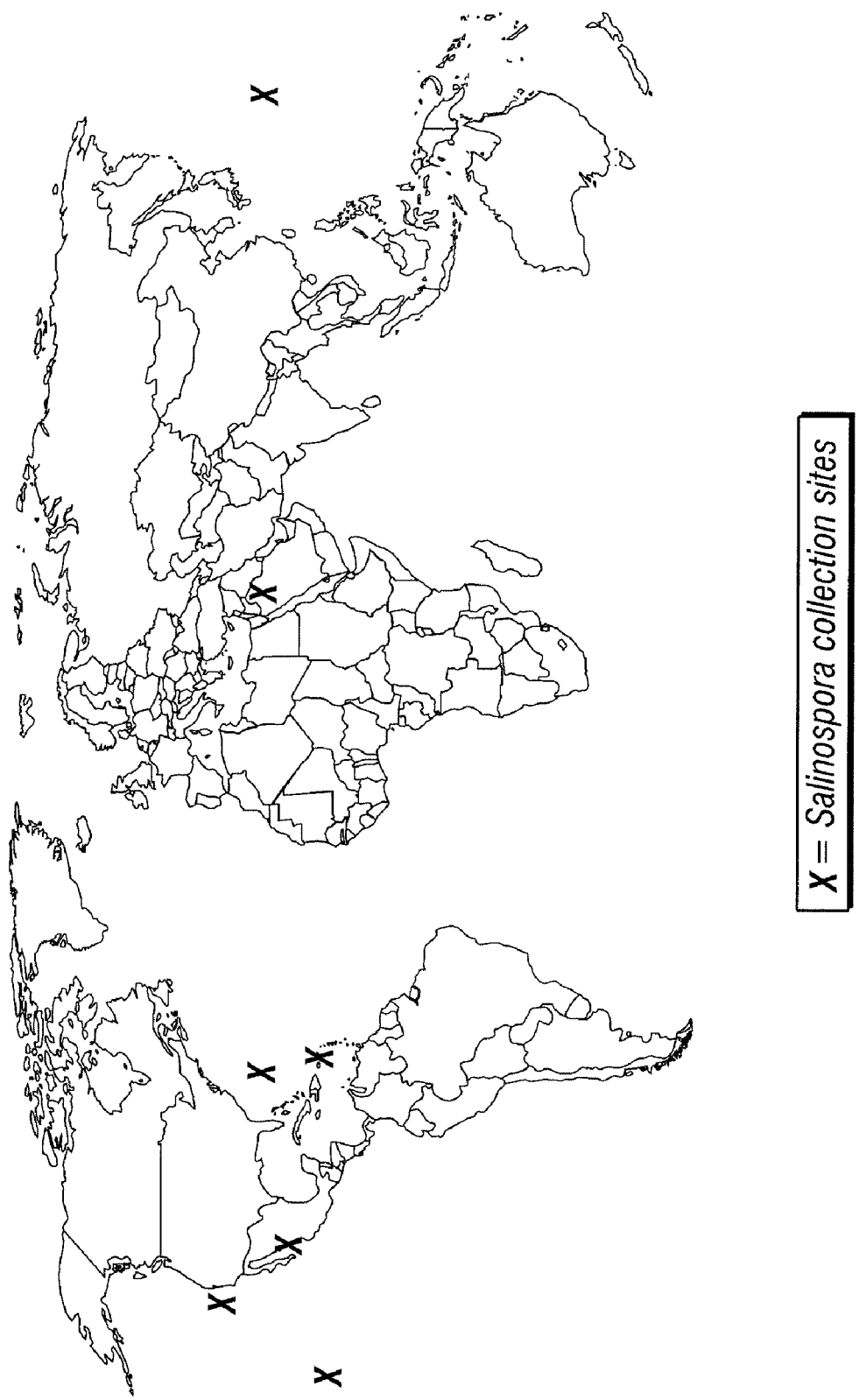
FIG. 2 shows the pan-tropical distribution of the *Salinospora*. "X" denotes *Salinospora* collection sites.

Numerous references are cited herein. The references cited herein, including the U.S. patents cited herein, are each to be considered incorporated by reference in their entirety into this specification.

Embodiments of the invention include, but are not limited to, providing a method for the preparation of compounds, including compounds, for example, those described herein and analogs thereof, and to providing a method for producing pharmaceutically acceptable anti-microbial, anti-cancer, and anti-inflammatory compositions, for example. The methods can include the compositions in relatively high yield, wherein the compounds and/or their derivatives are among the active ingredients in these compositions. Other embodiments relate to providing novel compounds not obtainable by currently available methods. Furthermore, embodiments relate to methods of treating cancer, inflammation, and infectious diseases, particularly those affecting humans. In some embodiments, one or more formulae, one or more compounds, or groups of compounds can be specifically excluded from use in any one or more of the methods of treating the conditions described herein. As one illustrative example, compounds of Formula II-16 can be excluded in some embodiments from the methods of treating cancer generally, for example, or a specific type of cancer. The methods may include, for example, the step of administering an effective amount of a member of a class of new compounds. Preferred embodiments relate to the compounds and methods of making and using such compounds disclosed herein, but not necessarily in all embodiments of the present invention, these objectives are met.

For the compounds described herein, each stereogenic carbon can be of R or S configuration. Although the specific compounds exemplified in this application can be depicted in a particular configuration, compounds having either the opposite stereochemistry at any given chiral center or mixtures thereof are also envisioned. When chiral centers are found in the derivatives of this invention, it is to be understood that the compounds encompasses all possible stereoisomers.

Compounds of Formula I

Some embodiments provide compounds, and methods of producing a class of compounds, pharmaceutically acceptable salts and pro-drug esters thereof, wherein the compounds are represented by Formula I:

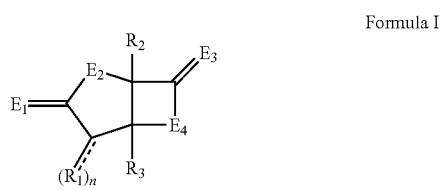

Formula I

In certain embodiments the substituent(s) $R_1$, $R_2$, and $R_3$ separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including for example, cyclohexylcarbinol), cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. Further, in certain embodiments, each of $E_1$, $E_2$, $E_3$ and $E_4$ can be a substituted or unsubstituted heteroatom, for example, a heteroatom separately selected from the group consisting of nitrogen, sulfur and oxygen.

In some embodiments n can be equal to 1 or equal to 2. When n is equal to 2, the substituents can be the same or can be different. Furthermore, in some embodiments $R_3$ is not a hydrogen.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

In some embodiments, $R_2$ is not cyclohex-2-enyl carbinol when one of the $R_1$ substituents is ethyl or chloroethyl and $R_3$ is methyl.

Preferably, $R_2$ can be a formyl. For example, the compound may have the following structure I-1:

Formula I-1

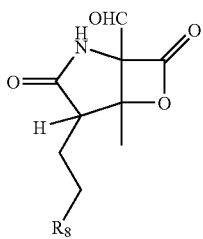

$R_8$ may include, for example, hydrogen, fluorine, chlorine, bromine and iodine.

Preferably, the structure of Formula I-1 may have the following stereochemistry:

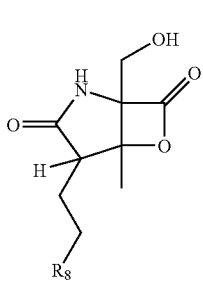

$R_8$ may include, for example, hydrogen, fluorine, chlorine, bromine and iodine.

Preferably, $R_2$ can be a carbinol. For example, the compound may have the following structure I-2:

Formula I-2

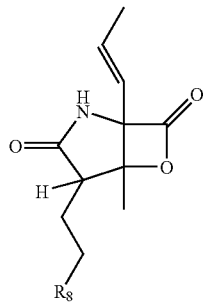

$R_8$ may include, for example, hydrogen, fluorine, chlorine, bromine and iodine.

As an example, the structure of Formula I-2 may have the following stereochemistry:

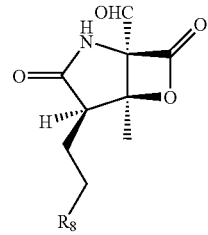

$R_8$ may include, for example, hydrogen, fluorine, chlorine, bromine and iodine.

As exemplary compound of Formula I can be the compound having the following structure I-3:

Formula I-3

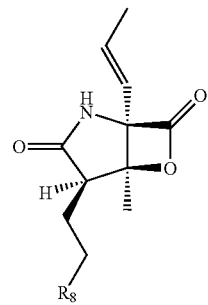

$R_8$ may include, for example, hydrogen, fluorine, chlorine, bromine and iodine.

The compound of Formula I-3 may have the following stereochemical structure:

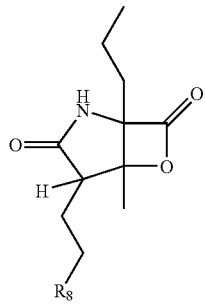

$R_8$ may include, for example, hydrogen, fluorine, chlorine, bromine and iodine.

Another exemplary compound Formula I can be the compound having the following structure I-4:

Formula I-4

$R_8$ may include, for example, hydrogen, fluorine, chlorine, bromine and iodine.

Preferably, the compound of Formula I-4 may have the following stereochemical structure:

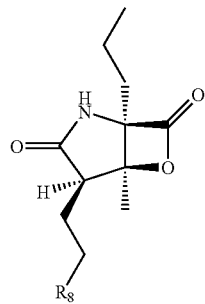

$R_8$ may include, for example, hydrogen, fluorine, chlorine, bromine and iodine.

Still a further exemplary compound of Formula I is the compound having the following structure I-5:

Formula I-5

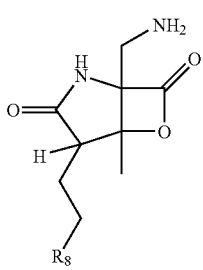

$R_8$ may include, for example, hydrogen, fluorine, chlorine, bromine and iodine.

For example, the compound of Formula I-5 may have the following stereochemistry:

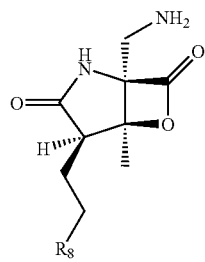

$R_8$ may include, for example, hydrogen, fluorine, chlorine, bromine and iodine.

In some embodiments, $R_2$ of Formula I can be, for example, a cyclohex-2-enyli denemethyl. For example, the compound may have the following structure of Formula I-6:

Formula I-6

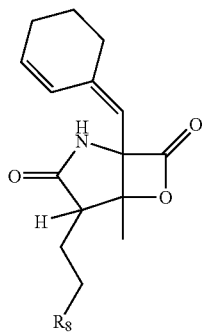

$R_8$ may include, for example, hydrogen, fluorine, chlorine, bromine and iodine.

Preferably, the compound of Formula I-6 may have the following stereochemistry:

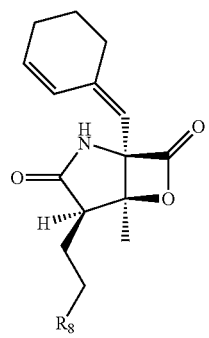

$R_8$ may include, for example, hydrogen, fluorine, chlorine, bromine and iodine.

In further embodiments, $R_2$ of Formula I can be, for example, a cyclohex-2-enylmethyl. For example, the compound may have the following structure of Formula I-7:

Formula I-7

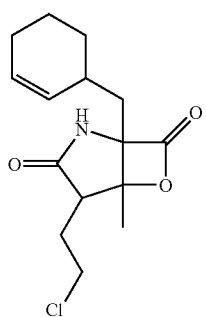

$R_8$ may include, for example, hydrogen, fluorine, chlorine, bromine and iodine.

Preferably, the compound of Formula I-7 may have the following stereochemistry:

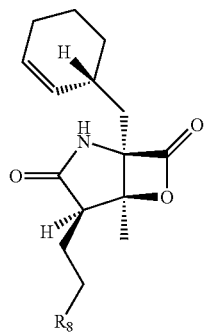

$R_8$ may include, for example, hydrogen, fluorine, chlorine, bromine and iodine.

In other embodiments, $R_2$ can be a cyclohexylalkylamine.

Also, in other embodiments, $R_2$ can be a C-Cyclohexyl-methyleneamine. In others, $R_2$ can be a cyclohexenecarbaldehyde O-oxime.

Furthermore, in some embodiments, $R_2$ can be a cycloalkylacyl.

Compounds of Formula II

Other embodiments provide compounds, and methods of producing a class of compounds, pharmaceutically acceptable salts and pro-drug esters thereof, wherein the compounds are represented by Formula II:

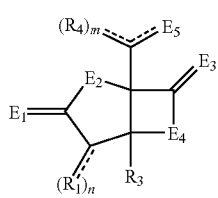

Formula II

In certain embodiments the substituent(s) $R_1$, $R_3$, and $R_4$ separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. Further, in certain embodiments, each of $E_1$, $E_2$, $E_3$ and $E_4$ can be a substituted or unsubstituted heteroatom, for example, a heteroatom or substituted heteroatom selected from the group consisting of nitrogen, sulfur and oxygen.

In some embodiments n can be equal to 1, while in others it can be equal to 2. When n is equal to 2, the substituents can be the same or can be different. Furthermore, in some embodiments $R_3$ is not a hydrogen. m can be equal to 1 or 2, and when m is equal to 2, $R_4$ can be the same or different.

$E_5$ can be, for example, OH, O, $OR_{10}$, S, $SR_{11}$, $SO_2R_{11}$, NH, $NH_2$, NOH, NHOH, $NR_{12}$, and $NHOR_{13}$, wherein $R_{10-13}$ may separately include, for example, hydrogen, a substituted or unsubstituted of any of the following: alkyl, an aryl, a heteroaryl, and the like. Also, $R_1$ can be $CH_2CH_2X$, wherein X can be, for example, H, F, Cl, Br, and I. $R_3$ can be methyl. Furthermore, $R_4$ may include a cyclohexyl. Also, each of $E_1$, $E_3$ and $E_4$ can be O and $E_2$ can be NH. Preferably, $R_1$ can be $CH_2CH_2X$, wherein X is selected from the group consisting of H, F, Cl Br, and I; wherein $R_4$ may include a cyclohexyl; wherein $R_3$ can be methyl; and wherein each of $E_1$, $E_3$ and $E_4$ separately can be O and $E_2$ can be NH.

In some embodiments, $R_2$ is not cyclohex-2-enyl carbinol when one of the $R_1$ substituents is ethyl or chloroethyl and $R_3$ is methyl.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, R1 is not a substituted or unsubstituted, unbranched $C_6$ alkyl.

For example, an exemplary compound of Formula II has the following structure II-1:

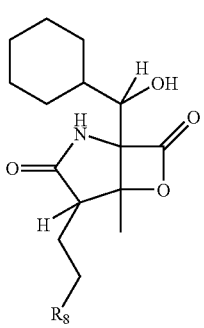

Formula II-1

$R_8$ may include, for example, hydrogen, fluorine, chlorine, bromine and iodine.

Exemplary stereochemistry can be as follows:

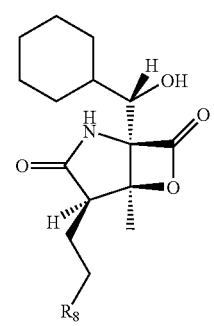

In preferred embodiments, the compound of Formula II has any of the following structures:

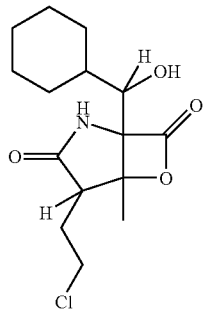 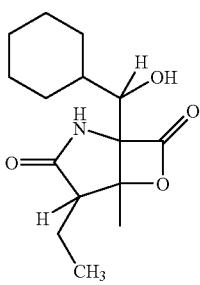

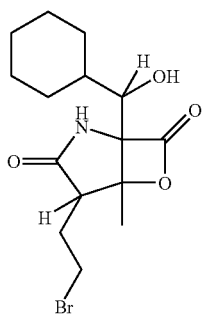

The following is exemplary stereochemistry for compounds having the structures II-2, II-3, and II-4, respectively:

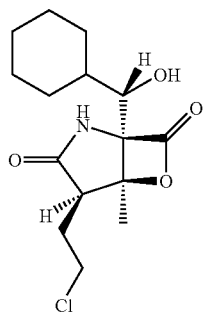 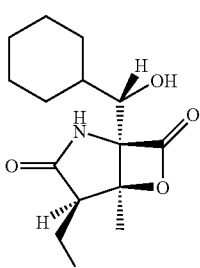

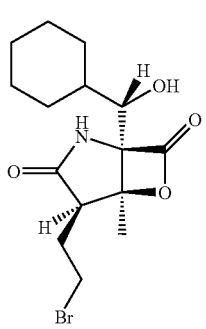

In other embodiments wherein $R_4$ may include a 7-oxabicyclo[4.1.0]hept-2-yl). An exemplary compound of Formula II is the following structure II-5:

Formula II-5

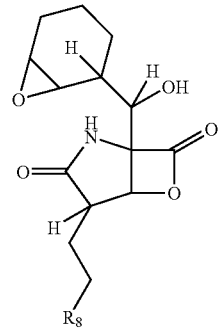

$R_8$ may include, for example, hydrogen, fluorine, chlorine, bromine and iodine.

The following are examples of compounds having the structure of Formula II-5:

Formulae II-5A and II-5B

II-5A

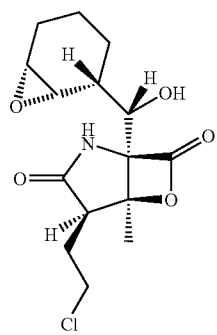

II-5B

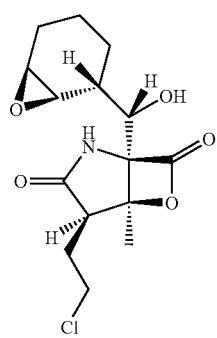

In still further embodiments, at least one $R_4$ may include a substituted or an unsubstituted branched alkyl. For example, a compound of Formula II can be the following structure II-6:

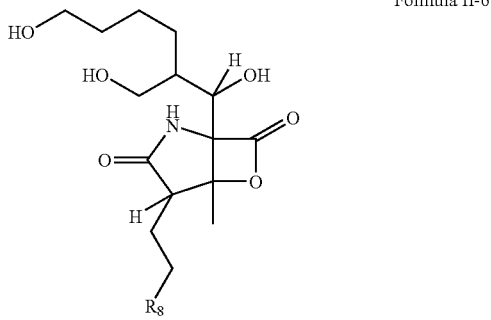

Formula II-6

$R_8$ may include, for example, hydrogen, fluorine, chlorine, bromine and iodine.

The following is exemplary stereochemistry for a compound having the structure of Formula II-6:

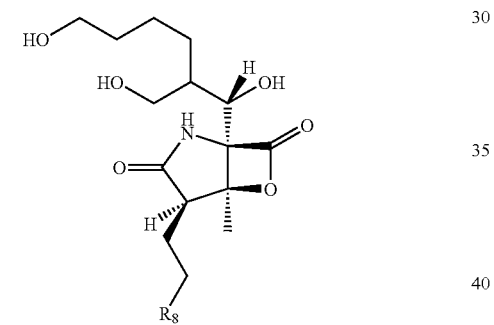

As another example, the compound of Formula II can be the following structure II-7:

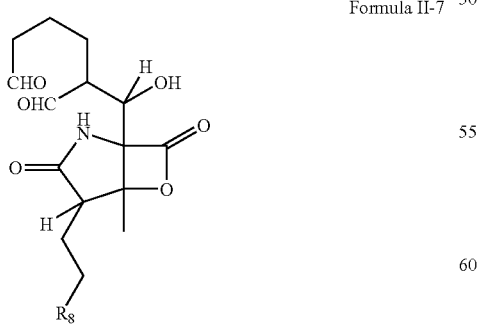

Formula II-7

$R_8$ may include, for example, hydrogen, fluorine, chlorine, bromine and iodine.

The following is exemplary stereochemistry for a compound having the structure of Formula II-7:

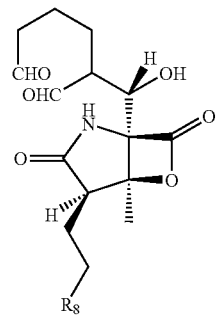

In other embodiments, at least one $R_4$ can be a cycloalkyl and $E_5$ can be an oxygen. An exemplary compound of Formula II can be the following structure II-8:

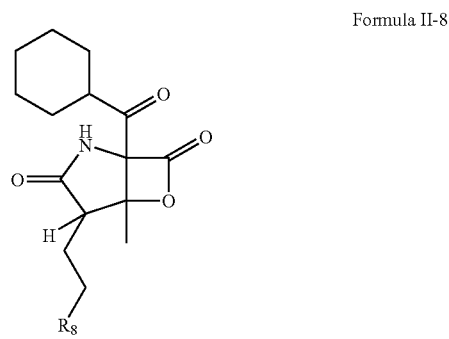

Formula II-8

$R_8$ may include, for example, hydrogen (II-8A), fluorine (II-8B), chlorine (II-8C), bromine (II-8D) and iodine (II-8E).

The following is exemplary stereochemistry for a compound having the structure of Formula II-8:

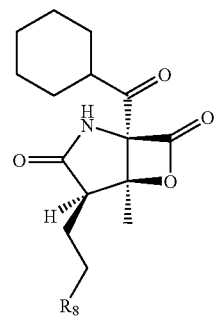

In some embodiments E5 can be an amine oxide, giving rise to an oxime. An exemplary compound of Formula II has the following structure II-9:

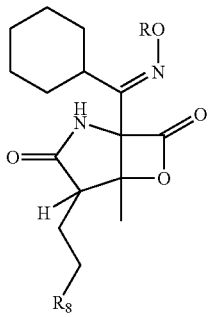

Formula II-9

$R_8$ may include, for example, hydrogen, fluorine, chlorine, bromine and iodine; R can be hydrogen, and a substituted or unsubstituted alkyl, aryl, or heteroaryl, and the like.

The following is exemplary stereochemistry for a compound having the structure of Formula II-9:

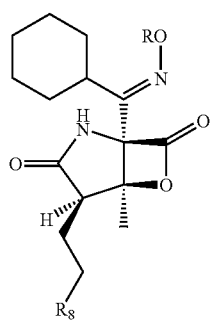

A further exemplary compound of Formula II has the following structure II-10:

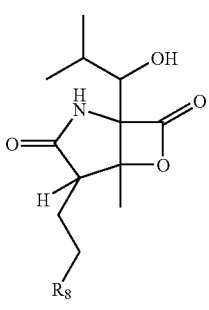

Formula II-10

$R_8$ may include, for example, hydrogen, fluorine, chlorine, bromine and iodine.

The following is exemplary stereochemistry for a compound having the structure of Formula II-10:

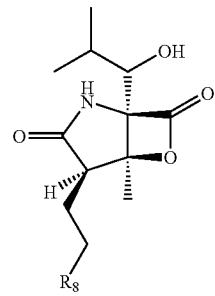

In some embodiments, $E_5$ can be $NH_2$. An exemplary compound of Formula II has the following structure II-11:

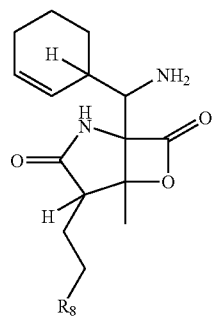

Formula II-11

$R_8$ may include, for example, hydrogen, fluorine, chlorine, bromine and iodine.

The following is exemplary stereochemistry for a compound having the structure of Formula II-11:

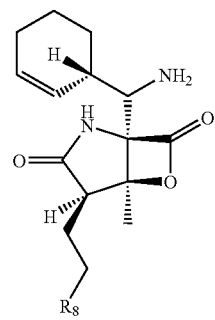

In some embodiments, at least one $R_4$ may include a cycloalkyl and $E_5$ can be $NH_2$. An exemplary compound of Formula II has the following structure II-12:

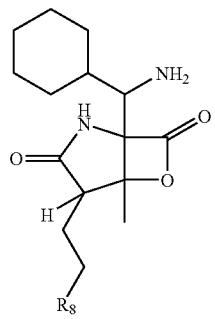

$R_8$ may include, for example, hydrogen, fluorine, chlorine, bromine and iodine.

The following is exemplary stereochemistry for a compound having the structure of Formula II-12:

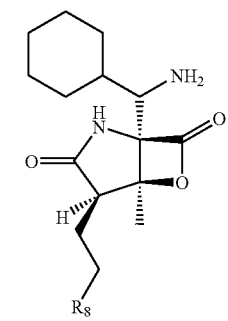

A further exemplary compound of Formula II has the following structure II-13:

Formula II-13

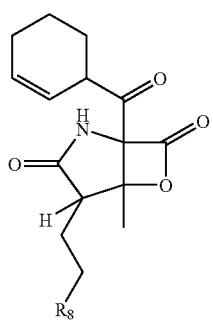

$R_8$ may include, for example, hydrogen (II-13A), fluorine (II-13B), chlorine (II-13C), bromine (II-13D) and iodine (II-13E).

The following is exemplary stereochemistry for a compound having the structure of Formula II-13:

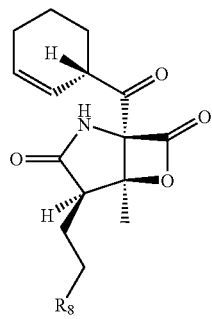

A still further exemplary compound of Formula II has the following structure II-14:

Formula II-14

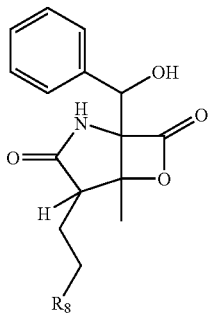

$R_8$ may include, for example, hydrogen, fluorine, chlorine, bromine and iodine.

The following is exemplary stereochemistry for a compound having the structure of Formula II-14:

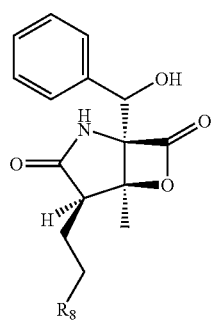

In some embodiments, the compounds of Formula II, may include as $R_4$ at least one cycloalkene, for example. Furthermore, in some embodiments, the compounds may include a hydroxy at $E_5$, for example. A further exemplary compound of Formula II has the following structure II-15:

Formula II-15

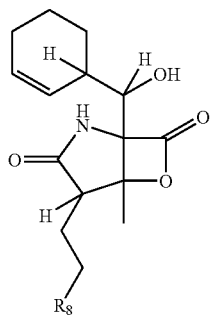

$R_8$ may include, for example, hydrogen, fluorine, chlorine, bromine and iodine.

Exemplary stereochemistry can be as follows:

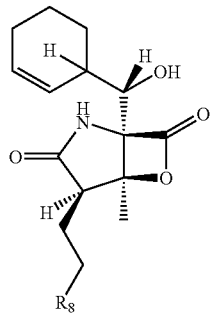

The following is exemplary stereochemistry for compounds having the structures II-16, II-17, II-18, and II-19, respectively:

II-16

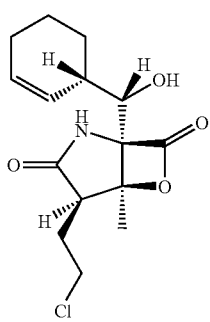

II-17

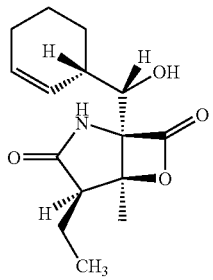

II-18

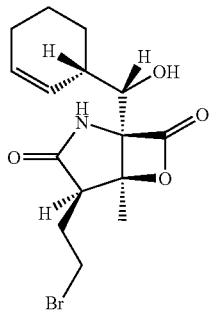

II-19

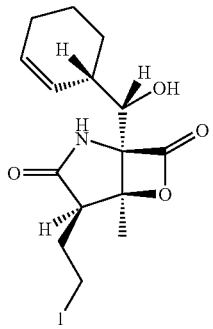

The compounds of Formulae II-16, II-17, II-18 and II-19 can be obtained by fermentation, synthesis, or semi-synthesis and isolated/purified as set forth below. Furthermore, the compounds of Formulae II-16, II-17, II-18 and II-19 can be used, and are referred to, as "starting materials" to make other compounds described herein.

In some embodiments, the compounds of Formula II, may include a methyl group as $R_1$, for example. A further exemplary compound, Formula II-20, has the following structure and stereochemistry:

II-20

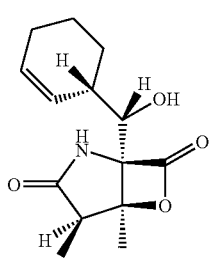

In some embodiments, the compounds of Formula II, may include hydroxyethyl as $R_1$, for example. A further exemplary compound, Formula II-21, has the following structure and stereochemistry:

II-21

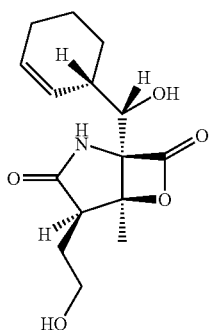

In some embodiments, the hydroxyl group of Formula II-21 can be esterified such that $R_1$ may include ethylpropionate, for example. An exemplary compound, Formula II-22, has the following structure and stereochemistry:

II-22

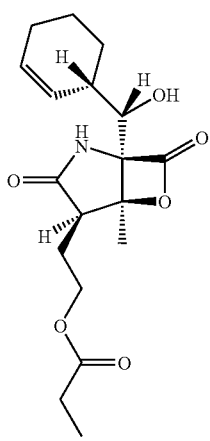

In some embodiments, the compounds of Formula II may include an ethyl group as $R_3$, for example. A further exemplary compound of Formula II has the following structure II-23:

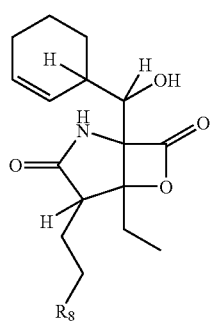

$R_8$ may include, for example, hydrogen, fluorine, chlorine, bromine and iodine. Exemplary stereochemistry can be as follows:

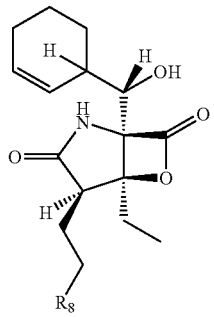

In some embodiments, the compounds of Formula II-23 may have the following structure and stereochemistry, exemplified by Formula II-24C, where $R_8$ is chlorine:

II-24C

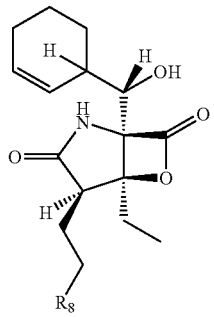

II-24C

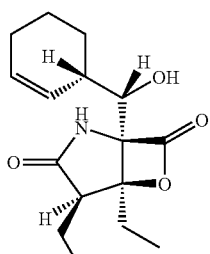

In some embodiments, the compounds of Formula II-15 may have the following stereochemistry, exemplified by the compound of Formula II-25, where $R_8$ is chlorine:

II-25

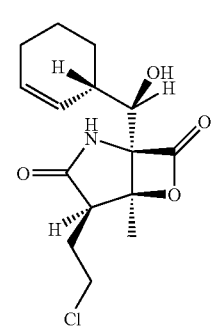

In some embodiments, the compound of Formula II-15 may have the following stereochemistry, exemplified by the compound of Formula II-26, where $R_8$ is chlorine:

II-26

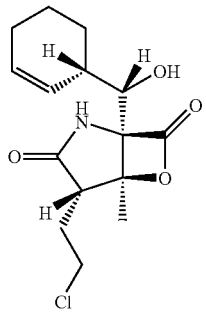

In some embodiments, the compound of Formula II may have the following structure and stereochemistry, exemplified by Formula II-27, where $R_1$ is ethyl:

II-27

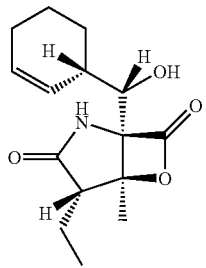

In some embodiments, the compound of Formula II may have the following structure and stereochemistry, exemplified by Formula II-28, where $R_1$ is methyl:

II-28

II-28

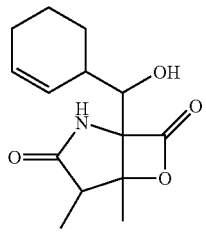

In some embodiments, the compounds of Formula II may include azidoethyl as $R_1$, for example. A further exemplary compound, Formula II-29, has the following structure and stereochemistry:

II-29

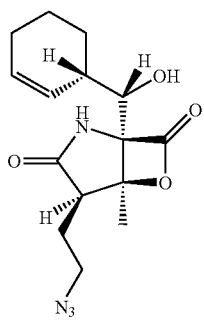

In some embodiments, the compounds of Formula II may include propyl as $R_1$, for example. A further exemplary compound, Formula II-30, has the following structure and stereochemistry:

II-30

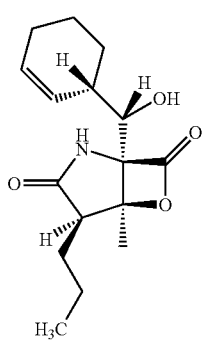

Still further exemplary compounds, Formulae II-31 and II-32, have the following structure and stereochemistry:

Formula II-31 and II-32

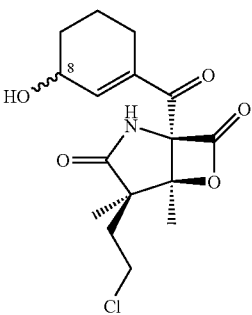

Other exemplary compounds, Formulae II-33, II-34, II-35 and II-36, have the following structure and stereochemistry:

Formula II-33 - II-36

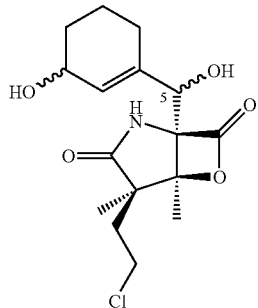

In some embodiments, the compound of Formula II may include cyanoethyl as $R_1$; for example, the compound of Formula II-37 has the following structure and stereochemistry:

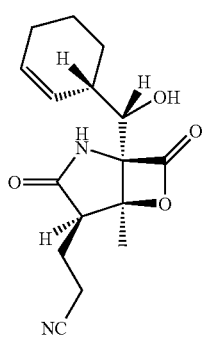

II-37

In another embodiment, the compound of Formula II may include ethylthiocyanate as $R_1$; for example, the compound of Formula II-38 has the following structure and stereochemistry:

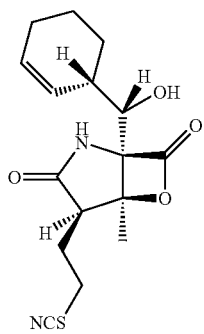

II-38

In some embodiments, the compounds of Formula II may include a thiol as $R_1$, for example. A further exemplary compound, Formula II-39, has the following structure and stereochemistry, where R=H, alkyl, aryl, or substituted alkyl or aryl:

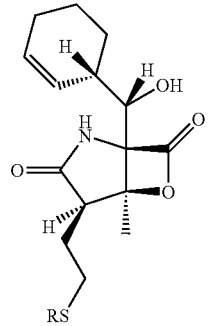

II-39

In a further exemplary compound, the sulfur of the compound of Formula II-39 can be oxidized to a sulfoxide (n=1) or sulfone (n=2), for example, as in the compound of Formula II-40:

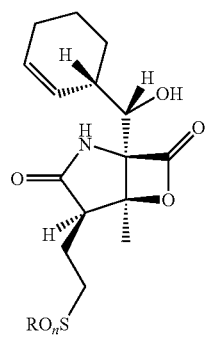

II-40

In some embodiments, the substituent $R_1$ of the compound of Formula II may include a leaving group, for example, a halogen, as in compounds II-18 or II-19, or another leaving group, such as a sulfonate ester. One example is the methane sulfonate (mesylate) of Formula II-41:

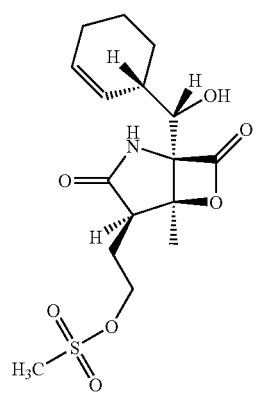

II-41

In some embodiments, the substituent $R_1$ of the compound of Formula II may include electron acceptors. The electron acceptor can be, for example, a Lewis acid, such as a boronic acid or ester. An exemplary compound, Formula II-42, has the following structure and stereochemistry, where n=0, 1, 2, 3, 4, 5, or 6, for example, and where R=H or alkyl, for example:

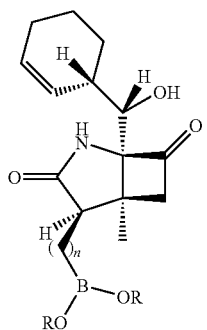

II-42

Further exemplary compounds of Formula II-42 are the compounds of Formula II-42A, where n=2 and R=H, and the compound of Formula II-42B, where n=1 and R=H:

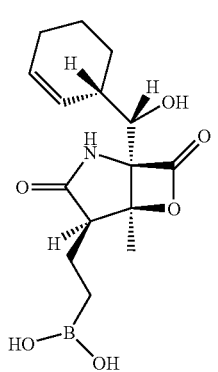

II-42A

II-42B

In some embodiments where the substituent $R_1$ of the compound of Formula II includes an electron acceptor, the electron acceptor can be, for example, a Michael acceptor. An exemplary compound, Formula II-43 has the following structure, where n=0, 1, 2, 3, 4, 5, 6, and where Z is an electron withdrawing group, for example, CHO, COR, COOR, $CONH_2$, CN, $NO_2$, SOR, $SO_2R$, etc:

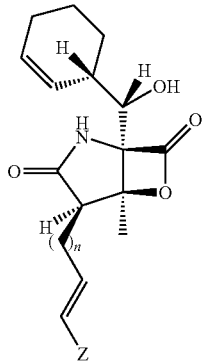

II-43

A further exemplary compound of Formula II-43 is the compound of Formula II-43A, where n=1 and Z=$CO_2CH_3$:

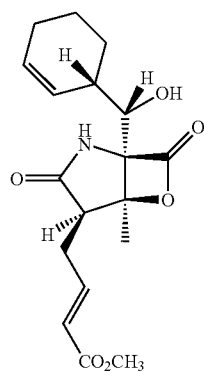

II-43A

In some embodiments, the compounds can be prodrug esters or thioesters of the compounds of Formula II. For example, the compound of Formula II-44 (a prodrug thioester of the compound of Formula II-16) has the following structure and stereochemistry:

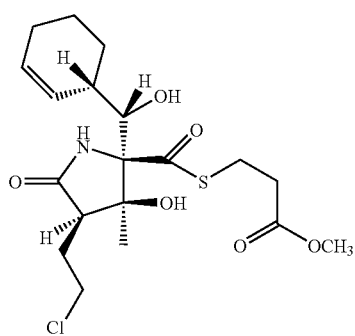

II-44

In some embodiments, the compounds of Formula II may include an alkenyl group as $R_1$, for example, ethylenyl. A further exemplary compound, Formula II-46, has the following structure and stereochemistry:

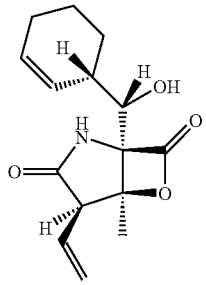

II-46

In some embodiments, the compounds can be prodrug esters or thioesters of the compounds of Formula II. For example, the compound of Formula II-47 (a prodrug thioester of the compound of Formula II-17) has the following structure and stereochemistry:

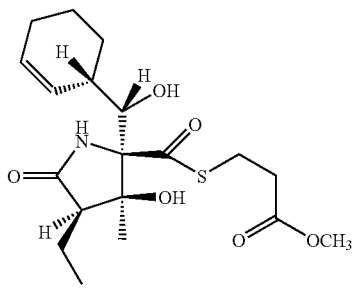

II-47

In some embodiments, the compounds can be prodrug esters or thioesters of the compounds of Formula II. For example, the compound of Formula II-48 has the following structure and stereochemistry:

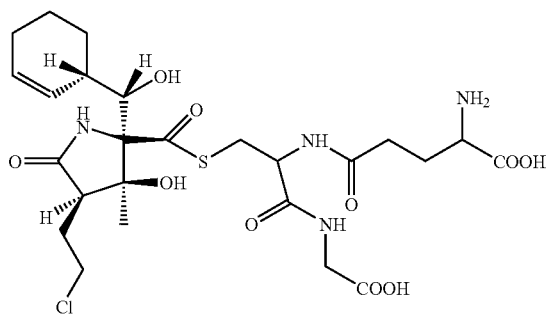

II-48

Other exemplary compound, Formula II-49 has the following structure and stereochemistry:

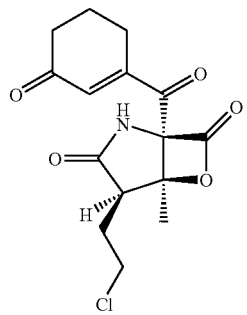

II-49

In some embodiments, the compound can be prodrug ester or thioester of the compounds of Formula II. For example, the compound of Formula II-50 (prodrug ester of the compound of Formula II-16) has the following structure and stereochemistry:

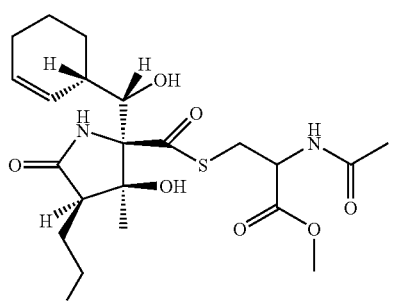

II-50

Compounds of Formula III

Other embodiments provide compounds, and methods of producing a class of compounds, pharmaceutically acceptable salts and pro-drug esters thereof, wherein the compounds are represented by Formula III:

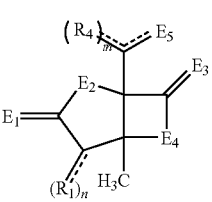

Formula III

In certain embodiments, the substituent(s) $R_1$ separately may include, for example, a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. For example, n can be equal to 1 or 2.

In certain embodiments, $R_4$ can be, for example, a hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. In some embodiments m can be equal to 1 or 2, and where m is equal to 2, the substituents can the same or different. Also, each of $E_1$, $E_2$, $E_3$, $E_4$ and $E_5$ can be, for example, a substituted or unsubstituted heteroatom. For example, the heteroatom can be nitrogen, sulfur or oxygen.

In some embodiments, $R_2$ is not cyclohex-2-enyl carbinol when one of the $R_1$ substituents is ethyl or chloroethyl.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

Compounds of Formula IV

Other embodiments provide compounds, and methods of producing a class of compounds, pharmaceutically acceptable salts and pro-drug esters thereof, wherein the compounds are represented by Formula IV:

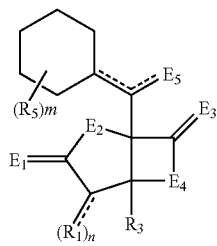

Formula IV

In certain embodiments, the substituent(s) $R_1$ $R_3$, and $R_5$ may separately include a hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. Also, each of $E_1$, $E_2$, $E_3$, $E_4$ and $E_5$ can be a heteroatom or substituted heteroatom, for example, nitrogen, sulfur or oxygen. In some embodiments, $R_3$ is not a hydrogen. n is equal to 1 or 2. When n is equal to 2, the substituents can be the same or can be different. Also, m can be 0, 1, 2, 3, 4, 5, 6, 7, 8, 9, 10, or 11. When m is greater than 1, the substituents can be the same or different.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

In some embodiments $R_5$ may give rise to a di-substituted cyclohexyl. An exemplary compound of Formula IV is the following structure IV-1, with and without exemplary stereochemistry:

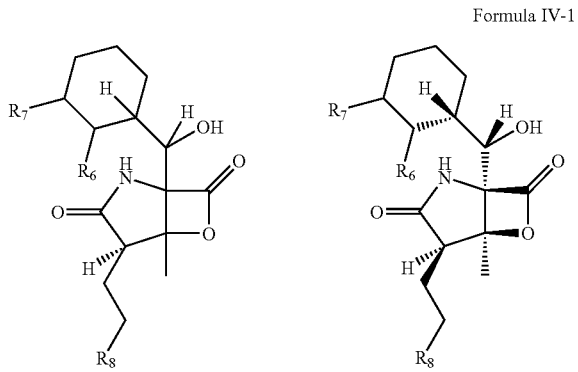

Formula IV-1

$R_8$ may include, for example, hydrogen, fluorine, chlorine, bromine and iodine. The substituent(s) $R_6$ and $R_7$ may separately include a hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl. Further, $R_6$ and $R_7$ both can be the same or different.

For example, an exemplary compound of Formula IV has the following structure IV-2:

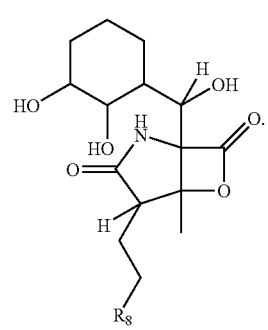

Formula IV-2

$R_8$ may include, for example, hydrogen, fluorine, chlorine, bromine and iodine.

Exemplary stereochemistry can be as follows:

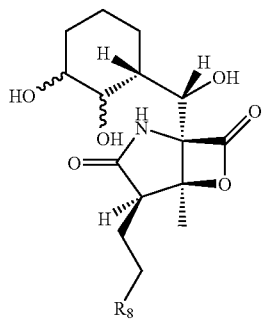

For example, an exemplary compound of Formula IV has the following structure IV-3:

Formula IV-3

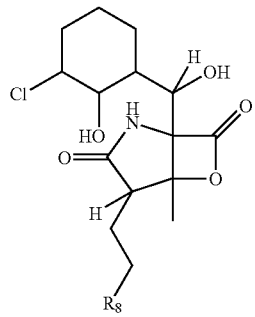

R₈ may include, for example, hydrogen (IV-3A), fluorine (IV-3B), chlorine (IV-3C), bromine (IV-3D) and iodine (IV-3E).

Exemplary structure and stereochemistry can be as follows:

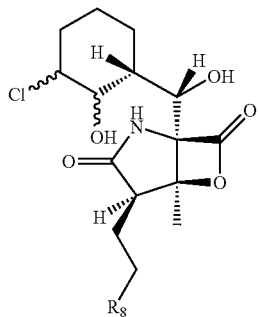

Additional exemplary structure and stereochemistry can be as follows:

Formula IV-3C

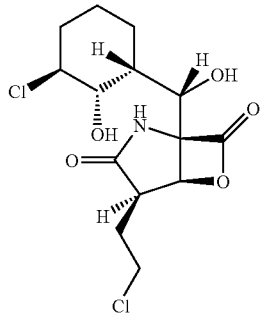

For example, an exemplary compound of Formula IV has the following structure IV-4:

Formula IV-4

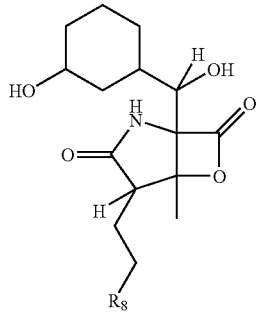

R₈ may include, for example, hydrogen, fluorine, chlorine, bromine and iodine.

Exemplary stereochemistry can be as follows:

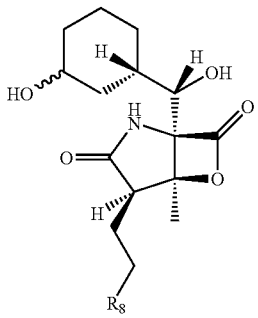

Compounds of Formula V

Some embodiments provide compounds, and methods of producing a class of compounds, pharmaceutically acceptable salts and pro-drug esters thereof, wherein the compounds are represented by Formula V:

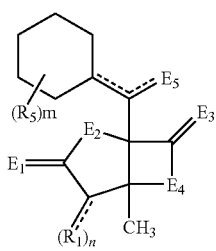

Formula V

In certain embodiments, the substituent(s) $R_1$ and $R_5$ may separately include a hydrogen, a halogen, a mono-substituted, a poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. In certain embodiments, each of $E_1$, $E_2$, $E_3$, $E_4$ and $E_5$ can be a heteroatom or substituted heteroatom, for example, nitrogen, sulfur or oxygen. n can be equal to 1 or 2, and when n is equal to 2, the substituents can be the same or different. Preferably, m can be, for example, 0, 1, 2, 3, 4, 5, 6, 7, 8, 9, 10, or 11. When m is greater than 1, $R_5$ can be the same or different.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

Compounds of Formula VI

Some embodiments provide compounds, and methods of producing a class of compounds, pharmaceutically acceptable salts and pro-drug esters thereof, wherein the compounds are represented by Formula VI:

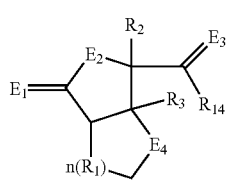

Formula VI wherein $R_1$ can be separately selected from the group consisting of a mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, phenyl, cycloalkylacyl, alkylthio, arylthio, oxysulfonyl, carboxy, thio, sulfoxide, sulfoneboronic acid esters, and halogenated alkyl including polyhalogenated alkyl. n is equal to 1 or 2, and if n is equal to 2, then $R_1$ can be the same or different;

wherein $R_2$, can be selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including, for example, cyclohexylcarbinol), cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl; wherein each of $E_1$, $E_2$, $E_3$ and $E_4$ can be a substituted or unsubstituted heteroatom.)

In some embodiments, $R_2$ is not cyclohex-2-enyl carbinol when one of the $R_1$ substituents is ethyl or chloroethyl and $R_3$ is methyl.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred.

wherein $R_{14}$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, thioesters, sulfoxide, sulfone, sulfonate esters, thiocyano, and halogenated alkyl including polyhalogenated alkyl.

In some embodiments, preferably $R_{14}$ is an alkylthiol or substituted alkylthiol, and $E_3$ is an oxygen.

For example, in some embodiments some of the compounds of Formula VI can have the following structure referred to as Formula VI-1:

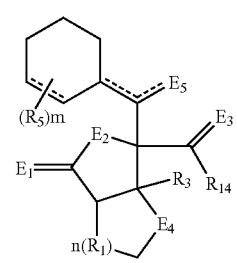

VI-1 wherein $R_1$ can be separately selected from the group consisting of a mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, phenyl, cycloalkylacyl, alkylthio, arylthio, oxysulfonyl, carboxy, thio, sulfoxide, sulfone, boronic acid esters, and halogenated alkyl including polyhalogenated alkyl. n is equal to 1 or 2, and if n is equal to 2, then $R_1$ can be the same or different;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl; wherein each of $E_1$, $E_2$, $E_3$ and $E_4$ can be a substituted or unsubstituted heteroatom.

wherein $R_5$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, wherein m is 0, 1, 2, 3, 4, 5, 6, 7, 8, 9, 10, or 11 and if m is more than 1, then $R_5$ can be the same or different; and where the substituents $R_5$ can form a ring; and wherein each of $E_1$, $E_2$, $E_3$, $E_4$ and $E_5$ is a substituted or unsubstituted heteroatom.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred.

wherein $R_{14}$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, thioesters, sulfoxide, sulfone, sulfonate esters, thiocyano, and halogenated alkyl including polyhalogenated alkyl.

For example, the compound has the following structure VI-1A:

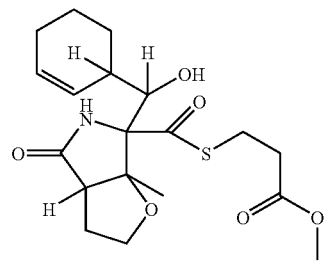

Formula VI-1A

Exemplary stereochemistry can be as follows:

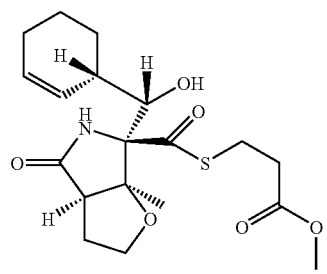

For example, an exemplary compound of Formula VI has the following structure and stereochemistry VI-1B:

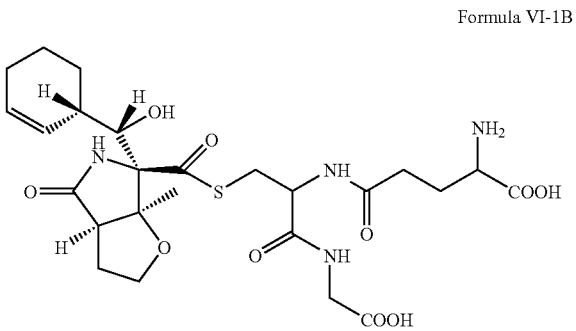

Formula VI-1B

Another example, the compound of Formula VI has the following structure and stereochemistry VI-1C:

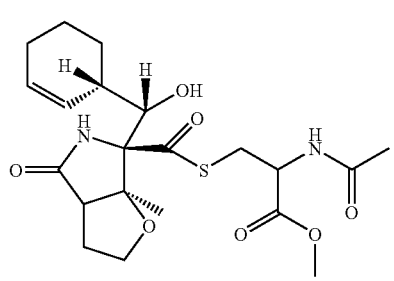

Formula VI-1C

Certain embodiments also provide pharmaceutically acceptable salts and pro-drug esters of the compound of Formulae I-VI, and provide methods of obtaining and purifying such compounds by the methods disclosed herein.

The term "pro-drug ester," especially when referring to a pro-drug ester of the compound of Formula I synthesized by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester- or thioester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl) methyl group. Other prodrugs can be prepared by preparing a corresponding thioester of the compound, for example, by reacting with an appropriate thiol, such as thiophenol, Cysteine or derivatives thereof, or propanethiol, for example. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is hereby incorporated by reference in its entirety.

The term "pro-drug ester," as used herein, also refers to a chemical derivative of the compound that is rapidly transformed in vivo to yield the compound, for example, by hydrolysis in blood.

The term "pharmaceutically acceptable salt," as used herein, and particularly when referring to a pharmaceutically acceptable salt of a compound, including Formulae I-VI, and Formula I-VI as produced and synthesized by the methods disclosed herein, refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. With respect to compounds synthesized by the method of this embodiment that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluenesulfonic or naphthalenesulfonic acid.

Preferred pharmaceutical compositions disclosed herein include pharmaceutically acceptable salts and pro-drug esters of the compound of Formulae I-VI obtained and purified by the methods disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

It will be also appreciated that the phrase "compounds and compositions comprising the compound," or any like phrase, is meant to encompass compounds in any suitable form for pharmaceutical delivery, as discussed in further detail herein. For example, in certain embodiments, the compounds or compositions comprising the same may include a pharmaceutically acceptable salt of the compound.

In one embodiment the compounds can be used to treat microbial diseases, cancer, and inflammation. Disease is meant to be construed broadly to cover infectious diseases, and also autoimmune diseases, non-infectious diseases and chronic conditions. In a preferred embodiment, the disease is caused by a microbe, such as a bacterium, a fungi, and protozoa, for example. The methods of use may also include the steps of administering a compound or composition comprising the compound to an individual with an infectious disease or cancer. The compound or composition can be administered in an amount effective to treat the particular infectious disease, cancer or inflammatory condition.

The infectious disease can be, for example, one caused by *Bacillus*, such as *B. anthracis* and *B. cereus*. The infectious disease can be one caused by a protozoa, for example, a *Leishmania*, a *Plasmodium* or a *Trypanosoma*. The compound or composition can be administered with a pharmaceutically acceptable carrier, diluent, excipient, and the like.

The cancer can be, for example, a multiple myeloma, a colorectal carcinoma, a prostate carcinoma, a breast adenocarcinoma, a non-small cell lung carcinoma, an ovarian carcinoma, a melanoma, and the like.

The inflammatory condition can be, for example, rheumatoid arthritis, asthma, multiple sclerosis, psoriasis, stroke, myocardial infarction, reperfusion injury, and the like.

The term "halogen atom," as used herein, means any one of the radio-stable atoms of column 7 of the Periodic Table of the Elements, i.e., fluorine, chlorine, bromine, or iodine, with bromine and chlorine being preferred.

The term "alkyl," as used herein, means any unbranched or branched, substituted or unsubstituted, saturated hydrocarbon, with $C_1$-$C_{24}$ preferred, and $C_1$-$C_6$ hydrocarbons being preferred, with methyl, ethyl, propyl, isopropyl, butyl, isobutyl, and tert-butyl, and pentyl being most preferred. Among the substituted, saturated hydrocarbons, $C_1$-$C_{24}$ are preferred, with $C_1$-$C_6$ mono- and di- and per-halogen substituted saturated hydrocarbons and amino-substituted hydrocarbons more preferred.

The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Specifically, the definition of substituted is as broad as that provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. The other above-listed patents also provide standard definitions for the term "substituted" that are well-understood by those of skill in the art.

The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$-$C_6$ unbranched, mono-unsaturated and di-unsaturated, unsubstituted hydrocarbons being preferred, and mono-unsaturated, di-halogen substituted hydrocarbons being most preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom. The term "heterocycle" or "heterocyclic" refer to any cyclic compound containing one or more heteroatoms. The substituted aryls, heterocycles and heteroaryls can be substituted with any substituent, including those described above and those known in the art.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring. The term "alkoxy carbonyl" refers to any linear, branched, cyclic, saturated, unsaturated, aliphatic or aromatic alkoxy attached to a carbonyl group. The examples include methoxycarbonyl group, ethoxycarbonyl group, propyloxycarbonyl group, isopropyloxycarbonyl group, butoxycarbonyl group, sec-butoxycarbonyl group, tert-butoxycarbonyl group, cyclopentyloxycarbonyl group, cyclohexyloxycarbonyl group, benzyloxycarbonyl group, allyloxycarbonyl group, phenyloxycarbonyl group, pyridyloxycarbonyl group, and the like.

The terms "pure," "purified," "substantially purified," and "isolated" as used herein refer to the compound of the embodiment being free of other, dissimilar compounds with which the compound, if found in its natural state, would be associated in its natural state. In certain embodiments described as "pure," "purified," "substantially purified," or "isolated" herein, the compound may comprise at least 0.5%, 1%, 5%, 10%, or 20%, and most preferably at least 50% or 75% of the mass, by weight, of a given sample.

The terms "derivative," "variant," or other similar term refers to a compound that is an analog of the other compound.

Improved, Modified or Controlled Biosynthesis of Salinosporamide A and Analogs Thereof Certain of the compounds of Formula I-VI can be obtained selectively through modulation of biosynthesis of Salinosporamide A and analogs thereof. Salinosporamide A is shown in the following formula.

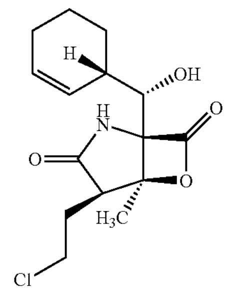

Other exemplary compounds made by or the production of which may be modified by these methods, include:

(II-17)

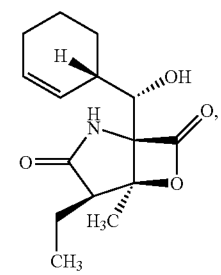

(II-20)

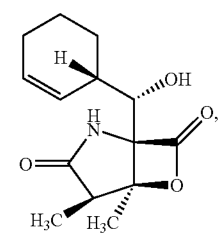

(II-28)

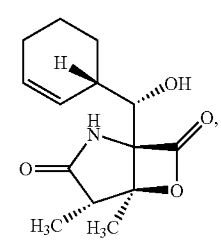

(II-24C)

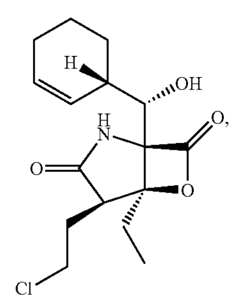

-continued

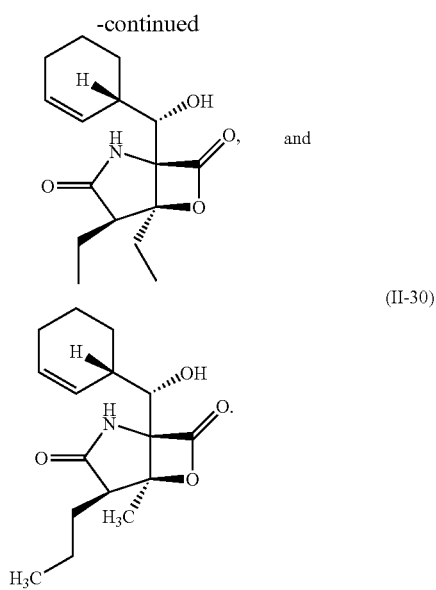

(II-30)

The genus *Salinospora*, with an excess of 2500 strains, has been discovered in several different oceanic systems. The compound salinosporamide A is produced by the bacteria. Accordingly, biosynthesis of salinosporamide A selectively and in high yield is desired. The production of Salinosporamide A and its analogs may be modulated by controlling fermentation conditions of the *salinospora* bacteria.

Salinosporamide A can be produced through a high-yield saline fermentation (~350-400 mg/L) and modifications of the conditions yield new analogs in the fermentation extracts. Different aspects of the fermentation conditions and genetic make-up or feed stock and feed schedule may be modulated to alter absolute and relative yields of Salinosporamide A and analogs thereof. These aspects include 1) improving production yield and 2) elimination of minor analogs.

In improving production yield of one select analog absolutely, or relative to other analogs, modulation of fermentation conditions favors production of a particular compound and may disfavor production of others. One tactic for improving production yield is to feed a particular intermediate preceding a rate determining step in the pathway. A buildup of a normally low-level intermediate can assist in the kinetics of the pathway, thus improving production yield.

In elimination of minor analogs, a particular compound may be favored over other analogs. Modulation of fermentation conditions can work to favor production of the particular compound. When minor analogs are disfavored or eliminated, then purification of the particular compounds is less cumbersome. For example, genes coding an essential enzyme may be "knocked-out," to eliminate producing undesired analogs. For example, the crotonly-CoA reductase (CCR) enzyme is responsible for catalyzing a step in the production of the erythrose-like precursor of the compound Formula II-17. Genetic engineering to reduce or eliminate production of CCR, through techniques known in the art, selectively inhibits production of the compound of Formula II-17.

Accordingly, in some embodiments, certain analogs of Salinosporamide A are produced by selectively feeding producing organisms (e.g., NPS21184 or CNB476) excesses of various agents, including but not limited to propionate, butyrate, and valerate. For example, in one embodiment, production of the compounds of formulae II-20 and II-29 is increased by feeding strain NPS21184 propionate. In another embodiment, production of the compound of formula II-17 is increased by feeding strain NPS21184 butyrate. In still another embodiment, production of the compound of formula II-30 is increased by feeding strain NPS21184 valerate.

In some embodiments, production yields of Salinosporamide A are increased by excluding from the fermentation broth agents that increase the yield of analogs also produced by the producing strain. For example, in some embodiments, production of Salinosporamide A is increased by excluding propionate, butyrate, and valerate from the fermentation broth.

Certain of the compounds of Formula I-VI can be obtained and purified or can be obtained via semi-synthesis from purified compounds as set forth herein. Generally, without being limited thereto, the compounds of Formula II-15, preferably, Formulae II-16, II-17, II-18 and II-19, can be obtained synthetically or by fermentation. Exemplary fermentation procedures are provided below. Further, the compounds of Formula II-15, preferably, Formulae II-16, II-17, II-18 and II-19 can be used as starting compounds in order to obtain/synthesize various of the other compounds described herein. Exemplary non-limiting syntheses are provided herein.

Formula II-16

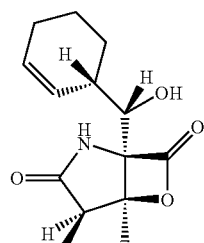

Formula II-17

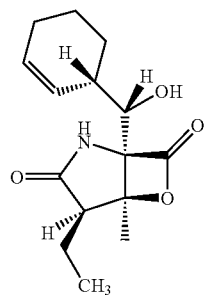

Formula II-18

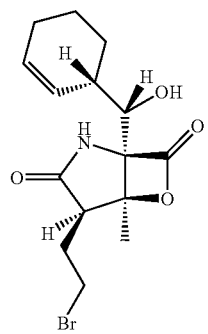

-continued

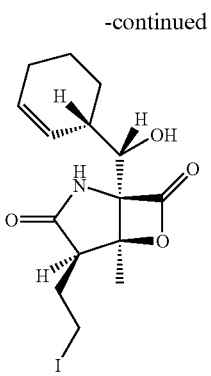

Formula II-19

Formula II-16 may be produced through a high-yield saline fermentation (~350-400 mg/L) and modifications of the conditions yields new analogs in the fermentation extracts. Additional analogs can be generated through directed biosynthesis. Directed biosynthesis is the modification of a natural product by adding biosynthetic precursor analogs to the fermentation of producing microorganisms (Lam, et al., *J Antibiot (Tokyo)* 44:934 (1991), Lam, et al., *J Antibiot (Tokyo)* 54:1 (2001); which is hereby incorporated by reference in its entirety).

Exposing the producing culture to analogs of acetic acid, phenylalanine, valine, butyric acid, shikimic acid, and halogens, preferably, other than chlorine, can lead to the formation of new analogs. The new analogs produced can be easily detected in crude extracts by HPLC and LC-MS. For example, after manipulating the medium with different concentrations of sodium bromide, a bromo-analog, Formula II-18, was successfully produced in shake-flask culture at a titer of 14 mg/L.

A second approach to generate new analogs is through biotransformation. Biotransformation reactions includes, but is not limited to, chemical reactions catalyzed by enzymes or whole cells containing these enzymes. Zaks, A., *Curr Opin Chem Biol* 5:130 (2001). Microbial natural products are ideal substrates for biotransformation reactions as they are synthesized by a series of enzymatic reactions inside microbial cells. Riva, S., *Curr Opin Chem Biol* 5:106 (2001).

Given the structure of the described compounds, including those of Formula II-15, for example, the possible biosynthetic origins are acetyl-CoA, ethylmalonyl-CoA, phenylalanine and chlorine. Ethylmalonyl-CoA is derived from butyryl-CoA, which can be derived either from valine or crotonyl-CoA. Liu, et al., *Metab Eng* 3:40 (2001). Phenylalanine is derived from shikimic acid.

Production of Compounds of Formulae I-7, II-16, II-17, II-18, II-20, II-24C, II-26, II-27 and II-28

The production of compounds of Formulae I-7, II-16, II-17, II-18, II-20, II-24C, II-26, II-27 and II-28 for example, can be carried out by cultivating strain CNB476 and strain NPS21184, a natural variant of strain CNB476, in a suitable nutrient medium under conditions described herein, preferably under submerged aerobic conditions, until a substantial amount of compounds are detected in the fermentation; harvesting by extracting the active components from the fermentation broth with a suitable solvent; concentrating the solvent containing the desired components; then subjecting the concentrated material to chromatographic separation to isolate the compounds from other metabolites also present in the cultivation medium.

A typical 16S rDNA sequence of the *Salinospora* is obtained. Bars represent characteristic signature nucleotides of the *Salinospora* that separate them from their nearest relatives.

The culture (CNB476) was deposited on Jun. 20, 2003 with the American Type Culture Collection (ATCC) in Rockville, Md. and assigned the ATCC patent deposition number PTA-5275. Strain NPS21184, a natural variant of strain CNB476, was derived from strain CNB476 as a single colony isolate. Strain NPS21184 has been deposited to ATCC on Apr. 27, 2005 and assigned the ATCC patent deposition number PTA-6685. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce the starting compounds of Formulae II-16, II-17, and II-18.

Fermentation of Strain CNB476 and Strain NPS21184

Production of compounds can be achieved at temperature conducive to satisfactory growth of the producing organism, e.g. from 16 C to 40 C, but it is preferable to conduct the fermentation at 22 C to 32 C. The aqueous medium can be incubated for a period of time necessary to complete the production of compounds as monitored by high pressure liquid chromatography (HPLC), preferably for a period of about 2 to 10 days, on a rotary shaker operating at about 50 rpm to 400 rpm, preferably at 150 rpm to 250 rpm, for example. The production of the compounds can also be achieved by cultivating the production strain in a bioreactor, such as a fermentor system that is suitable for the growth of the production strain.

Growth of the microorganisms is achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources can be combined in the same medium, for example. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cottonseed meal, fish meal, peptone, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Biological Activity and Uses of Compounds

Some embodiments relate to methods of treating cancer, inflammation, and infectious diseases, particularly those affecting humans. The methods may include, for example, the step of administering an effective amount of a member of a class of new compounds. Thus, the compounds disclosed herein can be used to treat cancer, inflammation, and infectious disease.

The compounds have various biological activities. For example, the compounds have chemosensitizing activity, anti-microbial, anti-inflammation, radiosensitizing, and anti-cancer activity.

The compounds have proteasome inhibitory activity. The proteasome inhibitory activity may, in whole or in part, contribute to the ability of the compounds to act as anti-cancer, anti-inflammatory, and anti-microbial agents.

The proteasome is a multisubunit protease that degrades intracellular proteins through its chymotrypsin-like, trypsin-like and peptidylglutamyl-peptide hydrolyzing (PGPH; and also know as the caspase-like activity) activities. The 26S proteasome contains a proteolytic core called the 20S proteasome and one or two 19S regulatory subunits. The 20S proteasome is responsible for the proteolytic activity against many substrates including damaged proteins, the transcription factor NF-κB and its inhibitor IκB, signaling molecules, tumor suppressors and cell cycle regulators. There are three distinct protease activities within the proteasome: 1) chymotrypsin-like; 2) trypsin-like; and the 3) peptidyl glutamyl peptide hydrolyzing (PGPH) activity.

Figure 5:
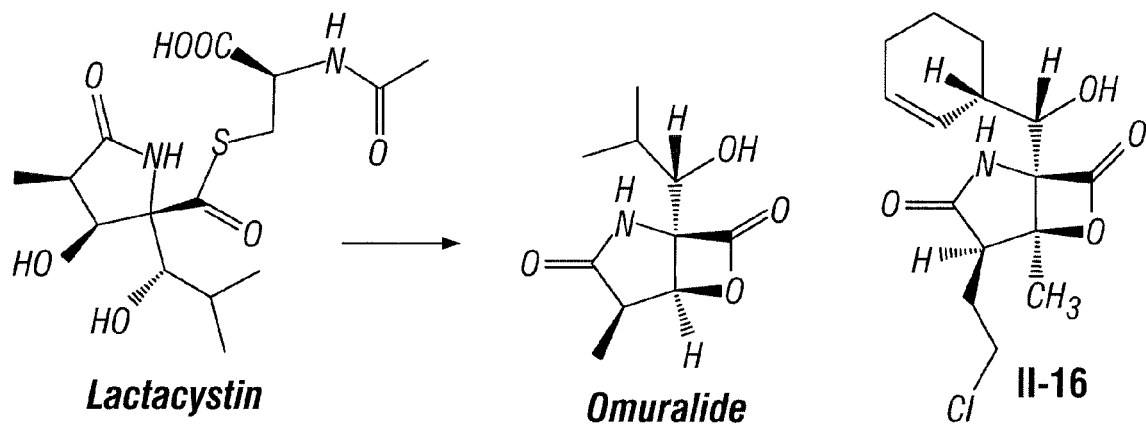
FIG. 5 shows Omuralide, a degradation product of the microbial metabolite Lactacystin. Also shown is a compound of Formula II-16, also referred to as Salinosporamide A.

As an example, compounds of Formula II-16 were more potent ($EC_{50}$ 2 nM) at inhibiting the chymotrypsin-like activity of rabbit muscle proteasomes than Omuralide ($EC_{50}$ 52 nM) and also inhibited the chymotrypsin-like activity of human erythrocyte derived proteasomes ($EC_{50}$~250 pM). FIG. 5 shows omuralide, which is a degradation product of Lactacystin, and it shows a compound of Formula II-16. Compounds of Formula II-16 exhibit a significant preference for inhibiting chymotrypsin-like activity of the proteasome over inhibiting the catalytic activity of chymotrypsin. Compounds of Formula II-16 also exhibit low nM trypsin-like inhibitory activity (~10 nM), but are less potent at inhibiting the PGPH activity of the proteasome ($EC_{50}$~350 nM).

Additional studies have characterized the effects of compounds described herein, including studies of Formula II-16 on the NF-κB/IκB signaling pathway. Treatment of HEK293 cells (human embryonic kidney) with Tumor Necrosis Factor-alpha (TNF-α) induces phosphorylation and proteasome-mediated degradation of IκBα followed by NF-κB activation. To confirm proteasome inhibition, HEK293 cells were pretreated for 1 hour with compounds of Formula II-16 followed by TNF-α stimulation. Treatment with compounds of Formula II-16 promoted the accumulation of phosphorylated IκBα suggesting that the proteasome-mediated IκBα degradation was inhibited.

Furthermore, a stable HEK293 clone (NF-κB/Luc 293) was generated carrying a luciferase reporter gene under the regulation of 5×NF-κB binding sites. Stimulation of NF-κB/Luc 293 cells with TNF-α increases luciferase activity as a result of NF-κB activation while pretreatment with compounds of Formula II-16 decreases activity. Western blot analyses demonstrated that compounds of Formula II-16 promoted the accumulation of phosphorylated-IκBα and decreased the degradation of total IκBα in the NF-κB/Luc 293 cells. Compounds of Formula II-16 were also shown to increase the levels of the cell cycle regulatory proteins, p21 and p27.

Tumor cells can be more sensitive to proteasome inhibitors than normal cells. Moreover, proteasome inhibition increases the sensitivity of cancer cells to anticancer agents. The cytotoxic activity of the compounds described herein, including Formula II-16, were examined for cytotoxic activity against various cancer cell lines. Formula II-16 was examined, for example, in the National Cancer Institute screen of 60 human tumor cell lines. Formula II-16 exhibited selective cytotoxic activity with a mean $GI_{50}$ value (the concentration to achieve 50% growth inhibition) of less than 10 nM. The greatest potency was observed against SK-MEL-28 melanoma and MDA-MB-235 breast cancer cells [both with $LC_{50}$ (the concentration with 50% cell lethality) <10 nM].

A panel of cell lines including human colorectal (HT-29 and LoVo), prostate (PC3), breast (MDA-MB-231), lung (NCI-H292), ovarian (OVCAR3), acute T-cell leukemia (Jurkat), murine melanoma (B16-F10) and normal human fibroblasts (CCD-27sk) was treated with Salinosporamide A for 48 h to assess cytotoxic activity. HT-29, LoVo, PC3, MDA-MB-231, NCI-H292, OVCAR3, Jurkat, and B16-F10 cells were sensitive with $EC_{50}$ values of 47, 69, 78, 67, 97, 69, 10, and 33 nM, respectively. In contrast, the $EC_{50}$ values for CCD-27sk cells were 196 nM. Treatment of Jurkat cells with Salinosporamide A at the approximate $EC_{50}$ resulted in Caspase-3 activation and cleavage of PARP confirming the induction of apoptosis.

The anti-anthrax activity of the described compounds was evaluated using an in vitro LeTx induced cytotoxicity assay. As one example, the results indicate that Formula II-16 is a potent inhibitor of LeTx-induced cytotoxicity of murine macrophage-like RAW264.7 cells. Treatment of RAW264.7 cells with Formula II-16 resulted in a 10-fold increase in the viability of LeTx-treated cells compared to LeTx treatment alone (average $EC_{50}$ of <4 nM).

Potential Chemosensitizing Effects of Formula II-16

Additional studies have characterized the effects of the compounds described herein on the NF-κB/IκB signaling pathway (see the Examples). In unstimulated cells, the transcription factor nuclear factor-kappa B (NF-?B) resides in the cytoplasm in an inactive complex with the inhibitory protein IκB (inhibitor of NF-κB). Various stimuli can cause I?B phosphorylation by I?B kinase, followed by ubiquitination and degradation by the proteasome. Following the degradation of I?B, NF-?B translocates to the nucleus and regulates gene expression, affecting many cellular processes including inhibition of apoptosis. Chemotherapy agents such as CPT-11 (Irinotecan) can activate NF-?B in human colon cancer cell lines including LoVo cells, resulting in a decreased ability of these cells to undergo apoptosis. Painter, R. B. *Cancer Res* 38:4445 (1978). Velcade™ is a dipeptidyl boronic acid that inhibits the chymotrypsin-like activity of the proteasome (Lightcap, et al., *Clin Chem* 46:673 (2000), Adams, et al., *Cancer Res* 59:2615 (1999), Adams, *Curr Opin Oncol* 14:628 (2002)) while enhancing the trypsin and PGPH activities. Recently approved as a proteasome inhibitor, Velcade™, (PS-341; Millennium Pharmaceuticals, Inc.) has been shown to be directly toxic to cancer cells and also enhance the cytotoxic activity of CPT-11 in LoVo cells in vitro and in a LoVo xenograft model by inhibiting I?B degradation by the proteasome. Blum, et al., *Ann Intern Med* 80:249 (1974). In addition, Velcade™ was found to inhibit the expression of proangiogenic chemokines/cytokines Growth Related Oncogene-alpha (GRO-α) and Vascular Endothelial Growth Factor (VEGF) in squamous cell carcinoma, presumably through inhibition of the NF-κB pathway. Dick, et al., *J Biol Chem*

271:7273 (1996). These data suggest that proteasome inhibition may not only decrease tumor cell survival and growth, but also angiogenesis.

Anti-Anthrax Activity

Another potential application for proteasome inhibitors comes from recent studies on the biodefense Category A agent B. anthracis (anthrax). Anthrax spores are inhaled and lodge in the lungs where they are ingested by macrophages. Within the macrophage, spores germinate, the organism replicates, resulting ultimately in killing of the cell. Before killing occurs, however, infected macrophages migrate to the lymph nodes where, upon death, they release their contents allowing the organism to enter the bloodstream, further replicate, and secrete lethal toxins. Hanna, et al., *Proc Natl Acad Sci USA* 90:10198 (1993). Anthrax toxins are responsible for the symptoms associated with anthrax. Two proteins that play a key role in the pathogenesis of anthrax are protective antigen (PA, 83 kDa) and lethal factor (LF, 90 kDa) which are collectively known as lethal toxin (LeTx). LF has an enzymatic function, but requires PA to achieve its biological effect. Neither PA or LF cause death individually; however, when combined they cause death when injected intravenously in animals. Kalns, et al., Biochem *Biophys Res Commun* 297:506 (2002), Kalns, et al., *Biochem Biophys Res Commun* 292:41 (2002).

Protective antigen (PA), the receptor-binding component of anthrax toxin, is responsible for transporting lethal factor into the host cell. PA oligomerizes into a ring-shaped heptamer (see FIG. 6). Each heptamer, bound to its receptor on the surface of a cell, has the ability to bind up to three molecules of LF. The complex formed between the PA heptamer and LF is taken into the cell by receptor-mediated endocytosis. Following endocytosis, LF is released into the cytosol where it attacks various cellular targets. Mogridge, et al., *Biochemistry* 41:1079 (2002), Lacy, et al., *J Biol Chem* 277: 3006 (2002), Bradley, et al., *Nature* 414:225 (2001).

Lethal factor (LF) is a zinc dependent metalloprotease, which in the cytosol can cleave and inactivate signaling proteins of the mitogen-activated protein kinase family (MAPKK). Duesbery, et al., *Science* 280:734 (1998), Bodart, et al., *Cell Cycle* 1:10 (2002), Vitale, et al., *J Appl Microbiol* 87:288 (1999), Vitale, et al., *Biochem J* 352 Pt 3:739 (2000). Of the seven different known MAPK kinases, six have been shown to be cleaved by LF. Within the cell, MAPK kinase pathways transduce various signals involved in cell death, proliferation, and differentiation making these proteins highly significant targets. However, certain inhibitors that prevent LeTx-induced cell death, do not prevent MAPKK cleavage by LF suggesting that this activity is not sufficient for induction of cell death. Kim, et al., *J Biol Chem* 278:7413 (2003), Lin, et al., *Curr Microbiol* 33:224 (1996).

Figure 6:
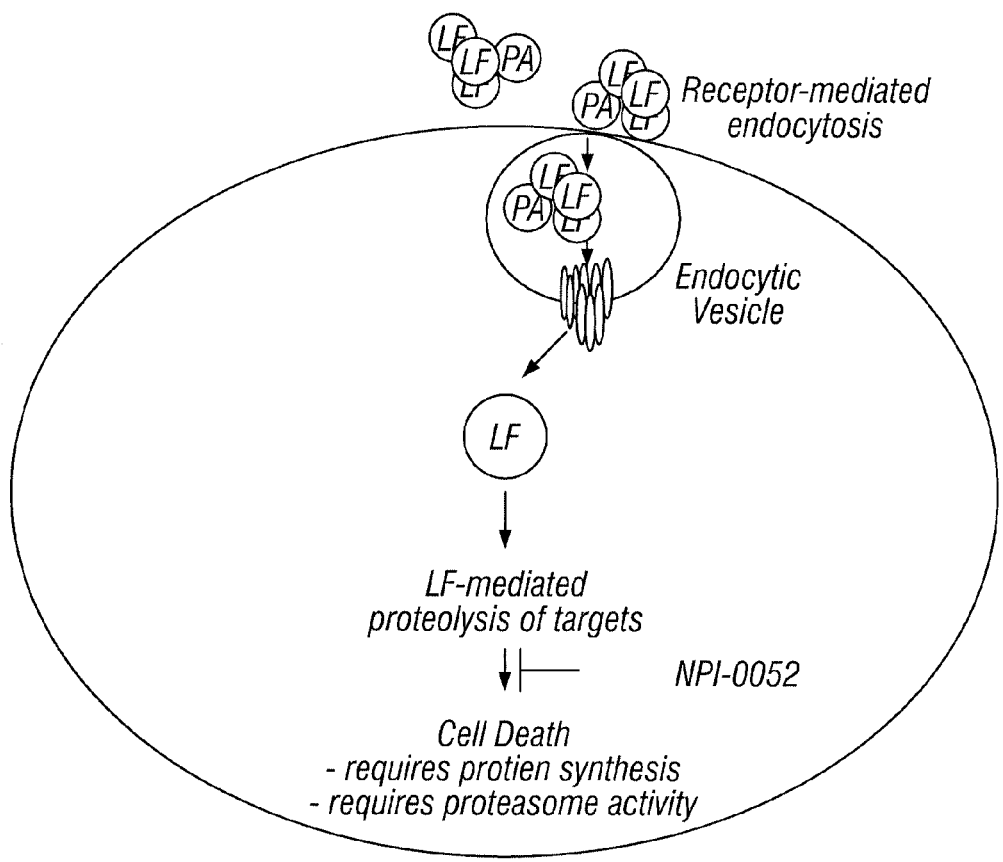
FIG. 6 illustrates lethal toxin-mediated macrophage cytotoxicity. NPI-0052 represents the compound of Formula II-16.

Studies have suggested that inhibition of the proteasome can prevent LeTx-induced cell death. Tang, et al., *Infect Immun* 67:3055 (1999). Data have shown that proteasome activity is required for LeTx-mediated killing of RAW264.7 macrophage-like cells and that proteasome inhibitors protect RAW264.7 cells from LeTx. Proteasome inhibition did not block MEK1 cleavage, suggesting the LeTx pathway is not blocked upstream of MEK1 cleavage in these studies. Additionally, there is no increase in proteasome activity in cells treated with LeTx. These data suggested that a novel, potent proteasome inhibitor like the compounds described herein, may also prevent LeTx-induced cell death as illustrated in FIG. 6.

The receptor for PA has been identified and is expressed by many cell types. Escuyer, et al., *Infect Immun* 59:3381 (1991). Lethal toxin is active in a few cell culture lines of macrophages causing cell death within a few hours. Hanna, et al., *Proc Natl Acad Sci USA* 90:10198 (1993), Kim, et al., *J Biol Chem* 278:7413 (2003), Lin, et al., *Curr Microbiol* 33:224 (1996). LeTx can induce both necrosis and apoptosis in mouse macrophage-like RAW264.7 and J774A.1 cells upon in vitro treatment.

The results indicate that the compounds described herein act as a potent inhibitor of LeTx-induced cytotoxicity of murine macrophage-like RAW264.7 cells. Treatment of RAW264.7 cells with, for example, compounds of Formula II-16, resulted in a 10-fold increase in the viability of LeTx-treated cells compared to LeTx treatment alone (average $EC_{50}$ of <4 nM) and therefore provide a valuable therapy for anthrax infections. Formula II-16, for example, promoted survival of RAW264.7 macrophage-like cells in the presence of LeTx indicating that this compound and its derivatives provide a valuable clinical therapeutic for anthrax infection.

Pharmaceutical Compositions

In one embodiment, the compounds disclosed herein are used in pharmaceutical compositions. The compounds preferably can be produced by the methods disclosed herein. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents can be provided in the pharmaceutical composition. For example, sodium benzoate, ascorbic acid and esters of p-hydroxybenzoic acid can be added as preservatives. In addition, antioxidants and suspending agents can be used.

The compositions, particularly those of Formulae I-VI, can be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. Such formulations can be made using methods known in the art (see, for example, U.S. Pat. Nos. 5,733,888 (injectable compositions); 5,726,181 (poorly water soluble compounds); 5,707,641 (therapeutically active proteins or peptides); 5,667,809 (lipophilic agents); 5,576,012 (solubilizing polymeric agents); 5,707,615 (anti-viral formulations); 5,683,676 (particulate medicaments); 5,654,286 (topical formulations); 5,688,529 (oral suspensions); 5,445,829 (extended release formulations); 5,653,987 (liquid formulations); 5,641,515 (controlled release formulations) and 5,601,845 (spheroid formulations); all of which are incorporated herein by reference in their entireties.

Further disclosed herein are various pharmaceutical compositions well known in the pharmaceutical art for uses that include topical, intraocular, intranasal, and intraauricular delivery. Pharmaceutical formulations include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Opthalmologica*, 210(2):101-3 (1996)); ophthalmic ointments; ophthalmic suspensions, such as microparticulates, drug-containing small polymeric particles that are suspended in a liquid carrier medium (Joshi, A. 1994 *J Ocul Pharmacol* 10:29-45), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences (Mack Publishing, 18$^{th}$ Edition), which is incorporated herein by reference in its entirety, and well-known to those skilled in the art, suitable formulations are most often and preferably isotonic, slightly buffered to maintain a pH of 5.5 to 6.5, and most often and preferably include anti-microbial preservatives and appropriate drug stabilizers. Pharmaceutical formulations for intraauricular delivery include suspensions and ointments for topical application in the ear. Common solvents for such aural formulations include glycerin and water.

When used as an anti-cancer, anti-inflammatory or anti-microbial compound, for example, the compounds of Formulae I-VI or compositions including Formulae I-VI can be administered by either oral or non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, or the like.

In one embodiment, the anti-cancer, anti-inflammatory or anti-microbial can be mixed with additional substances to enhance their effectiveness. In one embodiment, the anti-microbial is combined with an additional anti-microbial. In another embodiment, the anti-microbial is combined with a drug or medicament that is helpful to a patient that is taking anti-microbials.

Methods of Administration

In an alternative embodiment, the disclosed chemical compounds and the disclosed pharmaceutical compositions are administered by a particular method as an anti-microbial. Such methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the present embodiment into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the compositions that include the described compounds, including those of Formulae I-VI, required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the embodiment, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages can be between about 10 microgram/kg and 100 mg/kg body weight, preferably between about 100 microgram/kg and 10 mg/kg body weight. Alternatively dosages can be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above can be used in veterinary medicine.

Depending on the specific conditions being treated, such agents can be formulated and administered systemically or locally. A variety of techniques for formulation and administration can be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the embodiment can be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the embodiment into dosages suitable for systemic administration is within the scope of the embodiment. With proper choice of carrier and suitable manufacturing practice, the compositions disclosed herein, in particular, those formulated as solutions, can be administered parenterally, such as by intravenous injection. The compounds can be formulated readily using pharmaceutically acceptable carriers well known in the art into dosages suitable for oral administration. Such carriers enable the compounds of the embodiment to be formulated as tablets, pills, capsules, liquids, gels, syrups, slurries, suspensions and the like, for oral ingestion by a patient to be treated.

Agents intended to be administered intracellularly can be administered using techniques well known to those of ordinary skill in the art. For example, such agents can be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules can be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration can be in the form of tablets, dragees, capsules, or solutions. The pharmaceutical compositions can be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, can be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, can be determined using known methods. The efficacy of a particular compound can be established using several art recognized methods, such as in vitro methods, animal models, or human clinical trials. Art-recognized in vitro models exist for nearly every class of condition, including the conditions abated by the compounds disclosed herein, including cancer, cardiovascular disease, and various immune dysfunction, and infectious diseases. Similarly, acceptable animal models can be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an anti-microbial, anti-cancer, or anti-inflammatory agent, the compounds disclosed herein can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, intradermally, or the like. Controlled release formulations, depot formulations, and infusion pump delivery are similarly contemplated.

The compositions disclosed herein in pharmaceutical compositions may also comprise a pharmaceutically acceptable carrier. Such compositions can be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions can be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the embodiment, as described above, can be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions can be formulated and administered either systemically or locally. A variety of techniques for formulation and administration can be found in Remington's Pharmaceutical Sciences, 18th ed., Mack Publishing Co., Easton, Pa. (1990).

To formulate the compounds of Formulae I-VI as an antimicrobial, an anti-cancer, or an anti-inflammatory agent, known surface active agents, excipients, smoothing agents, suspension agents and pharmaceutically acceptable film-forming substances and coating assistants, and the like can be used. Preferably alcohols, esters, sulfated aliphatic alcohols, and the like can be used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like can be used as excipients; magnesium stearate, talc, hardened oil and the like can be used as smoothing agents; coconut oil, olive oil, sesame oil, peanut oil, soya can be used as suspension agents or lubricants; cellulose acetate phthalate as a derivative of a carbohydrate such as cellulose or sugar, or methylacetate-methacrylate copolymer as a derivative of polyvinyl can be used as suspension agents; and plasticizers such as ester phthalates and the like can be used as suspension agents. In addition to the foregoing preferred ingredients, sweeteners, fragrances, colorants, preservatives and the like can be added to the administered formulation of the compound produced by the method of the embodiment, particularly when the compound is to be administered orally.

The compounds and compositions can be orally or non-orally administered to a human patient in the amount of about 0.001 mg/kg/day to about 10,000 mg/kg/day of the active ingredient, and more preferably about 0.1 mg/kg/day to about 100 mg/kg/day of the active ingredient at, preferably, one time per day or, less preferably, over two to about ten times per day. Alternatively and also preferably, the compound produced by the method of the embodiment may preferably be administered in the stated amounts continuously by, for example, an intravenous drip. Thus, for the example of a patient weighing 70 kilograms, the preferred daily dose of the active or anti-infective ingredient would be about 0.07 mg/day to about 700 gm/day, and more preferable, 7 mg/day to about 7 grams/day. Nonetheless, as will be understood by those of skill in the art, in certain situations it can be necessary to administer the anti-cancer, anti-inflammatory or the anti-infective compound of the embodiment in amounts that excess, or even far exceed, the above-stated, preferred dosage range to effectively and aggressively treat particularly advanced cancers or infections.

In the case of using the anti-microbial produced by methods of the embodiment as a biochemical test reagent, the compound produced by methods of the embodiment inhibits the progression of the disease when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the embodiment for use as an anti-microbial, anticancer or anti-tumor compound is generally in the range of about 1 to about 100 μg/ml, the most appropriate use amount varies depending on the type of cultured cell system and the purpose of use, as will be appreciated by persons of ordinary skill in the art. Also, in certain applications it can be necessary or preferred to persons of ordinary skill in the art to use an amount outside the foregoing range.

In one embodiment, the method of using a compound as an anti-microbial, anti-cancer or anti-inflammatory involves administering an effective amount of any of the compounds of Formulae I-VI or compositions of those compounds. In a preferred embodiment, the method involves administering the compound represented by Formula II, to a patient in need of an anti-microbial, until the need is effectively reduced or more preferably removed.

As will be understood by one of skill in the art, "need" is not an absolute term and merely implies that the patient can benefit from the treatment of the anti-microbial, the anti-cancer, or anti-inflammatory in use. By "patient" what is meant is an organism that can benefit by the use of an anti-microbial, anti-cancer or anti-inflammatory agent. For example, any organism with *B. anthracis, Plasmodium, Leishmania, Trypanosoma*, and the like, may benefit from the application of an anti-microbial that may in turn reduce the amount of microbes present in the patient. As another example, any organism with cancer, such as, a colorectal carcinoma, a prostate carcinoma, a breast adenocarcinoma, a non-small cell lung carcinoma, an ovarian carcinoma, multiple myelomas, a melanoma, and the like, may benefit from the application of an anti-cancer agent that may in turn reduce the amount of cancer present in the patient. Furthermore, any organism with an inflammatory conditions, such as, rheumatoid arthritis, asthma, multiple sclerosis, psoriasis, stroke, reperfusion injury, myocardial infarction, and the like, may benefit from the application of an anti-inflammatory that may in turn reduce the amount of cells associated with the inflammatory response present in the patient. In one embodiment, the patient's health may not require that an anti-microbial, anti-cancer, or anti-inflammatory be administered, however, the patient may still obtain some benefit by the reduction of the level of microbes, cancer cells, or inflammatory cells present in the patient, and thus be in need. In one embodiment, the anti-microbial or anti-cancer agent is effective against one type of microbe or cancer, but not against other types; thus, allowing a high degree of selectivity in the treatment of the patient. In other embodiments, the anti-inflammatory can be effective against inflammatory conditions characterized by different cells associated with the inflammation. In choosing such an anti-microbial, anti-cancer or anti-inflammatory agent, the methods and results disclosed in the Examples can be useful. In an alternative embodiment, the anti-microbial can be effective against a broad spectrum of microbes, preferably a broad spectrum of foreign, and, more preferably, harmful bacteria, to the host organism. In embodiments, the anti-cancer and/or anti-inflammatory agent can be effective against a broad spectrum of cancers and inflammatory conditions/cells/substances. In yet another embodiment, the anti-microbial is effective against all microbes, even those native to the host. Examples of microbes that can be targets of anti-microbials, include, but are not limited to, *B. anthracis, Plasmodium, Leishmania, Trypanosoma*, and the like. In still further embodiments, the anti-cancer agent is effective against a broad spectrum of cancers or all cancers. Examples of cancers, against which the compounds can be effective include a colorectal carcinoma, a prostate carcinoma, a breast adenocarcinoma, a non-small cell lung carcinoma, an ovarian carcinoma, multiple myelomas, a melanoma, and the like. Exemplary inflammatory conditions against which the agents are effective include rheumatoid arthritis, asthma, multiple sclerosis, psoriasis, stroke, myocardial infarction, and the like.

"Therapeutically effective amount," "pharmaceutically effective amount," or similar term, means that amount of drug or pharmaceutical agent that will result in a biological or medical response of a cell, tissue, system, animal, or human that is being sought. In a preferred embodiment, the medical response is one sought by a researcher, veterinarian, medical doctor, or other clinician.

"Anti-microbial" refers to a compound that reduces the likelihood of survival of microbes, or blocks or alleviates the deleterious effects of a microbe. In one embodiment, the likelihood of survival is determined as a function of an individual microbe; thus, the anti-microbial will increase the chance that an individual microbe will die. In one embodiment, the likelihood of survival is determined as a function of a population of microbes; thus, the anti-microbial will increase the chances that there will be a decrease in the population of microbes. In one embodiment, anti-microbial means antibiotic or other similar term. Such anti-microbials are capable of blocking the harmful effects, destroying or suppressing the growth or reproduction of microorganisms, such as bacteria. For example, such antibacterials and other anti-microbials are described in Antibiotics, Chemotherapeutics and Antibacterial Agents for Disease Control (M. Grayson, editor, 1982), and E. Gale et al., The Molecular Basis of Antibiotic Action 2d edition (1981). In another embodiment, an anti-microbial will not change the likelihood of survival, but will change the chances that the microbes will be harmful to the host in some way. For instance, if the microbe secretes a substance that is harmful to the host, the anti-microbial may act upon the microbe to stop the secretion or may counteract or block the harmful effect. In one embodiment, an anti-microbial, while, increasing the likelihood that the microbe(s) will die, is minimally harmful to the surrounding, non-microbial, cells. In an alternative embodiment, it is not important how harmful the anti-microbial is to surrounding, nonmicrobial, cells, as long as it reduces the likelihood of survival of the microbe.

"Anti-cancer agent" refers to a compound or composition including the compound that reduces the likelihood of survival of a cancer cell. In one embodiment, the likelihood of survival is determined as a function of an individual cancer cell; thus, the anti-cancer agent will increase the chance that an individual cancer cell will die. In one embodiment, the likelihood of survival is determined as a function of a population of cancer cells; thus, the anti-cancer agent will increase the chances that there will be a decrease in the population of cancer cells. In one embodiment, anti-cancer agent means chemotherapeutic agent or other similar term.

A "chemotherapeutic agent" is a chemical compound useful in the treatment of a neoplastic disease, such as cancer. Examples of chemotherapeutic agents include alkylating agents, such as a nitrogen mustard, an ethyleneimine and a methylmelamine, an alkyl sulfonate, a nitrosourea, and a triazene, folic acid antagonists, anti-metabolites of nucleic acid metabolism, antibiotics, pyrimidine analogs, 5-fluorouracil, cisplatin, purine nucleosides, amines, amino acids, triazol nucleosides, corticosteroids, a natural product such as a vinca alkaloid, an epipodophyllotoxin, an antibiotic, an enzyme, a taxane, and a biological response modifier or antibodies to biological response modifiers or other agents; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gouadotropin-releasing hormone analog. Specific examples include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins, Melphalan, and other related nitrogen mustards. Also included in this definition are hormonal agents that act to regulate or inhibit hormone action on tumors, such as tamoxifen and onapristone.

The anti-cancer agent may act directly upon a cancer cell to kill the cell, induce death of the cell, to prevent division of the cell, and the like. Alternatively, the anti-cancer agent may indirectly act upon the cancer cell by limiting nutrient or blood supply to the cell, for example. Such anti-cancer agents are capable of destroying or suppressing the growth or reproduction of cancer cells, such as a colorectal carcinoma, a prostate carcinoma, a breast adenocarcinoma, a non-small cell lung carcinoma, an ovarian carcinoma, multiple myelomas, a melanoma, and the like.

A "neoplastic disease" or a "neoplasm" refers to a cell or a population of cells, including a tumor or tissue (including cell suspensions such as bone marrow and fluids such as blood or serum), that exhibits abnormal growth by cellular proliferation greater than normal tissue. Neoplasms can be benign or malignant.

An "inflammatory condition" includes, for example, conditions such as ischemia, septic shock, autoimmune diseases, rheumatoid arthritis, inflammatory bowel disease, systemic lupus erythematosus, multiple sclerosis, asthma, osteoarthritis, osteoporosis, fibrotic diseases, dermatosis, including psoriasis, atopic dermatitis and ultraviolet radiation (UV)-induced skin damage, psoriatic arthritis, alkylosing spondylitis, tissue and organ rejection, Alzheimer's disease, stroke, atherosclerosis, restenosis, diabetes, glomerulonephritis, cancer, Hodgkins disease, cachexia, inflammation associated with infection and certain viral infections, including acquired immune deficiency syndrome (AIDS), adult respiratory distress syndrome and Ataxia Telangiestasia.

In one embodiment, a described compound, preferably a compound having the Formulae I-VI, including those as described herein, is considered an effective anti-microbial, anti-cancer, or anti-inflammatory if the compound can influence 10% of the microbes, cancer cells, or inflammatory cells, for example. In a more preferred embodiment, the compound is effective if it can influence 10 to 50% of the microbes, cancer cells, or inflammatory cells. In an even more preferred embodiment, the compound is effective if it can influence 50-80% of the microbes, cancer cells, or inflammatory cells. In an even more preferred embodiment, the compound is effective if it can influence 80-95% of the microbes, cancer cells, or inflammatory cells. In an even more preferred embodiment, the compound is effective if it can influence 95-99% of the microbes, cancer cells, or inflammatory cells. "Influence" is defined by the mechanism of action for each compound. Thus, for example, if a compound prevents the reproduction of microbes, then influence is a measure of prevention of reproduction. Likewise, if a compound destroys microbes, then influence is a measure of microbe death. Also, for example, if a compound prevents the division of cancer cells, then influence is a measure of prevention of cancer cell division. Further, for example, if a compound prevents the proliferation of inflammatory cells, then influence is a measure of prevention of inflammatory cell proliferation. Not all mechanisms of action need be at the same percentage of effectiveness. In an alternative embodiment, a low percentage effectiveness can be desirable if the lower degree of effectiveness is offset by other factors, such as the specificity of the compound, for example. Thus a compound that is only 10% effective, for example, but displays little in the way of harmful side-effects to the host, or non-harmful microbes or cells, can still be considered effective.

In one embodiment, the compounds described herein are administered simply to remove microbes, cancer cells or inflammatory cells, and need not be administered to a patient. For example, in situations where microbes can present a problem, such as in food products, the compounds described herein can be administered directly to the products to reduce the risk of microbes in the products. Alternatively, the compounds can be used to reduce the level of microbes present in the surrounding environment, such working surfaces. As another example, the compounds can be administered ex vivo to a cell sample, such as a bone marrow or stem cell transplant to ensure that only non-cancerous cells are introduced into the recipient. After the compounds are administered they may optionally be removed. This can be particularly desirable in situations where work surfaces or food products may come into contact with other surfaces or organisms that could risk being harmed by the compounds. In an alternative embodiment, the compounds can be left in the food products or on the work surfaces to allow for a more protection. Whether or not this is an option will depend upon the relative needs of the situation and the risks associated with the compound, which in part can be determined as described in the Examples below.

The following non-limiting examples are meant to describe the preferred embodiments of the methods. Variations in the details of the particular methods employed and in the precise chemical compositions obtained will undoubtedly be appreciated by those of skill in the art.

EXAMPLES

Example 1

Fermentation of Compound of Formulae I-7, II-16, II-17, II-20, II-24C, II-26 and II-28 Using Strain CNB476

Strain CNB476 was grown in a 500-ml flask containing 100 ml of vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml each of the first seed culture was inoculated into three 500-ml flasks containing of 100 ml of the vegetative medium. The second seed cultures were incubated at 28 degree C. and 250 rpm on a rotary shaker for 2 days. Five ml each of the second seed culture was inoculated into thirty-five 500-ml flasks containing of 100 ml of the vegetative medium. The third seed cultures were incubated at 28 degree and 250 rpm on a rotary shaker for 2 days. Five ml each of the third seed culture was inoculated into four hundred 500-ml flasks containing 100 ml of the Production Medium A consisting of the following per liter of deionized water: starch, 10 g; yeast extract, 4 g; Hy-Soy, 4 g; ferric sulfate, 40 mg; potassium bromide, 100 mg; calcium carbonate, 1 g; and synthetic sea salt (Instant Ocean, Aquarium Systems), 30 g. The production cultures were incubated at 28 degree C. and 250 rpm on rotary shakers for 1 day. Approximately 2 to 3 grams of sterile Amberlite XAD-7 resin were added to the production cultures. The production cultures were further incubated at 28 degree C. and 250 rpm on rotary shakers for 5 days and achieved a titer of Compound II-16 of about 200 mg/L. The culture broth was filtered through cheese cloth to recover the Amberlite XAD-7 resin. The resin was extracted with 2 times 6 liters ethyl acetate followed by 1 time 1.5 liters ethyl acetate. The combined extracts were dried in vacuo. The dried extract, containing 3.8 grams the compound of Formula II-16 and lesser quantities of compounds of formulae II-20 and II-24C, was then processed for the recovery of the compounds of Formula I-7, II-16, II-20, II-24C, II-26 and II-28.

Example 2

Fermentation of Compounds I-7, II-16, II-17, II-20, II-24C, II-26 and II-28 Using Strain NPS21184

Strain NPS21184 was grown in a 500-ml flask containing 100 ml of vegetative medium consisting of the following per liter of deionized water: glucose, 8 g; yeast extract, 6 g; Hy-Soy, 6 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into 500-ml flask containing of 100 ml of the vegetative medium. The second seed cultures were incubated at 28 degree C. and 250 rpm on a rotary shaker for 2 days. Five ml each of the second seed culture was inoculated into 500-ml flask containing of 100 ml of the vegetative medium. The third seed cultures were incubated at 28 degree and 250 rpm on a rotary shaker for 2 days. Five ml each of the third seed culture was inoculated into 500-ml flask containing 100 ml of the Production Medium B consisting of the following per liter of deionized water: starch, 20 g; yeast extract, 4 g; Hy-Soy, 8 g; ferric sulfate, 40 mg; potassium bromide, 100 mg; calcium carbonate, 1 g; and synthetic sea salt (Instant Ocean, Aquarium Systems), 30 g. The production cultures were incubated at 28 degree C. and 250 rpm on rotary shakers for 1 day. Approximately 2 to 3 grams of sterile Amberlite XAD-7 resin were added to the production culture. The production culture was further incubated at 28 degree C. and 250 rpm on rotary shaker for 4 days and achieved a titer of 350-400 mg/L for Compound II-16.

Alternatively, the production of the compounds can be achieved in a 42 L fermentor system using strain NPS21184. Strain NPS21184 was grown in a 500-ml flask containing 100 ml of vegetative medium consisting of the following per liter of deionized water: glucose, 8 g; yeast extract, 6 g; Hy-Soy, 6 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into 500-ml flask containing of 100 ml of the vegetative medium. The second seed cultures were incubated at 28 degree C. and 250 rpm on a rotary shaker for 2 days. Twenty ml each of the second seed culture was inoculated into 2.8 L Fernbach flask containing of 400 ml of the vegetative medium. The third seed cultures were incubated at 28 degree and 250 rpm on a rotary shaker for 2 days. 1.2 L of the third seed culture was inoculated into a 42 L fermentor containing 26 L of Production Medium A. Production Medium B and Production Medium C, with the following composition, can also be used. Production Medium C consisting of the following per liter of deionized water: starch, 15 g; yeast extract 6 g; Hy-Soy, 6 g; ferric sulfate, 40 mg; potassium bromide, 100 mg; calcium carbonate, 1 g; and synthetic sea salt (Instant Ocean, Aquarium Systems), 30 g. The fermentor cultures were operated at the following parameters: temperature, 28 degree C.; agitation, 200 rpm; aeration, 13 L/min and back pressure, 4.5 psi. At 36 to 44 hours of the production cycle, approximately 600 grams of sterile Amberlite XAD-7 resin were added to the fermentor culture. The production culture was further incubated at the above operating parameters until day 4 of the production cycle. The aeration rate was lowered to 8 L/min. At day 5 of the production cycle, the fermentor culture achieved a titer of about 300 mg/L for Compound II-16. The culture broth was filtered through cheese cloth to recover the Amberlite XAD-7 resin. The resin was extracted with 2 times 4.5 L liters ethyl acetate followed by 1 time 1.5 liters ethyl acetate. The combined extracts were dried in vacuo. The dried extract was then processed for the recovery of the Compounds of Formulae I-7, II-16, II-17, II-20, II-24C, II-26 and II-28.

Example 3

Purification of Compound of Formulae I-7, II-16, II-20, II-24C, II-26 and II-28

3A: Purification of Compound of Formulae II-16, II-20, II-24C, II-26 and II-28

The pure compounds of Formulae II-16, II-20, II-24C, II-26 and II-28 were obtained by flash chromatography followed by HPLC. Eight grams crude extract containing 3.8 grams of the compound of Formula II-16 and lesser quantities of II-20, II-24C, II-26 and II-28 was processed by flash chromatography using Biotage Flash40i system and Flash 40M cartridge (KP-Sil Silica, 32-63 µm, 90 grams). The flash chromatography was developed by the following step gradient:

1. Hexane (1 L)
2. 10% Ethyl acetate in hexane (1 L)
3. 20% Ethyl acetate in hexane, first elution (1 L)
4. 20% Ethyl acetate in hexane, second elution (1 L)
5. 20% Ethyl acetate in hexane, third elution (1 L)
6. 25% Ethyl acetate in hexane (1 L)
7. 50% Ethyl acetate in hexane (1 L)
8. Ethyl acetate (1 L)

Fractions containing the compound of Formula II-16 in greater or equal to 70% UV purity by HPLC were pooled and subject to HPLC purification, as described below, to obtain II-16, along with II-20 and II-24C, each as pure compounds

| | |
|---|---|
| Column | Phenomenex Luna 10u Silica |
| Dimensions | 25 cm × 21.2 mm ID |
| Flow rate | 25 ml/min |
| Detection | ELSD |
| Solvent | Gradient of 24% EtOAc/hexane for 19 min, 24% EtOAc/hexane to 100% EtOAc in 1 min, then 100% EtOAc for 4 min |

The fraction enriched in compound of Formula II-16 (described above; ~70% pure with respect to II-16) was dissolved in acetone (60 mg/ml). Aliquots (950 ul) of this solution were injected onto a normal-phase HPLC column using the conditions described above. Compound II-16 typically eluted after 14 minutes and compounds II-24C and II-26 co-eluted as a single peak at 11 min. When parent samples containing compounds II-17, II-20 and II-28 were processed, compound II-17 eluted at 22 minutes, while II-20 and II-28 co-eluted at 23 minutes during the 100% ethyl acetate wash. Fractions containing compound II-16 and minor analogs were pooled based on composition of compounds present, and evaporated under reduced pressure on a rotary evaporator. This process yielded pure Compound A, as well as separate fractions containing minor compounds II-20, II-24C, II-26 and II-28, which were further purified as described below.

Sample containing II-24C and II-26 generated from the process described above were further separated using reversed-phase preparative HPLC as follows. The sample containing II-24C (70 mg) was dissolved in acetonitrile at a concentration of 10 mg/ml, and 500 μl was loaded on an HPLC column of dimensions 21 mm i.d. by 15 cm length containing Eclipse XDB-C18 support. The solvent gradient increased linearly from 15% acetonitrile/85% water to 100% acetonitrile over 23 minutes at a flow rate of 14.5 ml/min. The solvent composition was held at 100% acetonitrile for 3 minutes before returning to the starting solvent mixture. Compound II-26 eluted at 17.5 minutes while compound II-24C eluted at 19 minutes under these conditions.

Crystalline II-26 was obtained using a vapor diffusion method. Compound II-26 (15 mg) was dissolved in 100 μl of acetone in a 1.5 ml v-bottom HPLC vial. This vial was then placed inside a larger sealed vessel containing 1 ml of pentane. Crystals suitable for X-ray crystallography experiments were observed along the sides and bottom of the inner vial after 48 hours of incubation at 4° C. Crystallography data was collected on a Bruker SMART APEX CCD X-ray diffractometer (F(000)=2656, Mo$_{K\alpha}$ radiation, λ=0.71073 Å, μ=0.264 mm$^{-1}$, T=100K) at the UCSD Crystallography Lab and the refinement method used was full-matrix least-squares on F$^2$. Crystal data NPI-2065: C$_{15}$H$_{20}$ClNO$_4$, MW=313.77, tetragonal, space group P4(1)2(1)2, a=b=11.4901(3) Å, c=46.444(2) Å, α=β=γ=90°, vol=6131.6(3) Å$^3$, Z=16, ρ$_{calcd}$=1.360 g cm$^{-3}$, crystal size, 0.30×0.15×0.07 mm$^3$, θ range, 1.75-26.00°, 35367 reflections collected, 6025 independent reflections (R$_{int}$=0.0480), final R indices (I>2σ(I)): R$_1$=0.0369, wR$_2$=0.0794, GOF=1.060.

In order to separate II-28 from II-20, a reverse-phase isocratic method was employed. Sample (69.2 mg) containing both compounds was dissolved in acetonitrile to a concentration of 10 mg/ml, and 500 μl was loaded on a reverse-phase HPLC column (ACE 5 C18-HL, 15 cm×21 mm ID) per injection. An isocratic solvent system of 27% acetonitrile/63% water at flow rate of 14.5 ml/min was used to separate compounds II-28 and II-20, which eluted after 14 and 16 minutes, respectively. Fractions containing compounds of interest were immediately evaporated under reduced pressure at room temperature on a rotary evaporator. Samples were then loaded onto a small column of silica and eluted with 10 ml of 70% hexane/30% acetone to remove additional impurities.

Samples generated from the preparative normal-phase HPLC method described above that contained II-20, but which were free of II-28 could also be triturated with 100% EtOAc to remove minor lipophilic impurities.

Compound of Formula II-16: UV (Acetonitrile/H$_2$O) λ$_{max}$ 225(sh) nm. Low Res. Mass: m/z 314 (M+H), 336 (M+Na).

Figure 7:
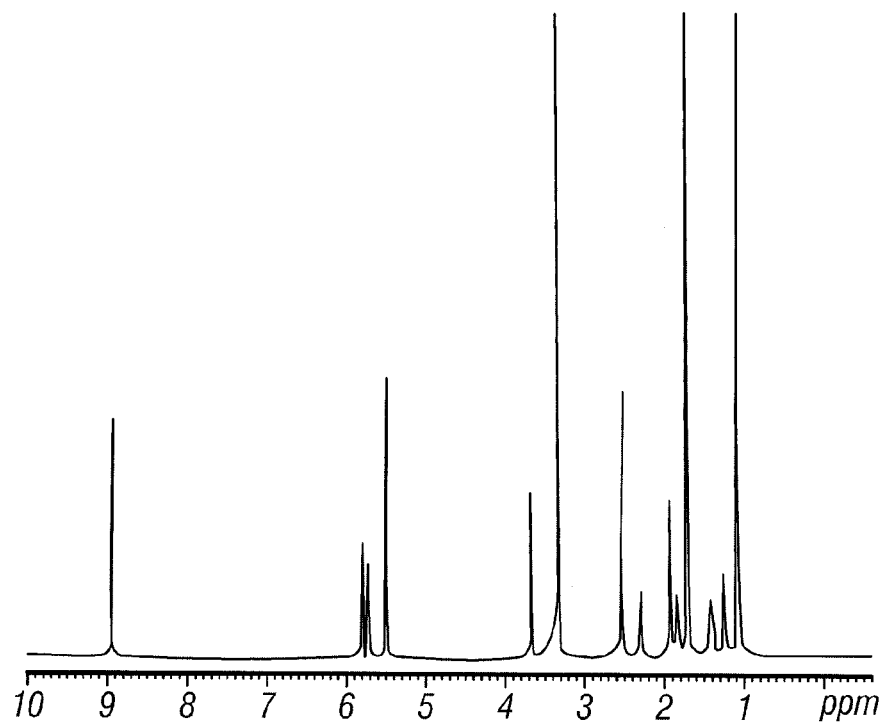
FIG. 7 depicts the $^1$H NMR spectrum of a compound having structure Formula II-20.

Compound of Formula II-20: UV (Acetonitrile/H$_2$O) λ$_{max}$ 225(sh) nm. Low Res. Mass: m/z 266 (M+H); HRMS (ESI), m/z 266.1396 (M+H), Δ$_{calc}$=1.2 ppm. FIG. 7 depicts the 1H NMR spectrum of a compound having the structure of Formula II-20.

Figure 8:
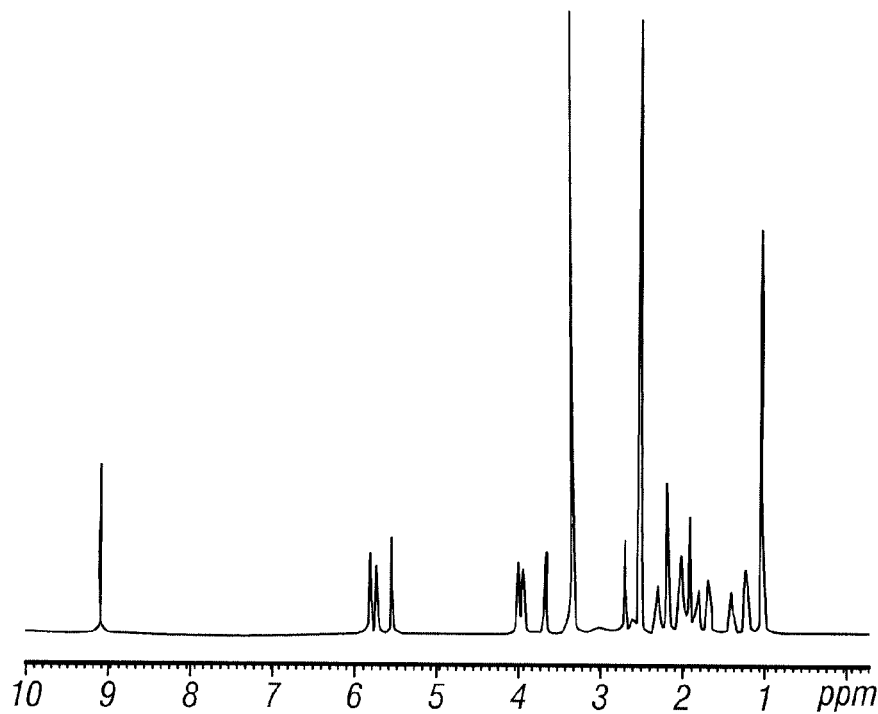
FIG. 8 depicts the $^1$H NMR spectrum of a compound having structure Formula II-24C.

Compound of Formula II-24C: UV (Acetonitrile/H$_2$O) λ$_{max}$ 225(sh) nm. Low Res. Mass: m/z 328 (M+H), 350 (M+Na); HRMS (ESI), m/z 328.1309 (M+H), Δ$_{calc}$=−2.0 ppm, C$_{16}$H$_{23}$NO$_4$Cl. FIG. 8 depicts the 1H NMR spectrum of a compound having the structure of Formula II-24C.

Figure 51:
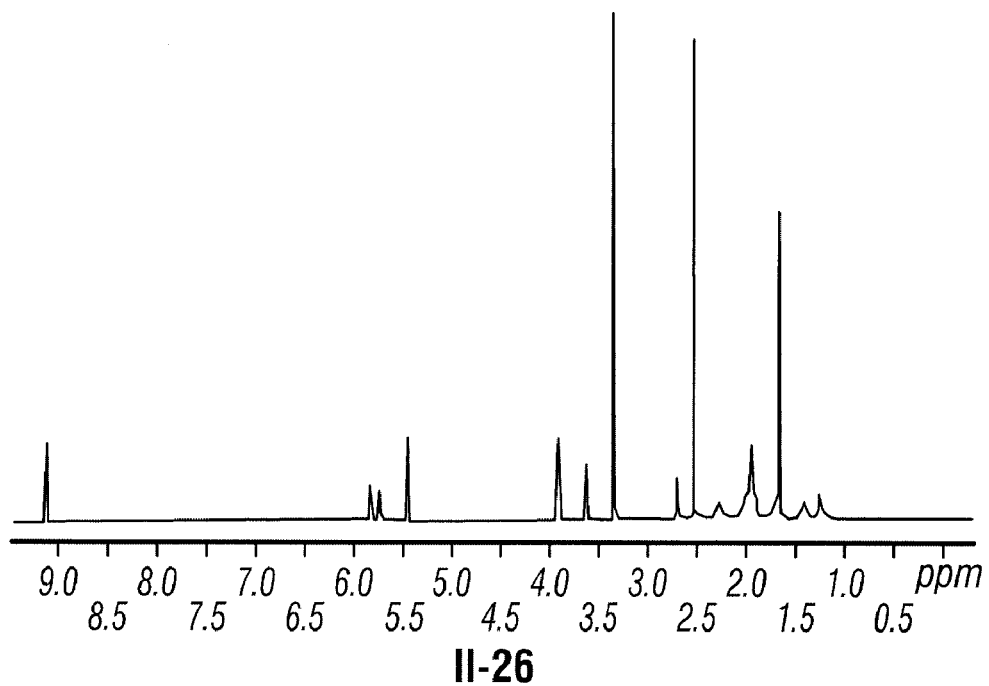
FIG. 51 depicts the $^1$H NMR spectrum of the compound of Formula II-26 in DMSO-$d_6$.
Figure 52:
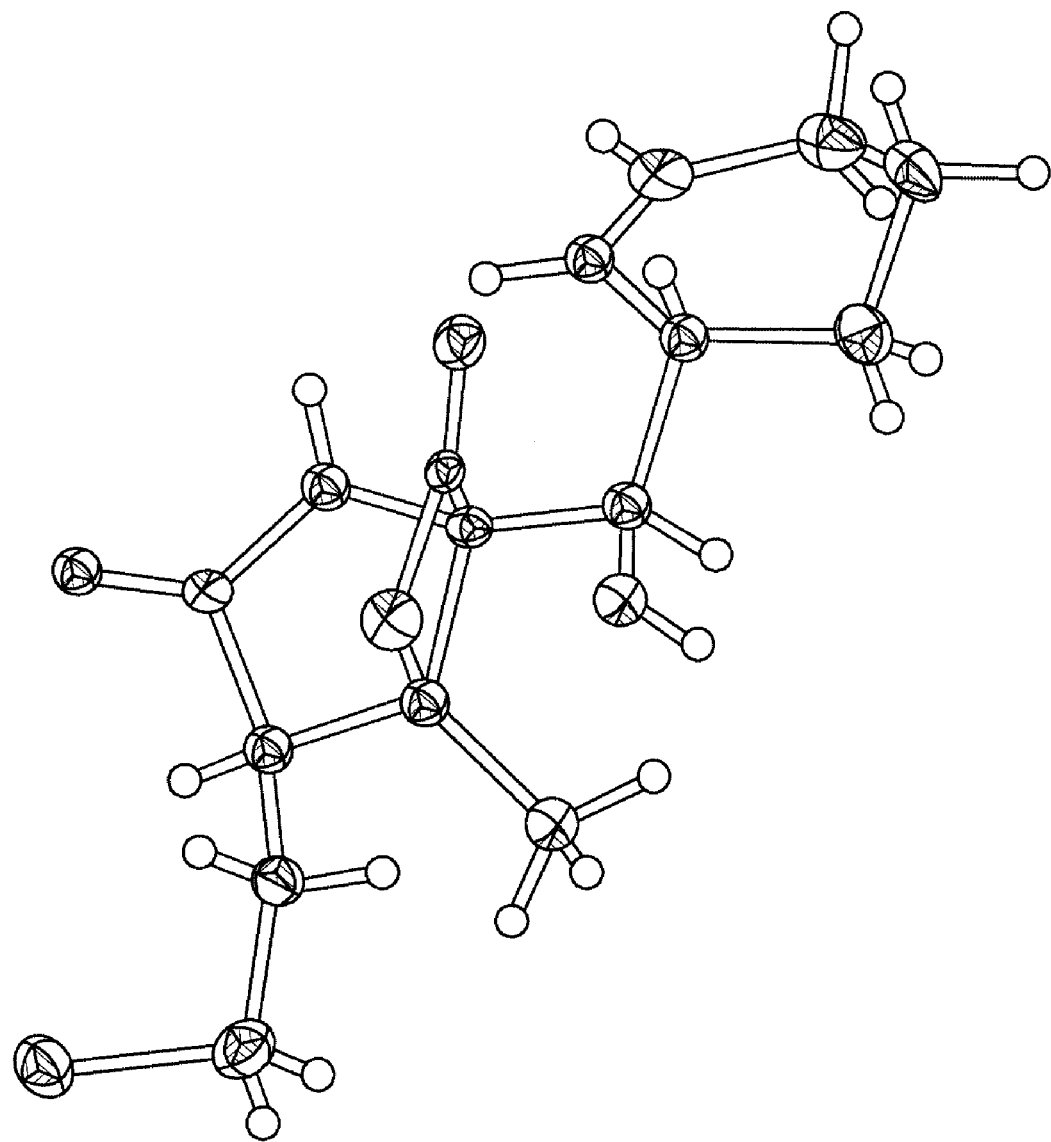
FIG. 52 depicts the computer-generated ORTEP plot of the compound of Formula II-26.

Compound of Formula II-26: UV (Acetonitrile/H$_2$O) λ$_{max}$ 225(sh) nm; HRMS (ESI), m/z 314.1158 (M+H), Δ$_{calc}$=−0.4 ppm, C$_{15}$H$_{21}$NO$_4$Cl; FIG. 51 depicts the $^1$H NMR spectrum of a compound having the structure of Formula II-26 in DMSO-d$_6$. FIG. 52 depicts the computer-generated ORTEP plot of the compound of Formula II-26.

Figure 54:
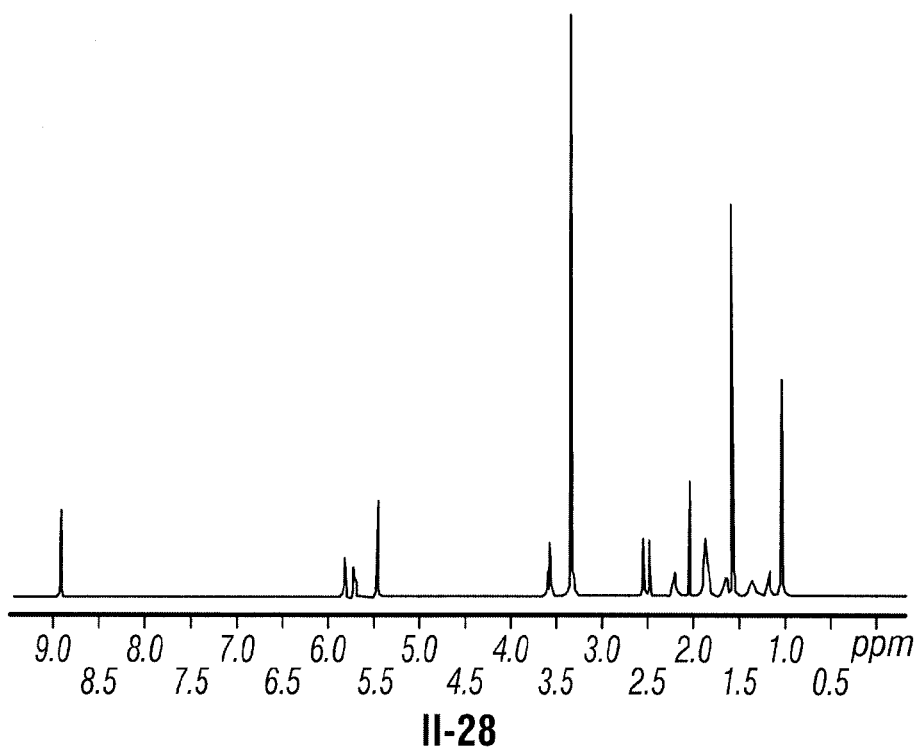
FIG. 54 depicts the $^1$H NMR spectrum of the compound of Formula II-28 in DMSO-$d_6$.

Compound of Formula II-28: UV (Acetonitrile/H$_2$O) λ$_{max}$ 225(sh) nm; HRMS (ESI), m/z 266.1388 (M+H), Δ$_{calc}$=−1.8 ppm, C$_{14}$H$_{20}$NO$_4$. FIG. 54 depicts the $^1$H NMR spectrum of a compound having the structure of Formula II-28 in DMSO-d$_6$.

3B: Purification of Compound of Formula I-7

A Biotage Flash 75Li system with a Flash 75L KP-Sil cartridge was used to process the filtered crude extract (10.0 g), enriched in Compound II-16 and containing Compound of Formula I-7. The crude extract was dissolved to a concentration of 107 mg/ml in acetone and loaded directly onto the cartridge. The following solvent step gradient was then run through the cartridge at a flow rate between 235 ml/min and 250 ml/min 1. 10% EtOAc in n-Heptane (3.2 L)
2. 25% EtOAc in n-Heptane (16 L)
3. 30% EtOAc in n-Heptane (5.4 L)

Fractions enriched in Compound II-16 were pooled and concentrated by rotavapor until ~5% of the total pooled volume of solvent remained. The solvent was removed, leaving behind the white solid.

A crystallization was then performed on the solid by dissolving the sample (4.56 g) in 1:1 acetone:n-heptane (910 ml). The solvent was slowly evaporated using a rotary evaporator until the solvent was reduced to about 43% of its original volume. The solution (supernatant) was removed and concentrated (598 mg).

The supernatant was dissolved in acetone (80 mg/ml). Aliquots (500 ul) of this solution were injected onto a normal-phase HPLC column using the conditions described above for normal phase purification of Compounds II-16, II-24C, II-26 and II-28. Compound of Formula I-7 eluted at 7.5 minutes as a pure compound.

Figure 58:
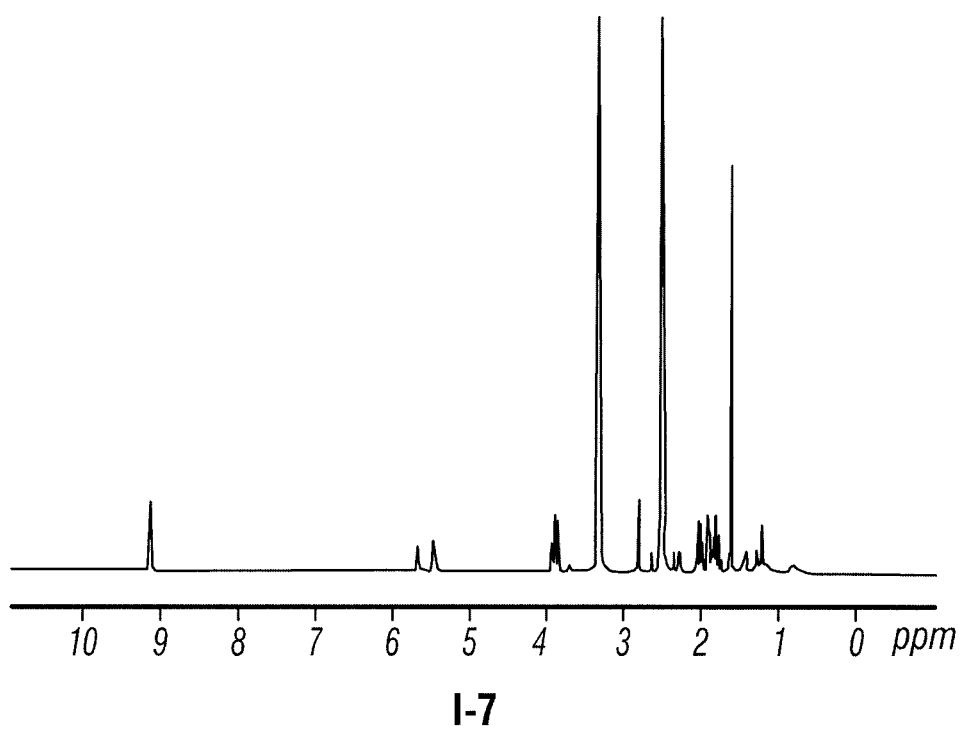
FIG. 58 depicts the $^1$H NMR spectrum of the compound of Formula I-7 in DMSO-$d_6$.
Figure 59:
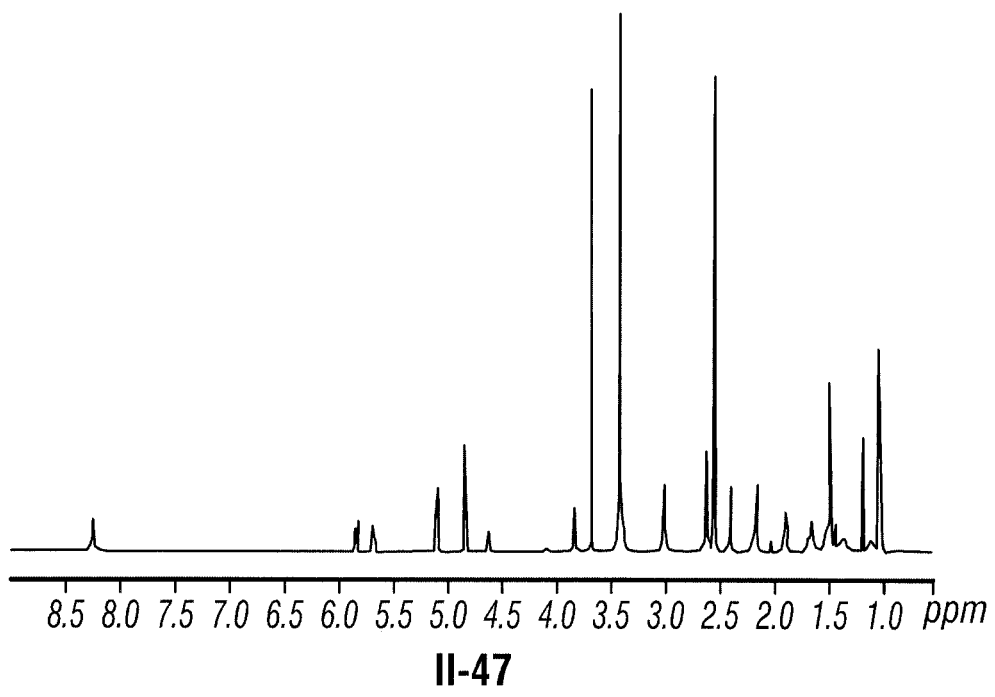
FIG. 59 depicts the $^1$H NMR spectrum of the compound of Formula II-47 in DMSO-$d_6$.
Figure 60:
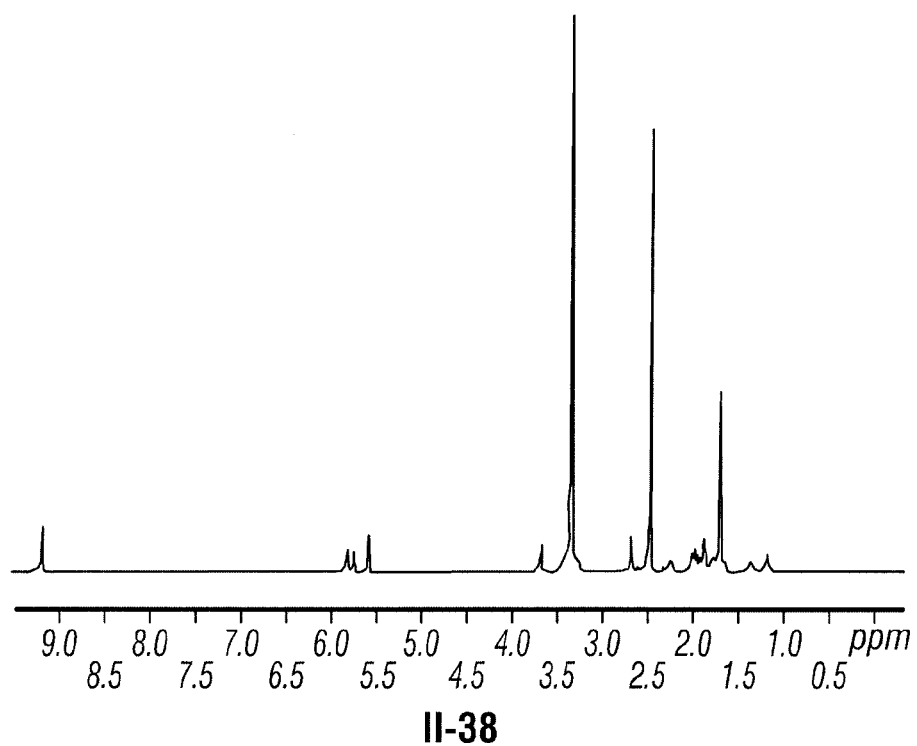
FIG. 60 depicts the $^1$H NMR spectrum of the compound of Formula II-38 in DMSO-$d_6$.
Figure 61:
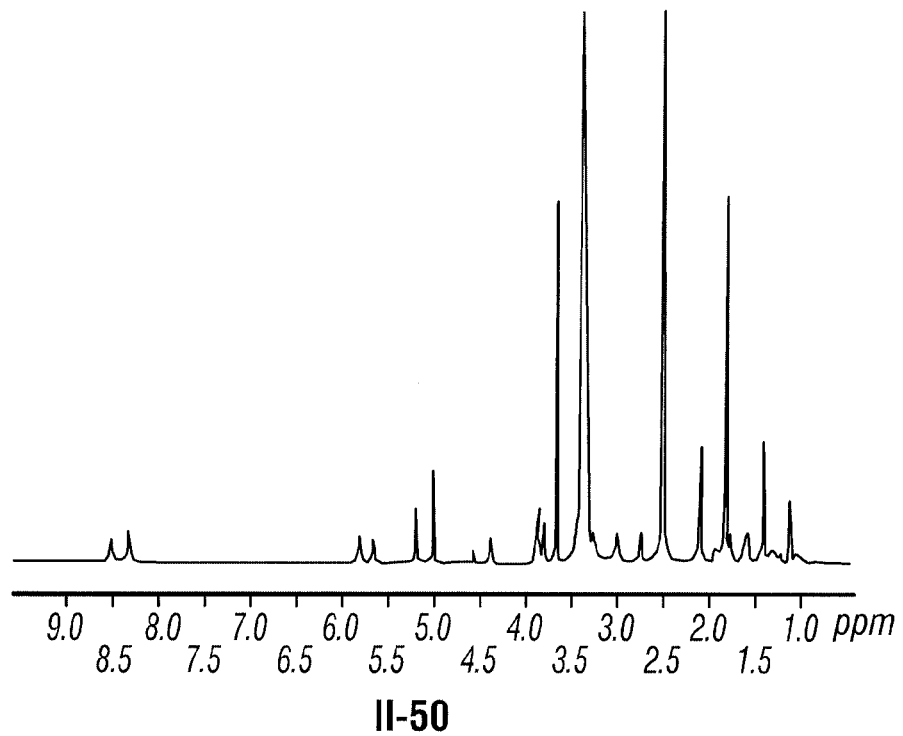
FIG. 61 depicts the $^1$H NMR spectrum of the compound of Formula II-50 in DMSO-$d_6$.

Compound of Formula I-7 (FIG. 58): UV (Acetonitrile/H$_2$O) λ$_{max}$ 225(sh) nm. Low Res. Mass: m/z 298 (M+H), 320 (M+Na).

Example 4

Fermentation of Compounds of Formulae II-17, II-18, and II-27

Strain CNB476 was grown in a 500-ml flask containing 100 ml of the first vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into a 500-ml flask containing 100 ml of the second vegetative medium consisting of the following per liter of deionized water: starch, 10 g; yeast extract, 4 g; peptone, 2 g; ferric sulfate, 40 mg; potassium bromide, 100 mg; calcium carbonate, 1 g; and sodium bromide, 30 g. The second seed cultures were incubated at 28° C. for 7 days on a rotary shaker operating at 250 rpm. Approximately 2 to 3 gram of sterile Amberlite XAD-7 resin were added to the second seed culture. The second seed culture was further incubated at 28° C. for 2 days on a rotary shaker operating at 250 rpm. Five ml of the second seed culture was inoculated into a 500-ml flask containing 100 ml of the second vegetative medium. The third seed culture was incubated at 28° C. for 1 day on a rotary shaker operating at 250 rpm. Approximately 2 to 3 gram of sterile Amberlite XAD-7 resin were added to the third seed culture. The third seed culture was further incubated at 28° C.

for 2 days on a rotary shaker operating at 250 rpm. Five ml of the third culture was inoculated into a 500-ml flask containing 100 ml of the second vegetative medium. The fourth seed culture was incubated at 28° C. for 1 day on a rotary shaker operating at 250 rpm. Approximately 2 to 3 gram of sterile Amberlite XAD-7 resin were added to the fourth seed culture. The fourth seed culture was further incubated at 28° C. for 1 day on a rotary shaker operating at 250 rpm. Five ml each of the fourth seed culture was inoculated into ten 500-ml flasks containing 100 ml of the second vegetative medium. The fifth seed cultures were incubated at 28° C. for 1 day on a rotary shaker operating at 250 rpm. Approximately 2 to 3 grams of sterile Amberlite XAD-7 resin were added to the fifth seed cultures. The fifth seed cultures were further incubated at 28° C. for 3 days on a rotary shaker operating at 250 rpm. Four ml each of the fifth seed culture was inoculated into one hundred and fifty 500-ml flasks containing 100 ml of the production medium having the same composition as the second vegetative medium. Approximately 2 to 3 grams of sterile Amberlite XAD-7 resin were also added to the production culture. The production cultures were incubated at 28° C. for 6 day on a rotary shaker operating at 250 rpm. The culture broth was filtered through cheese cloth to recover the Amberlite XAD-7 resin. The resin was extracted with 2 times 3 liters ethyl acetate followed by 1 time 1 liter ethyl acetate. The combined extracts were dried in vacuo. The dried extract, containing 0.42 g of the compound Formula II-17 and 0.16 gram the compound of Formula II-18, was then processed for the recovery of the compounds.

Example 5

Purification of Compounds of Formula II-17, II-18 and II-27

The pure compounds of Formula II-17 and II-18 were obtained by reversed-phase HPLC as described below:

| Column | ACE 5 C18-HL |
|---|---|
| Dimensions | 15 cm × 21 mm ID |
| Flow rate | 14.5 ml/min |
| Detection | 214 nm |
| Solvent | Gradient of 35% Acetonitrile/65% $H_2O$ to 90% Acetonitrile/10% $H_2O$ over 15 min |

Crude extract (100 mg) was dissolved in 15 ml of acetonitrile. Aliquots (900 ul) of this solution were injected onto a reversed-phase HPLC column using the conditions described above. Compounds of Formulae II-17 and II-18 eluted at 7.5 and 9 minutes, respectively. Fractions containing the pure compounds were first concentrated using nitrogen to remove organic solvent. The remaining solution was then frozen and lyophilized to dryness.

An alternative purification method for Compound II-17 and II-18 was developed for larger scale purification and involved fractionation of the crude extract on a normal phase VLC column. Under these conditions, sufficient amounts of several minor metabolites were identified, including compound II-27. The crude extract (2.4 g) was dissolved in acetone (10 ml) and this solution adsorbed onto silica gel (10 cc) by drying in vacuo. The adsorbed crude extract was loaded on a normal phase silica VLC column (250 cc silica gel, column dimensions 2.5 cm diameter by 15 cm length) and washed with a step gradient of hexane/EtOAc, increasing in the percentage of hexane in steps of 5% (100 ml solvent per step). The majority of compound II-16 eluted in the 60% hexane/40% EtOAc wash while the majority of compound II-17 eluted in the 50% hexane/50% ethyl acetate wash. Final separation of the compounds was achieved using C18 HPLC chromatography (ACE 5μ C18-HL, 150 mm×21 mm ID) using an isocratic solvent system consisting of 35% ACN/ 65% H2O. Under these conditions, compound II-27 eluted at 11 minutes, compound II-17 eluted at 12.00 minutes, traces of compound A eluted at 23.5 minutes, and compound II-18 eluted at 25.5 minutes. The resulting samples were dried in vacuo using no heat to remove the aqueous solvent mixture. The spectroscopic data for these samples of compound II-16 and compound II-18 were found to be identical with those of samples prepared from earlier purification methods. The sample of compound II-18 was found to contain 8% of the lactone hydrolysis product and was further purified by washing through a normal phase silica plug (1 cm diameter by 2 cm height) and eluting using a solvent mixture of 20% EtOAc/ 80% Hexanes (25 ml). The resulting sample was found to contain pure compound II-18.

The fractions containing compound II-27 described above were further purified using normal phase semipreparative HPLC (Phenomenex Luna Si 10μ, 100 Å; 250×10 mm id) using a solvent gradient increasing from 100% hexane to 100% EtOAc over 20 minutes with a flowrate of 4 ml/min. Compound II-27 eluted as a pure compound after 11.5 minutes (0.8 mg, 0.03% isolated yield from dried extract weight).

Figure 49:
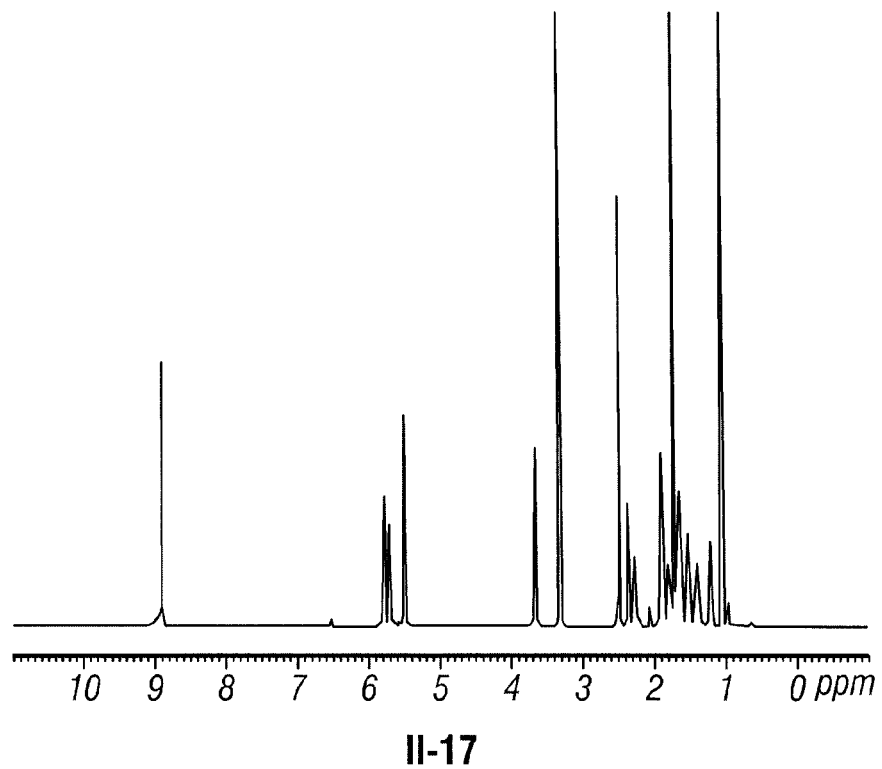
FIG. 49 depicts the $^1$H NMR spectrum of a compound having structure Formula II-17.

Compound of Formula II-17: UV (Acetonitrile/$H_2O$) $\lambda_{max}$ 225(sh) nm. High Res. Mass (APCI): m/z 280.156 (M+H), $\Delta_{calc}$=2.2 ppm, $C_{15}H_{22}NO_4$. FIG. 49 depicts the $^1$H NMR spectrum of a compound having the structure of Formula II-17.

Figure 50:
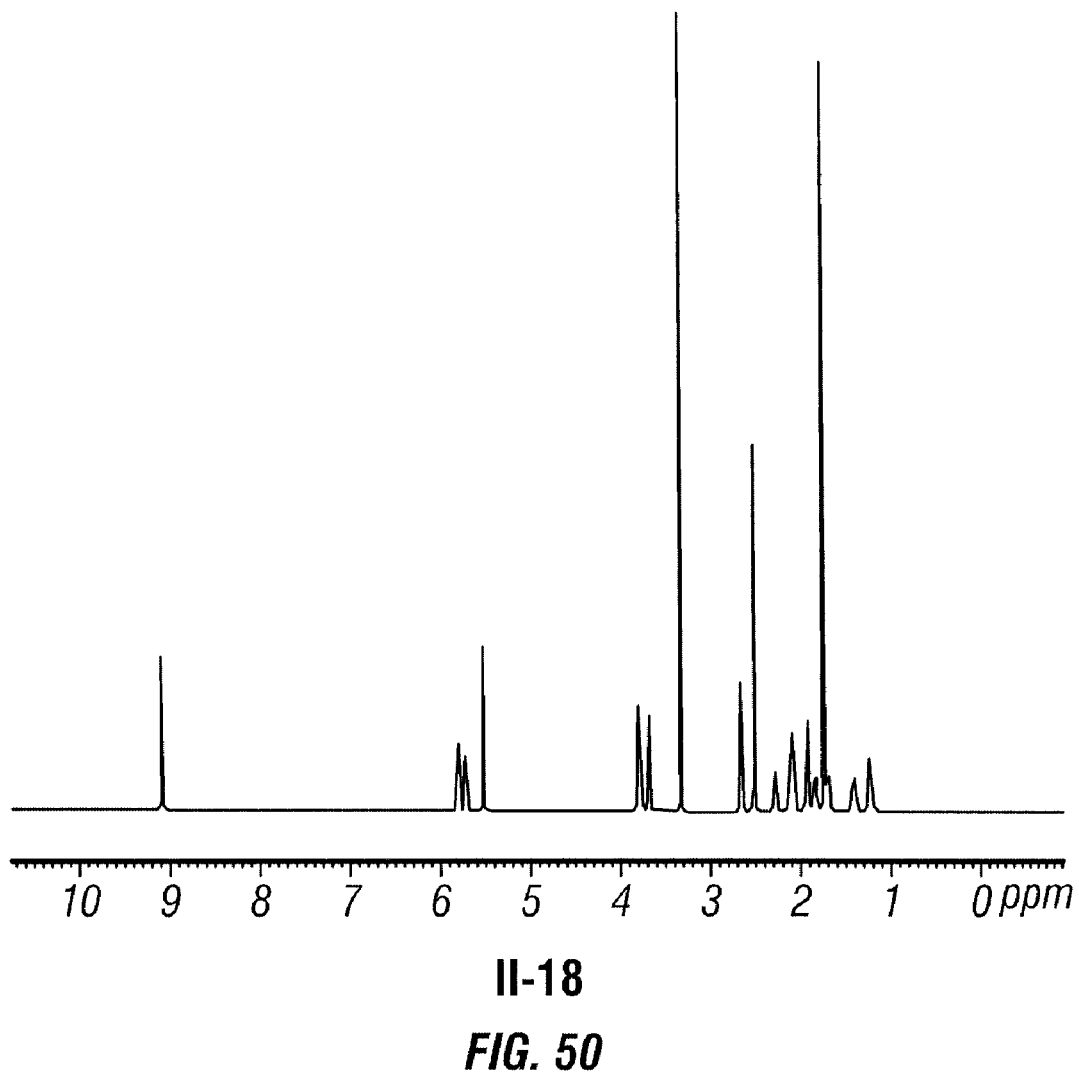
FIG. 50 depicts the $^1$H NMR spectrum of a compound having structure Formula II-18.

Compound of Formula II-18: UV (Acetonitrile/$H_2O$) $\lambda_{max}$ 225(sh) nm. High Res. Mass (APCI): m/z 358.065 (M+H), $\Delta_{calc}$=−1.9 ppm, $C_{15}H_{21}NO_4Br$. FIG. 50 depicts the $^1$H NMR spectrum of a compound having the structure of Formula II-18.

Figure 53:
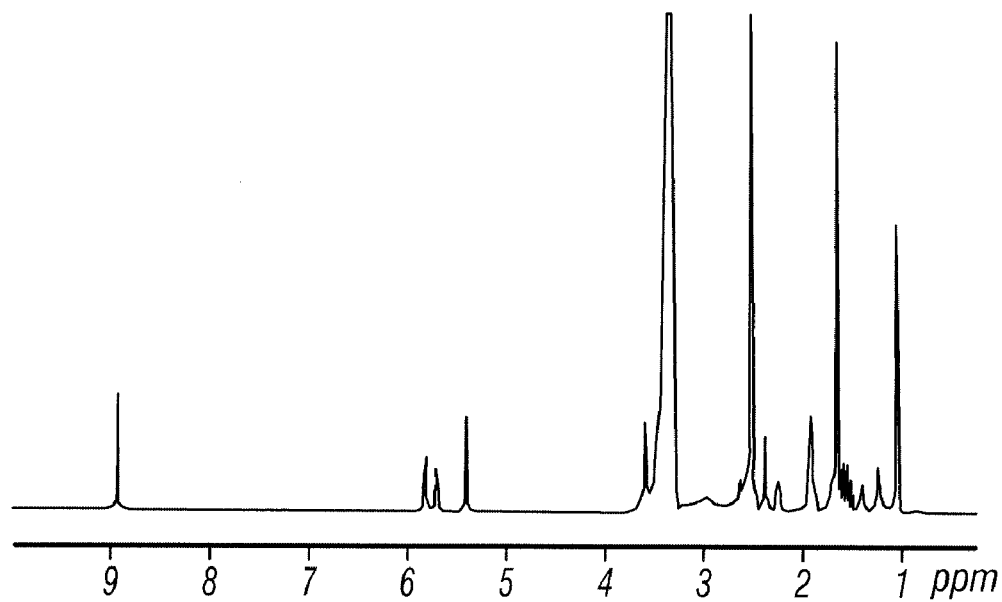
FIG. 53 depicts the $^1$H NMR spectrum of the compound of Formula II-27 in DMSO-$d_6$.

Compound II-27: UV (Acetonitrile/$H_2O$) $\lambda_{max}$ 225(sh) nm; MS (HR-ESI), m/z 280.1556 (M+H) $\Delta_{calc}$=2.7 ppm ($C_{15}H_{22}NO_4$); $^1$H NMR (DMSO-$d_6$) see FIG. 53.

Example 6

Preparation of Compound of Formula II-19 from II-16

Figure 9:
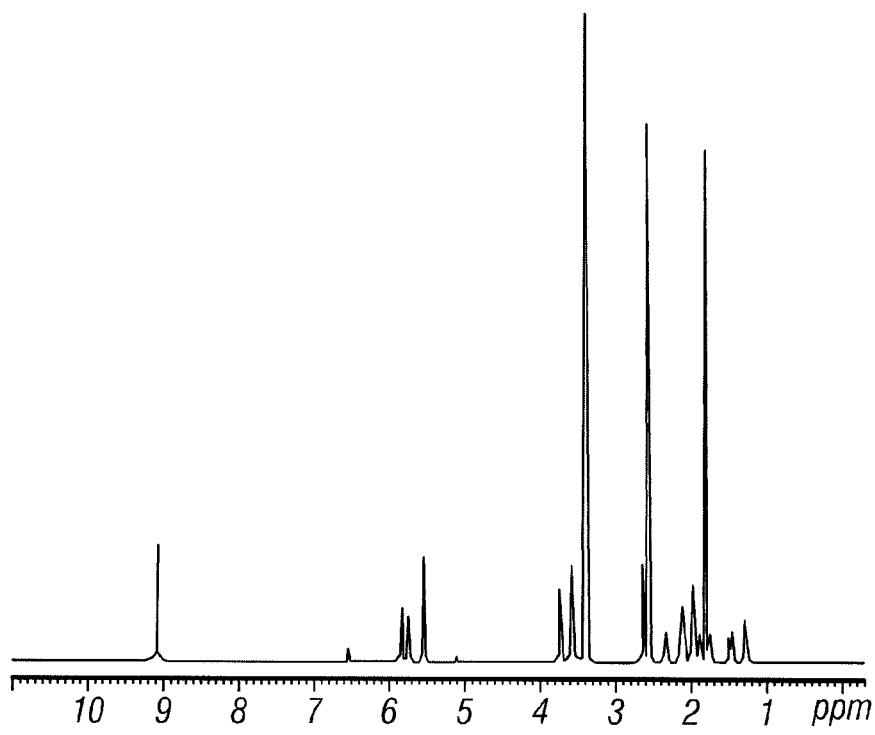
FIG. 9 depicts the $^1$H NMR spectrum of a compound having structure Formula II-19.

A sample of compound of Formula II-16 (250 mg) was added to an acetone solution of sodium iodide (1.5 g in 10 ml) and the resulting mixture stirred for 6 days. The solution was then filtered through a 0.45 micron syringe filter and injected directly on a normal phase silica HPLC column (Phenomenex Luna 10u Silica, 25 cm×21.2 mm) in 0.95 ml aliquots. The HPLC conditions for the separation of compound formula II-19 from unreacted II-16 employed an isocratic HPLC method consisting of 24% ethyl acetate and 76% hexane, in which the majority of compound II-19 eluted 2.5 minutes before compound II-16. Equivalent fractions from each of 10 injections were pooled to yield 35 mg compound II-19. Compound II-19: UV (Acetonitrile/$H_2O$) 225 (sh), 255 (sh) nm; ESMS, m/z 406.0 (M+H); HRMS (ESI), m/z 406.0513 [M+H]$^+$, $\Delta_{calc}$=−0.5 ppm, $C_{15}H_{21}NO_4I$; $^1$H NMR in DMSO-$d_6$ (see FIG. 9).

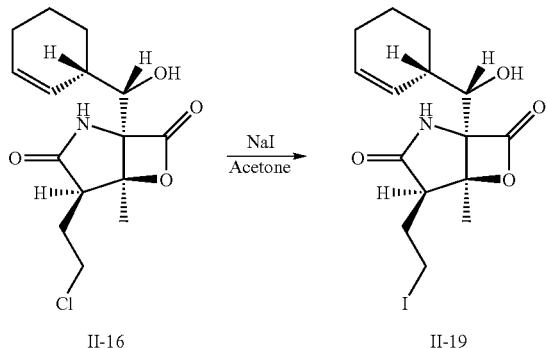

II-16    II-19

Example 7

Synthesis of the Compounds of Formulae II-2, II-3, and II-4

Compounds of Formulae II-2, II-3 and II-4 can be synthesized from compounds of Formulae II-16, II-17 and II-18, respectively, by catalytic hydrogenation.

Exemplary Depiction of Synthesis

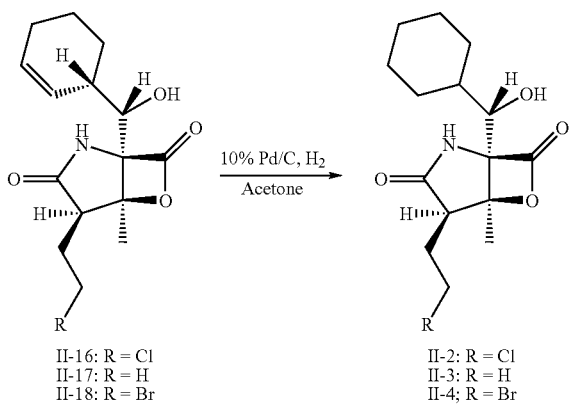

II-16: R = Cl
II-17: R = H
II-18: R = Br

II-2: R = Cl
II-3: R = H
II-4; R = Br

Example 7A

Catalytic Hydrogenation of Compound of Formula II-16

Figure 10:
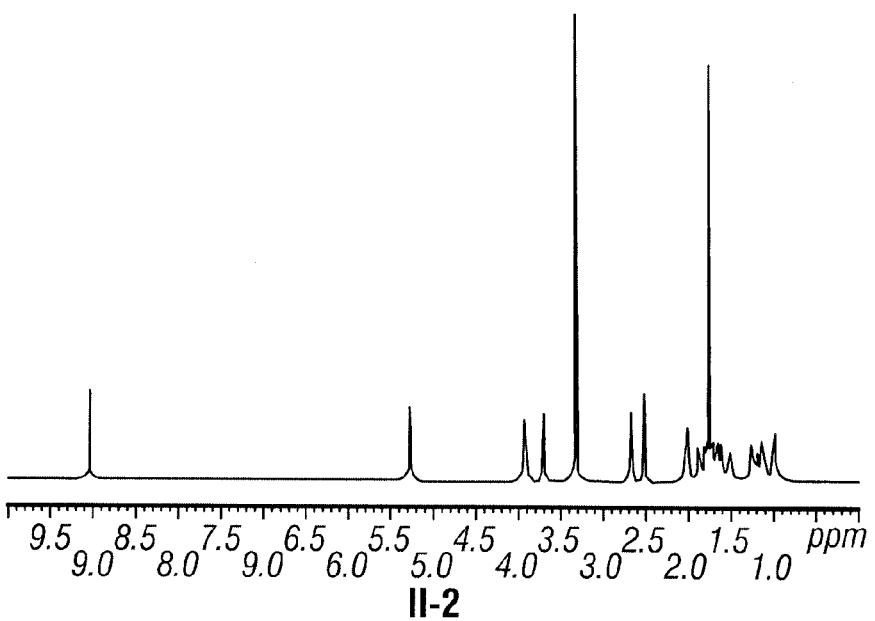
FIG. 10 depicts the $^1$H NMR spectrum of a compound having structure Formula II-2.
Figure 11:
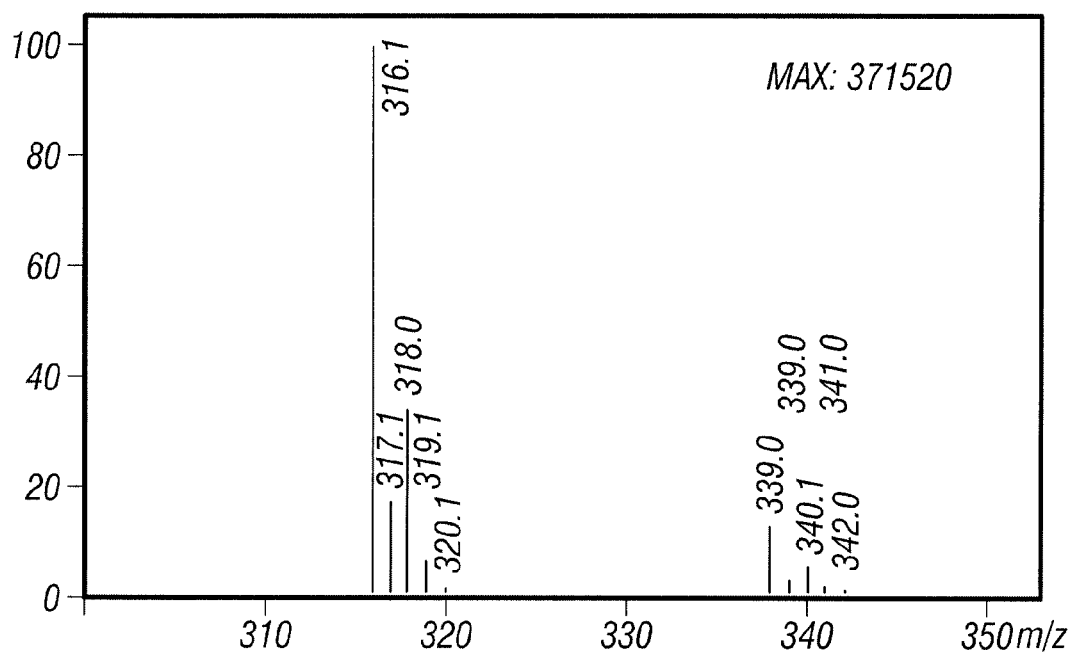
FIG. 11 depicts the mass spectrum of a compound having structure Formula II-2.

Compound of Formula II-16 (10 mg) was dissolved in acetone (5 mL) in a scintillation vial (20 mL) to which was added the 10% (w/w) Pd/C (1-2 mg) and a magnetic stirrer bar. The reaction mixture was stirred in a hydrogen atmosphere at room temperature for about 15 hours. The reaction mixture was filtered through a 3 cc silica column and washed with acetone. The filtrate was filtered again through 0.2 μm Gelman Acrodisc to remove any traces of catalyst. The solvent was evaporated off from filtrate under reduced pressure to yield the compound of Formula II-2 as a pure white powder: UV (acetonitrile/H$_2$O): λ$_{man}$ 225 (sh) rim. FIG. 10 depicts the NMR spectrum of the compound of Formula II-2 in DMSO-d6. FIG. 11 depicts the low resolution mass spectrum of the compound of Formula II-2: m/z 316 (M+H), 338 (M+Na).

Example 7B

Catalytic Hydrogenation of Compound of Formula II-17

Compound of Formula II-17 (5 mg) was dissolved in acetone (3 mL) in a scintillation vial (20 mL) to which was added the 10% (w/w) Pd/C (about 1 mg) and a magnetic stirrer bar. The reaction mixture was stirred in a hydrogen atmosphere at room temperature for about 15 hours. The reaction mixture was filtered through a 0.2 μm Gelman Acrodisc to remove the catalyst. The solvent was evaporated off from filtrate to yield the compound of Formula II-3 as a white powder which was purified by normal phase HPLC using the following conditions:

| Column: | Phenomenex Luna 10u Silica |
|---|---|
| Dimensions: | 25 cm × 21.2 mm ID |
| Flow rate: | 14.5 ml/min |
| Detection: | ELSD |
| Solvent: | 5% to 60% EtOAc/Hex for 19 min, 60 to 100% EtOAc in 1 min, then 4 min at 100% EtOAc |

Figure 12:
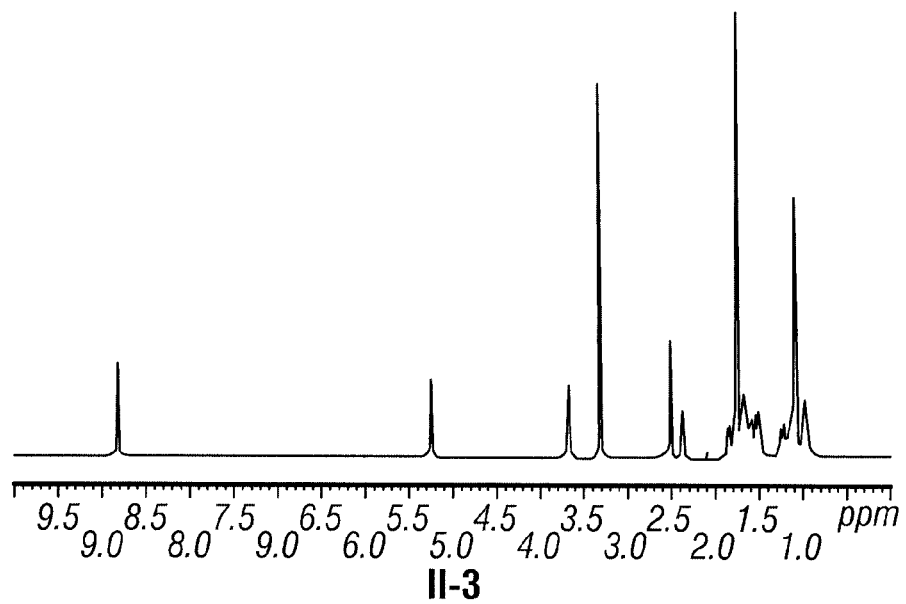
FIG. 12 depicts the $^1$H NMR spectrum of a compound having structure Formula II-3.
Figure 13:
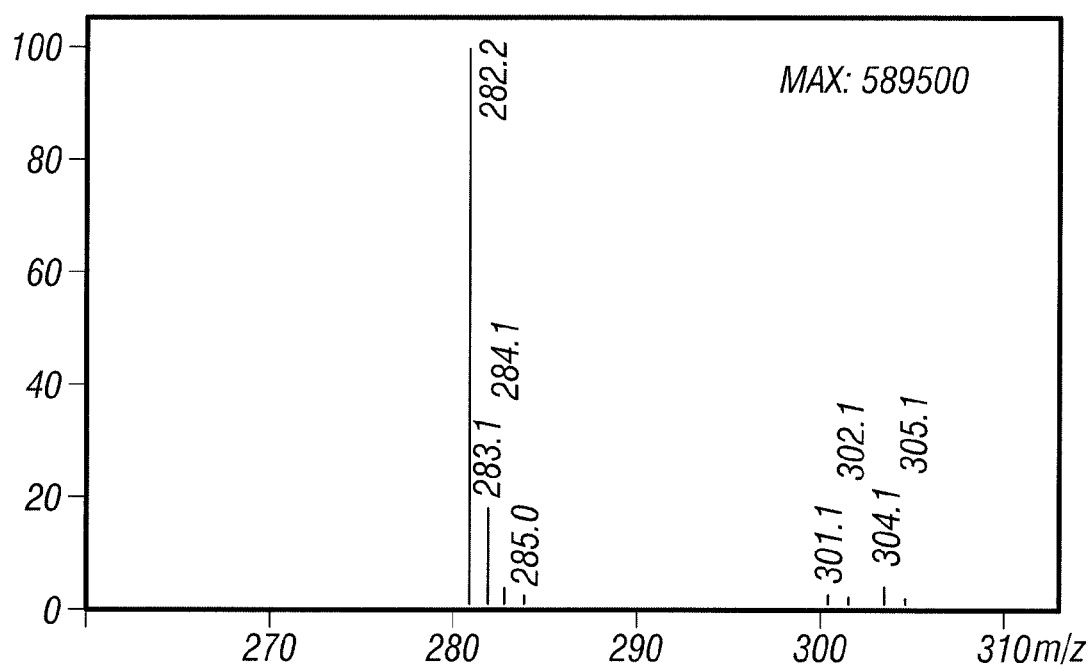
FIG. 13 depicts the mass spectrum of a compound having structure Formula II-3.

Compound of Formula II-3 eluted at 22.5 min as a pure compound: UV (acetonitrile/H$_2$O): λ$_{max}$ 225 (sh) nm. FIG. 12 depicts the NMR spectrum of the compound of Formula II-3 in DMSO-d$_6$. FIG. 13 depicts the low resolution mass spectrum of the compound of Formula II-3: m/z 282 (M+H), 304 (M+Na).

Example 7C

Catalytic Hydrogenation of Compound of Formula II-18

3.2 mg of compound of Formula I-18 was dissolved in acetone (3 mL) in a scintillation vial (20 mL) to which was added the 10% (w/w) Pd/C (about 1 mg) and a magnetic stirrer bar. The reaction mixture was stirred in hydrogen atmosphere at room temperature for about 15 hours. The reaction mixture was filtered through a 0.2 μm Gelman Acrodisc to remove the catalyst. The solvent was evaporated off from filtrate to yield the compound of Formula II-4 as a white powder which was further purified by normal phase HPLC using the following conditions:

| Column: | Phenomenex Luna 10u Silica |
|---|---|
| Dimensions: | 25 cm × 21.2 mm ID |
| Flow rate: | 14.5 ml/min |
| Detection: | ELSD |
| Solvent: | 5% to 80% EtOAc/Hex for 19 min, 80 to 100% EtOAc in 1 min, then 4 min at 100% EtOAc |

Figure 14:
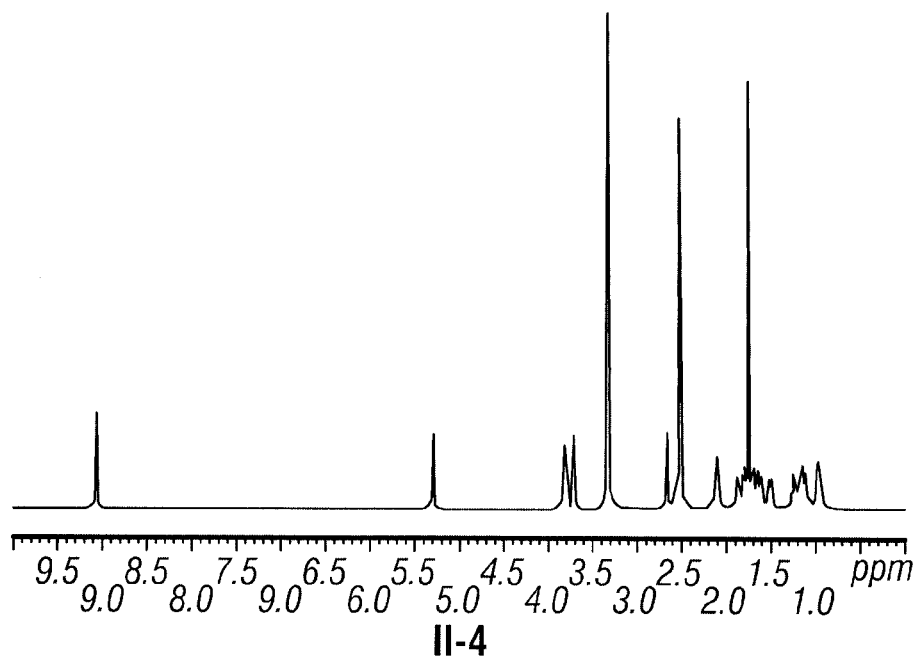
FIG. 14 depicts the $^1$H NMR spectrum of a compound having structure Formula II-4.
Figure 15:
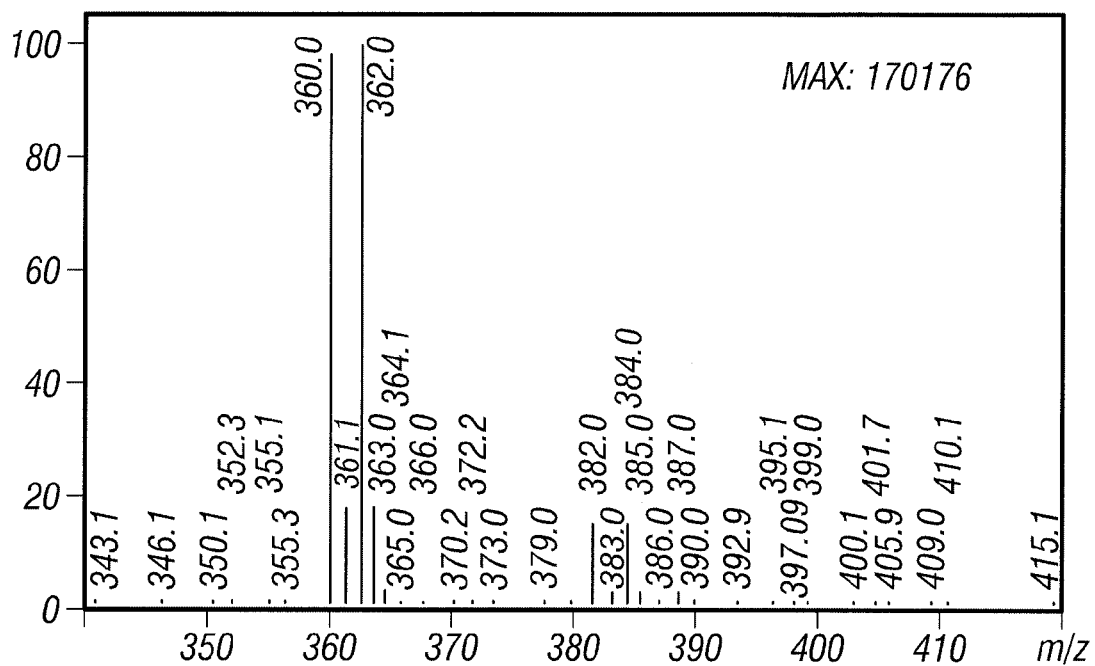
FIG. 15 depicts the mass spectrum of a compound having structure Formula II-4.

Compound of Formula II-4 eluted at 16.5 min as a pure compound: UV (acetonitrile/H$_2$O): λ$_{max}$ 225 (sh) nm. FIG. 14 depicts the NMR spectrum of the compound of Formula II-4 in DMSO-d$_6$. FIG. 15 depicts the low resolution mass of the compound of Formula II-4: m/z 360 (M+H), 382 (M+Na).

In addition, high resolution mass spectrometry data were obtained for compounds II-2, II-3, and II-4. Compound II-2: HRMS (ESI), m/z 316.1305 [M+H]$^+$, $\Delta_{calc}$=−3.5 ppm, $C_{15}H_{23}NO_4Cl$. Compound II-3: HRMS (ESI), m/z 282.1706 [M+H]$^+$, $\Delta_{calc}$=0.3 ppm, $C_{15}H_{24}NO_4$. Compound II-4: HRMS (ESI), m/z 360.0798 [M+H]$^+$, $\Delta_{calc}$=−3.4 ppm, $C_{15}H_{23}NO_4Br$.

Example 8

Synthesis of the Compounds of Formulae II-5A and II-5B

Compounds of Formula II-5A and Formula II-5B can be synthesized from compound of Formula II-16 by epoxidation with mCPBA.

Compound of Formula II-16 (101 mg, 0.32 mmole) was dissolved in methylenechloride (30 mL) in a 100 ml of round bottom flask to which was added 79 mg (0.46 mmole) of meta-chloroperbenzoic acid (mCPBA) and a magnetic stir bar. The reaction mixture was stirred at room temperature for about 18 hours. The reaction mixture was poured onto a 20 cc silica flash column and eluted with 120 ml of $CH_2Cl_2$, 75 ml of 1:1 ethyl acetate/hexane and finally with 40 ml of 100% ethyl acetate. The 1:1 ethyl acetate/hexane fractions yield a mixture of diastereomers of epoxyderivatives, Formula II-5A and II-5B, which were separated by normal phase HPLC using the following conditions:

| | |
|---|---|
| Column | Phenomenex Luna 10u Silica |
| Dimensions | 25 cm × 21.2 mm ID |
| Flow rate | 14.5 ml/min |
| Detection | ELSD |
| Solvent | 25% to 80% EtOAc/Hex over 19 min, 80 to 100% EtOAc in 1 min, then 5 min at 100% EtOAc |

Compound Formula II-5A (major product) and II-5B (minor product) eluted at 21.5 and 19 min, respectively, as pure compounds. Compound II-5B was further chromatographed on a 3 cc silica flash column to remove traces of chlorobenzoic acid reagent.

Chemical Structures:

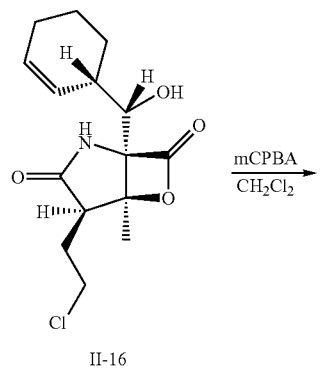

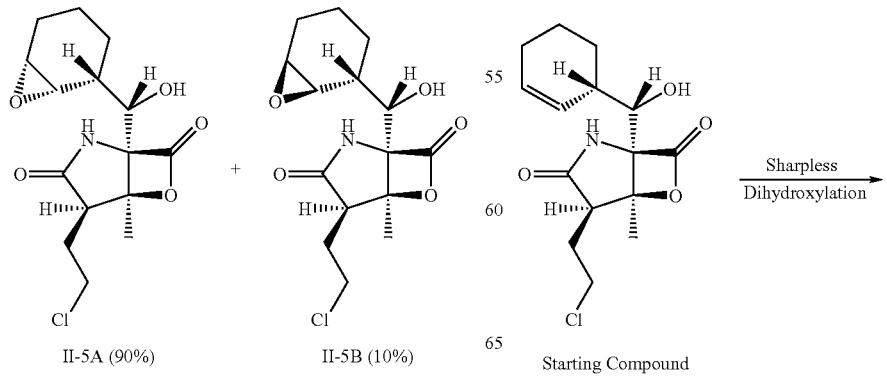

Structural Characterization

Figure 16:
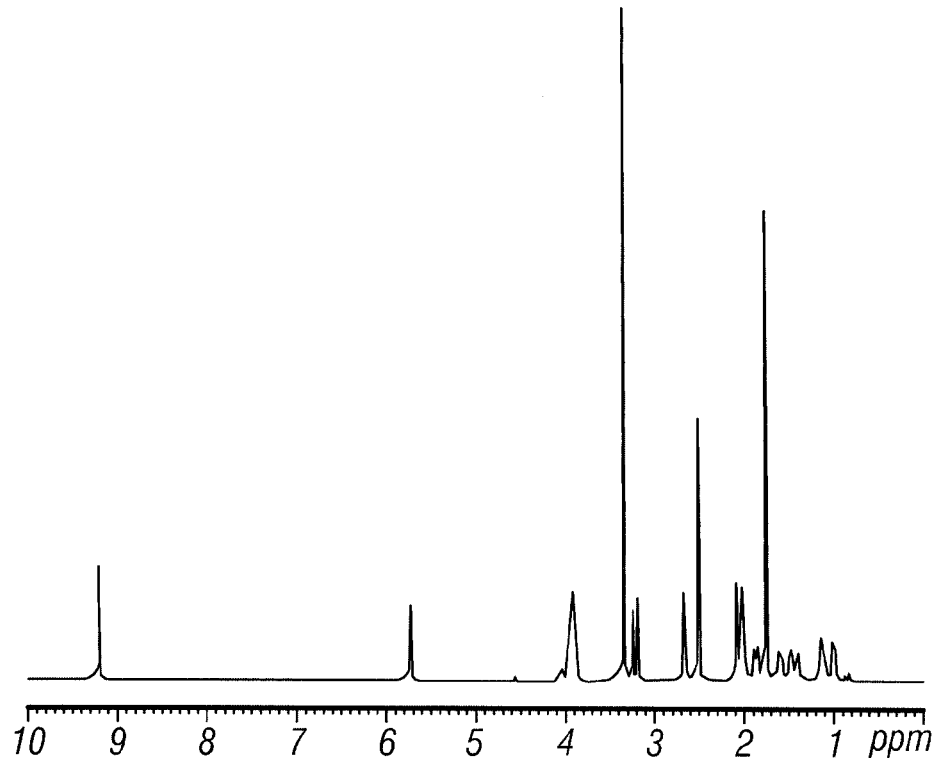
FIG. 16 depicts the $^1$H NMR spectrum of a compound having structure Formula II-5A.
Figure 17:
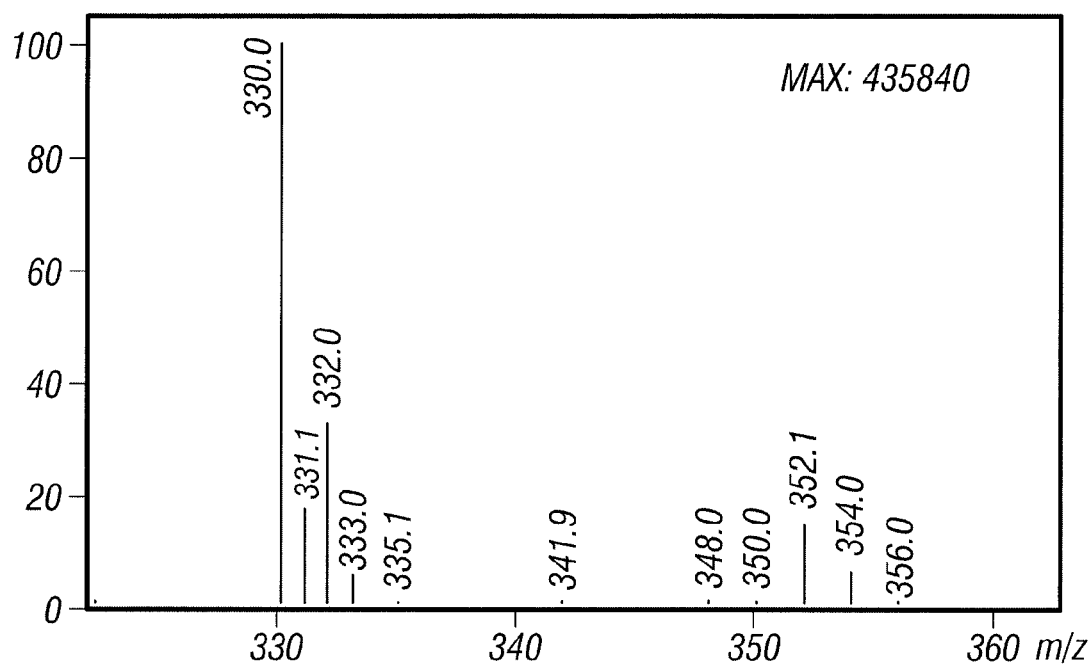
FIG. 17 depicts the mass spectrum of a compound having structure Formula II-5A.

Formula II-5A: UV (Acetonitrile/$H_2O$) $\lambda_{max}$ 225 (sh) nm. Low Res. Mass: m/z 330 (M+H), 352 (M+Na); HRMS (ESI), m/z 330.1099 [M+H]$^+$, $\Delta_{calc}$=−2.9 ppm, $C_{15}H_{21}NO_5Cl$. FIGS. 16-17, respectively depict the 1H NMR spectrum of Formula II-5A and the mass spectrum of Formula II-5A.

Figure 18:
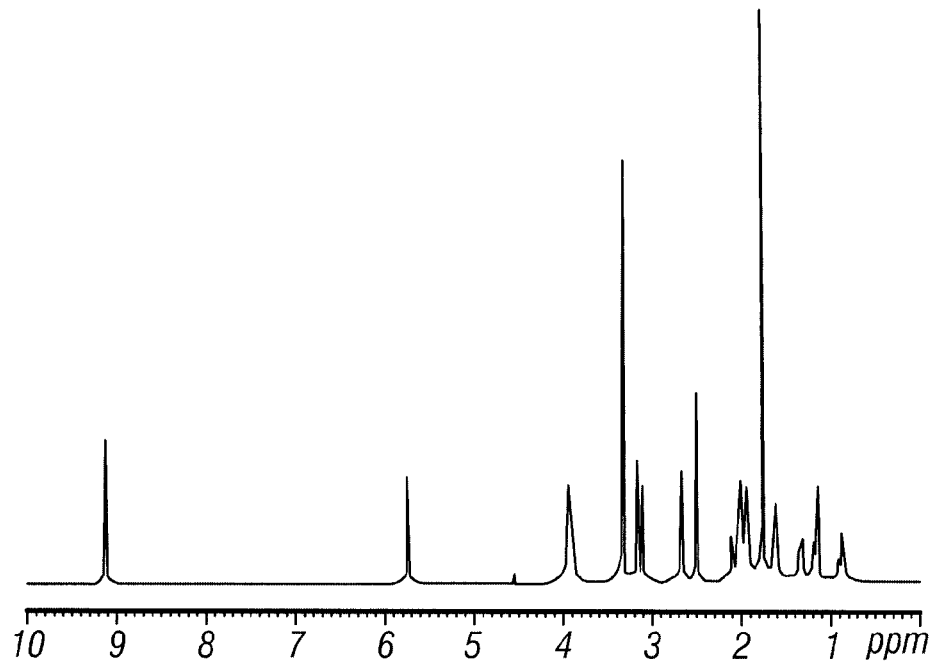
FIG. 18 depicts the $^1$H NMR spectrum of a compound having structure Formula II-5B.
Figure 19:
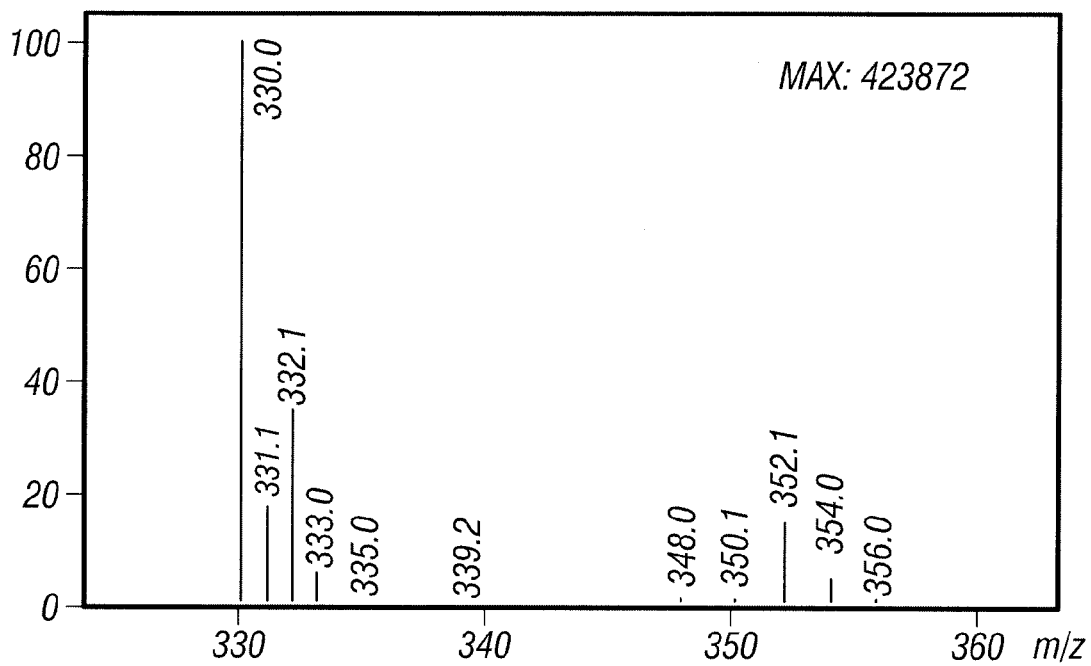
FIG. 19 depicts the mass spectrum of a compound having structure Formula II-5B.

Formula II-5B: UV (Acetonitrile/$H_2O$) $\lambda_{max}$ 225 (sh) nm. Low Res. Mass: m/z 330 (M+H), 352 (M+Na); HRMS (ESI), m/z 330.1105 [M+H]$^+$, $\Delta_{calc}$=−0.9 ppm, $C_{15}H_{21}NO_5Cl$. FIGS. 18-19, respectively depict the 1H NMR spectrum of II-5B and the mass spectrum of II-5B.

Example 9

Synthesis of the Compounds of Formulae IV-1, IV-2, IV-3 and IV-4

Synthesis of diol derivatives (Formula IV-2)

Diols can be synthesized by Sharpless dihydroxylation using AD mix-α and β: AD mix-α is a premix of four reagents, $K_2OsO_2(OH)_4$; $K_2CO_3$; $K_3Fe(CN)_6$; (DHQ)$_2$-PHAL [1,4-bis(9-O-dihydroquinine)phthalazine] and AD mix-β is a premix of $K_2OsO_2(OH)_4$; $K_2CO_3$; $K_3Fe(CN)_6$; (DHQD)$_2$—PHAL [1,4-bis(9-O-dihydroquinidine)phthalazine] which are commercially available from Aldrich. Diol can also be synthesized by acid or base hydrolysis of epoxy compounds (Formula II-5A and II-5B) which may be different to that of products obtained in Sharpless dihydroxylation in their stereochemistry at carbons bearing hydroxyl groups Sharpless Dihydroxylation of Compounds II-16, II-17 and II-18

Any of the compounds of Formulae II-16, II-17 and II-18 can be used as the starting compound. In the example below, compound of Formula II-16 is used. The starting compound is dissolved in t-butanol/water in a round bottom flask to which is added AD mix-α or β and a magnetic stir bar. The reaction is monitored by silica TLC as well as mass spectrometer. The pure diols are obtained by usual workup and purification by flash chromatography or HPLC. The structures are confirmed by NMR spectroscopy and mass spectrometry. In this method both hydroxyl groups are on same side.

-continued

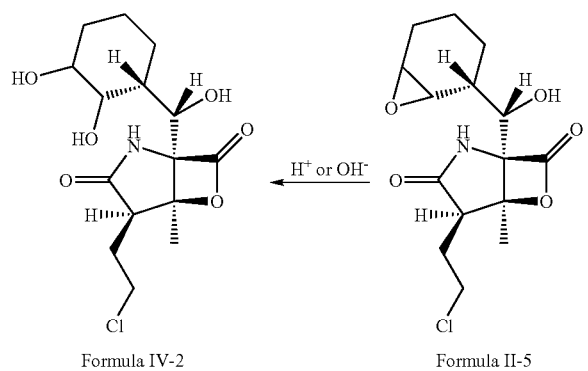

Formula IV-2    Formula II-5

Nucleophilic Ring Opening of Epoxy Compounds (II-5):

The epoxy ring is opened with various nucleophiles like NaCN, NaN$_3$, NaOAc, HBr, HCl, etc. to create various substituents on the cyclohexane ring, including a hydroxyl substituent.

Examples:

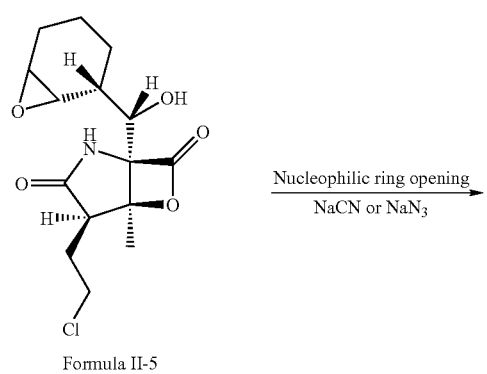

Formula II-5

R7: CN or N3 if R6 is OH
R6: CN or N3 if R7 is OH

Formula IV-1

The epoxy is opened with HCl to make Formula IV-3:

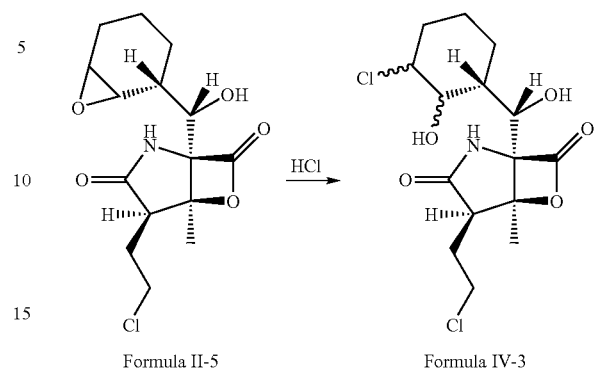

Formula II-5    Formula IV-3

Figure 20:
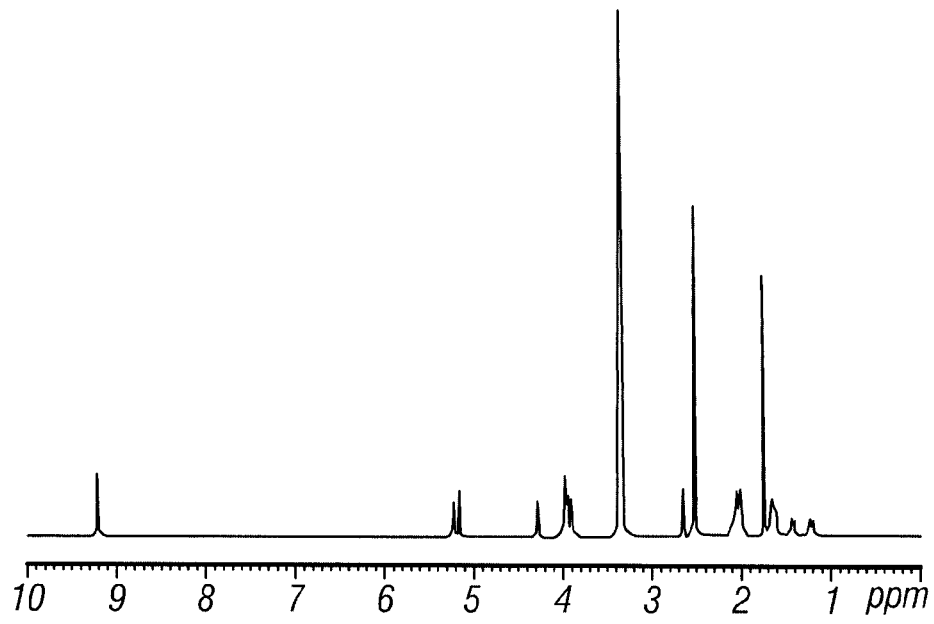
FIG. 20 depicts the $^1$H NMR spectrum of a compound having structure Formula IV-3C in DMSO-$d_6$.
Figure 21:
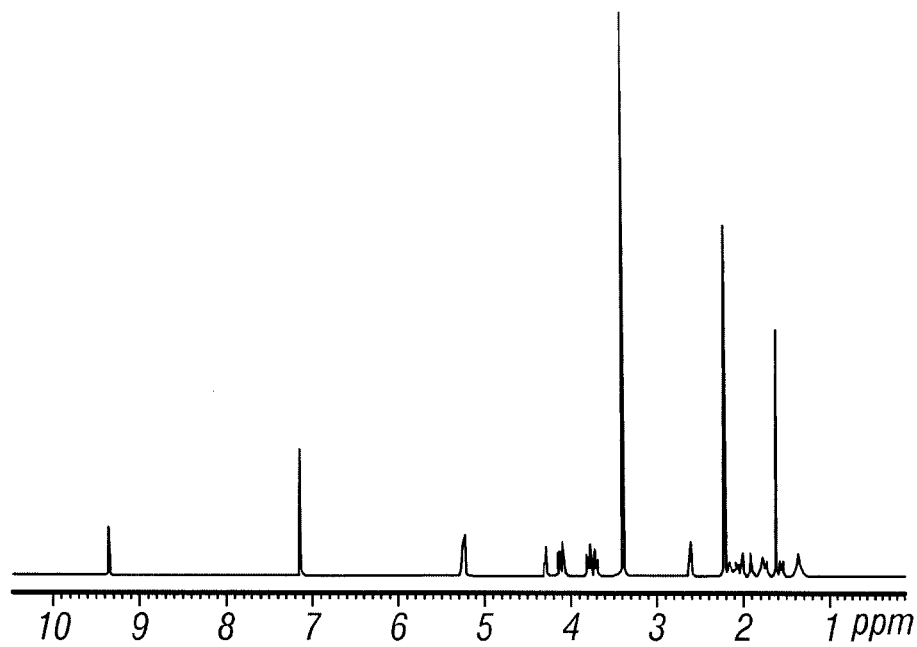
FIG. 21 depicts the $^1$H NMR spectrum of a compound having structure Formula IV-3C in $C_6D_6$/DMSO-$d_6$.

Compound of Formula II-5A (3.3 mg) was dissolved in acetonitrile (0.5 ml) in a 1 dram vial to which was added 5% HCl (500 ul) and a magnetic stir bar. The reaction mixture was stirred at room temperature for about an hour. The reaction was monitored by mass spectrometry. The reaction mixture was directly injected on normal phase HPLC to obtain compound of Formula IV-3C as a pure compound without any work up. The HPLC conditions used for the purification were as follows: Phenomenex Luna 10u Silica column (25 cm×21.2 mm ID) with a solvent gradient of 25% to 80% EtOAc/Hex over 19 min, 80 to 100% EtOAc in 1 min, then 5 min at 100% EtOAc at a flow rate of 14.5 ml/min. An ELSD was used to monitor the purification process. Compound of Formula IV-3C eluted at about 18 min (2.2 mg). Compound of Formula IV-3C: UV (Acetonitrile/H$_2$O) $\lambda_{max}$ 225 (sh) nm; ESMS, m/z 366 (M+H), 388 (M+Na); HRMS (ESI), m/z 366.0875 [M+H]$^+$, $\Delta_{calc}$=0.0 ppm, C$_{15}$H$_{22}$NO$_5$Cl$_2$; $^1$H NMR in DMSO-d$_6$ (FIG. 20) The stereochemistry of the compound of Formula IV-3C was determined based on coupling constants observed in the cyclohexane ring in 1:1 C$_6$D$_6$/DMSO-d$_6$ (FIG. 21)

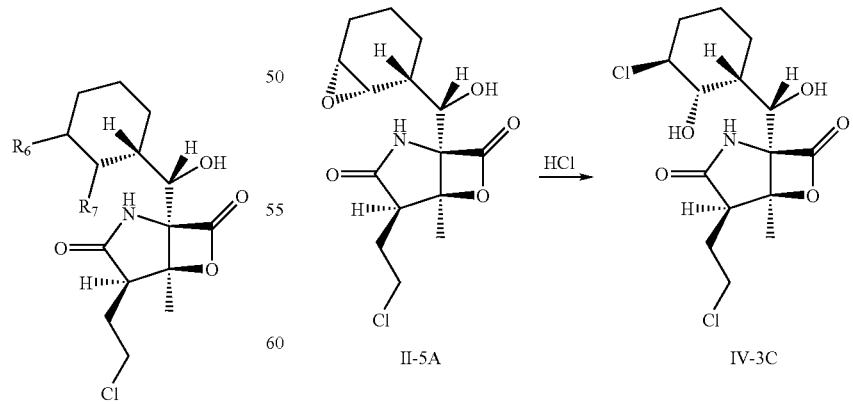

II-5A    IV-3C

Reductive ring opening of epoxides (II-5): The compound of Formula is treated with metalhydrides like BH$_3$-THF complex to make compound of Formula IV-4.

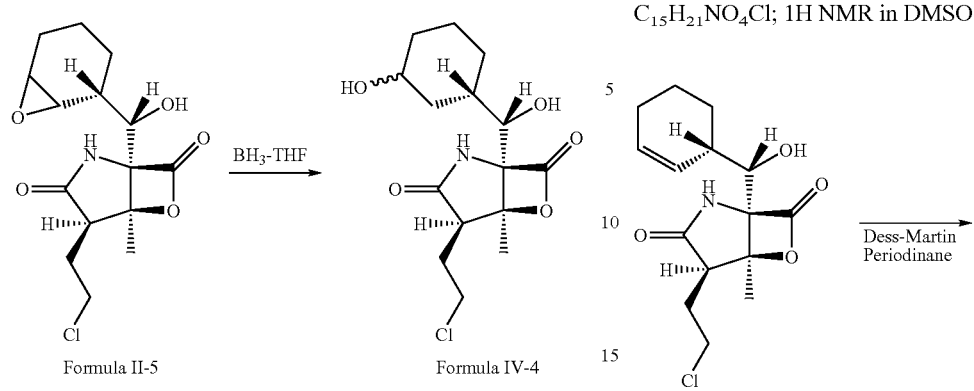

Formula II-5 → Formula IV-4 (BH₃-THF)

Example 10

Synthesis of the Compounds of Formulae II-13C and II-8C

Figure 22:
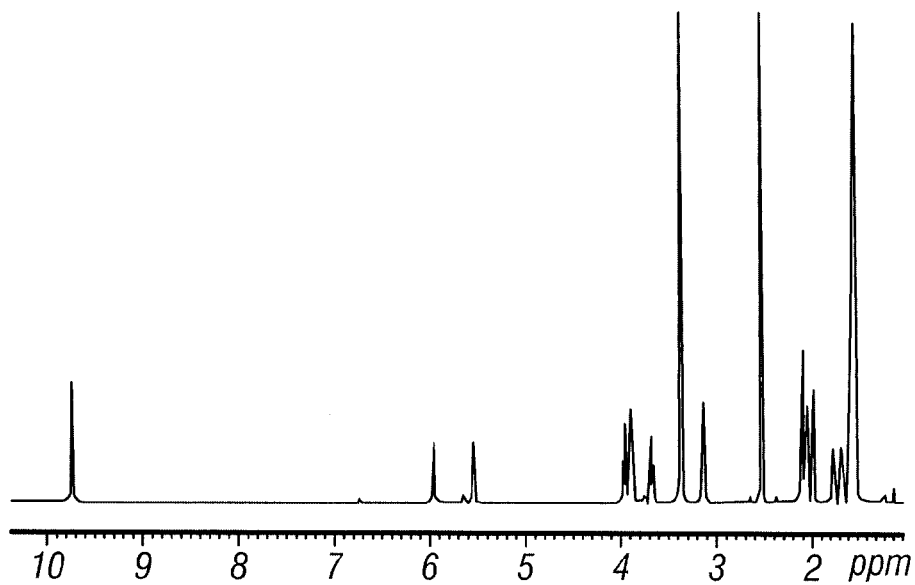
FIG. 22 depicts the $^1$H NMR spectrum of a compound having structure Formula II-13C.

Compound of Formula II-16 (30 mg) was dissolved in CH$_2$Cl$_2$ (6 ml) in a scintillation vial (20 ml) to which Dess-Martin Periodinane (122 mg) and a magnetic stir bar were added. The reaction mixture was stirred at room temperature for about 2 hours. The progress of the reaction was monitored by TLC (Hex:EtOAc, 6:4) and analytical HPLC. From the reaction mixture, the solvent volume was reduced to one third, absorbed on silica gel, poured on top of a 20 cc silica flash column and eluted in 20 ml fractions using a gradient of Hexane/EtOAc from 10 to 100%. The fraction eluted with 30% EtOAc in Hexane contained a mixture of rotamers of Formula II-13C in a ratio of 1.5:8.5. The mixture was further purified by normal phase HPLC using the Phenomenex Luna 10u Silica column (25 cm×21.2 mm ID) with a solvent gradient of 25% to 80% EtOAc/Hex over 19 min, 80 to 100% EtOAc over 1 min, holding at 100% EtOAc for 5 min, at a flow rate of 14.5 ml/min. An ELSD was used to monitor the purification process. Compound of Formula II-13C eluted at 13.0 and 13.2 mins as a mixture of rotamers with in a ratio of 1.5:8.5 (7 mg). Formula II-13C: UV (Acetonitrile/H$_2$O) λ$_{max}$ 226 (sh) & 300 (sh) nm; ESMS, m/z 312 (M+H)$^+$, 334 (M+Na)$^+$; HRMS (ESI), m/z 312.1017 [M+H]$^+$, Δ$_{calc}$=4.5 ppm, C$_{15}$H$_{19}$NO$_4$Cl; 1H NMR in DMSO-d$_6$ (see FIG. 22).

Figure 23:
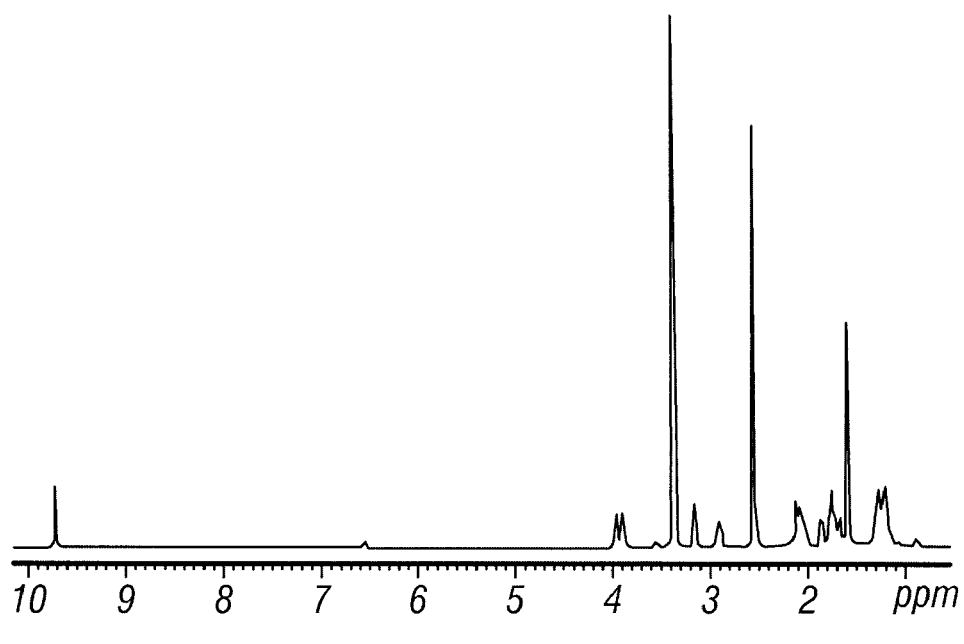
FIG. 23 depicts the $^1$H NMR spectrum of a compound having structure Formula II-8C.

The rotamer mixture of Formula II-13C (4 mg) was dissolved in acetone (1 ml) in a scintillation vial (20 ml) to which a catalytic amount (0.5 mg) of 10% (w/w) Pd/C and a magnetic stir bar were added. The reaction mixture was stirred in a hydrogen atmosphere at room temperature for about 15 hours. The reaction mixture was filtered through a 0.2 μm Gelman Acrodisc to remove the catalyst. The solvent was evaporated from the filtrate to yield compound of Formula II-8C as a colorless gum which was further purified by normal phase HPLC using a Phenomenex Luna 10u Silica column (25 cm×21.2 mm ID) with a solvent gradient of 25% to 80% EtOAc/Hex over 19 min, 80 to 100% EtOAc over 1 min, holding at 100% EtOAc for 5 min, at a flow rate of 14.5 ml/min. An ELSD was used to monitor the purification process. Compound of Formula II-8C (1 mg) eluted at 13.5 min as a pure compound. Formula II-8C: UV (Acetonitrile/H$_2$O) λ$_{max}$ 225 (sh) nm; ESMS, m/z 314 (M+H)$^+$, 336 (M+Na)$^+$; HRMS (ESI), m/z 314.1149 [M+H]$^+$, Δ$_{calc}$=3.3 ppm, C$_{15}$H$_{21}$NO$_4$Cl; 1H NMR in DMSO-d$_6$ (See FIG. 23).

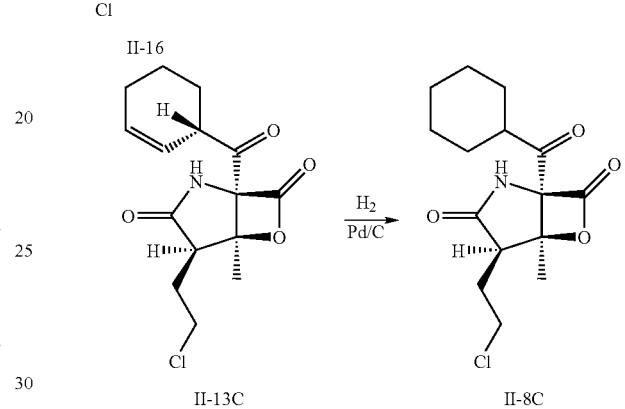

II-16 → II-13C (Dess-Martin Periodinane) → II-8C (H$_2$, Pd/C)

Example 11

Synthesis of the Compound of Formula II-25 from II-13C

Figure 24:
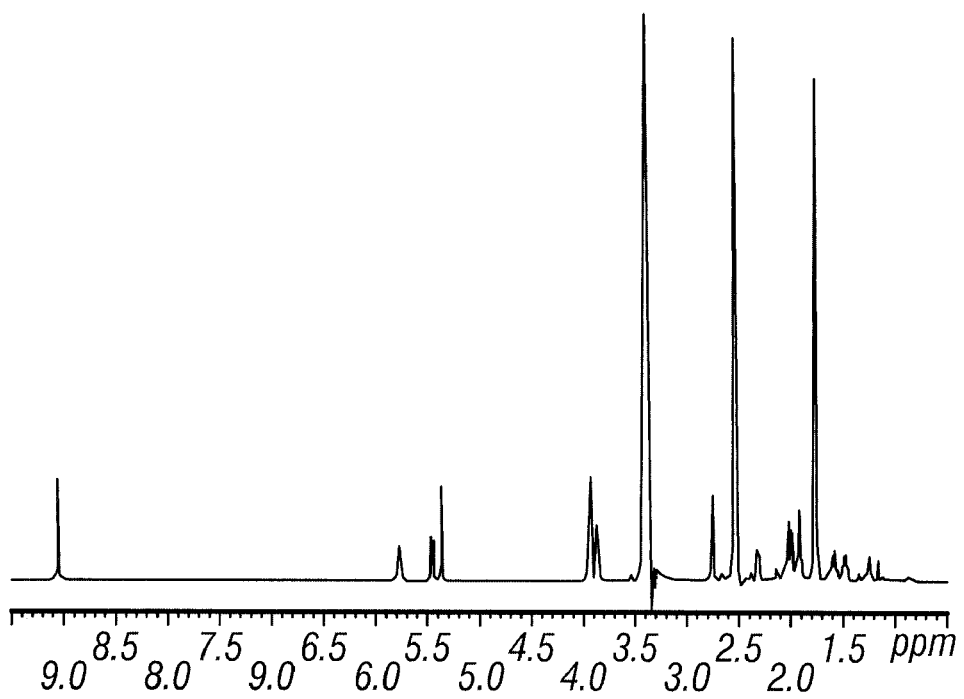
FIG. 24 depicts the $^1$H NMR spectrum of a compound having structure Formula II-25.

The rotamer mixture of Formula II-13C (5 mg) was dissolved in dimethoxy ethane (monoglyme; 1.5 ml) in a scintillation vial (20 ml) to which water (15 μl (1% of the final solution concentration)) and a magnetic stir bar were added. The above solution was cooled to −78° C. on a dry ice-acetone bath, and a sodium borohydride solution (3.7 mg of NaBH$_4$ in 0.5 ml of monoglyme (created to allow for slow addition)) was added drop-wise. The reaction mixture was stirred at −78° C. for about 14 minutes. The reaction mixture was acidified using 2 ml of 4% HCl solution in water and extracted with CH$_2$Cl$_2$. The organic layer was evaporated to yield mixture of compound of formulae II-25 and II-16 in a 9.5:0.5 ratio as a white solid, which was further purified by normal phase HPLC using a Phenomenex Luna 10u Silica column (25 cm×21.2 mm ID). The mobile phase was 24% EtOAc/76% Hexane, which was held isocratic for 19 min, followed by a linear gradient of 24% to 100% EtOAc over 1 min, and held at 100% EtOAc for 3 min; the flow rate was 25 ml/min. An ELSD was used to monitor the purification process. Compound of formula II-25 (1.5 mg) eluted at 11.64 min as a pure compound. Compound of Formula II-25: UV (Acetonitrile/H$_2$O) λ$_{max}$ 225 (sh) nm; ESMS, m/z 314 (M+H)$^+$, 336 (M+Na)$^+$; HRMS (ESI), m/z 314.1154 [M+H]$^+$, Δ$_{calc}$=−0.6 ppm, C$_{15}$H$_{21}$NO$_4$Cl; $^1$H NMR in DMSO-d$_6$ (see FIG. 24).

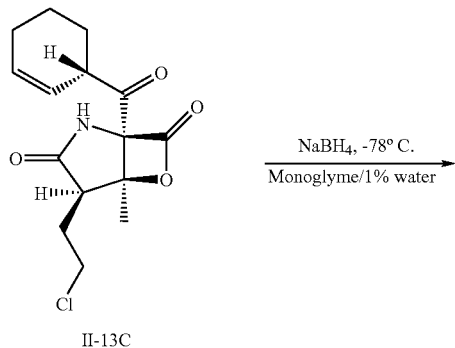

II-13C

II-25 (95%)

Example 12

Synthesis of the Compounds of Formulae II-31, II-32 and II-49 from II-13C; and Compounds of Formulae II-33, II-34, II-35 and II-36 from II-31 and II-32

A rotamer mixture of the Compound of Formula II-13C (20 mg) was dissolved in acetone (4 ml) in a scintillation vial (20 ml) to which a catalytic amount (3 mg) of 10% (w/w) Pd/C and a magnetic stir bar were added. The reaction mixture was stirred at room temperature for about 15 hours. The reaction mixture was filtered through a 0.2 μm Gelman Acrodisc to remove the catalyst. The solvent was evaporated from the filtrate to yield a mixture of diastereomers of hydroxy derivatives of Formulae II-31 and II-32 (1:1) and a minor compound II-49, which were separated by reversed phase HPLC using Ace 5u C18 column (150 mm×22 mm ID) with a solvent gradient of 90% to 30% $H_2O$/Acetonitrile over 15 min, 70 to 100% Acetonitrile over 5 min, holding at 100% Acetonitrile for 4 min, at a flow rate of 14.5 ml/min. A diode array detector was used to monitor the purification process. Compound II-31 (2 mg), II-32 (2 mg) and II-49 (0.2 mg) eluted at 10.6, 10.8 and 11.54 min, respectively, as pure compounds. II-31: UV (Acetonitrile/$H_2O$) $\lambda_{max}$ 250 (sh) nm; ESMS m/z 328.1 $(M+H)^+$ & 350.0 $(M+Na)^+$. II-32: UV (Acetonitrile/$H_2O$) max 250 (sh) nm; ESMS, m/z 328.1 $(M+H)^+$ & 350.0 $(M+Na)^+$. II-49: UV (Acetonitrile/$H_2O$) $\lambda_{max}$ 250 (sh) and 320 nm; ESMS, m/z 326.0 $(M+H)^+$, 343.1 $(M+H_2O)^+$ & 348.0 $(M+Na)^+$.

In an alternate method, compounds II-31, II-32 and II-49 were separated by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process.

The ketone of the compounds of formula II-31 and II-32 can be reduced by using sodium borohydride at 0 to −10° C. in monoglyme solvent for about 14 minutes. The reaction mixture can be acidified using 4% HCl solution in water and extracted with $CH_2Cl_2$. The organic layer can be evaporated to yield the mixtures of compounds of formulae II-33, II-34, II-35 and II-36 which can be separated by chromatographic methods.

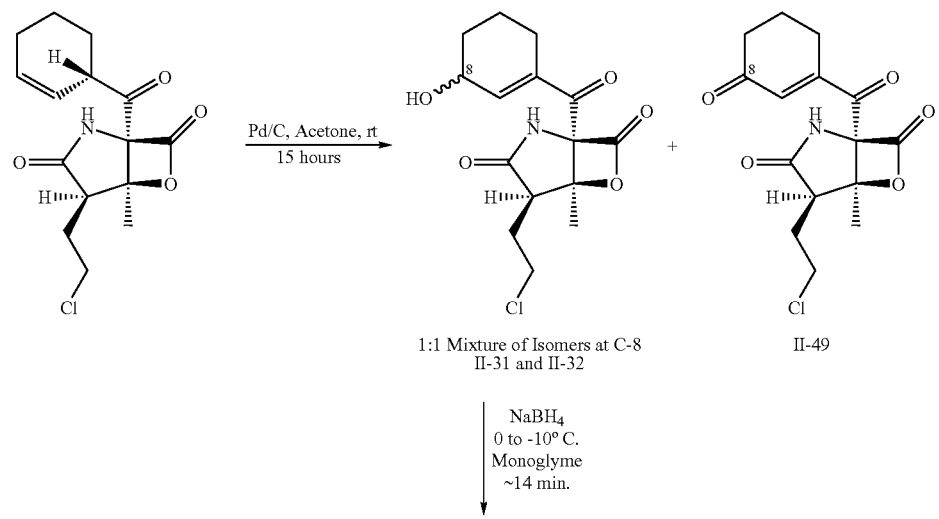

1:1 Mixture of Isomers at C-8
II-31 and II-32

II-49

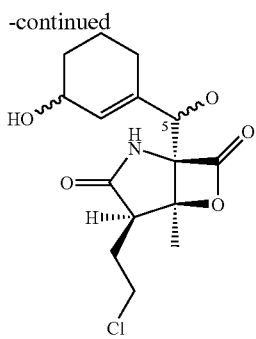

II-33, II-34, II-35 and II-36

Example 13

Synthesis of the Compound of Formulae II-21 from II-19

Figure 25:
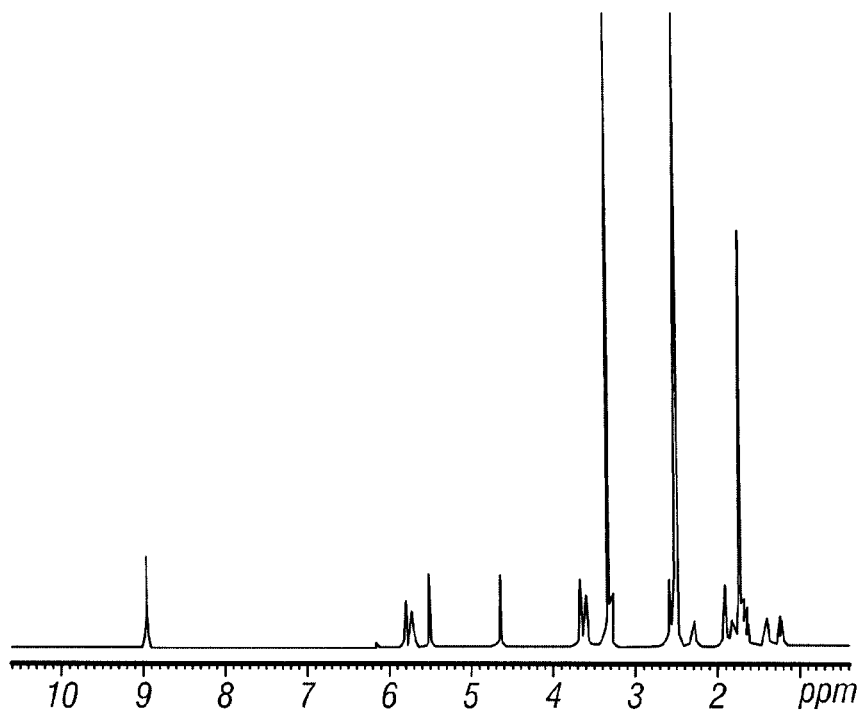
FIG. 25 depicts the $^1$H NMR spectrum of a compound having structure Formula II-21.

Acetone (7.5 ml) was vigorously mixed with 5 N NaOH (3 ml) and the resulting mixture evaporated to a minimum volume in vacuo. A sample of 100 µl of this solution was mixed with compound of Formula II-19 (6.2 mg) in acetone (1 ml) and the resulting biphasic mixture vortexed for 2 minutes. The reaction solution was immediately subjected to preparative C18 HPLC. Conditions for the purification involved a linear gradient if 10% acetonitrile/90% water to 90% acetonitrile/10% water over 17 minutes using an Ace 5µ C18 HPLC column of dimensions 22 mm id by 150 mm length. Compound of Formula II-21 eluted at 9.1 minutes under these conditions to yield 0.55 mg compound. Compound of Formula II-21: UV (Acetonitrile/H$_2$O) 225 (sh), ESMS, m/z 296.1 (M+H); $^1$H NMR in DMSO-d$_6$ (see FIG. 25).

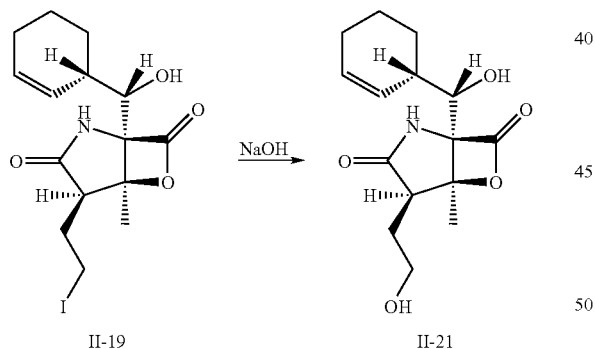

Example 14

Synthesis of the Compound of Formulae II-22 from II-19

Figure 26:
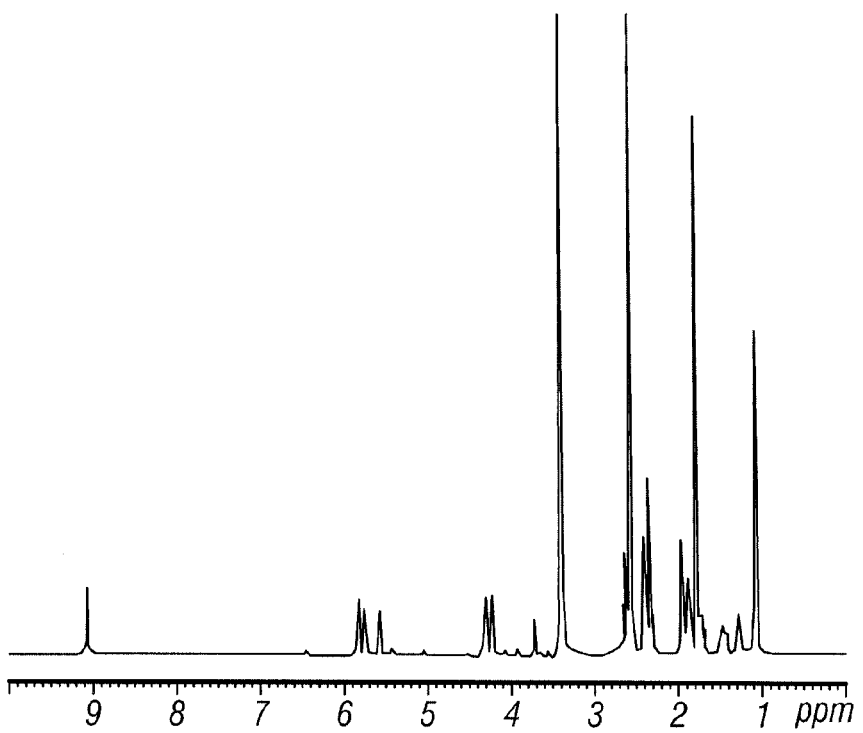
FIG. 26 depicts the $^1$H NMR spectrum of a compound having structure Formula II-22.

A sample of 60 mg sodium propionate was added to a solution of compound of Formula II-19 (5.3 mg) in DMSO (1 ml) and the mixture sonicated for 5 minutes, though the sodium propionate did not completely dissolve. After 45 minutes, the solution was filtered through a 0.45µ syringe filter and purified directly using HPLC. Conditions for the purification involved a linear gradient if 10% acetonitrile/90% water to 90% acetonitrile/10% water over 17 minutes using an Ace 5µ C18 HPLC column of dimensions 22 mm id by 150 mm length. Under these conditions, compound of Formula II-22 eluted at 12.3 minutes to yield 0.7 mg compound (15% isolated yield). UV (Acetonitrile/H$_2$O) 225 (sh), ESMS, m/z 352.2 (M+H); HRMS (ESI), m/z 352.1762 [M+H]$^+$, $\Delta_{calc}$=0.6 ppm, C$_{18}$H$_{26}$NO$_6$; $^1$H NMR in DMSO-d$_6$ (see FIG. 26).

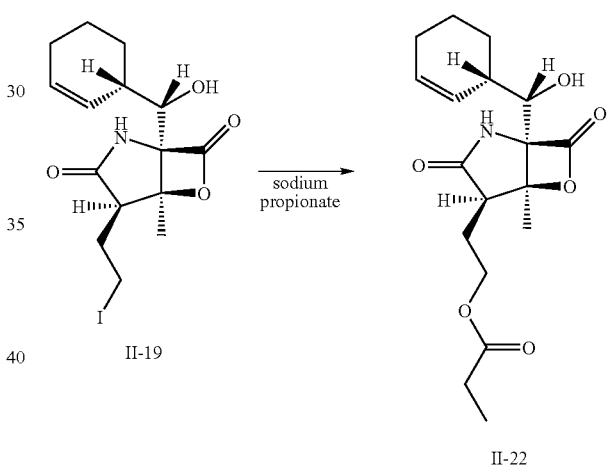

Example 15

Synthesis of the Compound of Formula II-29 from II-19

A sample of NaN$_3$ (80 mg) was dissolved in DMSO (1 ml) and transferred to a vial containing Compound II-19 (6.2 mg) which was contaminated with approximately 10% Compound II-16. The solution was incubated at room temperature for 1 hr prior to purification on C18 HPLC (ACE 5µ C18-HL, 150 mm×21 mm ID) using a solvent gradient of 10% acetonitrile/90% H$_2$O to 90% acetonitrile/10% H$_2$O over 17 minutes. Using this method, the desired azido derivative II-29 co-eluted with Compound II-16 contaminant at 12.5 minutes (4.2 mg, 85% yield). A 2.4 mg portion of compound II-29 was further purified using additional C18 HPLC chromatography (ACE 5µ C18-HL, 150 mm×21 mm ID) using an isocratic solvent gradient consisting of 35% acetonitrile/65% H$_2$O. Under these conditions compound II-29 eluted after 20 minutes, while Compound II-16 eluted after 21.5 minutes. The resulting sample consisted of 1.1 mg Compound II-29 was used for characterization in biological assays.

Figure 55:
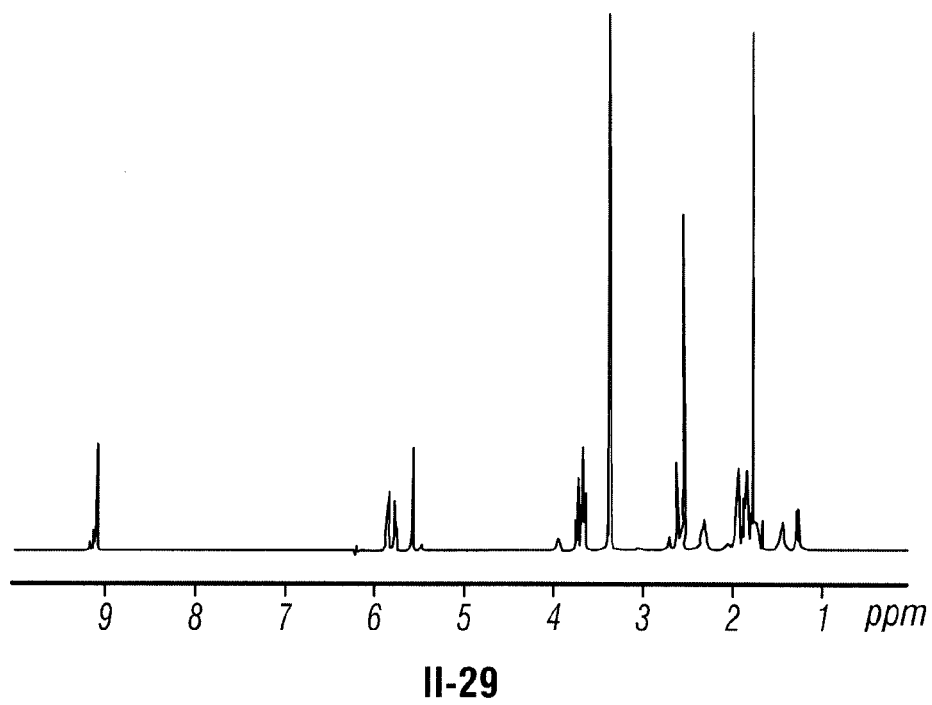
FIG. 55 depicts the $^1$H NMR spectrum of the compound of Formula II-29 in DMSO-$d_6$.

Compound II-29: UV (Acetonitrile/H$_2$O) 225 (sh), ESMS, m/z 321.1 (M+H); $^1$H NMR in DMSO-d$_6$ (see FIG. 55).

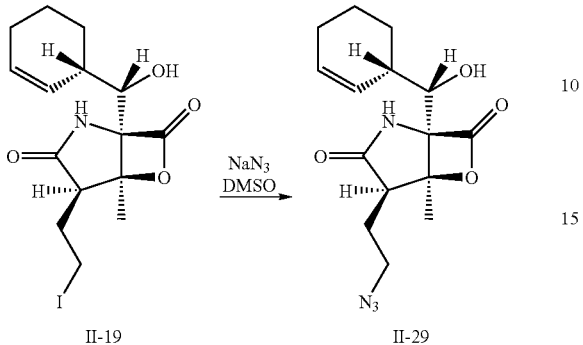

Example 16

Synthesis of the Compounds of Formulae II-37 and II-38 from II-19

The compounds of Formulae II-37 and II-38 can be prepared from the compound of Formula II-19 by cyano-de-halogenation or thiocyanato-de-halogenation, respectively. Compound II-19 can be treated with NaCN or KCN to obtain compound II-37. Alternatively, Compound II-19 can be treated with NaSCN or KSCN to obtain compound II-38.

Synthesis of the compound of Formula II-38 from II-19:

The compound of formula II-19 (10.6 mg, 0.02616 mmol) was dissolved in 1.5 ml of acetone in a scintillation vial (20 ml) to which sodium thiocyanate (10.0 mg, 0.1234 mmol), triethylamine (5 µl, 0.03597 mmol) and a magnetic stir bar were added. The reaction mixture was stirred at room temperature for 72 hours. The reaction mixture was concentrated in vacuo to yield the compound II-38. Compound II-38 was purified by normal phase HPLC using a Phenomenex Luna 10µ Silica column (25 cm×21.2 mm ID) with a solvent gradient of 0 to 95% H$_2$O/Acetonitrile over 21 min, at a flow rate of 14.5 ml/min. Diode array detector was used to monitor the purification process. Compound II-38 (3.0 mg, 34% yield) eluted at 18.0 min as a pure compound. II-38: UV Acetonitrile/H$_2$O $\lambda_{max}$ 203 (sh) nm; ESMS m/z 337.1 (M+H)$^+$ & 359.1 (M+Na)$^+$.

-continued

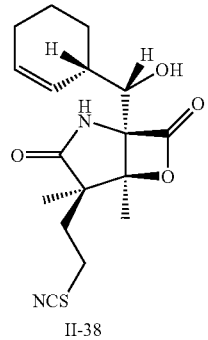

II-38

Example 17

Synthesis of the Compound of Formula II-39 from II-19

Thiols and thioethers of the Formula II-39 can be formed by dehalogenation of the compound of Formula II-19. Thiols (R=H) can be formed by treatment of Compound II-19 with NaSH, for example, while thioethers (R=alkyl) can be formed by treatment of Compound II-19 with salts of thiols, or alternatively, by treatment with thiols themselves by running the reaction in benzene in the presence of DBU.

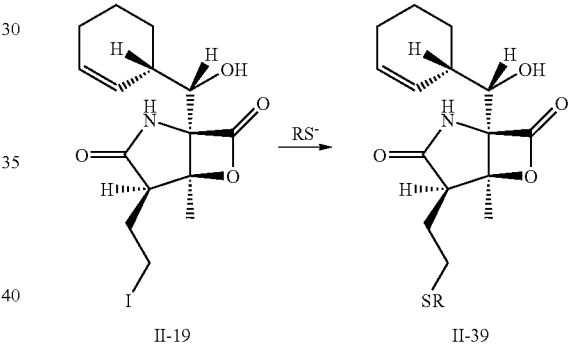

Example 18

Synthesis of the Compound of Formula II-40 from II-39

Sulfoxides (n=1) and sulfones (n=2) of the Formula II-40 can be formed by oxidation of thioethers of the Formula II-39, for example, with hydrogen peroxide or other oxidizing agents.

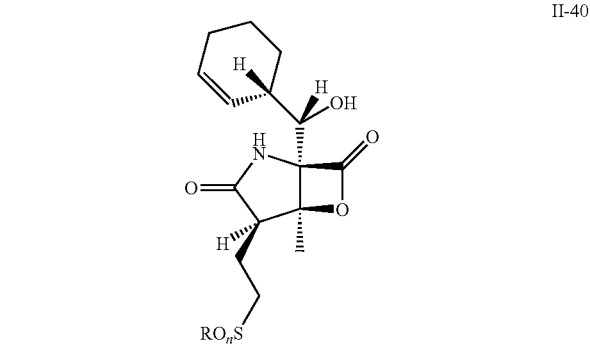

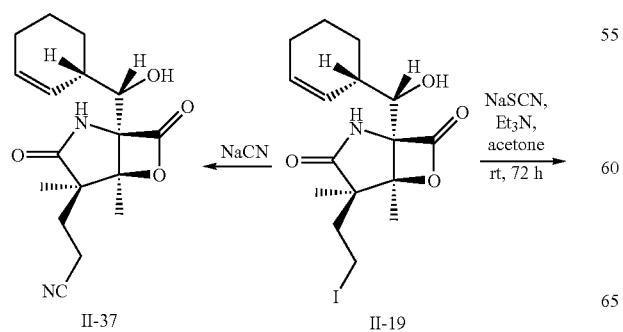

Example 19

Synthesis of the Compound of Formula II-41 from II-21

The compound of the Formula II-41 can be prepared by treatment of the compound of Formula II-21 (or a protected derivative of II-21, where the C-5 alcohol or lactam NH are protected, for example) with methyl sulfonyl chloride (mesyl chloride) in pyridine, for example, or by treatment with mesyl chloride in the presence of triethylaminde. Other sulfonate esters can be similarly prepared.

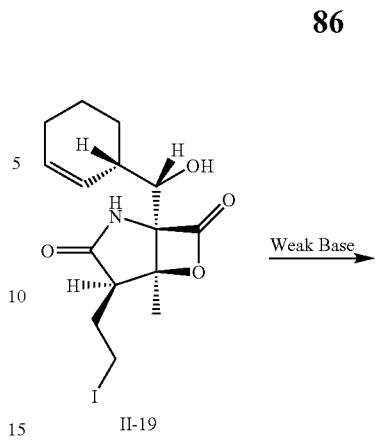

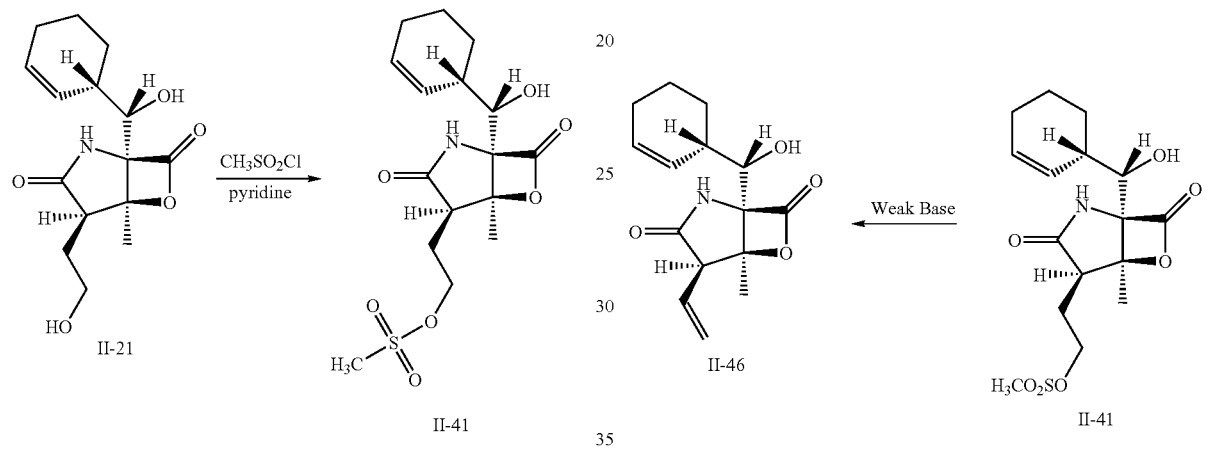

Example 20

Synthesis of the Compound of Formula II-46 from II-19 or II-41

The alkene of the Formula II-46 can be prepared by dehydroiodination of the compound of Formula II-19, or by hydromesyloxy elimination of the compound of Formula II-41, for example, by treatment with base.

Example 21

Synthesis of the Compound of Formula II-42A

Synthesis of boronic acids or esters, for example, the compound of the Formula II-42A, can be achieved as outlined in the retrosynthetic scheme below. Hydroboration of the alkene of Formula II-46 gives the corresponding alkyl borane, which can be converted to the corresponding boronic acid or ester, for example, the compound of the Formula II-42A.

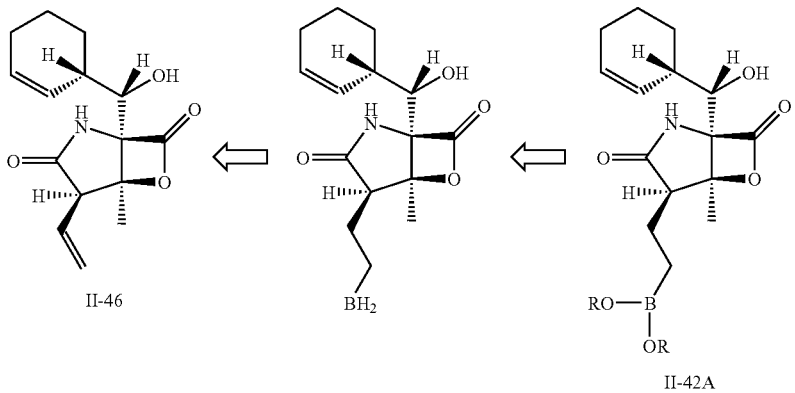

Example 22

Synthesis of the Compound of Formula II-43A

The compound of the Formula II-43A can be prepared by treatment of the compound of Formula II-19 with triphenyl phosphine to make a phosphorus ylide, which can be treated with various aldehydes, for example, glyoxylic acid methyl ester, to make Formula II-43A.

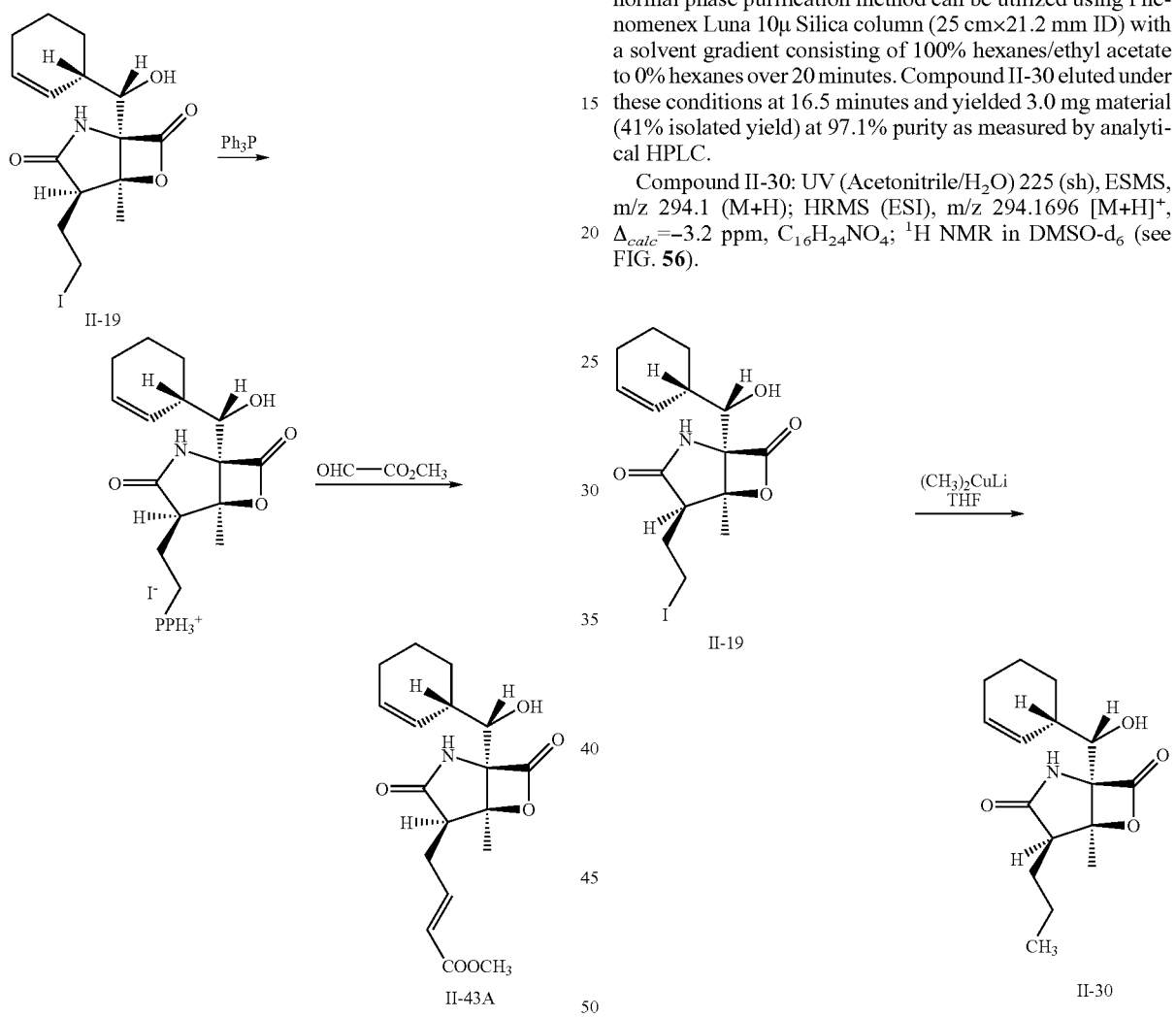

Example 23

Synthesis of the Compound of Formula II-30 from II-19

A portion of CuI (100 mg) was placed in a 25 ml pear bottom flask and flushed with Ar gas for 30 minutes. Ar gas flow was maintained through the flask throughout the course of the reaction. The vessel was cooled to −78° C. prior to addition of dry THF (5 ml) followed by the immediate dropwise addition of a solution of methyllithium in dry THF (5.0 ml, 1.6 M) with vigorous stirring. A solution of Compound II-19 in dry THF (12 mg Compound II-19, 1 ml THF) was added slowly to the clear dialkylcuprate solution and the resulting mixture stirred at −78° C. for 1 hr. The reaction was quenched by washing the THF solution through a plug of silica gel (1 cm diameter by 2 cm length) along with further washing using a solution of 50% EtOAc/50% hexanes (50 ml). The combined silica plug washes were dried in vacuo and subjected to further C18 HPLC purification in 2 injections (ACE 5μ C18-HL, 150 mm×21 mm ID) using an isocratic solvent gradient consisting of 35% acetonitrile/65% H$_2$O. Compound II-30 eluted under these conditions at 23.5 minutes and yielded 2.4 mg material (27% isolated yield) at 90.8% purity as measured by analytical HPLC. An alternative normal phase purification method can be utilized using Phenomenex Luna 10μ Silica column (25 cm×21.2 mm ID) with a solvent gradient consisting of 100% hexanes/ethyl acetate to 0% hexanes over 20 minutes. Compound II-30 eluted under these conditions at 16.5 minutes and yielded 3.0 mg material (41% isolated yield) at 97.1% purity as measured by analytical HPLC.

Figure 56:
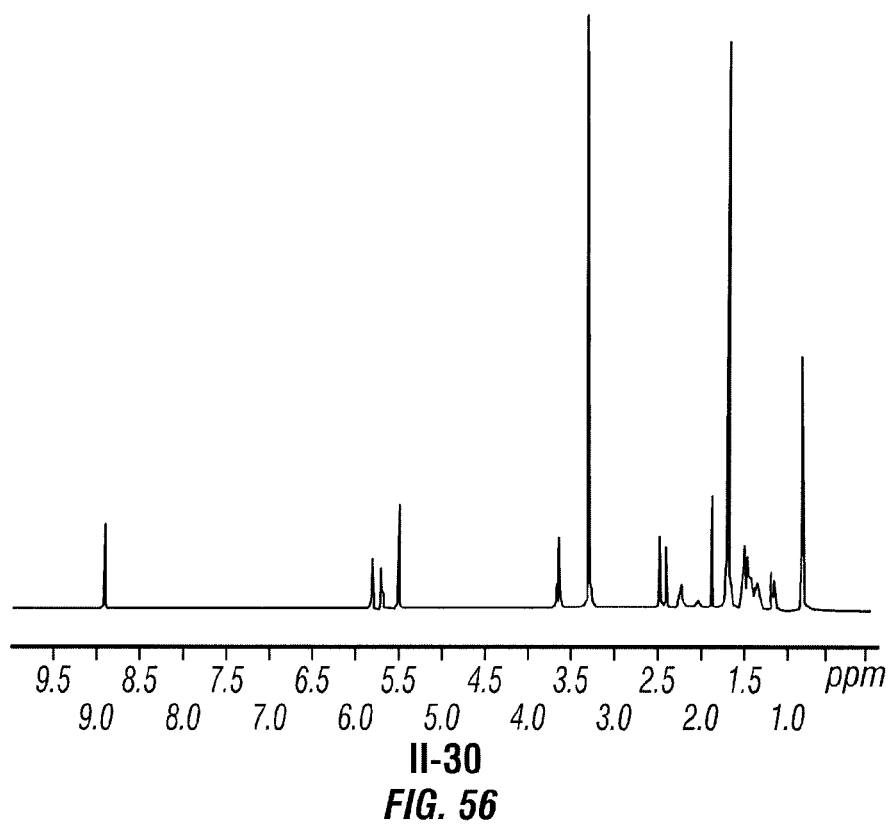
FIG. 56 depicts the $^1$H NMR spectrum of the compound of Formula II-30 in DMSO-$d_6$.
Figure 57:
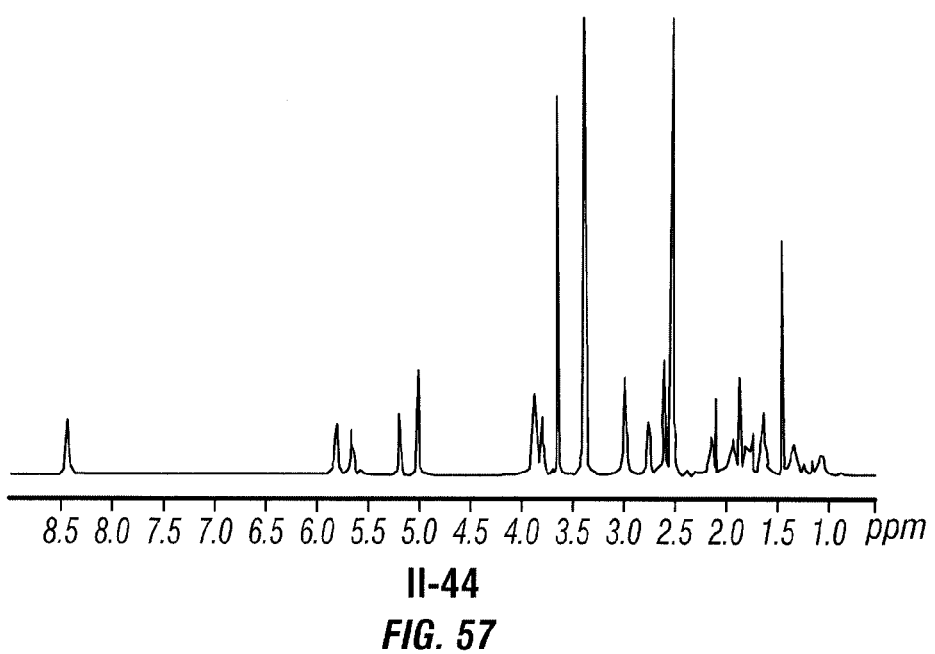
FIG. 57 depicts the $^1$H NMR spectrum of the compound of Formula II-44 in DMSO-$d_6$.

Compound II-30: UV (Acetonitrile/H$_2$O) 225 (sh), ESMS, m/z 294.1 (M+H); HRMS (ESI), m/z 294.1696 [M+H]$^+$, $\Delta_{calc}$=−3.2 ppm, C$_{16}$H$_{24}$NO$_4$; $^1$H NMR in DMSO-d$_6$ (see FIG. 56).

Example 24

Synthesis of the Compound of Formulae II-44 and VI-1A from II-16

The compound of Formula II-16 (30 mg, 0.096 mmol) was dissolved in CH$_2$Cl$_2$ (9 ml) in a scintillation vial (20 ml) to which triethylamine (40 μl, 0.29 mmol), methyl-3-mercapto propionate (thiol, 250 μl) and a magnetic stir bar were added. The reaction mixture was stirred at room temperature for about 4 hours. The solvent was evaporated from the reaction mixture to yield a mixture of compounds of Formulae II-44 and VI-1A (19:1), which were separated by reversed phase HPLC using Ace 5u C18 column (150 mm×22 mm ID) with a solvent gradient of 35% to 90% H$_2$O/Acetonitrile over 17 min, 90 to 100% Acetonitrile over 1 min, holding at 100% Acetonitrile for 1 min, at a flow rate of 14.5 ml/min. Diode array detector was used to monitor the purification process. Compounds II-44 (20 mg) and VI-1A (1 mg) eluted at 11.68 and 10.88 min, respectively, as pure compounds. Compound II-44: UV (Acetonitrile/H$_2$O) $\lambda_{max}$ 240 (sh) nm; ESMS m/z 434.0 (M+H)$^+$ & 456.0 (M+Na)$^+$. Compound VI-1A: UV (Acetonitrile/H$_2$O) $\lambda_{max}$ 220 (sh) nm; ESMS, m/z 398.0 (M+H)$^+$ & 420.0 (M+Na)$^+$.

Dess-Martin periodinane can be used as a reagent for this reaction. (Ref: Fenteany G. et al. Science, 1995, 268, 726-73). The resulting keto compound is treated with hydroxylamine or methoxy amine to generate oximes.

Examples:

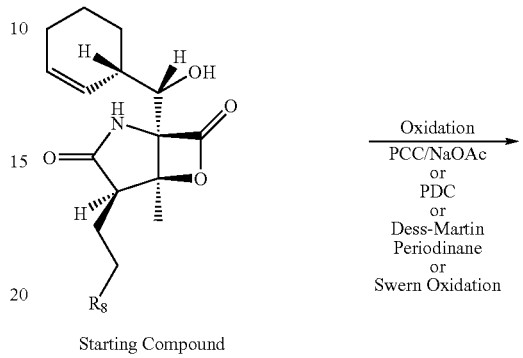

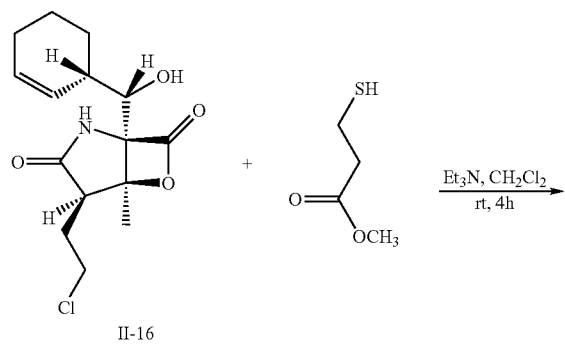

II-16

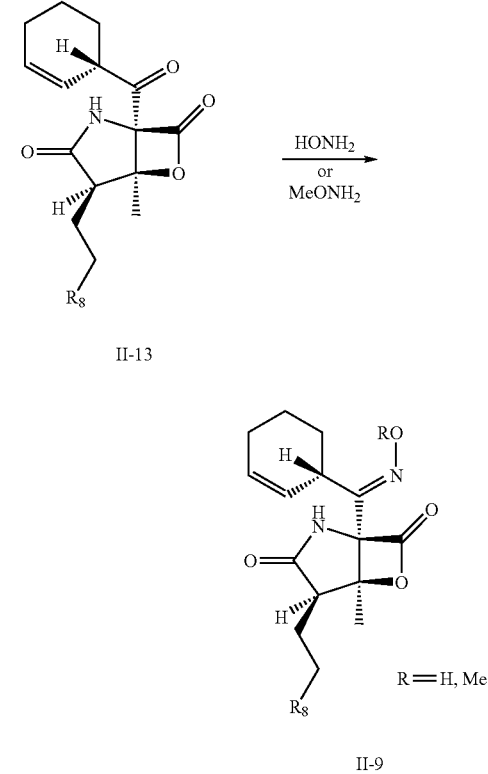

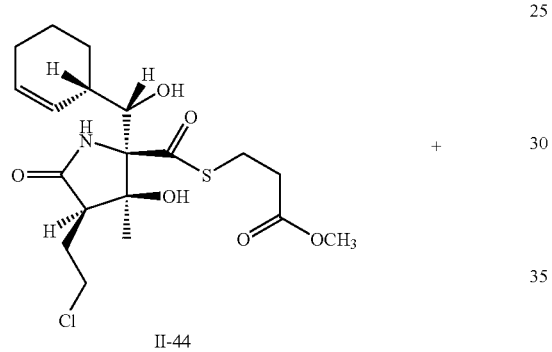

II-44

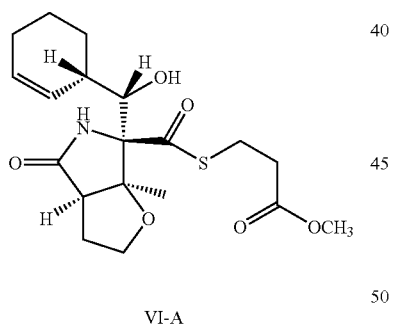

VI-A

Example 25

Oxidation of Secondary Hydroxyl group In Compounds of Formulae II-16, II-17 and II-18 and Reaction with Hydroxy or Methoxy Amines Any of the compounds of Formulae II-16, II-17 and II-18 can be used as the starting compound. The secondary hydroxyl group in the starting compound is oxidized using either of the following reagents: pyridinium dichromate (PDC), pyridinium chlorochromate (PCC), Dess-Martin periodinane or oxalyl chloride (Swern oxidation) (Ref: Organic Syntheses, collective volumes I-VIII). Preferably,

Example 26

Reductive Amination of Keto-Derivative

The keto derivatives, for example Formula II-8 and II-13, are treated with sodium cyanoborohydride (NaBH$_3$CN) in the presence of various bases to yield amine derivatives of the starting compounds which are subsequently hydrogenated with 10% Pd/C, H$_2$ to reduce the double bond in the cyclohexene ring.

Example:

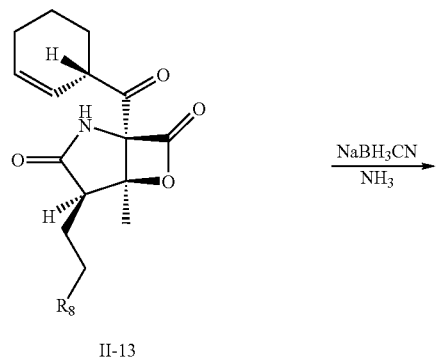

II-13

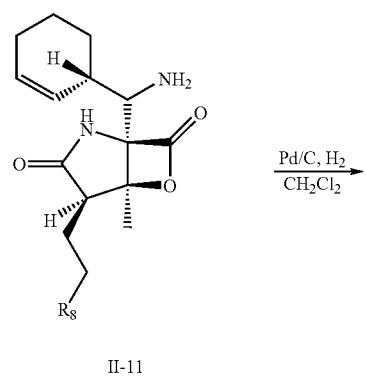

II-11

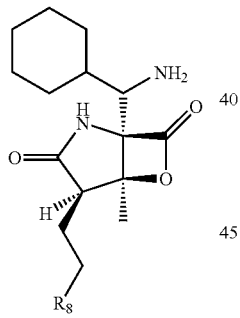

II-12

Example 27

Cyclohexene Ring Opening

Any compound of Formulae II-16, II-17 and II-18 can be used as a starting compound. The Starting Compounds can be protected, for example, at the alcohol and/or at the lactam nitrogen positions, and treated with $OsO_4$ and $NaIO_4$ in THF-$H_2O$ solution to yield dial derivatives which are reduced to the alcohol with $NaBH_4$. The protecting groups can be removed at the appropriate stage of the reaction sequence to produce II-7 or II-6.

Example:

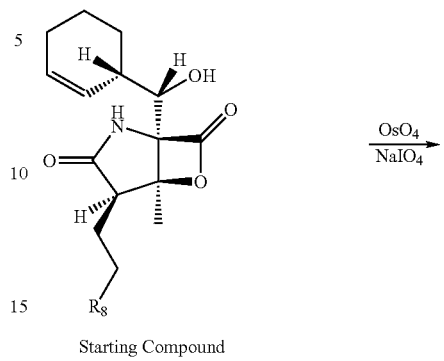

Starting Compound

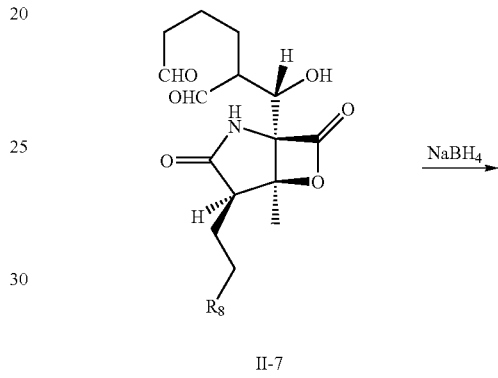

II-7

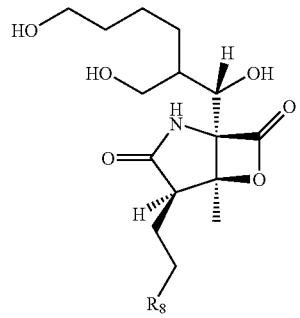

II-6

Example 28

Dehydration of Alcohol Followed by Aldehyde Formation at Lactone-Lactam Ring Junction A starting compound of any of Formulae II-16, II-17 or II-18 is dehydrated, for example, by treatment with mesyl-chloride in the presence of base, or, for example, by treatment with Burgess reagent or other dehydrating agents. The resulting dehydrated compound is treated with $OsO_4$, followed by $NaIO_4$, or alternatively by ozonolysis, to yield an aldehyde group at the lactone-lactam ring junction.

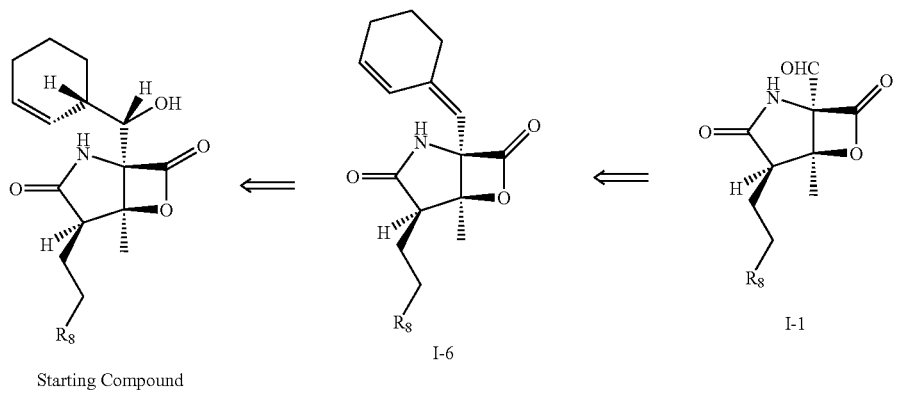

Starting Compound

Example 29

Oxidation of the Cyclohexene Ring to Produce Cyclohexadienes or a Phenyl Ring A Starting Compound, such as the ketone of Formula II-13C, is treated with Pd/C to produce a cyclohexadiene derivative. The new double bond can be at any position of the cyclohexene ring. The ketone can be reduced, for example, with sodium borohydride, to obtain the corresponding secondary alcohol(s). Alternatively, the cyclohexadiene derivative can be further treated, for example with DDQ, to aromatize the ring to a phenyl group. Similarly, the ketone can be reduced, for example, with sodium borohydride, to obtain the corresponding secondary alcohol(s).

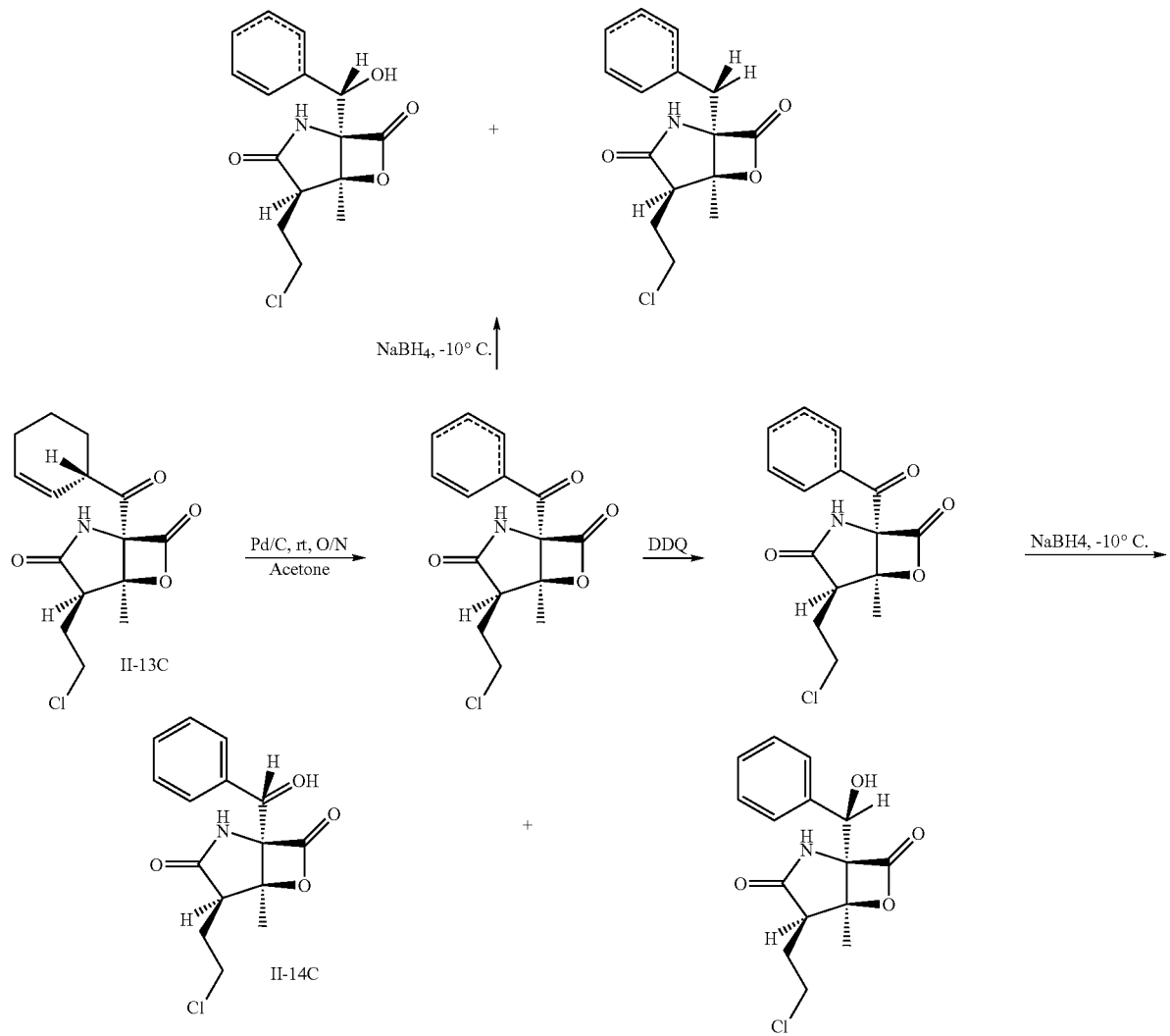

As an alternate method, the starting compound, such as the compound of Formula II-49, can be treated, for example with TMSCl to produce cyclohexadiene derivative. The cyclohexadiene derivative can be further treated, for example with DDQ, to aromatize the ring to a phenyl group. The OTMS on the phenyl group can be removed, for example, with acid or base. Similarly, the ketone can be reduced, for example, with sodium borohydride, to obtain the corresponding secondary alcohol(s).

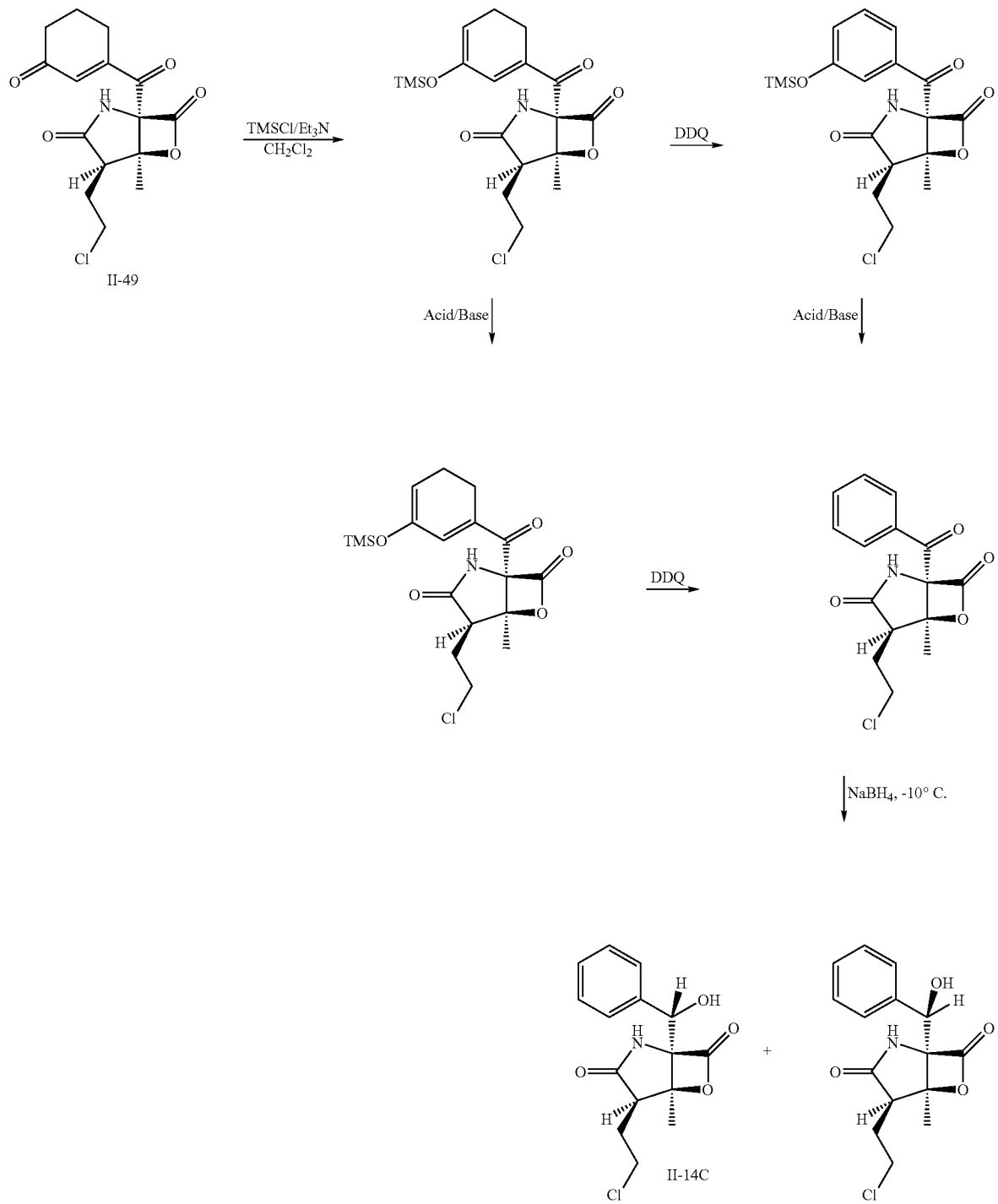

Example 30

Various reactions on aldehyde derivatives I-1

Wittig reactions are performed on the aldehyde group using various phosphorus ylides [e.g., (triphenylphosphoranylidene)ethane] to yield an olefin. The double bond in the side chain is reduced by catalytic hydrogenation.

Example:

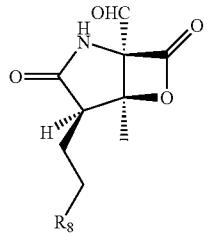

I-1

Wittig Reaction
CH₃CHPPh₃

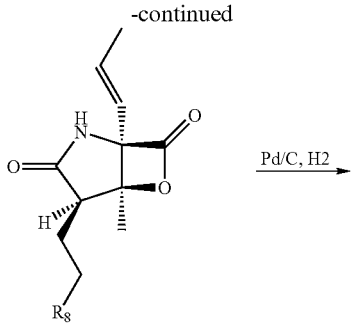

I-3

Pd/C, H2

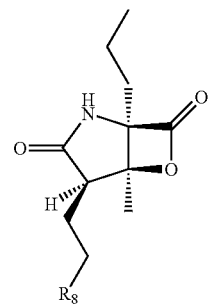

I-4

Reductive amination is performed on the aldehyde group using various bases (eg. NH₃) and sodium cyanoborohydride to yield amine derivatives. Alternatively, the aldehyde is reduced with NaBH₄ to form alcohols in the side chain.

Example:

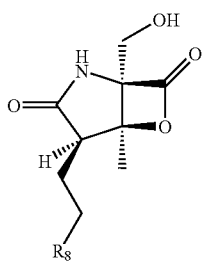

I-2

Reduction
NaBH₄

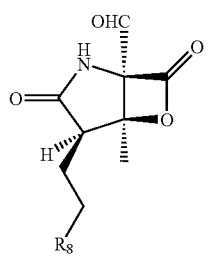

I-1

Reductive Amination
NaBH₃ON/NH₃

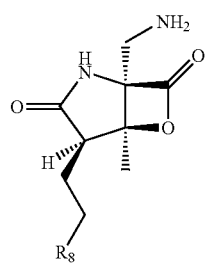

I-5

Organometallic addition reactions to the aldehyde carbonyl can be performed to yield various substituted secondary alcohols.

Examples:

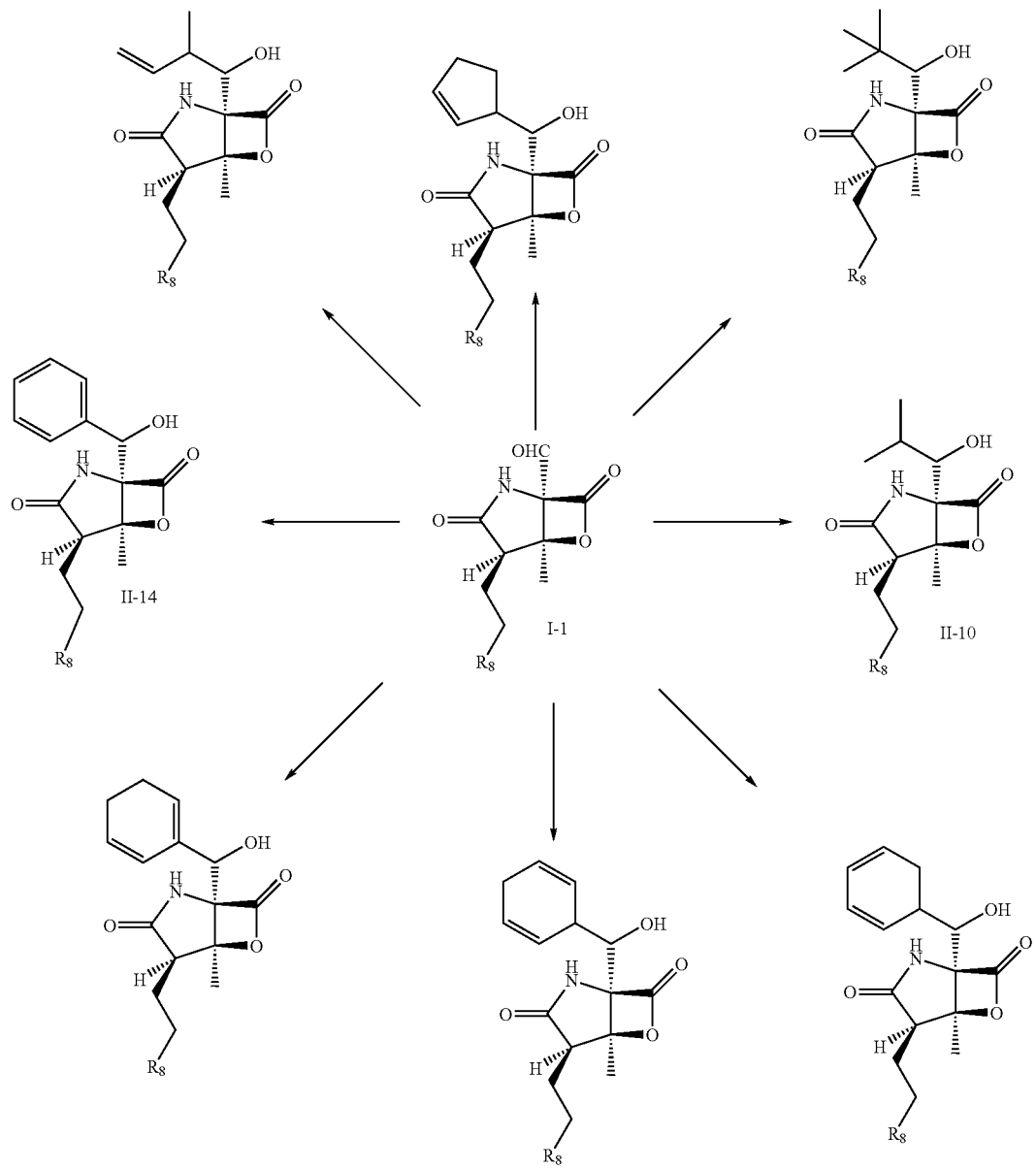

Example 31

Synthesis of the Compound of Formula II-47 from II-17

The compound of Formula II-17 (25 mg, 0.0896 mmol) was dissolved in $CH_2Cl_2$ (9 ml) in a scintillation vial (20 ml) to which triethylamine (38 μl, 0.27 mmol), methyl-3-mercapto propionate (thiol, 250 μl) and a magnetic stir bar were added. The reaction mixture was stirred at room temperature for about 4 hours. The solvent was evaporated from the reaction mixture to yield the compound of Formulae II-47, which was further purified by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process. Compound II-47 (15 mg) eluted at 10.98 min as pure compound. Compound II-47: UV (Acetonitrile/$H_2O$) $\lambda_{max}$ 240 (sh) nm; ESMS m/z 400.1 $(M+H)^+$ & 422.1 $(M+Na)^+$.

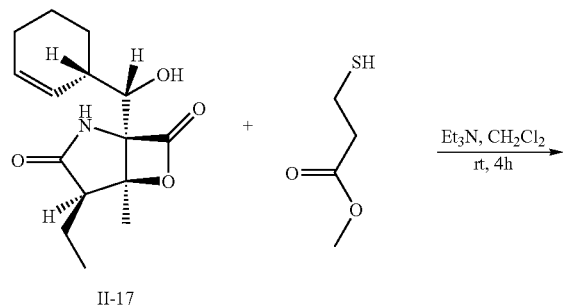
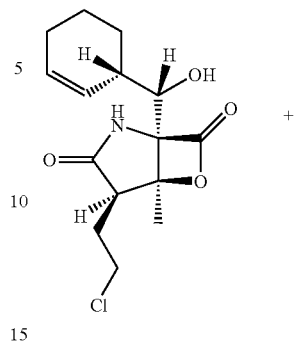
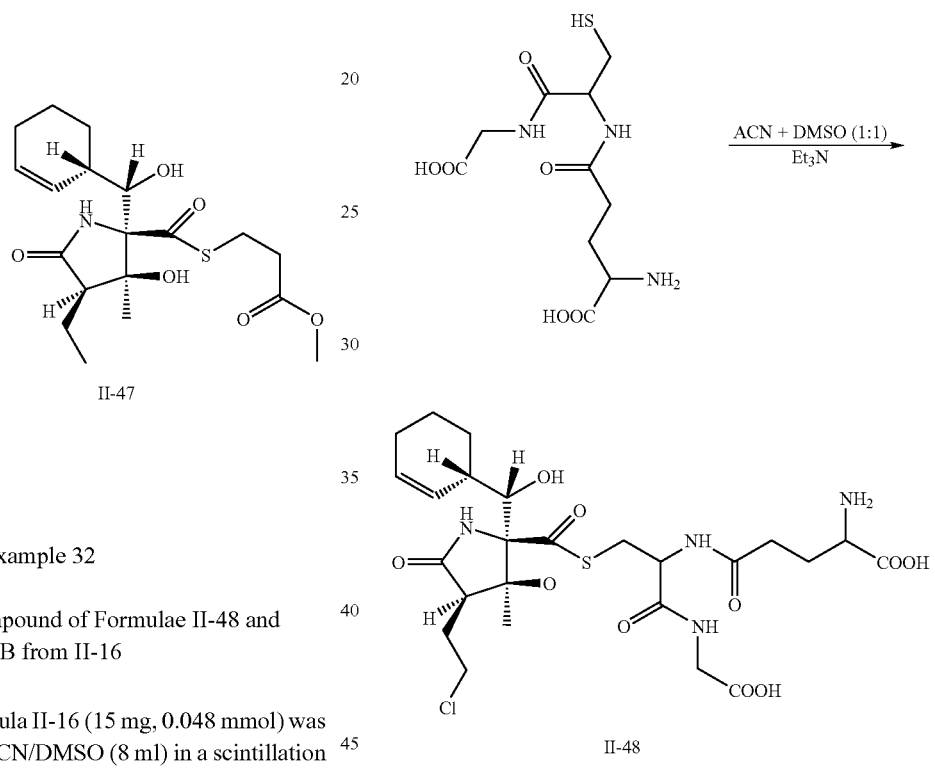

Example 32

Synthesis of the Compound of Formulae II-48 and VI-1B from II-16

The compound of Formula II-16 (15 mg, 0.048 mmol) was dissolved in 1:1 ratio of ACN/DMSO (8 ml) in a scintillation vial (20 ml) to which triethylamine (40 μl, 0.29 mmol), Glutathione (44.2 mg, 0.144 mmol) and a magnetic stir bar were added. The reaction mixture was stirred at room temperature for about 3 hours. The solvent was evaporated from the reaction mixture to yield the compound of Formula II-48, which was purified by reversed phase HPLC using Ace 5u C18 column (150 mm×22 mm ID) with a solvent gradient of 10% to 70% H$_2$O/Acetonitrile over 15 min, 70 to 100% Acetonitrile over 5 min, holding at 100% Acetonitrile for 4 min, at a flow rate of 14.5 ml/min. Diode array detector was used to monitor the purification process. Compound II-48 (10 mg) eluted as a pure compound at 8.255 min. Compound II-48: UV (Acetonitrile/H$_2$O) λ$_{max}$ 235 (sh) nm; ESMS m/z 621.0 (M+H)$^+$. Compound II-48 was unstable in solution and converted to compound VI-1B which appeared as a mixture of II-48 and VI-1B in the ratio of 7:3. Compound VI-1B: UV (Acetonitrile/H$_2$O) λ$_{max}$ 235 (sh) nm; ESMS, m/z 585.2 (M+H)$^+$.

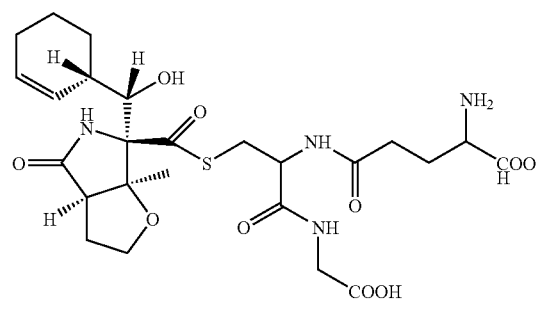

Example 33

Synthesis of the Compound of Formula II-50 and VI-1C from II-16

The compound of Formula II-16 (10 mg, 0.032 mmol) was dissolved in $CH_2Cl_2$ (9 ml) in scintillation vial (20 ml) to which triethylamine (26.5 μl, 0.192 mmol), N-Acetyl-L-Cysteine methyl ester (17 mg, 0.096 mmol) and a magnetic stir bar were added. The reaction mixture was stirred at room temperature for about 4 hours. The solvent was evaporated from the reaction mixture to yield the mixture of compounds of Formulae II-50 and VI-1C, which were further purified by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process. Compounds II-50 (2 mg) and VI-1C (0.2 mg) were eluted at 10.39 and 10.57 min, respectively as pure compounds. Compound II-50: UV (Acetonitrile/$H_2O$) $\lambda_{max}$ 230 (sh) nm; ESMS m/z 491.1 $(M+H)^+$ & 513.0 $(M+Na)^+$. Compound VI-1C: UV (Acetonitrile/$H_2O$) $\lambda_{max}$ 215 (sh) nm; ESMS m/z 455.1 $(M+H)^+$ & 577.0 $(M+Na)^+$

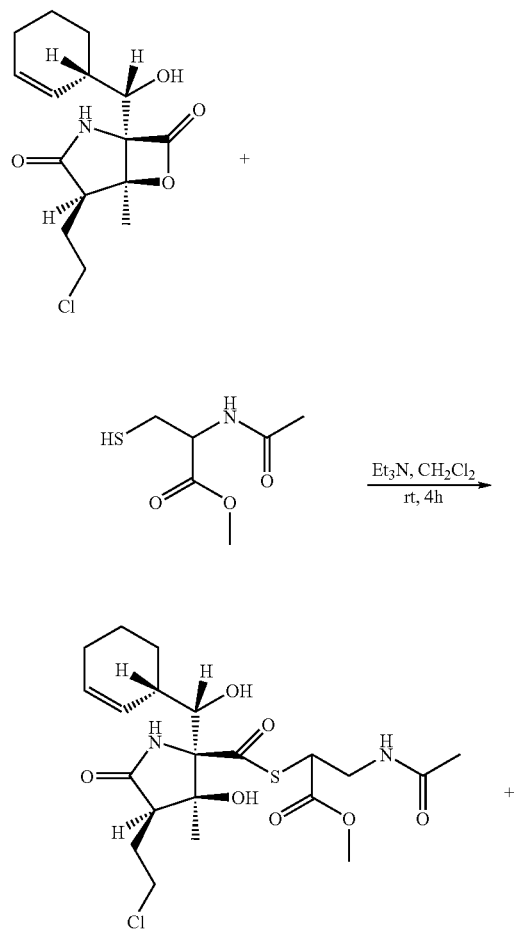

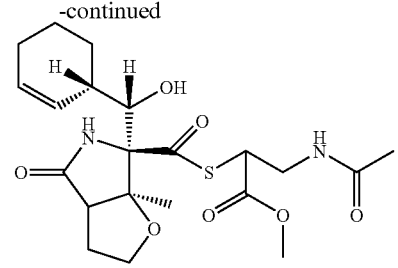

VI-1C

Example 34

In Vitro Biology

Initial studies of a compound of Formula II-16, which is also referred to as Salinosporamide A, employed the National Cancer Institute (NCI) screening panel, which consists of 60 human tumor cell lines that represent leukemia, melanoma and cancers of the lung, colon, brain, ovary, breast, prostate and kidney. A detailed description of the screening procedure can be found at hypertext transfer protocol (http://) "dtp.nci.nih.gov/branches/btb/ivclsp.html."

In brief, each of the 60 human tumor cell lines were grown in RPMI 1640 medium, supplemented with 5% fetal bovine serum and 2 mM L-glutamine. Cells were plated at their appropriate density in 96-well microtiter plates and incubated at 37° C., 5% $CO_2$, 95% air and 100% relative humidity. After 24 hours, 100 μL of various 10-fold serial dilutions of Salinosporamide A were added to the appropriate wells containing 100 μL of cells, resulting in a final Salinosporamide A concentration ranging from 10 nM to 100 μM. Cells were incubated for an additional 48 hours and a sulforhodamine B protein assay was used to estimate cell viability or growth.

Three dose response parameters were calculated as follows:

$GI_{50}$ indicates the concentration that inhibits growth by 50%.

TGI indicates the concentration that completely inhibits growth.

$LC_{50}$ indicates the concentration that is lethal to 50% of the cells.

An example of a study evaluating Salinosporamide A in the NCI screen is shown in Table 1 below.

Data indicate that the mean $GI_{50}$ value of Salinosporamide A was less than 10 nM. The wide range (>1000-fold difference) observed in both the mean TGI and mean $LC_{50}$ values for the most sensitive and the most resistant tumor cell lines illustrates that Salinosporamide A displays good selectivity and does not appear to be a general toxin. Furthermore, the mean TGI data suggest that Salinosporamide A shows preferred specificity towards melanoma and breast cancer cell lines. The assay was repeated and showed similar results.

The results of the NCI tumor screen show that Salinosporamide A: (1) is a potent compound with a mean $GI_{50}$ value of <10 nM, and (2) displays good tumor selectivity of more than 1000-fold difference in both the mean TGI and mean $LC_{50}$ values between the most sensitive and resistant tumor cell lines.

TABLE 1

Relative Sensitivity of the NCI 60 Human Tumor Cell Lines to Salinosporamide A

| National Cancer Institute Development Therapeutics Program Mean Graphs | | | NSC: D- 721267/1 | Units: Molar | SSPL: 075T | Exp. ID: 0108RS09-1 |
|---|---|---|---|---|---|---|
| | | | Report Date: Sept. 17, 2001 | | Test Date: Aug. 6, 2001 | |
| Pinel/Cell Line | $\log_{10}$ G150 | G150 | $\log_{10}$ TGI | TGI | $\log_{10}$ LC50 | LC50 |
| Leukemia | | | | | | |
| CCRF-CEM | <-8.00 | | <-8.00 | | >-4.00 | |
| HL-60(TB) | <-8.00 | | -4.32 | | >-4.00 | |
| K-562 | <-8.00 | | -5.59 | | >-4.00 | |
| MOLT-4 | <-8.00 | | <-8.00 | | >-4.00 | |
| RPMI-8226 | <-8.00 | | <-8.00 | | >-4.00 | |
| SR | <-8.00 | | <-8.00 | | -4.19 | |
| Non-Small Cell Lung Cancer | | | | | | |
| A549/ATCC | <-8.00 | | -4.70 | | >-4.00 | |
| EKVX | <-8.00 | | -5.67 | | >-4.00 | |
| HDP-62 | <-8.00 | | -4.89 | | >-4.00 | |
| HDP-92 | <-8.00 | | -7.77 | | -5.36 | |
| NCI-H236 | <-8.00 | | <-8.00 | | <-8.00 | |
| HCI-H23 | <-8.00 | | -7.85 | | -6.31 | |
| NCI-H322M | <-8.00 | | -5.48 | | -4.37 | |
| NCI-H460 | <-8.00 | | -6.97 | | >-4.00 | |
| NCI-H522 | <-8.00 | | <-8.00 | | -7.37 | |
| Colon Cancer | | | | | | |
| COLO 205 | <-8.00 | | -6.19 | | -4.06 | |
| HCC-2998 | <-8.00 | | <-8.00 | | -7.75 | |
| HCT-116 | <-8.00 | | -7.14 | | -4.99 | |
| HCT-15 | <-8.00 | | -6.06 | | -4.25 | |
| HT29 | <-8.00 | | -7.37 | | -4.42 | |
| KM12 | <-8.00 | | -6.00 | | -4.23 | |
| SW-620 | <-8.00 | | >-4.00 | | >-4.00 | |
| CNS Cancer | | | | | | |
| SF-268 | <-8.00 | | -6.92 | | >-4.00 | |
| SF-295 | <-8.00 | | <-8.00 | | -6.63 | |
| SF-539 | <-8.00 | | <-8.00 | | <-8.00 | |
| SNB-19 | <-8.00 | | >-4.00 | | >-4.00 | |
| SNB-75 | <-8.00 | | <-8.00 | | -7.50 | |
| U251 | <-8.00 | | -5.99 | | >-4.00 | |
| Melanoma | | | | | | |
| LOX IMVI | <-8.00 | | -7.87 | | >-4.00 | |
| MALME-3M | <-8.00 | | <-8.00 | | -4.19 | |
| M14 | <-8.00 | | -7.94 | | -6.73 | |
| SK-MEL-2 | <-8.00 | | <-8.00 | | -6.79 | |
| SK-MEL-21 | <-8.00 | | <-8.00 | | <-8.00 | |
| UACC-257 | <-8.00 | | <-8.00 | | -6.37 | |
| UACC-62 | <-8.00 | | <-8.00 | | -7.04 | |
| Ovarian Cancer | | | | | | |
| tGROV1 | <-8.00 | | -5.18 | | >-4.00 | |
| OVCAR-3 | <-8.00 | | -4.83 | | >-4.00 | |
| OVCAR-4 | <-8.00 | | <-8.00 | | -5.52 | |
| OVCAR-5 | <-8.00 | | -7.28 | | >-4.00 | |
| OVCAR-8 | <-8.00 | | -7.70 | | -6.55 | |
| SK-OV-3 | <-8.00 | | <-8.00 | | >-4.00 | |
| Renal Cancer | | | | | | |
| T86-0 | <-8.00 | | -5.37 | | >-4.00 | |
| A498 | <-8.00 | | <-8.00 | | -7.94 | |
| ACHN | <-8.00 | | -5.27 | | >-4.00 | |
| CAK1-1 | <-8.00 | | >-4.00 | | >-4.00 | |
| RXF393 | <-8.00 | | <-8.00 | | -7.64 | |
| SN12C | <-8.00 | | <-8.00 | | -6.20 | |
| TK-10 | <-8.00 | | -7.13 | | >-4.00 | |
| UO-11 | <-8.00 | | -5.83 | | -4.59 | |
| Prostate Cancer | | | | | | |
| PC-3 | <-8.00 | | -5.81 | | -4.93 | |
| DU-145 | <-8.00 | | >-4.00 | | >-4.00 | |
| Breast Cancer | | | | | | |
| MCF7 | <-8.00 | | >-4.00 | | >-4.00 | |
| NCVADR-RES | <-8.00 | | <-8.00 | | -6.75 | |
| MDA-MB-231/ATCC | <-8.00 | | <-8.00 | | -6.86 | |
| MDA-MB-435 | <-8.00 | | <-8.00 | | <-8.00 | |
| MDA-N | <-8.00 | | <-8.00 | | >-4.00 | |
| BT-459 | <-8.00 | | <-8.00 | | -7.22 | |
| T-47D | <-8.00 | | >-4.00 | | >-4.00 | |
| MG_MID | -8.00 | | -6.79 | | -3.20 | |
| Deka | 0.00 | | 1.21 | | 2.80 | |
| Range | 0.00 | | 4.00 | | 4.00 | |

Example 35

Growth Inhibition of Tumor Cell Lines

B16-F10 (ATCC; CRL-6475), DU 145 (ATCC; HTB-81), HEK293 (ATCC; CRL-1573), HT-29 (ATCC; HTB-38), LoVo (ATCC; CCL-229), MDA-MB-231 (ATCC; HTB-26), MIA PaCa-2 (ATCC; CRL-1420), NCI-H292 (ATCC; CRL-1848), OVCAR-3 (ATCC, HTB-161), PANC-1 (ATCC; CRL-1469), PC-3 (ATCC; CRL-1435), RPMI 8226 (ATCC; CCL-155) and U266 (ATCC; TIB-196) were maintained in appropriate culture media. The cells were cultured in an incubator at 37° C. in 5% CO2 and 95% humidified air.

For cell growth inhibition assays, B16-F10, DU 145, HEK293, HT-29, LoVo, MDA-MB-231, MIA PaCa-2, NCI-H292, OVCAR-3, PANC-1, PC-3, RPMI 8226 and U266 cells were seeded at $1.25 \times 10^3$, $5 \times 10^3$, $1.5 \times 10^4$, $5 \times 10^3$, $5 \times 10^3$, $1 \times 10^4$, $2 \times 10^3$, $4 \times 10^3$, $1 \times 10^4$, $7.5 \times 10^3$, $5 \times 10^3$, $2 \times 10^4$, $2.5 \times 10^4$ cells/well respectively in 90 µl complete media into Corning 3904 black-walled, clear-bottom tissue culture plates. 20 mM stock solutions of Formula II-16 were prepared in 100% DMSO, aliquoted and stored at −80° C. Formula II-16 was serially diluted and added in triplicate to the test wells resulting in final concentrations ranging from of 20 µM to 0.2 µM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and $EC_{50}$ values (the drug concentration at which 50% of the maximal observed growth inhibition is established) were determined using a standard sigmoidal dose response curve fitting algorithm (generated by XLfit 3.0, ID Business Solutions Ltd or Prism 3.0, GraphPad Software Inc).

The data in Table 2 summarize the growth inhibitory effects of Formula II-16 against diverse tumor cell lines, including 12 human and 1 murine.

TABLE 2

Mean $EC_{50}$ values of Formula II-16 against various tumor cell lines

| Cell line | Source | $EC_{50}$ (nM), mean ± SD* | n |
|---|---|---|---|
| B16-F10 | Mouse, melanoma | 47 ± 20 | 12 |
| DU 145 | Human, prostate carcinoma | 37 ± 10 | 3 |
| HEK293 | Human, embryonic kidney | 47 | 2 |
| HT-29 | Human, colorectal adenocarcinoma | 40 ± 26 | 5 |
| LoVo | Human, colorectal adenocarcinoma | 70 ± 8 | 3 |
| MDA-MB-231 | Human, breast adenocarcinoma | 87 ± 40 | 12 |
| MIA PaCa-2 | Human, pancreatic carcinoma | 46 | 2 |
| NCI-H292 | Human, non small cell lung carcinoma | 66 ± 29 | 12 |
| OVCAR-3 | Human, ovarian adenocarcinoma | 49 ± 31 | 6 |
| PANC-1 | Human, pancreatic carcinoma | 60 | 2 |
| PC-3 | Human, prostate adenocarcinoma | 64 ± 26 | 19 |
| RPMI 8226 | Human, multiple myeloma | 8.6 ± 1.9 | 26 |
| U266 | Human, multiple myeloma | 4.7 ± 0.7 | 6 |

*Where n (number of independent experiments) = 2, the mean value is presented

The $EC_{50}$ values indicate that Formula II-16 was cytotoxic against B16-F10, DU 145, HEK293, HT-29, LoVo, MDA-MB-231, MIA PaCa-2, NCI-H292, OVCAR-3, PANC-1, PC-3, RPMI 8226 and U266 cells.

Example 36

In Vitro Inhibition of Proteasome Activity by Formulae I-7, II-2, II-3, II-4, II-5A, II-5B, II-8C, II-13C, II-16, II-17, II-18, II-19, II-20, II-21, II-22, II-24C, II-25, II-26, II-27, II-28, II-29, II-30, II-31, II-32, II-38, IV-3C, II-44, VI-1A and II-47

All the compounds were prepared as 20 mM stock solution in DMSO and stored in small aliquots at −80° C. Purified rabbit muscle 20S proteasome was obtained from CalBiochem or Boston Biochem. To enhance the chymotrypsin-like activity of the proteasome, the assay buffer (20 mM HEPES, pH7.3, 0.5 mM EDTA, and 0.05% Triton X100) was supplemented with SDS resulting in a final SDS concentration of 0.035%. The substrate used was suc-LLVY-AMC, a fluorogenic peptide substrate specifically cleaved by the chymotrypsin-like activity of the proteasome. Assays were performed at a proteasome concentration of 1 µg/ml in a final volume of 200 µl in 96-well Costar microtiter plates. Formulae II-2, II-4, II-16, II-17, II-18, II-19, II-21, II-22 and II-44 were tested as eight-point dose response curves with final concentrations ranging from 500 nM to 158 pM. Formulae I-7, II-5A, II-5B, II-20, II-29, II-30 and II-38 were tested at concentrations ranging from 1 µM to 0.32 nM. Formulae II-3 and VI-1A were tested as an eight-dose response curve with final concentrations ranging from 10 µM to 3.2 nM. Formula II-47 was tested at concentrations ranging from 5 µM to 1.6 nM, while Formulae II-8C, II-13C, II-24C, II-25, II-26, II-27, II-28, II-31, II-32 and IV-3C were tested with final concentrations ranging from 20 µM to 6.3 nM. The samples were incubated at 37° C. for five minutes in a temperature controlled Fluoroskan Ascent 96-well microplate reader (Thermo Electron, Waltham, Mass.). During the preincubation step, the substrate was diluted 25-fold in SDS-containing assay buffer. After the preincubation period, the reactions were initiated by the addition of 10 µl of the diluted substrate and the plates were returned to the plate reader. The final concentration of substrate in the reactions was 20 µM. Fluorescence of the cleaved peptide substrate was measured at $\lambda_{ex}$=390 nm and $\lambda_{em}$=460 nm. All data were collected every five minutes for more than 1.5 hour and plotted as the mean of triplicate data points. The $EC_{50}$ values (the drug concentration at which 50% of the maximal relative fluorescence is inhibited) were calculated by Prism (GraphPad Software) using a sigmoidal dose-response, variable slope model. To evaluate the activity of the compounds against the caspase-like activity of the 20S proteasomes, reactions were performed as described above except that Z-LLE-AMC was used as the peptide substrate. Formulae II-3, II-4, II-5A, II-5B, II-8C, II-13C, II-17, II-18, II-20, II-21, II-22, II-24C, II-25, II-26, II-27, II-28, II-29, II-30, IV-3C, II-44 and VI-1A were tested at concentrations ranging from 20 μM to 6.3 nM. Formula II-2 was tested at concentrations ranging from 10 μM to 3.2 nM, while Formula II-16 and Formula II-19 were tested at concentrations ranging from 5 μM to 1.58 nM. For the evaluation of the compounds against the trypsin-like activity of the proteasome, the SDS was omitted from the assay buffer and Boc-LRR-AMC was used as the peptide substrate. Formula II-20 was tested at concentrations ranging from 5 μM to 1.6 nM. Formulae II-3, II-8C, II-13C, II-17, II-21, II-22, II-24C, II-25, II-26, II-27, II-28, II-29, II-30, IV-3C and VI-1A were tested at concentrations ranging from 20 μM to 6.3 nM. For Formulae II-2 and II-5B the concentrations tested ranged from 10 μM to 3.2 nM, while Formulae II-4, II-5A, II-16, II-18 and II-19 were tested at concentrations ranging from 1 μM to 0.32 nM. II-44 was tested at concentrations ranging from 2 μM to 632 pM.

Results ($EC_{50}$ values) are shown in Table 3 and illustrate that among the tested compounds, Formulae II-5A, II-16, II-18, II-19, II-20, II-21, II-22, II-29, II-38 and II-44 are the most potent inhibitors of the chymotrypsin-like activity of the 20S proteasome with $EC_{50}$ values ranging from 2 nM to 11 nM. Formulae I-7, II-2, II-4, II-5B, II-17, II-30 and II-47 inhibit the proteasomal chymotrypsin-like activity with $EC_{50}$ values ranging from 13 nM to 88 nM, while the $EC_{50}$ values of Formulae II-3, II-26 and VI-1A ranged from 207 nM to 964 nM. Formulae II-13C, II-24C, II-27, II-28 and IV-3C inhibited the chymotrypsin-like activity with $EC_{50}$ values ranging from 1.4 μM to 10.6 μM. $EC_{50}$ values for Formulae II-8C, II-25, II-31 and II-32 were greater than 20 μM. Under the conditions tested, Formulae II-2, II-3, II-4, II-5A, II-5B, II-13C, II-16, II-17, II-18, II-19, II-20, II-21, II-22, II-24C, II-26, II-29, II-30, II-44 and VI-1A were able to inhibit the trypsin-like activity of the 20S proteasome. Formulae II-4, II-5A, II-16, II-18, II-19 and II-29 inhibited the caspase-like activity with $EC_{50}$ values ranging from 213 nM to 850 nM, while Formulae II-2, II-5B, II-17, II-20, II-21, II-22, II-30, II-44 and VI-1A had $EC_{50}$ values ranging from 956 nM to 8.7 μM.

TABLE 3

Effects of Formulae I-7, II-2, II-3, II-4, II-5A, II-5B, II-8C, II-13C, II-16, II-17, II-18, II-19, II-20, II-21, II-22, II-24C, II-25, II-26, II-27, II-28, II-29, II-30, II-31, II-32, II-38, IV-3C, II-44, VI-1A and II-47 on the various enzymatic activities of purified rabbit 20S proteasomes

| Analog | $EC_{50}$ Values* | | |
|---|---|---|---|
| | Chymotrypsin-like | Trypsin-like | Caspase-like |
| Formula I-7 | 52 ± 2 nM | ND | ND |
| Formula II-2 | 18 nM | 230 nM | 1.3 μM |
| | 19 nM | 230 nM | 1.7 μM |
| Formula II-3 | 964 nM | 5.5 μM | >20 μM |
| | 890 nM | 7.7 μM | >20 μM |
| Formula II-4 | 13 nM | 107 nM | 850 nM |
| | 15 nM | 110 nM | 637 nM |
| Formula II-5A | 6 nM | 87 nM | 535 nM |
| | 7 nM | 90 nM | 438 nM |
| Formula II-5B | 88 nM | 762 nM | 3.8 μM |
| | 85 nM | 716 nM | 2.9 μM |
| Formula II-8C | >20 μM | >20 μM | >20 μM |
| | >20 μM | >20 μM | >20 μM |
| Formula II-13C | 7.6 μM | 8.6 μM | >20 μM |
| | 8.8 μM | 12.8 μM | >20 μM |
| Formula II-16 | 2.6 ± 0.2 nM | 21 ± 2.6 nM | 427 ± 61 nM |
| Formula II-17 | 26 ± 6.7 nM | 573 nM | 1.2 μM |
| | | 602 nM | 1.2 μM |
| Formula II-18 | 2.3 nM | 14 nM | 286 nM |
| | 2 nM | 14 nM | 213 nM |
| Formula II-19 | 3 nM | 13 nM | 573 nM |
| | 3 nM | 15 nM | 739 nM |
| Formula II-20 | 7.7 ± 3.0 nM | 318 nM | 1.4 μM |
| | | 321 nM | 1.4 μM |
| Formula II-21 | 7 nM | 720 nM | 2.6 μM |
| | 8 nM | 879 nM | 2.3 μM |
| Formula II-22 | 7 nM | 308 nM | 1.3 μM |
| | 3 nM | 289 nM | 1.4 μM |
| Formula II-24C | 2.2 μM | 3.3 μM | >20 μM |
| | 2.0 μM | 3.1 μM | >20 μM |
| Formula II-25 | >20 μM | >20 μM | >20 μM |
| | >20 μM | >20 μM | >20 μM |
| Formula II-26 | 349 nM | 2.0 μM | >20 μM |
| | 319 nM | 3.0 μM | >20 μM |
| Formula II-27 | 1.4 μM | >20 μM | >20 μM |
| Formula II-28 | 3.2 μM | >20 μM | >20 μM |
| | 3.3 μM | >20 μM | >20 μM |
| Formula II-29 | 6 nM | 175 nM | 535 nM |
| | 8 nM | 254 nM | 520 nM |
| Formula II-30 | 21 nM | 905 nM | 956 nM |
| | 21 nM | 1.2 μM | 1.3 μM |
| Formula II-31 | >20 μM** | ND | ND |
| Formula II-32 | >20 μM** | ND | ND |
| Formula II-38 | 3.4 ± 0.2 nM | ND | ND |
| Formula IV-3C | 4.9 μM | >20 μM | >20 μM |
| | 10.6 μM | >20 μM | >20 μM |
| Formula II-44 | 11 nM | 55 nM | 1.4 μM |
| | 8.7 nM | 54 nM | 1.4 μM |
| Formula VI-1A | 274 nM | 3.1 μM | 7.9 μM |
| | 207 nM | 3.0 μM | 8.7 μM |
| Formula II-47 | 50 ± 10 nM | ND | ND |

Figure 46:
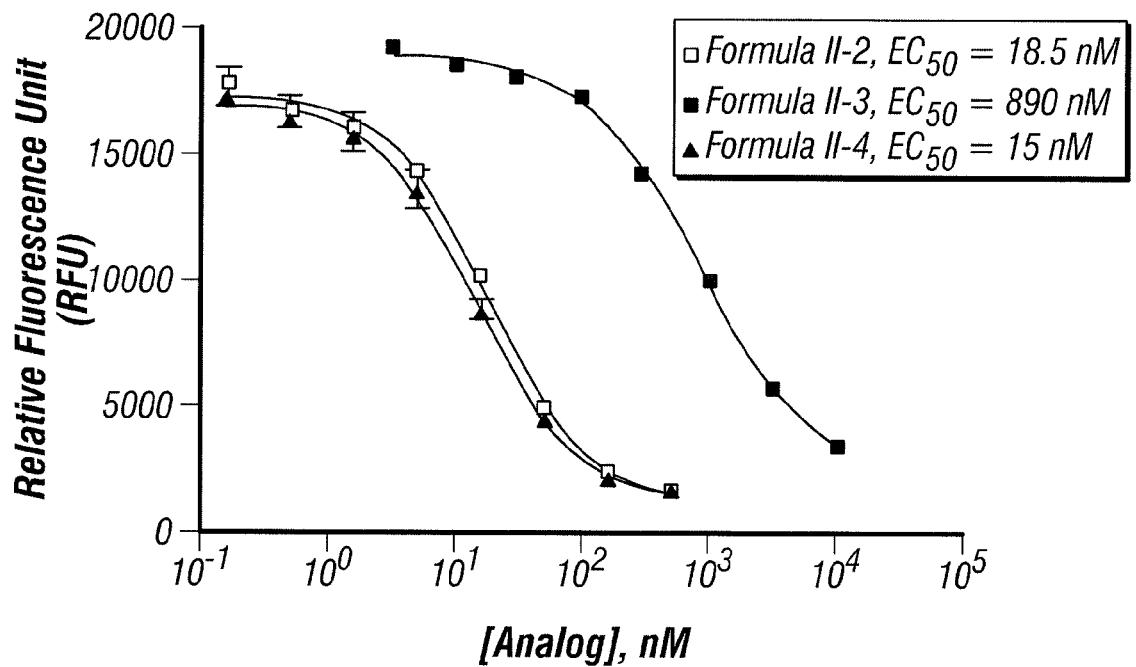
FIG. 46 depicts assay results showing the effect of Formula II-2, Formula II-3, and Formula II-4 on the chymotrypsin-like activity of rabbit 20S proteasome.

*$EC_{50}$ values of one or two independent experiments are shown. Where n ≥ 3, the mean $EC_{50}$ value ± standard deviation is presented,
**n = 3, standard deviation not applicable.
ND = not determined Results from a representative experiment evaluating Formula II-2, Formula II-3 and Formula II-4 are shown in FIG. 46 and illustrate that Formula II-2 and Formula II-4 inhibit the chymotrypsin-like activity of the proteasome with $EC_{50}$ values of 18.5 nM and 15 nM respectively. Formula II-3 is active in this assay with an $EC_{50}$ value of 890 nM. Similar results were obtained from an independent experiment.

Figure 47:
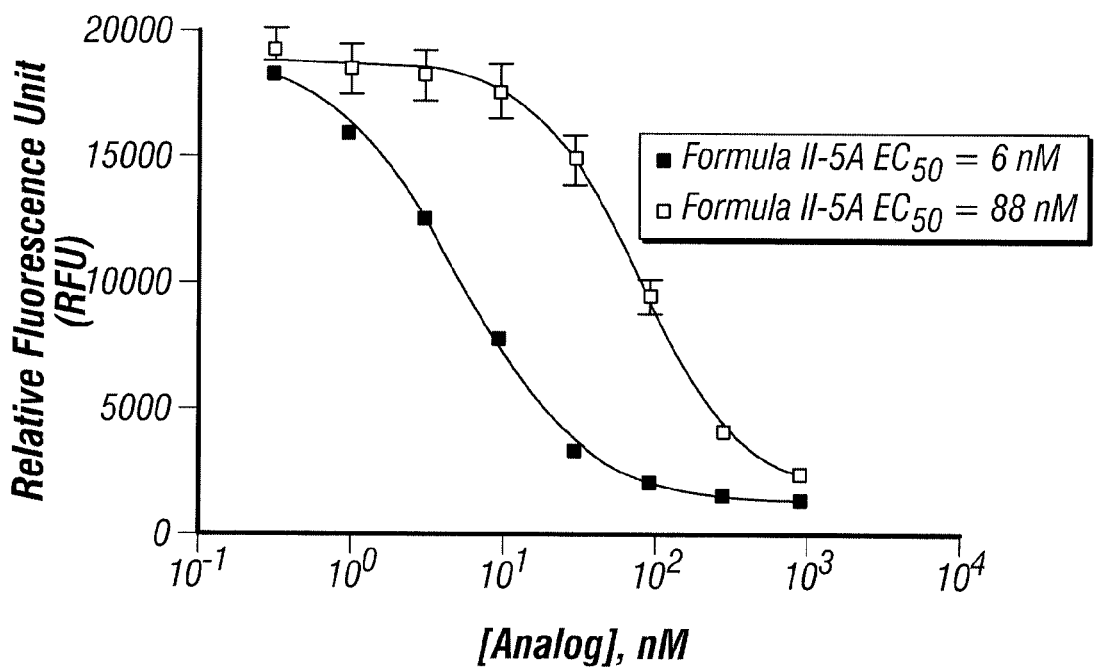
FIG. 47 depicts the effect of Formula II-5A and Formula II-5B on the chymotrypsin-like activity of rabbit 20S proteasome.
Figure 48:
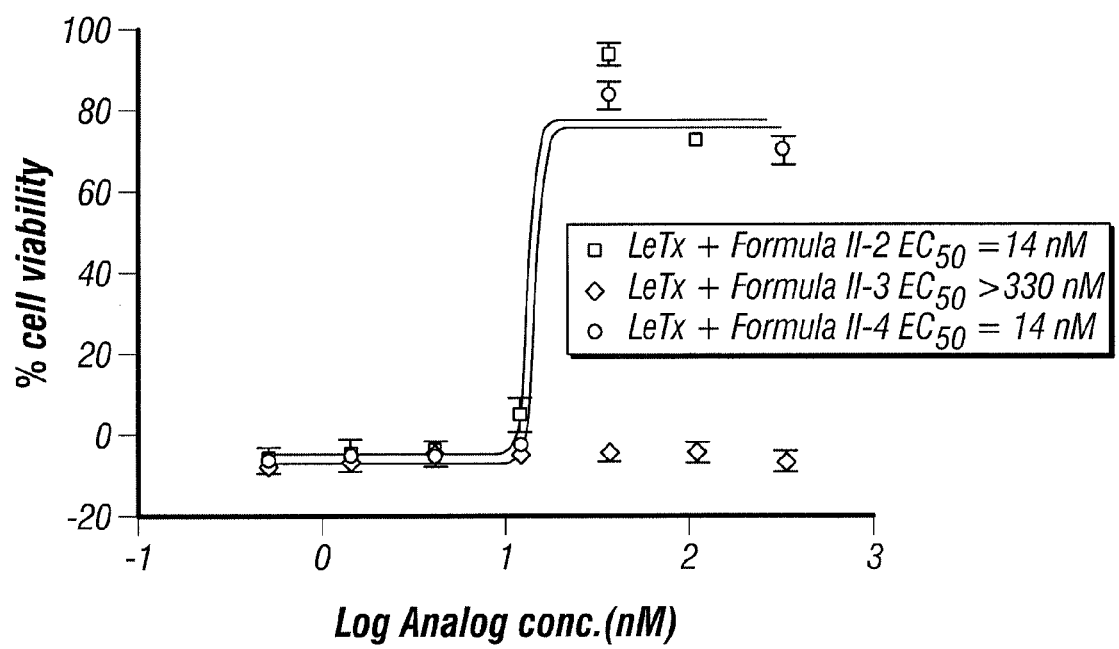
FIG. 48 depicts the effect of Formulae II-2, II-3, and II-4 against LeTx-mediated cytotoxicity.

Results from a representative experiment evaluating Formula II-5A and Formula II-5B are shown in FIG. 47 and illustrate that Formula II-5A and Formula II-5B inhibit the chymotrypsin-like activity of the proteasome with $EC_{50}$ values of 6 nM and 88 nM respectively. Similar results were obtained in an independent experiment.

Example 37

Salinosporamide A (II-16) Inhibits Chymotrypsin-Like Activity of Rabbit Muscle 20S Proteasomes The effect of Salinosporamide A (II-16) on proteasomes was examined using a commercially available kit from Calbiochem (catalog no. 539158), which uses a fluorogenic peptide substrate to measure the activity of rabbit muscle 20S proteasomes (Calbiochem 20S Proteasome Kit). This peptide substrate is specific for the chymotrypsin-like enzyme activity of the proteasome.

Omuralide was prepared as a 10 mM stock in DMSO and stored in 5 μL aliquots at −80° C. Salinosporamide A was prepared as a 25.5 mM solution in DMSO and stored in aliquots at −80° C. The assay measures the hydrolysis of Suc-LLVY-AMC into Suc-LLVY and AMC. The released coumarin (AMC) was measured fluorometrically by using $\lambda_{ex}$=390 nm and $\lambda_{em}$=460 nm. The assays were performed in a microtiter plate (Corning 3904), and followed kinetically with measurements every five minutes. The instrument used was a Thermo Lab Systems Fluoroskan, with the incubation chamber set to 37° C. The assays were performed according to the manufacturer's protocol, with the following changes. The proteasome was activated as described with SDS, and held on ice prior to the assay. Salinosporamide A and Omuralide were serially diluted in assay buffer to make an 8-point dose-response curve. Ten microliters of each dose were added in triplicate to the assay plate, and 190 μL of the activated proteasome was added and mixed. The samples were preincubated in the Fluoroskan for 5 minutes at 37° C. Substrate was added and the kinetics of AMC were followed for one hour. All data were collected and plotted as the mean of triplicate data points. The data were normalized to reactions performed in the absence of Salinosporamide A and modeled in Prism as a sigmoidal dose-response, variable slope.

Figure 27:
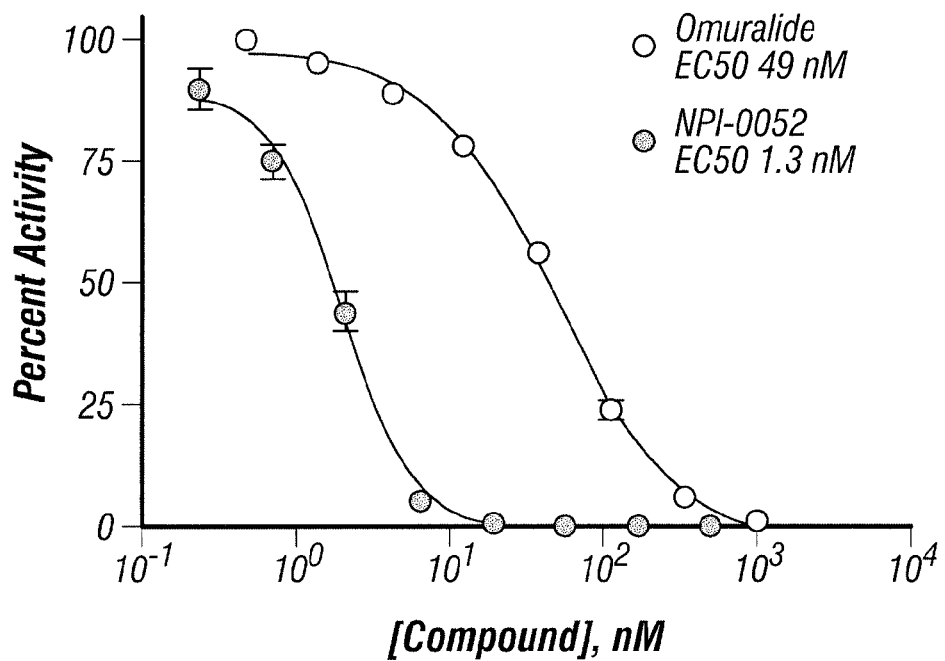
FIG. 27 shows inhibition of the chymotrypsin-like activity of rabbit muscle proteasomes.

Similar to the results obtained for the in vitro cytotoxicity (Table 2), Feling, et al., *Angew Chem Int Ed Engl* 42:355 (2003), the $EC_{50}$ values in the 20S proteasome assay showed that Salinosporamide A was approximately 40-fold more potent than Omuralide, with an average value of 1.3 nM versus 49 nM, respectively (FIG. 27). This experiment was repeated and the average $EC_{50}$ in the two assays was determined to be 2 nM for Salinosporamide A and 52 nM for Omuralide.

Salinosporamide A is a potent inhibitor of the chymotrypsin-like activity of the proteasome. The $EC_{50}$ values for cytotoxicity were in the 10-200 nM range suggesting that the ability of Salinosporamide A to induce cell death was due, at least in large part, to proteasome inhibition. The data suggest that Salinosporamide A is a potent small molecule inhibitor of the proteasome.

Example 38

Salinosporamide A (II-16) Inhibition of PGPH Activity of Rabbit Muscle 20S Proteasomes Omuralide can inhibit the PGPH activity (also known as the caspase-like) of the proteasome; therefore, the ability of Salinosporamide A to inhibit the PGPH activity of purified rabbit muscle 20S proteasomes was assessed. A commercially available fluorogenic substrate specific for the PGPH activity was used instead of the chymotrypsin substrate supplied in the proteasome assay kit described above.

Salinosporamide A (II-16) was prepared as a 20 mM solution in DMSO and stored in small aliquots at −80° C. The substrate Z-LLE-AMC was prepared as a 20 mM stock solution in DMSO, stored at −20° C. The source of the proteasomes was the commercially available kit from Calbiochem (Cat. # 539158). As with the chymotrypsin substrate, the proteasome can cleave Z-LLE-AMC into Z-LLE and free AMC. The activity can then be determined by measuring the fluorescence of the released AMC ($\lambda_{ex}$=390 nm and $\lambda_{em}$=460 nm). The proteasomes were activated with SDS and held on ice as per manufacturer's recommendation. Salinosporamide A was diluted in DMSO to generate a 400-fold concentrated 8-point dilution series. The series was diluted 20-fold with assay buffer and preincubated with the proteasomes as described for the chymotrypsin-like activity. After addition of substrate, the samples were incubated at 37° C., and release of the fluorescent AMC was monitored in a fluorimeter. All data were collected and plotted as the mean of triplicate points. In these experiments, the $EC_{50}$ was modeled in Prism as normalized activity, where the amount of AMC released in the absence of Salinosporamide A represents 100% activity. As before, the model chosen was a sigmoidal dose-response, with a variable slope.

Figure 28:
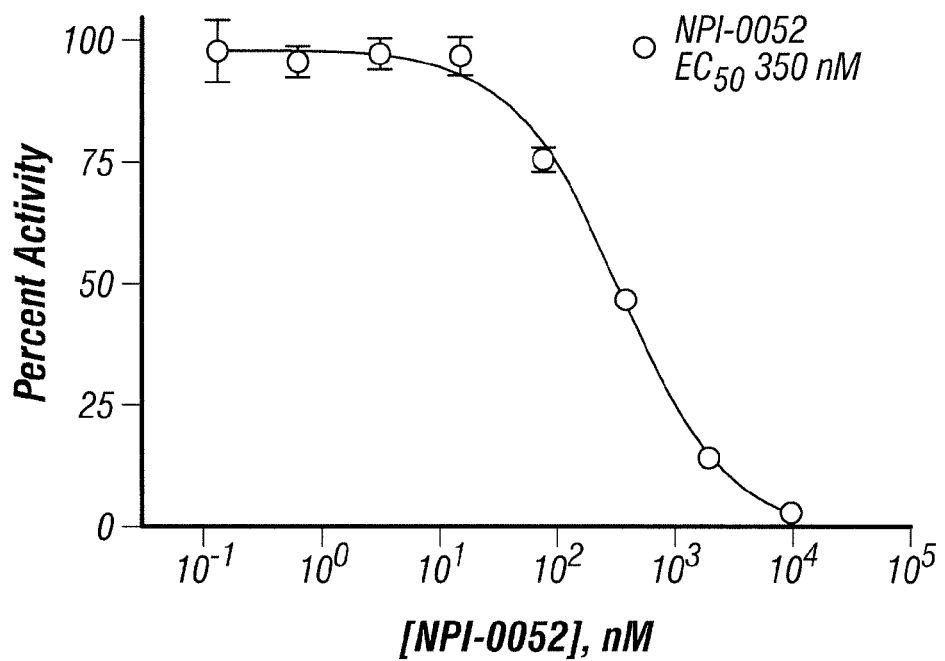
FIG. 28 shows inhibition of the PGPH and Caspase-like activity of rabbit muscle proteasomes.

Data revealed that Salinosporamide A inhibited the PGPH activity in rabbit muscle 20S proteasomes with an $EC_{50}$ of 350 nM (FIG. 28). A replicate experiment was performed, which gave a predicted $EC_{50}$ of 610 nM. These results indicate that Salinosporamide A does block the in vitro PGPH activity of purified rabbit muscle 20S proteasomes, albeit with lower potency than seen towards the chymotrypsin-like activity.

Example 39

Figure 29:
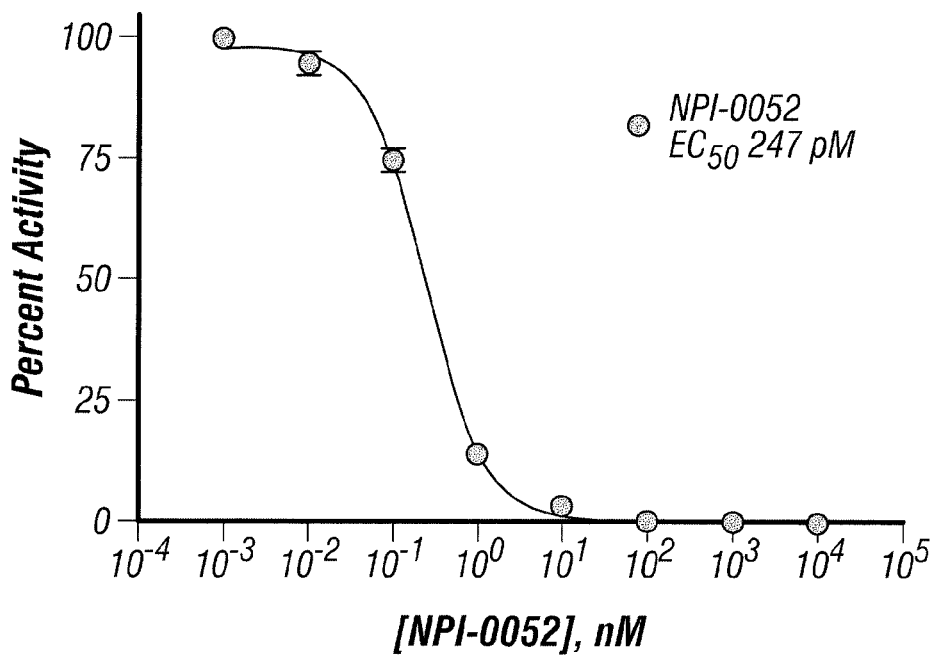
FIG. 29 shows inhibition of the chymotrypsin-like activity of human erythrocyte proteasomes.

Inhibition of the Chymotrypsin-Like Activity of Human Erythrocyte 20S Proteasomes The ability of Salinosporamide A (II-16) to inhibit the chymotrypsin-like activity of human erythrocyte 20S proteasomes was assessed in vitro. The calculated $EC_{50}$ value is approximately 3 nM (FIG. 29). These data indicate that the inhibitory effect of Salinosporamide A is not limited to rabbit skeletal muscle proteasomes.

Salinosporamide A was prepared as a 20 mM solution in DMSO and stored in small aliquots at −80° C. The substrate, suc-LLVY-AMC, was prepared as a 20 mM solution in DMSO and stored at −20° C. Human erythrocyte 20S proteasomes were obtained from BIOMOL (Cat. # SE-221). The proteasome can cleave suc-LLVY-AMC into suc-LLVY and free AMC and the activity can then be determined by measuring the fluorescence of the released AMC ($\lambda_{ex}$=390 nm and $\lambda_{em}$=460 nm). The proteasomes were activated by SDS and stored on ice as with the experiments using rabbit muscle proteasomes. Salinosporamide A was diluted in DMSO to generate a 400-fold concentrated 8-point dilution series. The series was then diluted 20-fold with assay buffer and preincubated with proteasomes at 37° C. The reaction was initiated with substrate, and the release of AMC was followed in a Fluoroskan microplate fluorimeter. Data were collected and plotted as the mean of triplicate points. Data were captured kinetically for 3 hours, and indicated that these reactions showed linear kinetics in this time regime. The data were normalized to reactions performed in the absence of Salinosporamide A and modeled in Prism as a sigmoidal dose-response, variable slope.

Replicate experiments performed using human erythrocyte proteasomes from separate lots resulted in a range of $EC_{50}$ values of approximately 4 nM. These results indicate that the in vitro chymotrypsin-like activity of human erythrocyte 20S proteasomes is sensitive to Salinosporamide A.

Formula II-16 also showed inhibition of the Trypsin-like and Caspase-like activity of human erythrocyte proteasomes. For Trypsin-like the studies showed an $EC_{50}$ value of about 9 nM, and for Caspase-like an $EC_{50}$ of about 390 nM. Additional studies of Chymotrypsin-like activity in human erythrocytes resulted in an $EC_{50}$ of about 250 pM. Furthermore, studies showed that Formula II-16 is specific for the proteasome, showing little or no effect on other proteolytic enzymes. For example, Formula II-16 when tested for inhibition of Chymotrypsin, Cathepsin B and Thrombin, respectively, had $EC_{50}$ values of 18,000 nM, >200,000 nm, and >200,000 nM, respectively.

Example 40

Salinosporamide A (II-16) Specificity

A possible mechanism by which Salinosporamide A inhibits the proteasome is by the reaction of the β-lactone functionality of Salinosporamide A with the active site threonine of the proteasome. This covalent modification of the proteasome would block the active site, as this residue is essential for the catalytic activity of the proteasome. Fenteany, et al., *J Biol Chem* 273:8545 (1998). A structurally related compound, Lactacystin, has been shown to also inhibit cathepsin A (Ostrowska, et al., *Int J Biochem Cell Biol* 32:747 (2000), Kozlowski, et al., *Tumour Biol* 22:211 (2001), Ostrowska, et al., *Biochem Biophys Res Commun* 234:729 (1997)) and TPPII (Geier, et al., *Science* 283:978 (1999)) but not trypsin, chymotrypsin, papain, calpain (Fenteany, et al., *Science* 268:726 (1995)), thrombin, or plasminogen activator (Omura, et al., *J Antibiot (Tokyo)* 44:113 (1991)). Similar studies were initiated to explore the specificity of Salinosporamide A for the proteasome by evaluating its ability to inhibit the catalytic activity of a prototypical serine protease, chymotrypsin.

Salinosporamide A was prepared as a 20 mM solution in DMSO and stored in small aliquots at −80° C. The substrate, suc-LLVY-AMC, was prepared as a 20 mM solution in DMSO and stored at −20° C. Proteolytic cleavage of this substrate by either proteasomes or chymotrypsin liberates the fluorescent product AMC, which can be monitored in a fluorimeter ($\lambda_{ex}$=390 nm and $\lambda_{em}$=460 nm). Bovine pancreatic chymotrypsin was obtained from Sigma (Cat. # C-4129), and prepared as a 5 mg/ml solution in assay buffer (10 mM HEPES, 0.5 mM EDTA, 0.05% Triton X-100, pH 7.5) daily. Immediately prior to the assay, the chymotrypsin was diluted to 1 μg/ml (0.2 μg/well) in assay buffer and held on ice. Salinosporamide A was diluted in DMSO to generate an 8-point dose-response curve. The high final Salinosporamide A concentrations needed to obtain complete inhibition of chymotrypsin required that the diluted enzyme be directly added to the compound dilution series. The inclusion of 1% DMSO (the final concentration of solvent in the test wells) into the reaction had no significant effect on chymotrypsin activity towards this substrate. The reactions were pre-incubated for 5 minutes at 37° C. and the reactions were initiated by the addition of substrate. Data were collected kinetically for one hour at 37° C. in the Fluoroskan and plotted as the mean of triplicate data points. The data were normalized to reactions performed in the absence of Salinosporamide A, and modeled in Prism as a sigmoidal dose-response, variable slope. Normalized data from Salinosporamide A inhibition of the chymotrypsin-like activity of rabbit 20S proteasomes has been included on the same graph.

Figure 30:
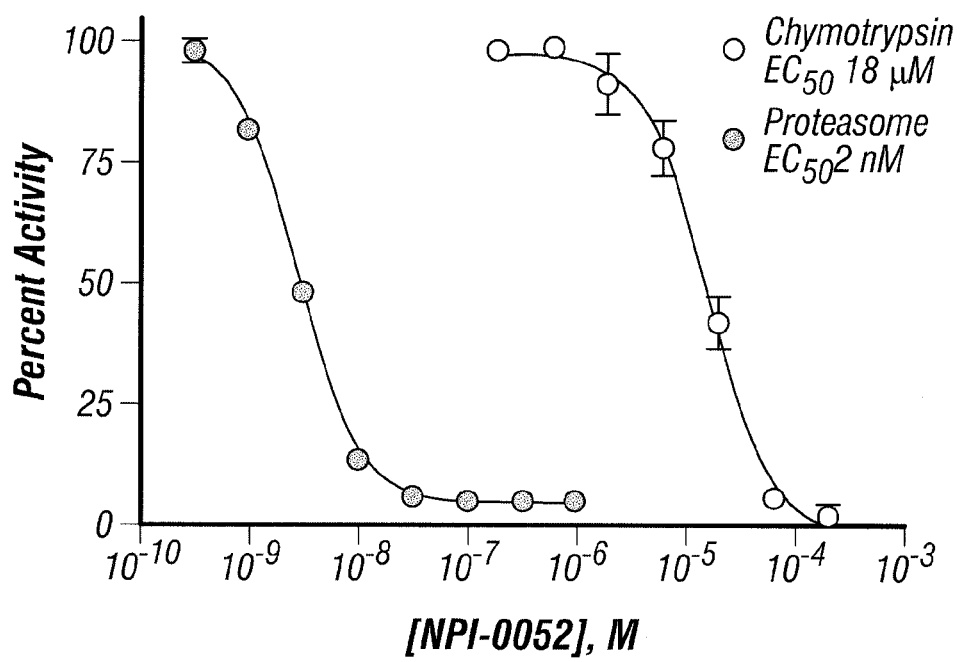
FIG. 30 shows the effect of II-16 treatment on chymotrypsin-mediated cleavage of LLVY-AMC substrate.

The average inhibition observed in two experiments using Salinosporamide A pretreatment of chymotrypsin was 17.5 μM (FIG. 30 shows a representative experiment). The data indicate that there is a preference for Salinosporamide A-mediated inhibition of the in vitro chymotrypsin-like activity of proteasomes over inhibition of the catalytic activity of chymotrypsin.

Thus, Salinosporamide A inhibits the chymotrypsin-like and PGPH activity of the proteasome. Preliminary studies indicate that Salinosporamide A also inhibits the trypsin-like activity of the proteasome with an $EC_{50}$ value of ~10 nM (data not shown).

Example 41

Inhibition of NF-κB-mediated Luciferase Activity by Formulae II-2, II-3, II-4, II-5A, II-5B, II-8C, II-13C, II-16, II-17, II-18, II-19, II-20, II-21, II-22, II-24C, II-25, II-26, II-27, II-28, II-29, II-30, II-44, VI-1A and IV-3C; HEK293 NF-κB/Luciferase Reporter Cell Line The HEK293 NF-κB/luciferase reporter cell line is a derivative of the human embryonic kidney cell line (ATCC; CRL-1573) and carries a luciferase reporter gene under the regulation of 5×NF-κB binding sites. The reporter cell line was routinely maintained in complete DMEM medium (DMEM plus 10% (v/v) Fetal bovine serum, 2 mM L-glutamine, 10 mM HEPES and Penicillin/Streptomycin at 100 IU/ml and 100 μg/ml, respectively) supplemented with 250 μg/ml G418. When performing the luciferase assay, the DMEM basal medium was replaced with phenol-red free DMEM basal medium and the G418 was omitted. The cells were cultured in an incubator at 37° C. in 5% $CO_2$ and 95% humidified air.

For NF-κB-mediated luciferase assays, HEK293 NF-κB/luciferase cells were seeded at $1.5 \times 10^4$ cells/well in 90 μl phenol-red free DMEM complete medium into Corning 3917 white opaque-bottom tissue culture plates. For Formulae II-2, II-4, II-5A and II-18, a 400 μM starting dilution was made in 100% DMSO and this dilution was used to generate an 8-point half log dilution series. This dilution series was further diluted 40× in appropriate culture medium and ten μl aliquots were added to the test wells in triplicate resulting in final test concentrations ranging from 1 μM to 320 pM. For Formulae II-3, II-5B, II-8C, II-13C, II-17, II-21, II-22, II-24C, II-25, II-26, II-27, II-28, II-29, II-30, VI-1A and IV-3C, a 8 mM starting dilution was made in 100% DMSO and the same procedure was followed as described above resulting in final test concentrations ranging from 20 μM to 6.3 nM. For Formulae II-16, II-19 and II-44, a 127 μM starting dilution was made in 100% DMSO and the final test concentrations ranging from 317 nM to 0.1 nM. For formula II-20, a 2.5 mM or 8 mM starting dilution was made in 100% DMSO and the final test concentrations ranged from 6.3 μM to 2.0 nM or 20 μM to 6.3 nM respectively. The plates were returned to the incubator for 1 hour. After 1 hr pretreatment, 10 μl of a 50 ng/ml TNF-α solution, prepared in the phenol-red free DMEM medium was added, and the plates were incubated for an additional 6 hours. The final concentration of DMSO was 0.25% in all samples.

At the end of the TNF-α stimulation, 100 μl of Steady Lite HTS luciferase reagent (Packard Bioscience) was added to each well and the plates were left undisturbed for 10 min at room temperature before measuring the luciferase activity. The relative luciferase units (RLU) were measured by using a Fusion microplate fluorometer (Packard Bioscience). The $EC_{50}$ values (the drug concentration at which 50% of the maximal relative luciferase activity is inhibited) were calculated in Prism (GraphPad Software) using a sigmoidal dose response, variable slope model.

Inhibition of NF-κB Activation by Formulae II-2, II-3, II-4, II-5A, II-5B, II-8C, II-13C, II-16, II-17, II-18, II-19, II-20, II-21, II-22, II-24C, II-25, II-26, II-27, II-28, II-29, II-30, II-44, VI-1A and IV-3C NF-κB regulates the expression of a large number of genes important in inflammation, apoptosis, tumorigenesis, and autoimmune diseases. Thus compounds capable of modulating or affecting NF-κB activity are useful in treating diseases related to inflammation, cancer, and autoimmune diseases, for example. In its inactive form, NF-κB complexes with IκB in the cytosol and upon stimulation, IκB is phosphorylated, ubiquitinated and subsequently degraded by the proteasome. The degradation of IκB leads to the activation of NF-κB and its translocation to the nucleus. The effects of Formulae II-2, II-3, II-4, II-5A, II-5B, II-8C, II-13C, II-16, II-17, II-18, II-19, II-20, II-21, II-22, II-24C, II-25, II-26, II-27, II-28, II-29, II-30, II-44, VI-1A and IV-3C on the activation of NF-κB were evaluated by assessing the NF-κB-mediated luciferase activity in HEK293 NF-κB/Luc cells upon TNF-α stimulation.

Pretreatment of NF-κB/Luc 293 cells with Formulae II-2, II-4, II-5A, II-5B, II-16, II-17, II-18, II-19, II-20, II-21, II-22, II-24C, II-26, II-29, II-30 and II-44 resulted in a dose-dependent decrease of luciferase activity upon TNF-α stimulation. The $EC_{50}$ values to inhibit NF-κB-mediated luciferase activity are shown in Table 4 and demonstrate that compounds of Formulae II-2, II-4, II-5A, II-5B, II-16, II-17, II-18, II-19, II-20, II-21, II-22, II-24C, II-26, II-29, II-30 and II-44 inhibited NF-κB activity in this cell-based assay.

TABLE 4

$EC_{50}$ values of Formulae II-2, II-3, II-4, II-5A, II-5B, II-8C, II-13C, II-16, II-17, II-18, II-19, II-20, II-21, II-22, II-24C, II-25, II-26, II-27, II-28, II-29, II-30, II-44, VI-1A and IV-3C from NF-κB-mediated luciferase reporter gene assay

| Compound | $EC_{50}$* |
|---|---|
| Formula II-2 | 71 ± 20 nM |
| Formula II-3 | >20 μM |
|  | >20 μM |
| Formula II-4 | 67 nM |
|  | 88 nM |
| Formula II-5A | 33 nM |
|  | 30 nM |
| Formula II-5B | 279 nM |
|  | 261 nM |
| Formula II-8C | >20 μM |
|  | >20 μM |
| Formula II-13C | >20 μM |
|  | >20 μM |
| Formula II-16 | 11 ± 3 nM |
| Formula II-17 | 960 ± 210 nM |
| Formula II-18 | 9 nM |
|  | 11 nM |
| Formula II-19 | 7 nM |
|  | 10 nM |
| Formula II-20 | 849 ± 225 nM** |
| Formula II-21 | 3.2 μM |
|  | 2.7 μM |
| Formula II-22 | 1 μM |
|  | 728 nM |
| Formula II-24C | 5.3 μM |
|  | 3.2 μM |
| Formula II-25 | >20 μM |
|  | >20 μM |
| Formula II-26 | 4.3 μM |
|  | 4.1 μM |
| Formula II-27 | >20 μM |
|  | >20 μM |
| Formula II-28 | >20 μM |
|  | >20 μM |

TABLE 4-continued $EC_{50}$ values of Formulae II-2, II-3, II-4, II-5A, II-5B, II-8C, II-13C, II-16, II-17, II-18, II-19, II-20, II-21, II-22, II-24C, II-25, II-26, II-27, II-28, II-29, II-30, II-44, VI-1A and IV-3C from NF-κB-mediated luciferase reporter gene assay

| Compound | $EC_{50}$* |
|---|---|
| Formula II-29 | 1.2 μM |
|  | 1.4 μM |
| Formula II-30 | 2.2 μM |
|  | 2.2 μM |
| Formula II-44 | 17 ± 4 nM |
| Formula VI-1A | >20 μM |
|  | >20 μM |
| Formula IV-3C | >20 μM |
|  | >20 μM |

*$EC_{50}$ values of two independent experiments are shown. Where n ≥ 3, the mean $EC_{50}$ value ± standard deviation is presented.
**The assay also was performed with compound II-20, and resulted in an $EC_{50}$ value of 154 nM, which value was not included in the calculation of the mean $EC_{50}$ value.

Figure 44:
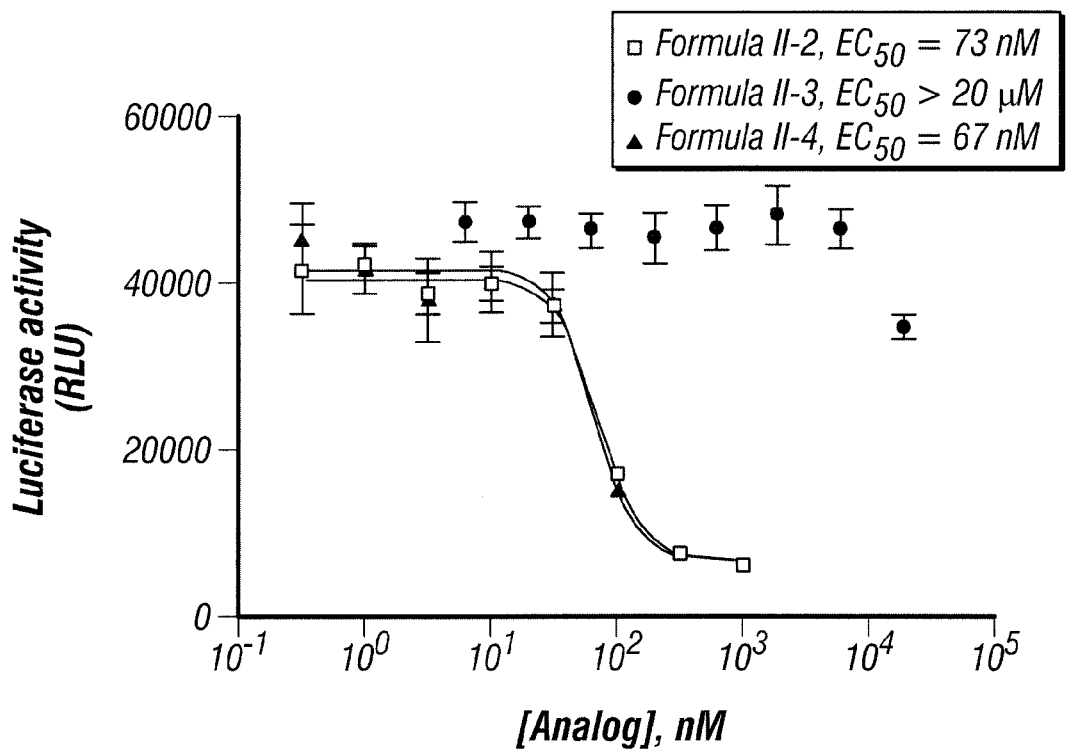
FIG. 44 depicts assay results showing the effect of Formula II-2, Formula II-3 and Formula II-4 on NF-κB mediated luciferase activity in HEK293 NF-κB/Luc Cells.

Results from a representative experiment evaluating Formula II-2, Formula II-3 and Formula II-4 (FIG. 44) revealed that pretreatment with Formula II-2 and Formula II-4 resulted in a dose-dependent decrease of luciferase activity in NF-κB/Luc 293 cells upon TNF-α stimulation. The calculated $EC_{50}$ to inhibit NF-κB inducible luciferase activity in this experiment was 73 nM for Formula II-2, while $EC_{50}$ value for Formula II-4 was 67 nM. Similar data were observed in a replicate experiment.

Figure 45:
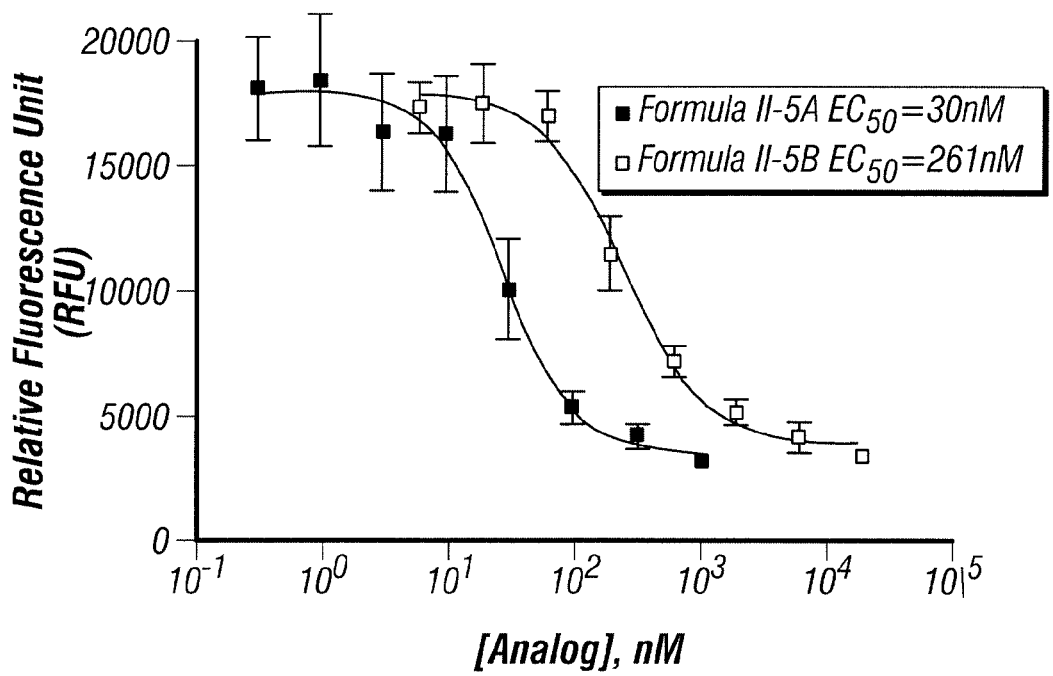
FIG. 45 depicts assay results showing the effect of Formula II-5A and Formula II-5B on NF-κB mediated luciferase activity in HEK293 NF-κB/Luc Cells

Results from a representative experiment evaluating Formula II-5A and Formula II-5B are shown in FIG. 45 and illustrate that Formula II-5A and Formula II-5B inhibit NF-κB inducible luciferase activity with $EC_{50}$ values of 30 nM and 261 nM respectively. Similar data were observed in a replicate experiment.

Example 42

Effect of Salinosporamide A on the NF-κB Signaling Pathway

Experiments were carried out to study the role of Salinosporamide A in the NF-κB signaling pathway. A stable HEK293 clone (NF-κB/Luc 293) was generated carrying a luciferase reporter gene under the regulation of 5×NF-κB binding sites. Stimulation of this cell line with TNF-α leads to increased luciferase activity as a result of NF-κB activation.

NF-κB/Luc 293 cells were pre-treated with 8-point half-log serial dilutions of Salinosporamide A (ranging from 1 μM to 317 pM) for 1 hour followed by a 6 hour stimulation with TNF-α (10 ng/mL). NF-κB inducible luciferase activity was measured at 6 hours. Viability of NF-κB/Luc 293 cells, after treatment with Salinosporamide A for 24 hr, was assessed by the addition of resazurin dye, as previously described.

Figure 31:
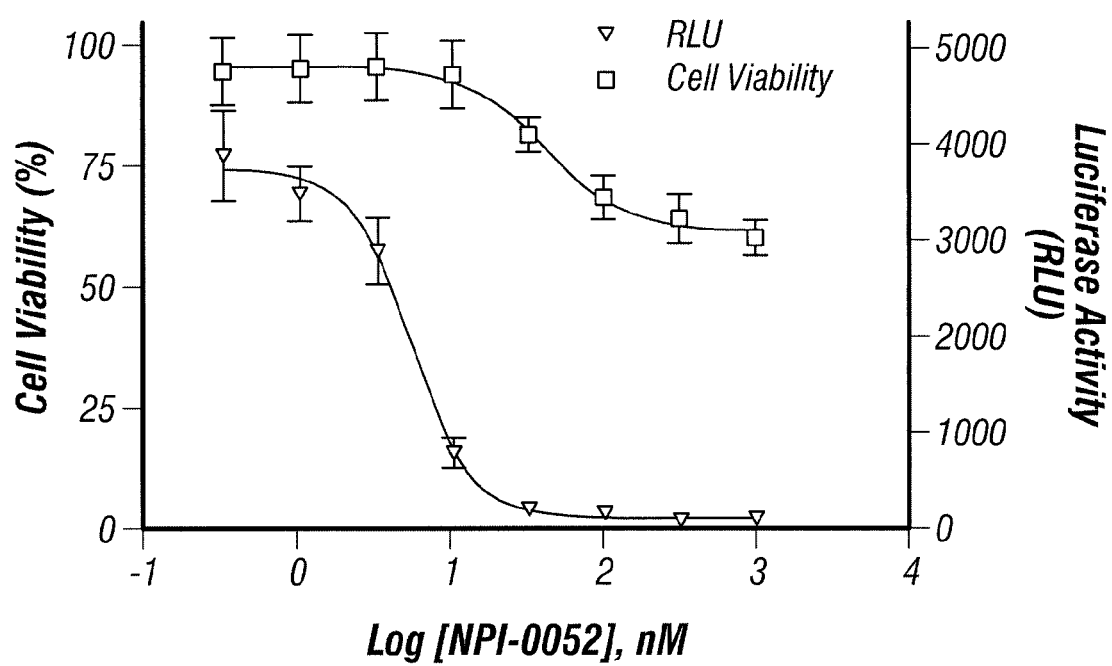
FIG. 31 shows nuclear factor-kappa B (NF-?B)/luciferase activity and cytotoxicity profiles of II-16.

Pretreatment of NF-κB/Luc 293 cells with Salinosporamide A resulted in a dose-dependent decrease of luciferase activity upon TNF-α stimulation (FIG. 31, right y-axis). The calculated $EC_{50}$ for inhibition of NF-κB/luciferase activity was ~7 nM. A cytotoxicity assay was simultaneously performed, and showed that this concentration of Salinosporamide A did not affect cell viability (FIG. 31, left y-axis). These representative data suggested that the observed decrease in luciferase activity by Salinosporamide A treatment was primarily due to an NF-κB mediated-signaling event rather than cell death.

Example 40

In addition to the NF-κB luciferase reporter gene assay, the effect of Salinosporamide A on the levels of phosphorylated-IκBα and total IκBα was evaluated by western blot. Endogenous protein levels were assessed in both HEK293 cells and the NF-κB/Luc 293 reporter clone.

Cells were pre-treated for 1 hour with Salinosporamide A at the indicated concentrations followed by stimulation with 10 ng/mL of TNF-α for 30 minutes. Antibodies against total and phosphorylated forms of IκBα were used to determine the endogenous level of each protein and anti-Tubulin antibody was used to confirm equal loading of protein.

As shown in FIG. 32, treatment of both cell lines with Salinosporamide A at 50 and 500 nM not only reduced the degradation of total IκBα but also retained the phospho-IκBα level when stimulated with TNF-α. These results strongly support the mechanism of action of Salinosporamide A as a proteasome inhibitor, which prevents the degradation of phosphorylated IκBα upon TNF-α stimulation.

Example 41

Effect of Salinosporamide A on Cell Cycle Regulatory Proteins

The ubiquitin-proteasome pathway is an essential proteolytic system involved in cell cycle control by regulating the degradation of cyclins and cyclin-dependent kinase (Cdk) inhibitors such as p21 and p27. Pagano, et al., *Science* 269: 682 (1995), Kisselev, et al., *Chem Biol* 8:739 (2001), King, et al., *Science* 274:1652 (1996). Furthermore, p21 and p27 protein levels are increased in the presence of proteasome inhibitors. Fukuchi, et al., *Biochim Biophys Acta* 1451:206 (1999), Takeuchi, et al., *Jpn J Cancer Res* 93:774 (2002). Therefore, western blot analysis was performed to evaluate the effect of Salinosporamide A treatment on endogenous levels of p21 and p27 using the HEK293 cells and the HEK293 NF-κB/Luciferase reporter clone.

The Western blots presented in FIG. 33 were reprobed using antibodies against p21 and p27 to determine the endogenous level of each protein and anti-Tubulin antibody was used to confirm equal loading of protein.

As shown in FIGS. 33A and 33B, preliminary results indicated that p21 and p27 protein levels were elevated when both cell lines were treated with Salinosporamide A at various concentrations. Data showed that Salinosporamide A acts by inhibiting proteasome activity thereby preventing the TNF-α induced activation of NF-κB. In addition, this proteasomal inhibition results in the accumulation of the Cdk inhibitors, p21 and p27, which has been reported to sensitize cells to apoptosis. Pagano, et al., supra (1995), King, et al., supra (1996).

Example 42

Activation of Caspase-3 by Salinosporamide A (II-16)

To address whether Salinosporamide A induces apoptosis, its effect on the induction of Caspase-3 activity was evaluated using Jurkat cells (American Type Culture Collection (ATCC) TIB-152, human acute T cell leukemia).

Jurkat cells were plated at $2 \times 10^6$ cells/3 mL per well in a 6-well plate and incubated at 37° C., 5% (v/v) $CO_2$ and 95% (v/v) humidity. Salinosporamide A and Mitoxantrone (Sigma, St. Louis, Mo. Cat # M6545), were prepared in DMSO at stock concentrations of 20 mM and 40 mM, respectively. Mitoxantrone is a chemotherapeutic drug that induces apoptosis in dividing and non-dividing cells via inhibition of DNA synthesis and repair and was included as a positive control. Bhalla, et al., *Blood* 82:3133 (1993). Cells were treated with $EC_{50}$ concentrations (Table 5) and incubated 19 hours prior to assessing of Caspase-3 activity. Cells treated with 0.25% DMSO served as the negative control. The cells were collected by centrifugation and the media removed. Cell pellets were processed for the Caspase-3 activity assay as described in the manufacturer's protocol (EnzChek Caspase-3 Assay Kit from Molecular Probes (E-13183; see Appendix G, which form a part of this application and is also available at hypertext transfer protocol on the worldwide web at "probes.com/media/pis/mp13183.pdf.". In brief, cell pellets were lysed on ice, mixed with the EnzChek Caspase-3 components in a 96-well plate, and then incubated in the dark for 30 minutes prior to reading fluorescence of cleaved benzyloxycarbonyl-DEVD-AMC using a Packard Fusion with $\lambda_{ex}$=485 nm and $\lambda_{em}$=530 nm filters. Protein concentrations for lysates were determined using the BCA Protein Assay Kit (Pierce) and these values were used for normalization.

Figure 34:
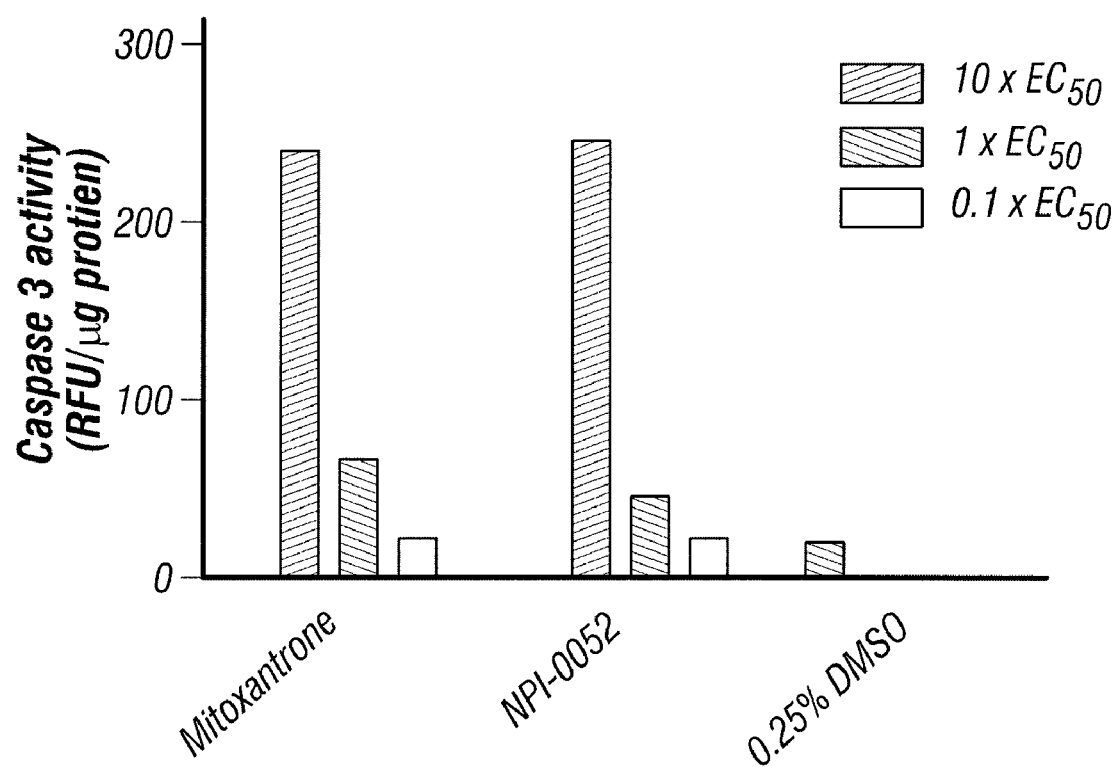
FIG. 34 shows activation of Caspase-3 by II-16 in Jurkat cells.

Data from representative experiments indicate that Salinosporamide A treatment of Jurkat cells results in cytotoxicity and activation of Caspase-3 (Table 5, FIG. 34).

TABLE 5

EC50 Values of Salinosporamide A and Mitoxantrone Cytotoxicity against Jurkat Cells

| | Jurkat Cells | |
|---|---|---|
| Compound | $EC_{50}$ (nM) | % max cell kill |
| Salinosporamide A | 10 | 97 |
| Mitoxantrone | 50 | 99 |

Example 43

PARP Cleavage by Salinosporamide A in Jurkat Cells

In order to assess the ability of Salinosporamide A to induce apoptosis in Jurkat cells, cleavage of poly (ADP-ribose) polymerase (PARP) was monitored. PARP is a 116 kDa nuclear protein that is one of the main intracellular targets of Caspase-3. Decker, et al., *J Biol Chem* 275:9043 (2000), Nicholson, D. W, *Nat Biotechnol* 14:297 (1996). The cleavage of PARP generates a stable 89 kDa product, and this process can be monitored by western blotting. Cleavage of PARP by caspases is a hallmark of apoptosis, and as such serves as an excellent marker for this process.

Jurkat cells were maintained in RPMI supplemented with 10% Fetal Bovine Serum (FBS) at low density ($2 \times 10^5$ cells per mL) prior to the experiment. Cells were harvested by centrifugation, and resuspended in media to $1 \times 10^6$ cells per 3 mL. Twenty mL of the cell suspension were treated with 100 nM Salinosporamide A (20 mM DMSO stock stored at −80° C.), and a 3 mL aliquot removed and placed on ice for the $T_0$ sample. Three mL aliquots of the cell suspension plus Salinosporamide A were placed in 6-well dishes and returned to the incubator. As a positive control for PARP cleavage, an identical cell suspension was treated with 350 nM Staurosporine, a known apoptosis inducer (Sigma S5921, 700 µM DMSO stock stored at −20° C.). Samples were removed at 2, 4, 6, 8, and 24 hrs in the case of Salinosporamide A treated cells, and at 4 hrs for the Staurosporine control. For each time point, the cells were recovered by brief centrifugation, the cells were washed with 400 µL of PBS, and the cells pelleted again. After removal of the PBS, the pellets were stored at −20° C. prior to SDS PAGE. Each cell pellet was resuspended in 100 µL of NuPAGE sample buffer (Invitrogen 46-5030) and 10 µL of each sample were separated on 10% NuPAGE BIS-Tris gels (Invitrogen NB302). After electrotransfer to nitrocellulose, the membrane was probed with a rabbit polyclonal antibody to PARP (Cell Signaling 9542), followed by goat anti-rabbit alkaline phosphatase conjugated secondary antibody (Jackson 11-055-045). Bound antibodies were detected colorimetrically using BCIP/NBT (Roche 1681451).

Figure 35:
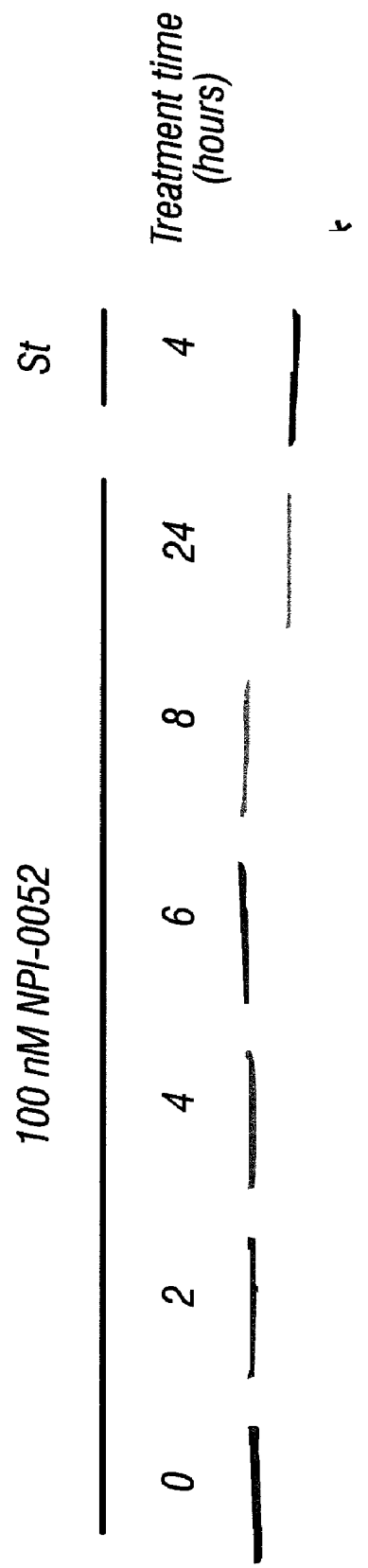
FIG. 35 shows PARP cleavage by II-16 in Jurkat cells.

The western blot presented in FIG. 35 shows the cleavage of PARP within the Jurkat cells in a time-dependent fashion. The cleaved form (denoted by the asterisk, *) appears in the treated cells between 2 and 4 hrs after exposure to Salinosporamide A while the majority of the remaining PARP is cleaved by 24 hrs. The Staurosporine treated cells (St) show rapid cleavage of PARP with most of this protein being cleaved within 4 hours. These data strongly suggest that Salinosporamide A can induce apoptosis in Jurkat cells.

Example 44

Anti-Anthrax Activity

In order to assay for the ability of Salinosporamide A or other compounds to prevent cell death resulting from LeTx exposure, RAW264.7 macrophage-like cells and recombinant LF and PA lethal toxin components were used as an in vitro model system assaying for cytotoxicity, as described below.

RAW264.7 cells (ATCC # TIB-71) were adapted to and maintained in Advanced Dulbecco's Modified Eagle Medium (Invitrogen, Carlsbad, Calif.) supplemented with 5% fetal bovine serum (ADMEM, Mediatech, Herndon, Va.) at 37° C. in a humidified 5% $CO_2$ incubator. Cells were plated overnight in ADMEM supplemented with 5% FBS at 37° C. in a humidified 5% $CO_2$ incubator at a concentration of 50,000 cells/well in a 96-well plate. Alternatively, cells cultured in DMEM supplemented with 10% fetal calf serum were also used and found to be amenable to this assay. Media was removed the following morning and replaced with serum-free ADMEM with or without Salinosporamide A or Omuralide at doses ranging from 1 µM to 0.5 nM for an 8-point dose-response. The compounds were prepared from a 1 mg/mL DMSO stock solution and diluted to the final concentration in ADMEM. After a 15 minute pre-incubation, 200 ng/mL LF or 400 ng/mL PA alone or in combination (LeTx) were added to cells. Recombinant LF and PA were obtained from List Biological Laboratories and stored as 1 mg/mL stock solutions in sterile water containing 1 mg/ml BSA at −80° C. as described by the manufacturer. Cells were incubated for 6 hours at 37° C., followed by addition of Resazurin as previously described. Plates were incubated an additional 6 hours prior to assessing cell viability by measuring fluorescence. The data are a summary of three experiments with three to six replicates per experiment and are expressed as the percent viability using the DMSO (negative) and the LeTx controls (positive) to normalize the data using the following equation: % viability=100*(observed OD−positive control)/(negative control−positive control).

Figure 36:
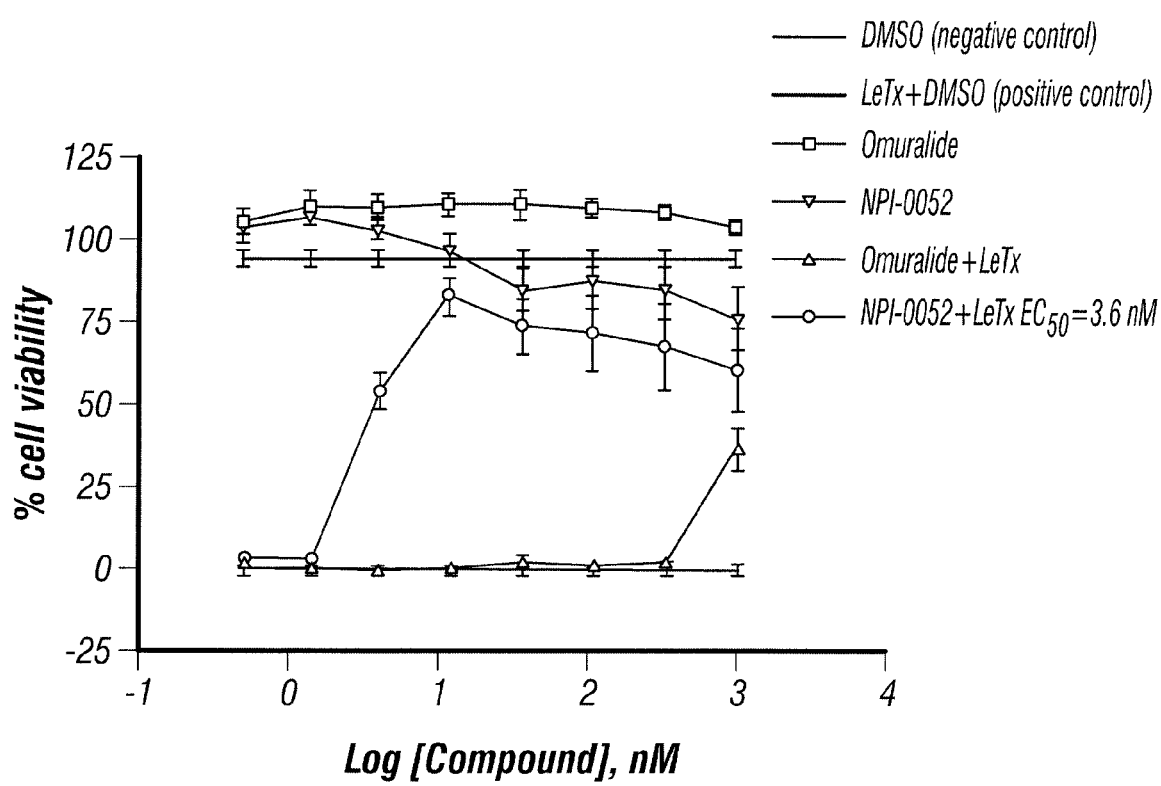
FIG. 36 shows inhibition of LeTx-induced cytotoxicity by II-16 in RAW264.7 cells.

The data represented in FIG. 36 indicate that treatment with Salinosporamide A can prevent LeTx-induced cell death of macrophage-like RAW264.7 cells in vitro. Treatment of RAW cells with either LF or PA alone or Salinosporamide A alone resulted in little reduction in cell viability, whereas treatment with LeTx resulted in approximately 0.27% cell viability as compared to controls. Salinosporamide A may enhance macrophage survival by inhibiting the degradation of specific proteins and decreasing the synthesis of cytokines, which will ultimately lead to the inhibition of the lethal effects of anthrax toxins in vivo.

Although Salinosporamide A treatment alone produced very modest cytotoxicity at concentrations of 100 nM and above, treatment with lower, relatively non-toxic levels revealed a marked increase in RAW 264.7 cell viability in LeTx treated cells (FIG. 36). For example, the Salinosporamide A+LeTx treated group showed 82% cell-viability when pretreated with 12 nM Salinosporamide A, which was a concentration that showed 96% viability with Salinosporamide A alone. The average $EC_{50}$ for Salinosporamide A in these studies was 3.6 nM. In contrast, Omuralide showed relatively little effect on cell viability until concentrations of 1 µM were reached. Even at this high concentration of Omuralide, only 37% viability was observed indicating that Salinosporamide A is a more potent inhibitor of LeTx-induced RAW264.7 cell death. Consistent with these data, Tang et. al., *Infect Immun* 67:3055 (1999), found that the $EC_{50}$ concentrations for MG132 and Lactacystin (the precursor to Omuralide) in the LeTx assay were 3 µM. Taken together, these data further illustrate that Salinosporamide A is a more potent inhibitor of LeTx-induced cytotoxicity than any other compound described to date.

Salinosporamide A promoted survival of RAW264.7 cells in the presence of LeTx indicating that this compound or it's derivatives can be a valuable clinical therapeutic for anthrax. In addition, it is worth noting that Salinosporamide A is much less cytotoxic on RAW 264.7 cells than for many tumor cells.

Example 45

Activity of Salinosporamide A Against Multiple Myeloma and Prostate Cancer Cell Lines NF-κB can be to be critical to the growth and resistance to apoptosis in Multiple Myeloma and has also been reported to be constitutively active in various prostate cancer cell lines (Hideshima T et al. 2002, Shimada K et al. 2002 and Palayoor S T et al. 1999). NF-κB activity is regulated by the proteasomal degradation of its inhibitor IκBα. Since Salinosporamide A has been shown to inhibit the proteasome in vitro and to interfere with the NF-κB signaling pathway, the activity of Salinosporamide A against the multiple myeloma cell line RPMI 8226 and the prostate cancer cell lines PC-3 and DU 145 was evaluated.

$EC_{50}$ values were determined in standard growth inhibition assays using Resazurin dye and 48 hour of drug exposure. Results from 2-5 independent experiments (Table 6) show that the $EC_{50}$ values for Salinosporamide A against RPMI 8226 and the prostate cell lines range from 10-37 nM.

TABLE 6

EC$_{50}$ values of Salinosporamide A (II-16) against Multiple Myeloma and Prostate Tumor cell lines

| Compound | RPMI 8226 (n = 5) | | DU 145 (n = 3) | | PC-3 (n = 2) | |
|---|---|---|---|---|---|---|
| | EC$_{50}$ (nM), mean ± SD | % cytotoxicity, mean ± SD | EC$_{50}$ (nM), mean ± SD | % cytotoxicity, mean ± SD | EC$_{50}$ (nM) | % cytotoxicity |
| Salinosporamide A | 10 ± 3 | 94 ± 1 | 37 ± 10 | 75 ± 4 | 31, 25 | 88, 89 |

The ability of Salinosporamide A to induce apoptosis in RPMI 8226 and PC-3 cells was evaluated by monitoring the cleavage of PARP and Pro-Caspase 3 using western blot analysis. Briefly, PC-3 and RPMI 8226 cells were treated with 100 nM Salinosporamide A (2345R01) for 0, 8 or 24 hours. Total protein lysates were made and 20 µg of the lysates were then resolved under reducing/denaturing conditions and blotted onto nitrocellulose. The blots were then probed with anti-PARP or anti-caspase 3 antibodies followed by stripping and reprobing with an anti-actin antibody.

Figure 37:
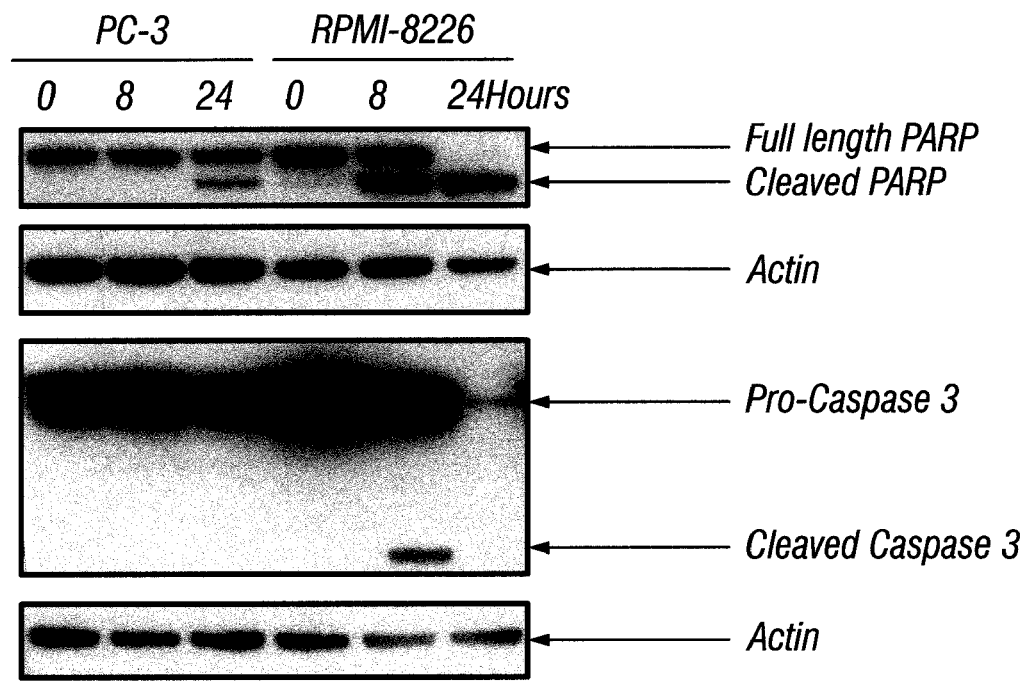
FIG. 37 shows the effects of II-16 treatment on PARP and Pro-Caspase 3 cleavage in RPMI 8226 and PC-3 cells.

Results of these experiments illustrate that Salinosporamide A treatment of RPMI 8226 cells leads to the cleavage of PARP and Pro-caspase 3 in a time-dependent manner (FIG. 37). RPMI 8226 cells seem to be more sensitive to Salinosporamide A than PC-3 cells since the induction of PARP cleavage is already noticeable at 8 hours and complete by 24 hours. In contrast, in PC-3 cells the cleavage of PARP is noticeable at 24 hours, while the cleavage of Pro-Caspase 3 is not detected in this experiment (FIG. 37).

Figure 38:
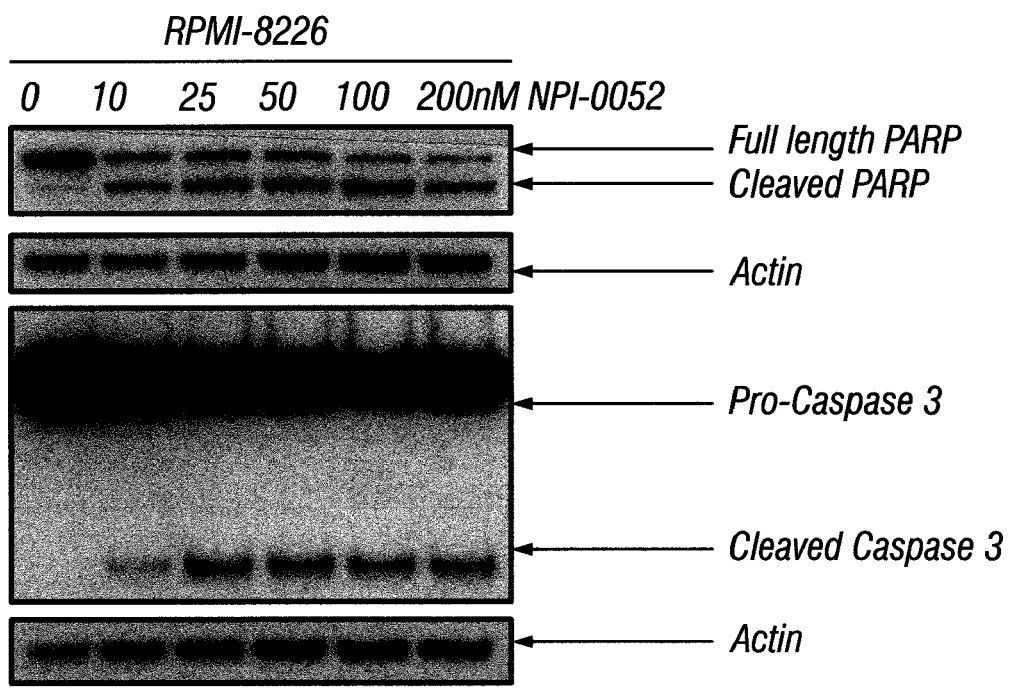
FIG. 38 shows II-16 treatment of RPMI 8226 results in a dose-dependent cleavage of PARP and Pro-Caspase 3.
Figure 39:
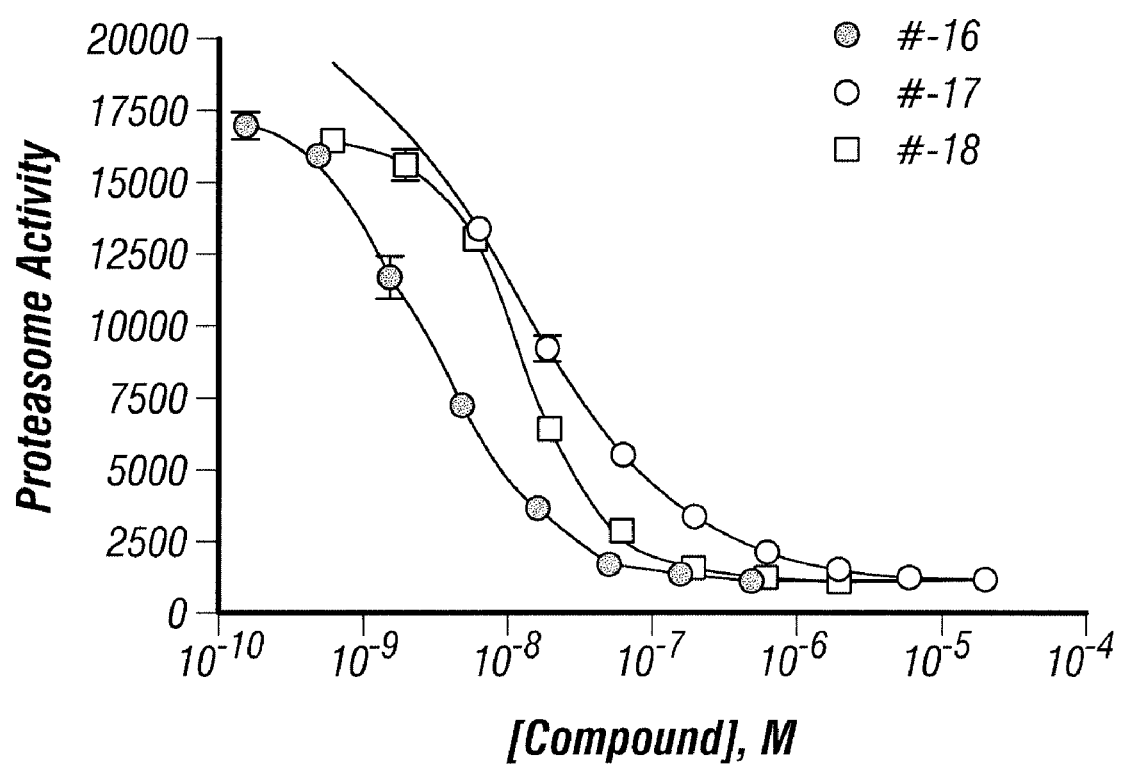
FIG. 39 shows in vitro proteasome inhibition by II-16, II-17, and II-18.

RPMI 8226 cells were used to evaluate the effect of treating the cells for 8 hours with various concentrations of Salinosporamide A. Briefly, RPMI 8226 cells were treated with varying concentrations of Salinosporamide A (2345R01) for 8 hours and protein lysates were made. 25 µg of the lysates were then resolved under reducing/denaturing conditions and blotted onto nitrocellulose. The blots were then probed with anti-PARP or anti-caspase 3 antibodies followed by stripping and reprobing with an anti-actin antibody. FIG. 38 demonstrates that Salinosporamide A induces a dose-dependent cleavage of both PARP and Pro-Caspase 3.

Example 46

Growth Inhibition of Human Multiple Myeloma by Formulae I-7, II-2, II-3, II-4, II-5A, II-5B, II-8C, II-13C, II-16, II-17, II-18, II-19, II-20, II-21, II-22, II-24C, II-25, II-26, II-28, II-29, II-30, II-31, II-32, II-38, IV-3C, II-44, VI-IA, II-47 and II-50; RPMI 8226 and U266 Cells The human multiple myeloma cell lines, RPMI 8226 (ATCC; CCL-155) and U266 (ATCC; TIB-196) were maintained in appropriate culture media. The cells were cultured in an incubator at 37° C. in 5% CO$_2$ and 95% humidified air.

For cell growth inhibition assays, RPMI 8226 cells and U266 were seeded at 2×10$^4$ and 2.5×10$^4$ cells/well respectively in 90 µl complete media into Corning 3904 black-walled, clear-bottom tissue culture plates. 20 mM stock solutions of the compounds were prepared in 100% DMSO, aliquoted and stored at −80° C. The compounds were serially diluted and added in triplicate to the test wells. The final concentration range of Formulae I-7, II-3, II-8C, II-5B, II-13C, II-17, II-20, II-21, II-22, II-24C, II-25, II-26, II-28, II-29, II-30, II-31, II-32, II-38, IV-3C, VI-1A and II-47 were from 20 µM to 6.32 nM. The final concentration of Formulae II-16, II-18, II-19, II-44 and II-50 ranged from 632 nM to 200 pM. The final concentration range of Formulae II-2, II-4 and II-5A were from 2 µM to 632 pM. The final concentration of DMSO was 0.25% in all samples.

Following 48 hours of drug exposure, 10 µl of 0.2 mg/ml resazurin (obtained from Sigma-Aldrich Chemical Co.) in Mg$^{2+}$, Ca$^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\mu_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and EC$_{50}$ values (the drug concentration at which 50% of the maximal observed growth inhibition is established) were determined using a standard sigmoidal dose response curve fitting algorithm (generated by XLfit 3.0 or XLfit 4.0, ID Business Solutions Ltd). The data are summarized in Tables 12 and 13.

Example 47

Salinosporamide A (II-16) Retains Activity Against Drug Resistant Cell Lines

The EC$_{50}$ values of Salinosporamide A against the human uterine sarcoma MES-SA cell line and its multidrug-resistant derivative MES-SA/Dx5 were determined to evaluate whether Salinosporamide A retains activity against a cell line overexpressing the P-glycoprotein efflux pump. Paclitaxel, a known substrate for the P-glycoprotein pump was included as a control.

TABLE 7

EC$_{50}$ values of Salinosporamide A against MES-SA and the drug-resistant derivative MES-SA/Dx5

| | MES-SA | | MES-SA/Dx5 | | |
|---|---|---|---|---|---|
| | EC$_{50}$ (nM), mean | % cytotoxicity, mean ± SD | EC$_{50}$ (nM), mean ± SD | % cytotoxicity, mean ± SD | Fold change |
| Salinosporamide A | 20 ± 5 | 94 ± 1 | 23 ± 1 | 92 ± 2 | 1.2 |
| Paclitaxel | 5 ± 2 | 63 ± 7 | 2040 ± 150 | 78 ± 1 | 408 |

Results from these growth inhibition assays (Table 7) show that, as expected, Paclitaxel did not retain its activity against MES-SA/Dx5 cells as reflected by the 408 fold increase in the $EC_{50}$ values. $EC_{50}$ values for Salinosporamide A against MES-SA and MES-SA/Dx5 were similar. This illustrates that Salinosporamide A is able to inhibit the growth of the multidrug resistant cell line MES-SA/Dx5 suggesting that Salinosporamide A does not seem to be a substrate for the P-glycoprotein efflux pump.

In addition, Salinosporamide A was evaluated against HL-60/MX2, the drug resistant derivative of the human leukemia cell line, HL-60, characterized by having a reduced Topoisomerase II activity and considered to have atypical multidrug resistance. $EC_{50}$ values for growth inhibition were determined for Salinosporamide A against the HL-60 and HL-60/MX2. The DNA binding agent Mitoxantrone was included as a control, as HL-60/MX2 cells are reported to be resistant to this chemotherapeutic agent (Harker W. G. et al. 1989).

TABLE 8

$EC_{50}$ values of Salinosporamide A against HL-60 and the drug resistant derivative HL-60/MX2

| | HL-60 | | HL-60/MX2 | | |
|---|---|---|---|---|---|
| | $EC_{50}$ (nM) | % cytotoxicity | $EC_{50}$ (nM) | % cytotoxicity | Fold change |
| Salinosporamide A | 27, 30 | 88, 91 | 28, 25 | 84, 89 | 1.0, 0.8 |
| Mitoxantrone | 59, 25 | 98, 100 | 1410, 827 | 98, 99 | 24, 33 |

The data in Table 8 reveals that Salinosporamide A was able to retain its activity against HL-60/MX2 cells relative to HL-60 cells, indicating that Salinosporamide A is active in cells expressing reduced Topoisomerase II activity. In contrast, Mitoxantrone was about 29 fold less active against HL-60/MX2 cells.

Salinosporamide A was also shown to have activity against drug resistant multiple myeloma cell lines. For example, Salinosporamide A was shown to be active against MM.1R and Doxorubicin-resistant Dox-40 cell lines. Furthermore, Salinosporamide A was shown to be active against cell lines obtained from human multiple myloma patients that had relapsed after multiple prior therapies with Dexamethasone, Bortezomib, and thalidomide. Thus, Salinosporamide A is active against drug resistant multiple myeloma including multiple myeloma exhibiting resistance to doxorubicin, dexamethasone, bortezomib, and thalidomide. Similarly, the other compounds disclosed herein are active against drug resistant multiple myeloma including multiple myeloma exhibiting resistance to doxorubicin, dexamethasone, bortezomib, and thalidomide.

Example 48

Salinosporamide A and Several Analogs

Structure Activity Relationship

To establish an initial structure activity relationship (SAR) for Salinosporamide A, a series of Salinosporamide A analogs were evaluated against the multiple myeloma cell line RPMI 8226. $EC_{50}$ values were determined in standard growth inhibition assays using Resazurin dye and 48 hour of drug exposure.

The results of this initial series of SAR (Table 9) indicate that the addition of a halogen group to the ethyl group seems to enhance the cytotoxic activity.

TABLE 9

Initial SAR series of Salinosporamide A

| Compound No. | Molecular Structure | $EC_{50}$, μM (mean ± SD) | % Cytotoxicity (mean ± SD) |
|---|---|---|---|
| II-16 | 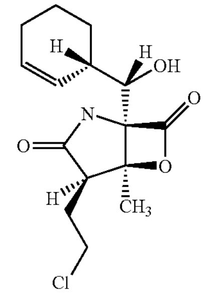 | 0.007 ± 0.0001 | 94 ± 0 |
| II-17 | 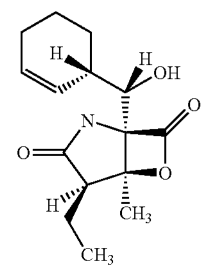 | 2.6, 2.3 | 94, 95 |
| II-18 | 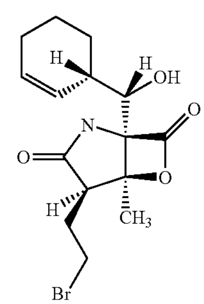 | 0.017, 0.022 | 94, 94 |

Where n > 2, mean ± standard deviation was determined

Example 49

In Vivo Biology

Maximum Tolerated Dose (MTD) Determination

In vivo studies were designed to determine the MTD of Salinosporamide A when administered intravenously to female BALB/c mice.

BALB/c mice were weighed and various Salinosporamide A concentrations (ranging from 0.01 mg/kg to 0.5 mg/kg) were administered intravenously as a single dose (qd×1) or daily for five consecutive days (qd×5). Animals were observed daily for clinical signs and were weighed individually twice weekly until the end of the experiment (maximum of 14 days after the last day of dosing). Results are shown in Table 10 and indicate that a single intravenous Salinosporamide A dose of up to 0.25 mg/kg was tolerated. When administered daily for five consecutive days, concentrations of Salinosporamide A up to 0.1 mg/kg were well tolerated. No behavioral changes were noted during the course of the experiment.

TABLE 10

MTD Determination of Salinosporamide A in female BALB/c Mice

| Group | Dose (mg/kg) | Route/Schedule | Deaths/Total | Days of Death |
|---|---|---|---|---|
| 1 | 0.5 | i.v.; qdx1 | 3/3 | 3, 3, 4 |
| 2 | 0.25 | i.v.; qdx1 | 0/3 | |
| 3 | 0.1 | i.v.; qdx1 | 0/3 | |
| 4 | 0.05 | i.v.; qdx1 | 0/3 | |
| 5 | 0.01 | i.v.; qdx1 | 0/3 | |
| 6 | 0 | i.v.; qdx1 | 0/3 | |
| 7 | 0.5 | i.v.; qdx5 | 3/3 | 4, 6, 7 |
| 8 | 0.25 | i.v.; qdx5 | 3/3 | 4, 5, 5 |
| 9 | 0.1 | i.v.; qdx5 | 0/3 | |
| 10 | 0.05 | i.v.; qdx5 | 0/3 | |
| 11 | 0.01 | i.v.; qdx5 | 0/3 | |
| 12 | 0 | i.v.; qdx5 | 0/3 | |

Example 50

Preliminary Assessment of Salinosporamide A Absorption, Distribution, Metabolism and Elimination (ADME) Characteristics Studies to initiate the evaluation of the ADME properties of Salinosporamide A were performed. These studies consisted of solubility assessment, Log $D^{7.4}$ determination and a preliminary screen to detect cytochrome P450 enzyme inhibition. Results from these studies showed an estimated solubility of Salinosporamide A in PBS (pH 7.4) of 9.6 µM (3 µg/ml) and a Log $D^{7.4}$ value of 2.4. This Log $D^{7.4}$ value is within the accepted limits compatible with drug development (Log $D^{7.4}$<5.0) and suggests oral availability. Results from the preliminary P450 inhibition screen showed that Salinosporamide A, when tested at 10 µM, showed no or low inhibition of all P450 isoforms: CYP1A2, CYP2C9 and CYP3A4 were inhibited by 3%, 6% and 6% respectively, while CYP2D6 and CYP2C19 were inhibited by 19% and 22% respectively.

Example 51

Salinosporamide A and its Effects In Vivo on Whole Blood Proteasome Activity

Salinosporamide A was previously demonstrated to be a potent and specific inhibitor of the proteasome in vitro, with an $IC_{50}$ of 2 nM towards the chymotrypsin-like activity of purified 20S proteasomes. To monitor the activity of Salinosporamide A in vivo, a rapid and reproducible assay (adapted from Lightcap et al. 2000) was developed to assess the proteosome activity in whole blood.

In brief, frozen whole blood samples were thawed on ice for one hour, and resuspended in 700 µL of ice cold 5 mM EDTA, pH 8.0 in order to lyse the cells by hypotonic shock. This represents approximately 2-3 times the volume of the packed whole blood cells. Lysis was allowed to proceed for one hour, and the cellular debris was removed by centrifugation at 14,000×g for 10 minutes. The supernatant (Packed Whole Blood Lysate, PWBL) was transferred to a fresh tube, and the pellet discarded. Protein concentration of the PWBL was determined by BCA assay (Pierce) using BSA as a standard. Approximately 80% of the samples had a total protein concentration between 800 and 1200 µg/mL.

Proteasome activity was determined by measuring the hydrolysis of a fluorogenic substrate specific for the chymotrypsin-like activity of proteasomes (suc-LLVY-AMC, Bachem Cat. I-1395). Control experiments indicated that >98% of the hydrolysis of this peptide in these extracts is mediated by the proteasome. Assays were set up by mixing 5 µL of a PWBL from an animal with 185 µL of assay buffer (20 mM HEPES, 0.5 mM EDTA, 0.05% Triton X-100, 0.05% SDS, pH 7.3) in Costar 3904 plates. Titration experiments revealed there is a linear relationship between protein concentration and hydrolysis rate if the protein concentration in the assay is between 200 and 1000 µg. The reactions were initiated by the addition of 10 µL of 0.4 mM suc-LLVY-AMC (prepared by diluting a 10 mM solution of the peptide in DMSO 1:25 with assay buffer), and incubated in a fluorometer (Labsystems Fluoroskan) at 37° C. Hydrolysis of the substrate results in the release of free AMC, which was measured fluorometrically by using $\lambda_{ex}$=390 nm and $\lambda_{em}$=460 nm. The rate of hydrolysis in this system is linear for at least one hour. The hydrolysis rate of each sample is then normalized to relative fluorescent units per milligram of protein (RFU/mg).

To explore the in vivo activity of Salinosporamide A, male Swiss-Webster mice (5 per group, 20-25 g in weight) were treated with various concentrations of Salinosporamide A. Salinosporamide A was administered intravenously and given its Log $D^{7.4}$ value of 2.4, suggestive of oral availability, Salinosporamide A was also administered orally. Salinosporamide A dosing solutions were generated immediately prior to administration by dilution of Salinosporamide A stock solutions (100% DMSO) using 10% solutol yielding a final concentration of 2% DMSO. The vehicle control consisted of 2% DMSO in 10% solutol. One group of animals was not dosed with either vehicle or Salinosporamide A in order to establish a baseline for proteasome activity. Salinosporamide A or vehicle was administered at 10 mL/kg and ninety minutes after administration the animals were anesthetized and blood withdrawn by cardiac puncture. Packed whole blood cells were collected by centrifugation, washed with PBS, and re-centrifuged. All samples were stored at –80° C. prior to the evaluation of the proteasome activity.

In order to be certain that the hydrolysis of the substrate observed in these experiments was due solely to the activity of the proteasome, dose response experiments on the extracts were performed using the highly specific proteasomal inhibitor Epoxomicin. PWBL lysates were diluted 1:40 in assay buffer, and 180 µL were added to Costar 3904 plates. Epoxomicin (Calbochem Cat. 324800) was serially diluted in DMSO to generate an eight point dose response curve, diluted 1:50 in assay buffer, and 10 µL added to the diluted PWBL in triplicate. The samples were preincubated for 5 minutes at 37° C., and the reactions initiated with substrate as above. The dose response curves were analyzed in Prism, using a sigmoidal dose response with variable slope as a model.

Figure 40:
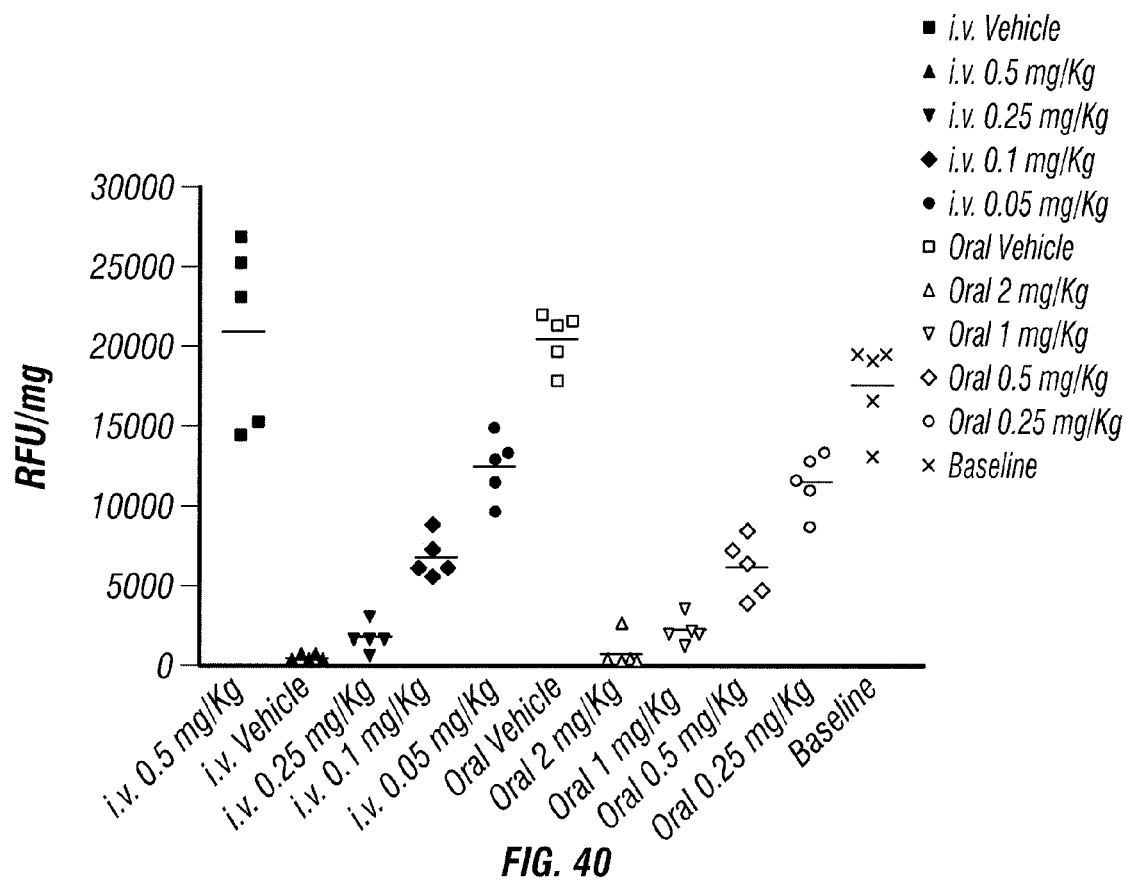
FIG. 40 shows proteasomal activity in PWBL prepared from II-16 treated mice.

FIG. 40 is a scatter plot displaying the normalized proteasome activity in PWBL's derived from the individual mice (5 mice per group). In each group, the horizontal bar represents the mean normalized activity. These data show that Salinosporamide A causes a profound decrease in proteasomal activity in PWBL, and that this inhibition is dose dependent. In addition, these data indicate that Salinosporamide A is active upon oral administration.

Figure 41:
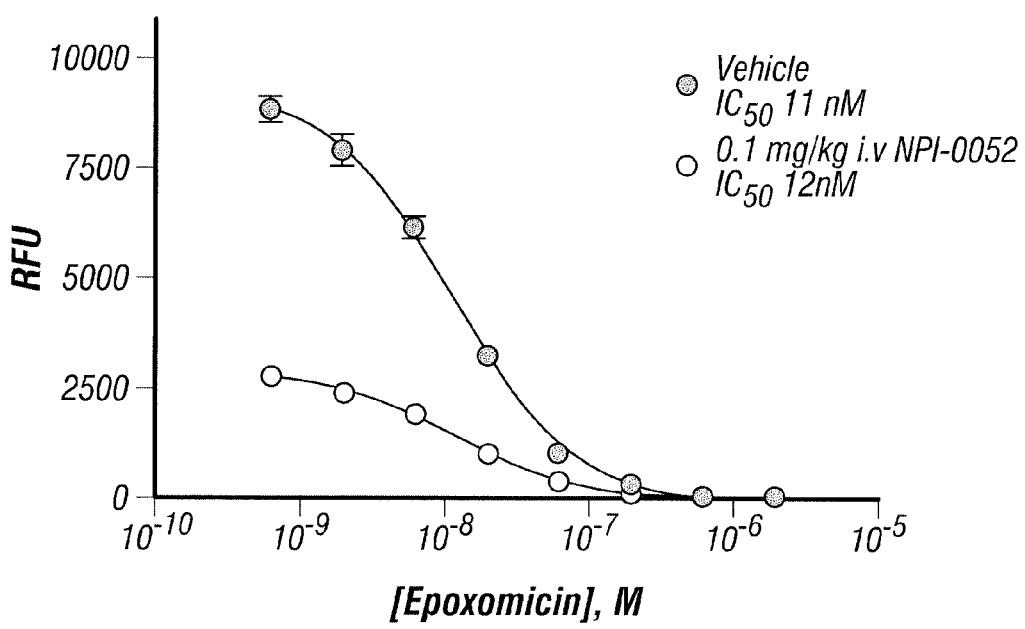
FIG. 41 shows epoxomicin treatment in the PWBL assay.

The specificity of the assay was shown by examining the effect of a known proteasome inhibitor, Epoxomicin, on hydrolysis of the peptide substrate. Epoxomicin is a peptide epoxide that has been shown to highly specific for the proteasome, with no inhibitory activity towards any other known protease (Meng et al., 1999). Lysates from a vehicle control and also from animals treated intravenous (i.v.) with 0.1 mg/kg Salinosporamide A were incubated with varying concentration of Epoxomicin, and $IC_{50}$ values were determined. Palayoor et al., *Oncogene* 18:7389-94 (1999). As shown in FIG. 41, Epoxomicin caused a dose dependent inhibition in the hydrolysis of the proteasome substrate. The $IC_{50}$ obtained in these experiments matches well with the 10 nM value observed using purified 20S proteasomes in vitro (not shown). These data also indicate that the remaining activity towards this substrate in these lysates prepared from animals treated with 0.1 mg/kg Salinosporamide A is due to the proteasome, and not some other protease. The residual activity seen in extracts treated with high doses of Epoxomicin is less than 2% of the total signal, indicating that over 98% of the activity observed with suc-LLVY-AMC as a substrate is due solely to the activity of the proteasomes present in the PWBL.

Figure 42:
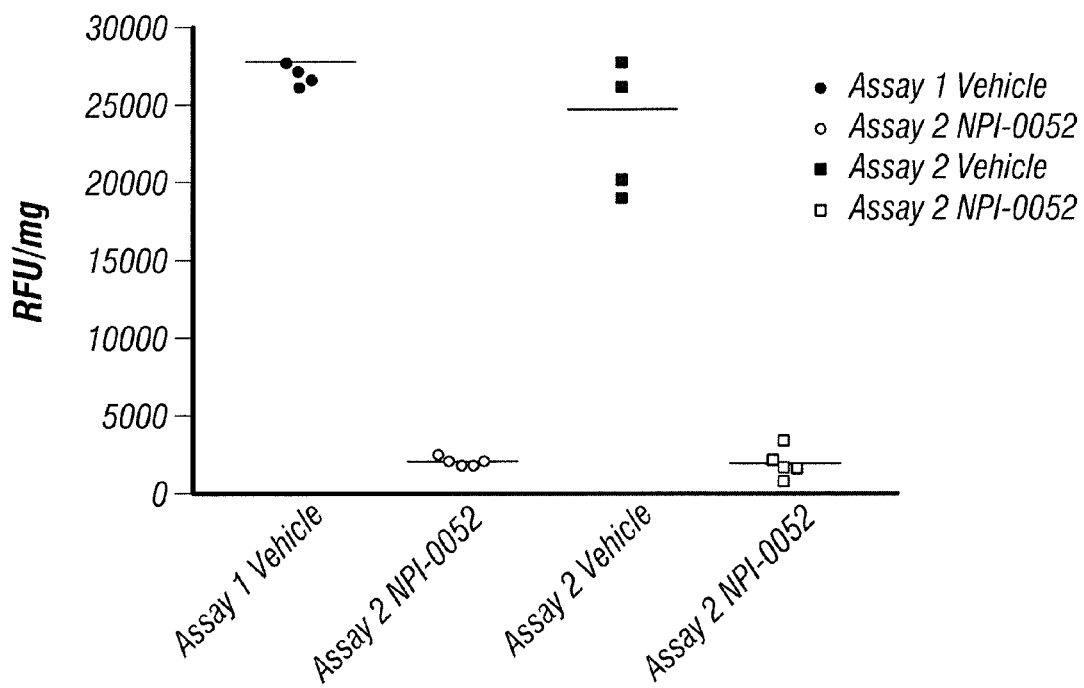
FIG. 42 shows intra-assay comparison.

Comparison of intra-run variation in baseline activity and the ability of Salinosporamide A to inhibit proteasomal activity was also assessed. In FIG. 42, the results of separate assays run several weeks apart are shown. Qureshi, et al., *J. Immunol.* 171(3):1515-25 (2003). For clarity, only the vehicle control and matching dose results are shown. While there was some variation in the proteasomal activity in PWBL derived from individual animals in the control groups, the overall mean was very similar between the two groups. The animals treated with Salinosporamide A (0.1 mg/kg i.v.) also show very similar residual activity and average inhibition. This suggests that results between assays can be compared with confidence.

Example 52

Inhibition of In Vivo LPS-Induced TNF by Salinosporamide A

Studies suggest that the proteasome plays a role in the activation of many signaling molecules, including the transcription factor NF-κB via protealytic degradation of the inhibitor of NF-κB (IκB). LPS signaling through the TLR4 receptor activates NF-κB and other transcriptional regulators resulting in the expression of a host of proinflammatory genes like TNF, IL-6, and IL-1β. The continued expression of proinflammatory cytokines has been identified as a major factor in many diseases. Inhibitors of TNF and IL-1β have shown efficacy in many inflammation models including the LPS murine model, as well as animal models of rheumatoid arthritis and inflammatory bowel disease. Recent studies have suggested that inhibition of the proteasome can prevent LPS-induced TNF secretion (Qureshi et al., 2003). These data suggest that Salinosporamide A, a novel potent proteasome inhibitor, may prevent TNF secretion in vivo in the high-dose LPS murine model.

To assess the ability of Salinosporamide A to inhibit in vivo LPS-induced plasma TNF levels in mice, in vivo studies were initiated at BolderBioPATH, Inc. in Boulder, Colo. The following methods outline the protocol design for these studies.

Male Swiss Webster mice (12/group weighing 20-25 g) were injected with LPS (2 mg/kg) by the i.p. route. Thirty minutes later, mice were injected i.v. (tail vein) with Salinosporamide A at 2.5 mg/kg after approximately 5 minutes under a heat lamp. Ninety minutes after LPS injection, the mice were anesthetized with Isoflurane and bled by cardiac puncture to obtain plasma. Remaining blood pellet was then resuspended in 500 µL of PBS to wash away residual serum proteins and centrifuged again. Supernatant was removed and blood pellet frozen for analysis of proteasome inhibition in packed whole blood lysate.

TABLE 11

| Group ID | Group | n = | Time 0 min | +30 min |
|---|---|---|---|---|
| No injections/baseline | 1 | 5 | | |
| Saline + solutol vehicle | 2 | 5 | saline | |
| Saline + solutol vehicles | 3 | 5 | saline | Solutol/DMSO |
| LPS ip./Vehicle (−30 min) | 4 | 12 | LPS | |
| LPS ip./Vehicle (+30 m) | 5 | 12 | LPS | Solutol/DMSO |
| saline/Salinosporamide A (−30 min) 0.25 mg/kg | 6 | 12 | saline | |
| saline/Salinosporamide A (+30 m) 0.25 mg/kg | 7 | 12 | saline | 0.25 mg/kg |
| LPS/Salinosporamide A (−30 min) 0.25 mg/kg | 8 | 12 | LPS | |
| LPS/Salinosporamide A (+30 m) 0.25 mg/kg | 9 | 12 | LPS | 0.25 mg/kg |

Dosing solutions were prepared using a 10 mg/mL Salinosporamide A stock solution in 100% DMSO. A 10% solutol solution was prepared by diluting w/w with endotoxin-free water and a 1:160 dilution was made of the 10 mg/ml Salinosporamide A stock. Animals were dosed i.v. with 4 ml/kg. A vehicle control solution was also prepared by making the same 1:160 dilution with 100% DMSO into 10% solutol solution giving a final concentration of 9.375% solutol in water and 0.625% DMSO. Measurements of plasma TNF were performed using the Biosource mTNF Cytoset kit (Biosource Intl., Camarillo, Calif.; catalog # CMC3014) according to manufacturer's instructions. Samples were diluted 1:60 for the assay.

Figure 43:
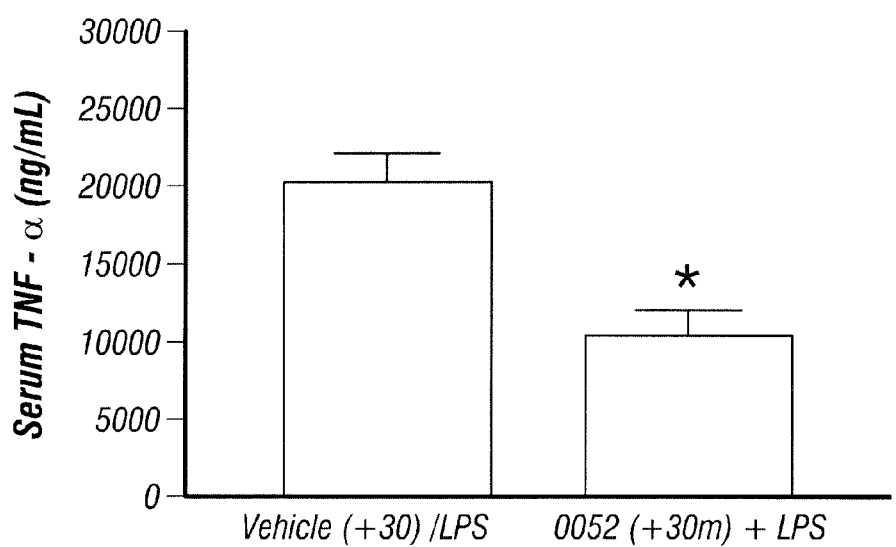
FIG. 43 shows decreased plasma TNF levels in mice treated with LPS.

Data from two independent experiments with at least ten replicate animals per group indicated that treatment with 0.125 or 0.25 mg/kg Salinosporamide A decreased LPS-induced TNF secretion in vivo. A representative experiment is shown in FIG. 43. These data reveal that treatment of animals with 0.25 mg/kg Salinosporamide A thirty minutes after 2 mg/kg LPS injection resulted in significant reduction in serum TNF levels. Packed whole blood samples were also analyzed for ex vivo proteasome inhibition revealing 70±3% inhibition in animals treated with 0.125 mg/kg and 94±3% in animals treated with 0.25 mg/kg. No significant differences were seen in proteasome inhibition in animals treated with or without LPS. Salinosporamide A reduces LPS-induced plasma TNF levels by approximately 65% when administered at 0.125 or 0.25 mg/kg i.v. into mice 30 minutes post-LPS treatment.

Example 53

In Vitro Chemosensitizing Effects of Salinosporamide A

Chemotherapy agents such as CPT-11 (Irinotecan) can activate the transcription factor nuclear factor-kappa B (NF-κB) in human colon cancer cell lines including LoVo cells, resulting in a decreased ability of these cells to undergo apoptosis. Cusack, et al., *Cancer Res* 61:3535 (2001). In unstimulated cells, NF-κB resides in the cytoplasm in an inactive complex with the inhibitory protein IκB (inhibitor of NF-κB). Various stimuli can cause IκB phosphorylation by IκB kinase, followed by ubiquitination and degradation of IκB by the proteasome. Following the degradation of IκB, NF-κB translocates to the nucleus and regulates gene expression, affecting many cellular processes, including upregulation of survival genes thereby inhibiting apoptosis.

The recently approved proteasome inhibitor, Velcade™ (PS-341; Millennium Pharmaceuticals, Inc.), is directly toxic to cancer cells and can also enhance the cytotoxic activity of CPT-11 against LoVo cells in vitro and in a LoVo xenograft model by inhibiting proteasome induced degradation of IκB. Adams, J., *Eur J Haematol* 70:265 (2003). In addition, Velcade™ was found to inhibit the expression of proangiogenic chemokines/cytokines GRO-α and VEGF in squamous cell carcinoma, presumably through inhibition of the NF-κB pathway. Sunwoo, et al., *Clin Cancer Res* 7:1419 (2001). The data indicate that proteasome inhibition may not only decrease tumor cell survival and growth, but also angiogenesis.

Example 54

Growth Inhibition of Colon, Prostate, Breast, Lung, Ovarian, Multiple Myeloma and Melanoma Human colon adenocarcinoma (HT-29; HTB-38), prostate adenocarcinoma (PC-3; CRL-1435), breast adenocarcinoma (MDA-MB-231; HTB-26), non-small cell lung carcinoma (NCI-H292; CRL-1848), ovarian adenocarcinoma (OVCAR-3; HTB-161), multiple myeloma (RPMI 8226; CCL-155), multiple myeloma (U266; TIB-196) and mouse melanoma (B16-F10; CRL-6475) cells were all purchased from ATCC and maintained in appropriate culture media. The cells were cultured in an incubator at 37° C. in 5% $CO_2$ and 95% humidified air.

For cell growth inhibition assays, HT-29, PC-3, MDA-MB-231, NCI-H292, OVCAR-3 and B16-F10 cells were seeded at $5\times10^3$, $5\times10^3$, $1\times10^4$, $4\times10^3$, $1\times10^4$ and $1.25\times10^3$ cells/well respectively in 90 μl complete media into 96 well (Corning; 3904) black-walled, clear-bottom tissue culture plates and the plates were incubated overnight to allow cells to establish and enter log phase growth. RPMI 8226 and U266 cells were seeded at $2\times10^4$ and $2.5\times10^4$ cells/well respectively in 90 μl complete media into 96 well plates on the day of the assay. 20 mM stock solutions of the compounds were prepared in 100% DMSO and stored at −80° C. The compounds were serially diluted and added in triplicate to the test wells. Concentrations ranging from 6.32 μM to 632 pM were tested for II-2 and II-4. II-3 and II-17 were tested at concentrations ranging from 20 μM to 6.32 nM. Formula II-18 and II-19 were tested at concentrations ranging from 2 μM to 200 pM. Formula II-5A and Formula II-5B were tested at final concentrations ranging from 2 μM to 632 pM and 20 μM to 6.32 nM respectively. The plates were returned to the incubator for 48 hours. The final concentration of DMSO was 0.25% in all samples.

Following 48 hours of drug exposure, 10 μl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and $EC_{50}$ values (the drug concentration at which 50% of the maximal observed growth inhibition is established) were determined using a standard sigmoidal dose response curve fitting algorithm (XLfit 3.0, ID Business Solutions Ltd). Where the maximum inhibition of cell growth was less than 50%, an $EC_{50}$ value was not determined.

The data in Table 12 summarize the growth inhibitory effects of Formulae II-2, II-3, II-4, II-5A, II-5B, II-17, II-18 and II-19 against the human colorectal carcinoma, HT-29, human prostate carcinoma, PC-3, human breast adenocarcinoma, MDA-MB-231, human non-small cell lung carcinoma, NCI-H292, human ovarian carcinoma, OVCAR-3, human multiple myelomas, RPMI 8226 and U266 and murine melanoma B16-F10 cell lines.

TABLE 12

$EC_{50}$ values of Formulae II-2, II-3, II-4, II-5A, II-5B, II-17, II-18 and II-19 against various tumor cell lines

| Cell line | $EC_{50}$ (nM)* | | | | | | | |
|---|---|---|---|---|---|---|---|---|
| | II-2 | II-3 | II-4 | II-5A | II-5B | II-17 | II-18 | II-19 |
| HT-29 | 129 ± 21 | >20000 | 132 ± 36 | 67 ± 17 | 1070 | >20000 | 18 ± 7.8 | 11 ± 1.6 |
| | | | | | 1210 | | | |
| PC-3 | 284 ± 110 | >20000 | 204 ± 49 | 109 ± 15 | 1330 | >20000 | 35 ± 5.6 | 29 ± 4.0 |
| | | | | | 1790 | | | |
| MDA-MB-231 | 121 ± 23 | >20000 | 114 ± 4 | 61 ± 4.6 | 1040 | 5900 ± 601 | 16 ± 2.8 | 14 ± 3.2 |
| | | | | | 957 | | | |
| NCI-H292 | 322 | >20000 | 192 | 102 ± 19 | 992 | >20000 | 29 | 27 ± 3.8 |
| | 395 | >20000 | 213 | | 1250 | >20000 | 41 | |
| OVCAR-3 | 188 | >20000 | >6320 | 80 | 1320 | >20000 | >2000 | 24 |
| | 251 | | >6320 | 64 | | | >20000 | >2000 | 20 |
| RPMI 8226 | 49 | >20000 | 57 | 36 | 326 | 6150 | 6.3 | 5.9 |
| | 45 | >20000 | 51 | 29 | 328 | 3460 | 6.3 | 7.1 |
| U266 | 39 | >20000 | 39 | 10 | 118 | 1620 | 4.2 | 3.2 |
| | 32 | >20000 | 34 | 9 | 111 | 1710 | 4.2 | 3.4 |
| B16-F10 | 194 | >20000 | 163 | 78 ± 11 | 1270 | 10500 | 19 | 13 ± 1.9 |
| | 180 | >20000 | 175 | | 1140 | 10300 | 36 | |

*Where n = 3, mean ± standard deviation is presented

The $EC_{50}$ values indicate that the Formulae II-2, II-4, II-5A, II-5B, II-18 and II-19 were cytotoxic against the HT-29, PC-3, MDA-MB-231, NCI-H292, RPMI 8226, U266 and B16-F10 tumor cell lines. II-2, II-5A, II-5B and II-19 were also cytotoxic against the OVCAR-3 tumor cells. Formula II-17 was cytotoxic against MDA-MB-231, RPMI 8226, U266 and B16-F10 tumor cell lines.

The data in Table 13 summarize the growth inhibitory effects of Formulae I-7, II-2, II-3, II-4, II-5A, II-5B, II-8C, II-13C, II-16, II-17, II-18, II-19, II-20, II-21, II-22, II-24C, II-25, II-26, II-28, II-29, II-30, II-31, II-32, II-38, IV-3C, II-44, VI-1A, II-47 and II-50 against the human multiple myeloma cell lines, RPMI 8226 and U266.

TABLE 13

EC$_{50}$ values of Formulae I-7, II-2, II-3, II-4, II-5A, II-5B, II-8C, II-13C, II-16, II-17, II-18, II-19, II-20, II-21, II-22, II-24C, II-25, II-26, II-28, II-29, II-30, II-31, II-32, II-38, IV-3C, II-44, VI-1A, II-47 and II-50 against RPMI 8226 and U266 cells

| Compound | RPMI 8226 EC$_{50}$ (nM) | U266 EC$_{50}$ (nM) |
|---|---|---|
| Formula I-7 | 250 | ND |
|  | 240 |  |
| Formula II-2 | 49 | 39 |
|  | 45 | 32 |
| Formula II-3 | >20000 | >20000 |
|  | >20000 | >20000 |
| Formula II-4 | 57 | 39 |
|  | 51 | 34 |
| Formula II-5A | 36 | 10 |
|  | 29 | 9 |
| Formula II-5B | 326 | 118 |
|  | 328 | 111 |
| Formula II-8C | >20000 | >20000 |
|  | >20000 | >20000 |
| Formula II-13C | >20000 | >20000 |
|  | >20000 | >20000 |
| Formula II-16 | 8.6 ± 1.9 | 4.7 ± 0.7 |
| Formula II-17 | 6150 | 1620 |
|  | 3460 | 1710 |
| Formula II-18 | 6.3 | 4.2 |
|  | 6.3 | 4.2 |
| Formula II-19 | 5.9 | 3.2 |
|  | 7.1 | 3.4 |
| Formula II-20 | 8510 ± 3260 | 310 |
|  |  | 442 |
| Formula II-21 | >20000 | 6090 |
|  | >20000 | 9670 |
| Formula II-22 | 9720 | 2860 |
|  | 11200 | 903 |
| Formula II-24C | 2320 | 1150 |
|  | 1640 | 825 |
| Formula II-25 | >20000 | >20000 |
|  | >20000 | >20000 |
| Formula II-26 | 2230 | 1300 |
|  | 1610 | 829 |
| Formula II-28 | >20000 | >20000 |
|  | >20000 | >20000 |
| Formula II-29 | 4280 | 624 |
|  | 6940 | 1420 |
| Formula II-30 | 4900 | 889 |
|  | 4160 | 1240 |
| Formula II-31 | >20000 | ND |
|  | >20000 |  |
| Formula II-32 | >20000 | ND |
|  | >20000 |  |
| Formula II-38 | 2600 | ND |
|  | 1800 |  |
| Formula IV-3C | >20000* | 7760 |
|  |  | 8290 |
| Formula II-44 | 12 | ND |
|  | 8.8 |  |
| Formula VI-1A | 8400 | ND |
|  | 7800 |  |
| Formula II-47 | 8000 ± 3400 | ND |
| Formula II-50 | 10 | ND |

Where n ≥ 3, mean EC$_{50}$ value ± standard deviation is presented;
*n = 3, standard deviation is not applicable;
ND not determined The EC$_{50}$ values indicate that Formulae II-2, II-4, II-5A, II-5B, II-16, II-17, II-18, II-19, II-20, II-22, II-24C, II-26, II-29 and II-30 were cytotoxic against RPMI 8226 and U266 cells. Formulae I-7, II-38, II-44, VI-1A, II-47 and II-50 were cytotoxic against RPMI 8226 cells. Formulae II-21 and IV-3C were cytotoxic against U266 cells.

Example 55

Growth Inhibition of MES-SA, MES-SA/Dx5, HL-60 and HL-60/MX2 Tumor Cell Lines

Human uterine sarcoma (MES-SA; CRL-1976), its multi-drug resistant derivative (MES-SA/Dx5; CRL-1977), human acute promyelocytic leukemia cells (HL-60; CCL-240) and its multidrug resistant derivative (HL-60/MX2; CRL-2257) were purchased from ATCC and maintained in appropriate culture media. The cells were cultured in an incubator at 37° C. in 5% CO$_2$ and 95% humidified air.

For cell growth inhibition assays, MES-SA and MES-SA/Dx5 cells were both seeded at $3 \times 10^3$ cells/well in 90 µl complete media into 96 well (Corning; 3904) black-walled, clear-bottom tissue culture plates and the plates were incubated overnight to allow cells to establish and enter log phase growth. HL-60 and HL-60/MX2 cells were both seeded at $5 \times 10^4$ cells/well in 90 µl complete media into 96 well plates on the day of compound addition. 20 mM stock solutions of the compounds were prepared in 100% DMSO and stored at −80° C. The compounds were serially diluted and added in triplicate to the test wells. Concentrations ranging from 6.32 µM to 2 nM were tested for II-2 and II-4. II-3 and II-17 were tested at concentrations ranging from 20 µM to 6.32 nM. Compound II-18 was tested at concentrations ranging from 2 µM to 632 pM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in Mg$^{2+}$, Ca$^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and EC$_{50}$ values (the drug concentration at which 50% of the maximal observed growth inhibition is established) were determined using a standard sigmoidal dose response curve fitting algorithm (XLfit 3.0, ID Business Solutions Ltd). Where the maximum inhibition of cell growth was less than 50%, an EC$_{50}$ value was not determined.

The multidrug resistant MES-SA/Dx5 tumor cell line was derived from the human uterine sarcoma MES-SA tumor cell line and expresses elevated P-Glycoprotein (P-gp), an ATP dependent efflux pump. The data in Table 14 summarize the growth inhibitory effects of Formulae II-2, II-3, II-4, II-17 and II-18 against MES-SA and its multidrug resistant derivative MES-SA/Dx5. Paclitaxel, a known substrate of the P-gp pump was included as a control.

TABLE 14

EC$_{50}$ values of Formulae II-2, II-3, II-4, II-17 and II-18 against MES-SA and MES-SA/Dx5 tumor cell lines

| Compound | EC$_{50}$ (nM) MES-SA | MES-SA/Dx5 | Fold change* |
|---|---|---|---|
| II-2 | 193 | 220 | 1.0 |
|  | 155 | 138 |  |
| II-3 | >20000 | >20000 | NA |
|  | >20000 | >20000 |  |
| II-4 | 163 | 178 | 0.9 |
|  | 140 | 93 |  |
| II-17 | 9230 | 9450 | 0.8 |
|  | 12900 | 7530 |  |
| II-18 | 22 | 32 | 1.2 |
|  | 17 | 14 |  |
| Paclitaxel | 5.6 | 2930 | 798 |
|  | 4.6 | 5210 |  |

*Fold change = the ratio of EC$_{50}$ values (MES-SA/Dx5 : MES-SA)

The EC$_{50}$ values indicate that II-2, II-4, II-17 and II-18 have cytotoxic activity against both MES-SA and MES-SA/Dx5 tumor cell lines. The multidrug resistant phenotype was confirmed by the observation that Paclitaxel was ~800 times less active against the resistant MES-SA/Dx5 cells.

HL-60/MX2 is a multidrug resistant tumor cell line derived from the human promyelocytic leukemia cell line, HL-60 and expresses reduced topoisomerase II activity. The data presented in Table 15 summarize the growth inhibitory effects of Formulae II-2, II-3, II-4, II-17 and II-18 against HL-60 and its multidrug resistant derivative HL-60/MX2. Mitoxantrone, the topoisomerase II targeting agent was included as a control.

TABLE 15

EC$_{50}$ values of Formulae II-2, II-3, II-4, II-17 and II-18 against HL-60 and HL-60/MX2 tumor cell lines

| Compound | EC$_{50}$ (nM) HL-60 | HL-60/MX2 | Fold change* |
|---|---|---|---|
| II-2 | 237 | 142 | 0.7 |
|  | 176 | 133 |  |
| II-3 | >20000 | >20000 | NA |
|  | >20000 | >20000 |  |
| II-4 | 143 | 103 | 0.8 |
|  | 111 | 97 |  |
| II-17 | >20000 | >20000 | NA |
| II-18 | 27 | 19 | 0.7 |
|  | 23 | 18 |  |
| Mitoxantrone | 42 | 1340 | 30.6 |
|  | 40 | 1170 |  |

*Fold change = the ratio of EC$_{50}$ values (HL-60/MX2 : HL-60)

The EC$_{50}$ values indicate that II-2, II-4 and II-18 retained cytotoxic activity against both HL-60 and HL-60/MX2 tumor cell lines. The multidrug resistant phenotype was confirmed by the observation that Mitoxantrone was ~30 times less active against the resistant HL-60/MX2 cells.

Example 56

The Effects of Formula II-16, Formula II-17, Formula II-20 and Omuralide on the Chymotrypsin-Like Activity of 20S Proteasomes in RPMI 8226 Cells RPMI 8226 (ATCC, CCL-155), the human multiple myeloma cell line, was cultured in RPMI 1640 medium supplemented with 2 mM L-glutamine, 100 units/ml penicillin, 100 µg/ml streptomycin, 1 mM sodium pyruvate and 10% heat inactivated fetal bovine serum at 37° C., 5% CO$_2$ and 95% humidified air. To evaluate the inhibitory effects on the chymotrypsin-like activity of the 20S proteasome, test compounds prepared in DMSO were appropriately diluted in culture medium and added to 2.5×10$^5$/ml RMPI 8226 cells. For Formula II-16, the final test concentrations ranged from 1 nM to 100 nM. For Formula II-17, Formula II-20 and Omuralide (Calbiochem, San Diego, Calif.), the final test concentrations ranged from 1 nM to 10 µM. DMSO was used as the vehicle control at a final concentration of 0.1%. Following 1 hr incubation of RMPI 8226 cells with the compounds, the cells were pelleted by centrifugation at 2,000 rpm for 10 sec at room temperature and washed 3× with ice-cold 1×Dulbecco's Phosphate-Buffered Saline (DPBS, Mediatech, Herndon, Va.). DPBS washed cells were lysed on ice for 15 min in lysis buffer (20 mM HEPES, 0.5 mM EDTA, 0.05% Triton X-100, pH 7.3) supplemented with protease inhibitor cocktail (Roche Diagnostics, Indianapolis, Ind.). Cell debris was pelleted by centrifugation at 14,000 rpm for 10 min, 4° C. and supernatants (=cell lysates) were transferred to a new tube. Protein concentration was determined by the BCA protein assay kit (Pierce Biotechnology, Rockford, Ill.). The chymotrypsin-like activity of the 20S proteasome was measured by using the Suc-LLVY-AMC fluorogenic peptide substrate (Boston Biochem, Cambridge, Mass.) in the proteasome assay buffer (20 mM HEPES, 0.5 mM EDTA, pH 8.0) containing a final concentration of 0.035% SDS. The reactions were initiated by the addition of 10 µL of 0.4 mM Suc-LLVY-AMC (prepared by diluting a 10 mM solution of the peptide in DMSO 1:25 with assay buffer) to 190 µL of the cell lysates and incubated in the Thermo Lab Systems Fluoroskan plate reader at 37° C. The released coumarin (AMC) was measured fluorometrically by using $\lambda_{ex}$=390 nm and $\lambda_{em}$=460 nm. The assay was performed in a microtiter plate (Corning 3904) and followed kinetically with measurements every five minutes for 2 hr. The total amount of protein used for each assay was 20 µg. The final concentration of Suc-LLVY-AMC and DMSO was 20 µM and 0.2%, respectively. Results are presented as the percent inhibition of the 20S proteasome chymotrypsin-like activity relative to the DMSO control.

Results in Table 16 show that exposure of RPMI 8226 cells to Formula II-16, Formula II-17, Formula II-20 and Omuralide resulted in inhibition of the chymotrypsin-like activity of the 20S proteasomes. Among them, Formula II-16 inhibits 85±7% of the chymotrypsin-like activity of the 20S proteasome at 5 nM. At 100 nM, Formula II-16 is able to completely inhibit the chymotrypsin-like activity of the 20S proteasome. At 100 nM, Formula II-17, Formula II-20 and Omuralide are only able to inhibit the chymotrypsin-like activity at 30±4%, 66±3% and 32±8%, respectively.

TABLE 16

Determination of the chymotrypsin-like activity of 20S proteasomes derived from RMPI 8226 cells treated with Formula II-16, Formula II-17, Formula II-20 and Omuralide

| | % inhibition of the chymotrypsin-like activity of 20S proteasomes in RPMI 8226 cell lysates (mean ± SD, n = 3) | | | | | | | |
|---|---|---|---|---|---|---|---|---|
| Compound | 10,000 nM | 1,000 nM | 500 nM | 100 nM | 50 nM | 10 nM | 5 nM | 1 nM |
| II-16 | ND | ND | ND | 98 ± 1 | 97 ± 0 | 94 ± 3 | 85 ± 7 | 30 ± 7 |
| II-17 | 65 ± 5 | 46 ± 4 | 39 ± 3 | 30 ± 4 | 26 ± 5 | 6 ± 6 | 10 ± 5 | 6 ± 6 |
| II-20 | 87 ± 4 | 73 ± 2 | 71 ± 2 | 66 ± 3 | 64 ± 3 | 37 ± 3 | 31 ± 9 | 3 ± 10 |
| Omuralide | 93 ± 1 | 80 ± 8 | 68 ± 11 | 32 ± 8 | 17 ± 11 | 4 ± 9 | 8 ± 9 | 5 ± 9 |

ND: not determined

Example 57

The Effects of Formula II-16, Formula II-17, Formula II-20 and Omuralide on the Chymotrypsin-Like Activity of 20S Proteasomes in PC-3 Cells PC-3 (ATCC, CRL-1435), the human prostate cancer cell line, was cultured in F12K medium supplemented with 2 mM L-glutamine, 100 units/ml penicillin, 100 µg/ml streptomycin and 10% heat inactivated fetal bovine serum at 37° C., 5% $CO_2$ and 95% humidified air. To evaluate the inhibitory effects on the chymotrypsin-like activity of the 20S proteasome, test compounds prepared in DMSO were appropriately diluted in culture medium and added to $1.25 \times 10^5$/ml PC-3 cells. For Formula II-16, the final test concentrations ranged from 1 nM to 50 nM. For Formula II-17, Formula II-20 and Omuralide (Calbiochem, San Diego, Calif.), the final test concentrations ranged from 1 nM to 10 µM. DMSO was used as the vehicle control at a final concentration of 0.1%. Following 1 hr incubation of PC-3 cells with the compounds, the cells were washed 3× with ice-cold 1×Dulbecco's Phosphate-Buffered Saline (DPBS, Mediatech, Herndon, Va.). DPBS washed cells were lysed on ice for 15 min in lysis buffer (20 mM HEPES, 0.5 mM EDTA, 0.05% Triton X-100, pH 7.3) supplemented with protease inhibitor cocktail (Roche Diagnostics, Indianapolis, Ind.). Cell debris was pelleted by centrifugation at 14,000 rpm for 10 min, 4° C. and supernatants (=cell lysates) were transferred to a new tube. Protein concentration was determined by the BCA protein assay kit (Pierce Biotechnology, Rockford, Ill.). The chymotrypsin-like activity of the 20S proteasome was measured by using the Suc-LLVY-AMC fluorogenic peptide substrate (Boston Biochem, Cambridge, Mass.) in the proteasome assay buffer (20 mM HEPES, 0.5 mM EDTA, pH 8.0) containing a final concentration of 0.035% SDS. The reactions were initiated by the addition of 10 µL of 0.4 mM Suc-LLVY-AMC (prepared by diluting a 10 mM solution of the peptide in DMSO 1:25 with assay buffer) to 190 µL of the cell lysates and incubated in the Thermo Lab Systems Fluoroskan plate reader at 37° C. The released coumarin (AMC) was measured fluorometrically by using $\lambda_{ex}$=390 nm and $\lambda_{em}$=460 nm. The assay was performed in a microtiter plate (Corning 3904) and followed kinetically with measurements every five minutes for 2 hr. The total amount of protein used for each assay was 20 µg. The final concentration of Suc-LLVY-AMC and DMSO was 20 µM and 0.2%, respectively. Results are presented as the percent inhibition of the 20S proteasome chymotrypsin-like activity relative to the DMSO control.

Results in Table 17 show that exposure of PC-3 cells to Formula II-16, Formula II-17, Formula II-20 and Omuralide resulted in inhibition of the chymotrypsin-like activity of the 20S proteasomes similar to results obtained from RPMI 8226 cell-based experiments. Formula II-16 inhibits 69% of the chymotrypsin-like activity of the 20S proteasome at 5 nM. At 50 nM, Formula II-16 is able to completely inhibit the chymotrypsin-like activity of the 20S proteasome. At 100 nM, Formula II-17, Formula II-20 and Omuralide inhibit the chymotrypsin-like activity at 26%, 57% and 36%, respectively.

TABLE 17

Determination of the chymotrypsin-like activity of 20S proteasomes derived from PC-3 cells treated with Formula II-16, Formula II-17, Formula II-20 and Omuralide

| | % inhibition of the chymotrypsin-like activity of 20S proteasomes in PC-3 cell lysates | | | | | | |
|---|---|---|---|---|---|---|---|
| Compound | 10,000 nM | 1,000 nM | 100 nM | 50 nM | 10 nM | 5 nM | 1 nM |
| II-16 | ND | ND | ND | 98 | ND | 69 | 19 |
| II-17 | 79 | 49 | 26 | ND | 16 | ND | ND |
| II-20 | 90 | 71 | 57 | ND | 38 | ND | ND |
| Omuralide | 90 | 80 | 36 | ND | 18 | ND | ND |

ND: not determined

Example 58

Growth Inhibition of Human Multiple Myeloma, RPMI 8226, Human Colon Adenocarcinoma, HT-29 and Murine Melanoma, B16-F10 Cells in Media Containing 1% or 10% Serum The growth inhibitory activity of Formulae II-16, II-17 and Formula II-18 against human multiple myeloma, RPMI 8226, human colon adenocarcinoma, HT-29 and mouse melanoma, B16-F10 cells in the presence of 1% or 10% fetal bovine serum (FBS) was determined.

RPMI 8226 (CCL-155), HT-29 (HTB-38), and B16-F10 (CRL-6475) cells were purchased from ATCC. RPMI 8226 cells were maintained in RPMI 1640 media supplemented with 10% (v/v) FBS, 2 mM L-glutamine, 1 mM sodium pyruvate and Penicillin/Streptomycin at 100 IU/ml and 100 µg/ml, respectively. HT-29 cells were maintained in McCoys 5A supplemented with 10% (v/v) FBS, 2 mM L-glutamine, 1 mM sodium pyruvate, 1% (v/v) non-essential amino acids, 10 mM HEPES and Penicillin/Streptomycin at 100 IU/ml and 100 µg/ml, respectively. B16-F10 cells were maintained in DMEM supplemented with 10% (v/v) FBS, 2 mM L-glutamine, 10 mM HEPES and Penicillin/Streptomycin at 100 IU/ml and 100 µg/ml, respectively. The cells were cultured in an incubator at 37° C. in 5% $CO_2$ and 95% humidified air.

For cell growth inhibition assays, HT-29 and B16-F10 cells were seeded $5 \times 10^3$, and $1.25 \times 10^3$ cells/well respectively in 90 µl media containing 10% (v/v) FBS or 1% (v/v) FBS into 96 well (Corning; 3904) black-walled, clear-bottom tissue culture plates. The plates were incubated overnight to allow cells to establish and enter log phase growth. RPMI 8226 cells were seeded at $2 \times 10^4$ cells/well in 90 µl RPMI media containing 10% (v/v) FBS or 1% (v/v) FBS into 96 well black-walled, clear-bottom tissue culture plates. 20 mM stock solutions of Formulae II-16, II-17 and Formula II-18 were prepared in 100% DMSO, aliquoted and stored at −80° C. Formulae II-16, II-17 and Formula II-18 were serially diluted in media containing 1% or 10% FBS and added in triplicate to the test wells. The final concentration of Formula II-16 ranged from 2 µM to 200 pM. The final concentration range of Formula II-17 was from 20 µM to 6.3 nM. The final concentration of Formula II-18 ranged from 2 µM to 630 pM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}=535$ nm and $\lambda_{em}=590$ nm filters. Resazurin dye in medium without cells was used to determine the background, which was subtracted from the data for all experimental wells. The data were normalized to the average fluorescence of the cells treated with media +0.25% DMSO (100% cell growth) and $EC_{50}$ values (the drug concentration at which 50% of the maximal observed growth inhibition is established) were determined using a standard sigmoidal dose response curve fitting algorithm (generated by XLfit 3.0, ID Business Solutions Ltd).

The data in Table 17 summarize the growth inhibitory effects of Formulae II-16, II-17 and Formula II-18 against the human multiple myeloma cell line, RPMI 8226 in media containing 1% or 10% FBS.

TABLE 17

$EC_{50}$ values of Formulae II-16, II-17 and Formula II-18 against RPMI 8226 cells in media containing 1% or 10% FBS

| Compound | 1% FBS, $EC_{50}$ (nM) | 10% FBS, $EC_{50}$ (nM) |
|---|---|---|
| II-16 | 6.2 | 12 |
|  | 6.8 | 9.6 |
| Mean | 6.5 | 11 |
| II-17 | 1100 | 3000 |
|  | 1300 | 2300 |
| Mean | 1200 | 2700 |
| II-18 | 15 | 20 |
|  | 13 | 20 |
| Mean | 14 | 20 |

The $EC_{50}$ values indicate that Formulae II-16, II-17 and Formula II-18 were cytotoxic against RPMI 8226 cells in media containing 1% or 10% FBS. There was a less than three fold decrease in the mean $EC_{50}$ of Formulae II-16, II-17 and Formula II-18 when tested in media containing 10% FBS relative to media containing 1% FBS.

The data in Table 18 summarize the growth inhibitory effects of Formula II-16 against the human colon adenocarcinoma, HT-29 and the murine melanoma, B16-F10 cell lines in media containing 1% or 10% FBS.

TABLE 18

Mean $EC_{50}$ values of Formula II-16 against HT-29 and B16-F10 cells in media containing 1% or 10% FBS

| Com-pound | HT-29, $EC_{50}$ (nM) mean ± SD | | B16-F10, $EC_{50}$ (nM) mean ± SD | |
|---|---|---|---|---|
|  | 1% FBS | 10% FBS | 1% FBS | 10% FBS |
| II-16 | 16 ± 5 | 23 ± 10 | 18 ± 9 | 13 ± 1 |

The mean $EC_{50}$ values indicate that Formula II-16 was cytotoxic against HT-29 and B16-F10 cells in media containing 1% or 10% FBS. There was a less than two fold decrease in the mean $EC_{50}$ of Formula II-16 when tested in media containing 10% FBS relative to media containing 1% FBS. Taken together, these data show that with respect to the in vitro cytotoxic activity against tumor cell lines, Formulae II-16, II-17 and Formula II-18 maintain similar biological activity in the presence of 1% or 10% FBS.

Example 59

Inhibition of Anthrax Lethal Toxin

Anthrax toxin is responsible for the symptoms associated with anthrax. In this disease, *B. anthracis* spores are inhaled and lodge in the lungs where they are ingested by macrophages. Within the macrophage, spores germinate, replicate, resulting in killing of the cell. Before killing occurs, however, infected macrophages migrate to the lymph nodes where, upon death, they release their contents, allowing the organism to enter the bloodstream, further replicate, and secrete lethal toxins.

Two proteins called protective antigen (PA 83 kDa) and lethal factor (LF, 90 kDa), play a key role in the pathogenesis of anthrax. These proteins are collectively known as lethal toxin (LeTx). When combined, PA and LF cause death when injected intravenously in animals. Lethal toxin is also active in a few cell culture lines of macrophages causing cell death within a few hours. LeTx can induce both necrosis and apoptosis in mouse macrophage-like RAW264.7 cells upon in vitro treatment.

In Vitro Cell-Based Assay for Inhibitors of Lethal Toxin-Mediated Cytotoxicity

RAW264.7 cells (obtained from the American Type Culture Collection) were adapted to and maintained in RPMI-1640 medium supplemented with 10% fetal bovine serum, 2 mM L-glutamine and 1% Penicillin/Streptomycin (complete medium) at 37° C. in a humidified 5% $CO_2$ incubator. For the assay, cells were plated overnight in complete medium at a concentration of 50,000 cells/well in a 96-well plate. Media was removed the following day and replaced with serum-free complete medium with or without varying concentrations of Formulae II-2, II-3, II-4, II-5A, II-5B, II-13C, II-17, II-18 and IV-3C starting at 330 nM and diluting at ½ log intervals for an 8-point dose-response. After a 45 minute preincubation, 1 μg/ml LF and 1 μg/ml PA alone or in combination (LF:PA, also termed lethal toxin (LeTx)) were added to cells. Recombinant LF and PA were obtained from List Biological Laboratories. Additional plates with no LeTx added were included as a control. Cells were then incubated for six hours followed by addition of 0.02 mg/ml resazurin dye (Molecular Probes, Eugene, Oreg.) prepared in Mg++, Ca++ free PBS (Mediatech, Herndon, Va.). Plates were then incubated an additional 1.5 hours prior to the assessment of cell viability. Since resazurin is metabolized by living cells, cytotoxicity or cell viability can be assessed by measuring fluorescence using 530 excitation and 590 emission filters. Data are expressed as the percent viability as compared to a DMSO alone control (high) and the LeTx alone control (low) using the following equation: Percent viability=100*((Measured OD−low control)/(high control−low control)).

Inhibition of Anthrax Lethal Toxin-Mediated Cytotoxicity in RAW 264.7 Cells

Data in FIG. 48 summarize the effects of Formula II-2, Formula II-3 and Formula II-4 against LeTx-mediated cytotoxicity of the RAW 264.7 murine macrophage-like cell line. Treatment of RAW 264.7 cells with Formula II-2 and Formula II-4 resulted in an increase in the viability of LeTx treated cells with $EC_{50}$ values of 14 nM (FIG. 48). The $EC_{50}$ values for Formula II-3 for LeTx protection was not be determined at the concentrations tested ($EC_{50}$>330 nM, the maximum concentration evaluated). Data in Table 19 show the effects of Formulae II-5A, II-5B, II-13C, II-17, II-18 and IV-3C against LeTx-mediated cytotoxicity of the RAW 264.7 murine macrophage-like cell line. Treatment of RAW 264.7 cells with Formula II-5A and II-18 showed an increase in the viability of LeTx treated RAW 264.7 cells with $EC_{50}$ values of 3 nM and 4 nM respectively. Treatment with Formula II-17 and Formula II-5B resulted in an increase in the viability of LeTx treated cells with $EC_{50}$ values of 42 nM and 45 nM respectively. The $EC_{50}$ values for Formulae II-13C and IV-3C for LeTx protection could not be determined at the concentrations tested ($EC_{50}$>330 nM, the maximum concentration evaluated).

TABLE 19

$EC_{50}$ values for inhibition of RAW 264.7 cell cytotoxicity mediated by anthrax lethal toxin

| Compound | $EC_{50}$ (nM) |
|---|---|
| Formula II-17 | 42 |
| Formula II-18 | 4 |
| Formula II-5A | 3 |
| Formula II-5B | 45 |
| Formula II-13C | >330 nM |
| Formula IV-3C | >330 nM |

Example 60

Structure-Activity Relationship of the $R_1$ Side Chain

A structure-activity relationship for the $R_1$ side chain of the disclosed compounds and specifically the compounds of Formulas (I), (II), (III), (IV), and (V) was inferred by analyzing the relative activity of various compounds having the formula:

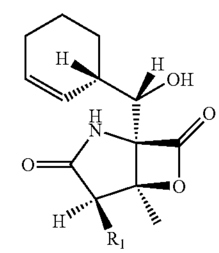

These compounds were assayed for cytotoxicity of RPMI cells and for inhibition of NF-κB and the chymotrypsin-, trypsin-, and caspase-like activities of the 20S proteasome. The results of 6 representative compounds are presented in Table 20.

TABLE 20

$EC_{50}$ values for compounds having varying $R_1$ groups

| Compound | $R_1$ | Cytotoxicity RPMI $EC_{50}$ (nM) | NF-κB $EC_{50}$ (nM) | Proteasome Chymotrypsin-like $EC_{50}$ (nM) | Proteasome Trypsin-like $EC_{50}$ (nM) | Proteasome Caspase-like $EC_{50}$ (nM) |
|---|---|---|---|---|---|---|
| II-16 | $CH_2CH_2Cl$ | 8.6 ± 1.9 | 11 ± 3 | 2.6 ± 0.2 | 21 ± 2.6 | 427 ± 61 |
| II-18 | $CH_2CH_2Br$ | 6.3, 6.3 | 11, 9 | 2.3, 2 | 14, 14 | 286, 213 |
| II-19 | $CH_2CH_2I$ | 6, 7 | 10, 7 | 3, 3 | 13, 15 | 573, 739 |
| II-17 | $CH_2CH_3$ | 6150, 3460 | 960 ± 210 | 26 ± 6.7 | 573, 602 | 1247, 1206 |
| II-20 | $CH_3$ | 8510 ± 3260 | 849 ± 225 | 7.7 ± 3.0 | 318, 321 | 1425, 1420 |
| II-21 | $CH_2CH_2OH$ | >20000, >20000 | 3172, 2707 | 7, 8 | 720, 879 | 2585, 2328 |

The results of the above assays can be interpreted to suggest that compounds having $R_1$ groups of chloroethyl, bromoethyl, or iodoethyl are potent inhibitors of proteasome and exhibit very potent cytotoxicity. In contrast, compounds having $R_1$ groups of methyl, ethyl, or hydroxyethyl exhibited relatively lower cytotoxicity (3-log decrease in potency), lower NF-κB inhibition (3-log decrease in potency), and a lower caspase-like (2 to 10 fold less potent) and trypsin-like (20 to 50 fold less potent) proteasome inhibition.

Without being bound to any particular theory, the Applicants note that the above results support the hypothesis that the increased activity of compounds containing Cl, Br, or I in the $R_1$ group can be due to the halogen's property of being a good leaving group. This hypothesis is supported by the fact that lactone ring opening of compound II-16 is observed to form a cyclic ether through nucleophilic substitution where chlorine is displaced according to the following reaction:

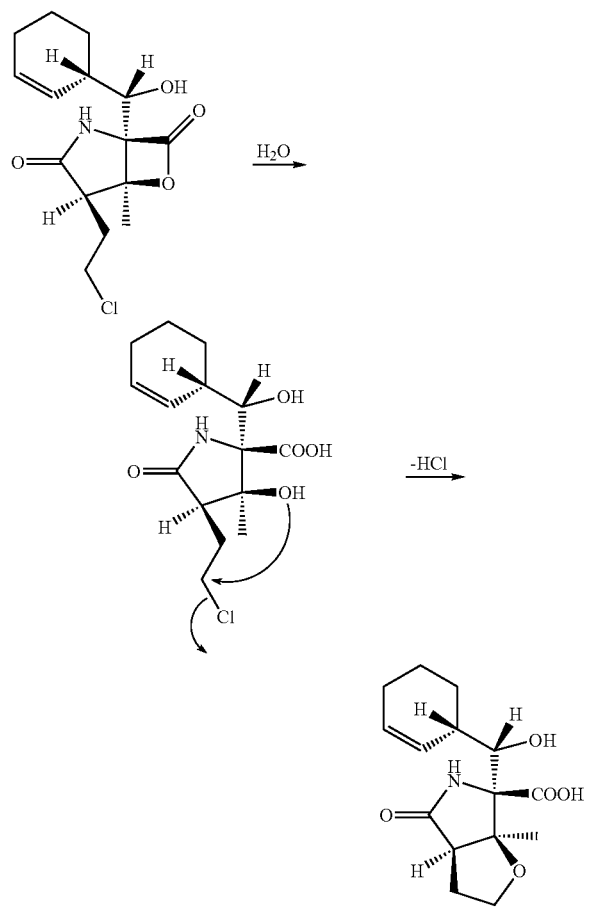

It is hypothesized that in compounds having a good leaving group in the $R_1$ side chain, such as compounds II-16, II-18, and II-19, nucleophilic addition of the proteasome to the β-lactone ring forms a cyclic ether in a manner similar to the above reaction. The cyclic ether is hypothesized to interact favorably with the proteasome.

Without being bound to any particular theory, the Applicants note that the above results also support the alternative hypothesis that a second nucleophile on the proteasome displaces the leaving group, thus forming a 2-point covalent adduct between the compound and the enzyme. In either case, leaving group functionality on the $R_1$ side chain promotes increased interaction between the compound and the enzyme and thus promotes increased activity. Therefore, compounds having other leaving groups on the $R_1$ side chain can be expected to exhibit high activity.

Without being bound to any particular theory, the Applicants note that the above results also support the hypothesis of a single-point leaving group. As one example, the presence of a halogen or other leaving group in the $R_1$ side chain promotes the delivery of the compound to its target, such as an intracellular or other biological target, thereby enhancing its therapeutic effect. An example of a single-point leaving group is illustrated in the diagram shown below.

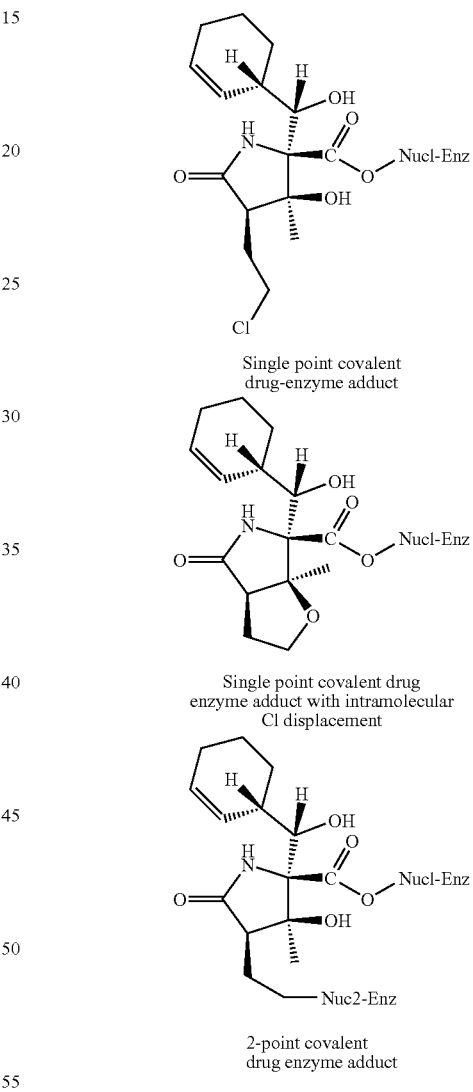

"Leaving groups" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of a strong acid. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5th ed., John McMurry (2000), pages 398 and 408; all of which are incorporated herein by reference in their entirety.

Example 61

Structure Activity Relationships

The data set forth in the above-listed Tables illustrate a number of preferred embodiments. With regard to Formula II, compounds having a halogenated substituent at $R_1$ are preferred and such compounds are generally equipotent across the above-described assays. Most preferred are n-halogenated ethyl at $R_1$.

Also, most preferred are compounds with a hydroxy group at $E_5$ and the attached carbon is in an S conformation (compounds having the stereochemistry of compound II-18, for example). Oxidation from a hydroxyl group to a ketone is less preferred.

In one preferred embodiment, the preferred substituent at $R_4$ is cyclohexene. In another preferred embodiment, the cyclohexene is oxidized to an epoxide. Less preferred are compounds with hydrogenation of the double bond of the cyclohexene substituent.

Furthermore in some embodiments, preferably, $R_3$ is methyl, with ethyl being less preferred.

Example 62

Inhibition of Angiogenesis

Angiogenesis is an important physiological process, without which embryonic development and wound healing would not occur. However, excessive or inappropriate angiogenesis is associated with a number of diseases, conditions, and adverse treatment results. Examples of disease types and conditions associated with excessive angiogenesis include inflammatory disorders such as immune and non-immune inflammation, rheumatoid arthritis, chronic articular rheumatism and psoriasis; disorders associated with inappropriate or inopportune invasion of vessels such as diabetic retinopathy, neovascular glaucoma, retinopathy of prematurity, macular degeneration, corneal graft rejection, retrolental fibroplasia, rubeosis, capillary proliferation in atherosclerotic plaques and osteoporosis; and cancer associated disorders, including for example, solid tumors, tumor metastases, blood born tumors such as leukemias, angiofibromas, Kaposi sarcoma, benign tumors such as hemangiomas, acoustic neuromas, neurofibromas, trachomas, and pyogenic granulomas, as well as other cancers which require neovascularization to support tumor growth. Additional examples of angiogenesis-dependent diseases include, for example, Osler-Webber Syndrome; myocardial angiogenesis; plaque neovascularization; telangiectasia; hemophiliac joints and wound granulation. Furthermore, excessive angiogenesis is also associated with clinical problems as part of biological and mechanical implants (tissue/organ implants, stents, etc.). The instant compositions can be used to inhibit angiogenesis, and thus in the treatment of such conditions. Other diseases in which angiogenesis plays a role, and to which the instant compounds and compositions can be used, are known by those of skill in the art.

Particular discussion of angiogenesis in a number of pathophysiological conditions such as cancer, rheumatoid arthritis, diabetic retinopathy, age related macular degeneration, endometriosis and obesity is found in Folkman J. (1985) Tumor angiogenesis. Adv Cancer Res. 1985; 43:175-203; Folkman, J. (2001). Angiogenesis-dependent diseases. *Semin Oncol*, 28, 536-42; Grosios, K., Wood, J., Esser, R., Raychaudhuri, A. & Dawson, J. (2004). Angiogenesis inhibition by the novel VEGF receptor tyrosine kinase inhibitor, PTK787/ZK222584, causes significant anti-arthritic effects in models of rheumatoid arthritis. *Inflamm Res*, 53, 133-42; Hull, M. L., Charnock-Jones, D. S., Chan, C. L., Bruner-Tran, K. L., Osteen, K. G., Tom, B. D., Fan, T. P. & Smith, S. K. (2003). Antiangiogenic agents are effective inhibitors of endometriosis. *J Clin Endocrinol Metab*, 88, 2889-99; Liu, L. & Meydani, M. (2003). Angiogenesis inhibitors may regulate adiposity. *Nutr Rev*, 61, 384-7; Mousa, S. A. & Mousa, A. S. (2004). Angiogenesis inhibitors: current & future directions. *Curr Pharm Des*, 10, 1-9. Each of the above-described references is incorporated herein by reference in its entirety.

The compounds disclosed herein inhibit angiogenesis. This is evidenced, for example, by the compound of Formula II-16 which blocked vascular endothelial growth-factor (VEGF)-induced migration of multiple myeloma cells in a transwell migration assay. The other compounds disclosed herein are tested in a transwell migration assay and inhibit migration.

The compounds disclosed herein show angiogenesis inhibitory activity in any of various other angiogenesis tests and assays, including one or more of the following.

The compounds disclosed herein show anti-angiogenic activity in various other in vitro and in vivo assays. Some examples include: in vitro assays for the evaluation of anti-angiogenesis compounds include, 1) the modified Boyden chamber assay which assesses the migration of endothelial cells in response to pro-angiogenic factors (Alessandri G, Raju K, Gullino P M. (1983), "Mobilization of capillary endothelium in vitro induced by effectors of angiogenesis in vivo" Cancer Res. 43(4):1790-7.), 2) differentiation assays such as the Matrigel assay in which the attachment, migration and differentiation of endothelial cells into tubules is analyzed (Lawley T J, Kubota Y. (1989), "Induction of morphologic differentiation of endothelial cells in culture" J Invest Dermatol. August; 93(2 Suppl):59S-61S) and 3) organ culture assays in which the outgrowth of endothelial (and other cells) is monitored (Nicosia R F, Ottinetti A. (1990), "Growth of microvessels in serum-free matrix culture of rat aorta. A quantitative assay of angiogenesis in vitro" Lab Invest. July; 63(1):115-22.). Some in vivo assays for the evaluation of angiogenesis inhibitors are 1) sponge implantation assays, during which sponges containing cells and/or angiogenic factors and the test substance are implanted subcutaneously in animals for study of in vivo angiogenesis (Plunkett M L, Hailey J A. (1990), "An in vivo quantitative angiogenesis model using tumor cells entrapped in alginate" Lab Invest. 1990 April; 62(4):510-7), 2) the chick chorioallantoic membrane assay in which test compounds are inserted through a window, cut in the eggshell. The lack of a mature, immune system in the 7-8 day old chick embryo allows for the study of tumor-induced angiogenesis (Folkman J. (1985) "Tumor angiogenesis" Adv Cancer Res. 1985; 43:175-203.) and 3) various tumor models in which specific histological analyses can be used to examine the effect on blood vessels, such as vascular density (CD31/CD34 staining), blood flow and concomitant tumor necrosis/apoptosis (TUNEL staining). In vitro assay examples include endothelial cell tests (HUVEC (human umbilical vein endothelial cell), aortic, capillary); endothelial cell proliferation assays; endothelial cell DNA synthesis assays; endothelial cell outgrowth assays (Aortic ring); endothelial cell migration assays (mentioned above; chemokinesis (colloidal gold), chemotaxis (Boyden chamber)); endothelial cell tube formation assays; endothelial apoptosis assays; endothelial cell viability assays (trypan blue);

angiogenesis factor-transfected endothelial cell lines; and magnetized microbeads on endothelial cells. Each of the references in this paragraph is incorporated herein by reference in its entirety.

Examples of in vivo assays include transparent chamber tests (e.g., rabbit ear, hamster cheek, cranial window, and dorsal skin); matrix implants (e.g., subcutaneous injection using sodium alginate, subcutaneous disc (polyvinyl foam implant), rat dorsal air sac, sponge implant); cornea micropocket assays, for example in rabbits and other rodents; anterior eye/iris chamber implant assays, mice and knock-out assays; ameroid constriction (heart) in pig and dog; rabbit hindlimb ischemia tests; vascularization into tissue (intradermal inoculation, peritoneal cavity/omentum with implant; tumor implants, for example in rabbits, mice or rats.

Also, ex vivo assays are performed using the disclosed compounds. Examples include CAM (chick chorioallantoic membrane assay) and vertical CAM with polymer gel. Immunoassays such as serum assays, urine assays cerebrospinal fluid assays and tissue immunohistochemical assays.

Some of the above assays are described in the following papers, each of which is incorporated herein by reference in its entirety. Grant et al., In Vitro Cell Dev. Biol. 27A:327-336 (1991); Min et al., Cancer Res. 56:2428-2433 (1996); Schnaper et al., J. Cell. Physiol. 165:107-118 (1995); Schnaper et al., J. Cell. Physiol. 165:107-118 (1995); Oikawa et al., Cancer Lett. 59:57-66 (1991).

Embodiments relate to methods of using the compounds and compositions described herein, alone or in combination with other agents, to inhibit angiogenesis and to treat or alleviate diseases and conditions associated with excessive or inappropriate angiogenesis. Preferably, the inhibition occurs in connection with vascularization in connection with a disease associated with angiogenesis, such as cancer or any of the other diseases described above, and those that are known by those of skill in the art. The compounds and compositions can be delivered in an appropriate inhibitory amount. Inhibitory amount is intended to mean an amount of a compound or composition required to effect a decrease in the extent, amount or rate of neovascularization when administered to a tissue, animal or individual. The dosage of compound or composition required to be therapeutically effective will depend, for example, on the angiogenesis-dependent disease to be treated, the route and form of administration, the potency and big-active half-life of the molecule being administered, the weight and condition of the tissue, animal or individual, and previous or concurrent therapies. The appropriate amount application of the method can be determined by those skilled in the art, using the guidance provided herein. For example, the amount can be extrapolated from in vitro or in vivo angiogenesis assays described above. One skilled in the art will recognize that the condition of the patient needs to be monitored throughout the course of therapy and that the amount of the composition administered can be adjusted accordingly.

The present compounds and compositions can be and are used as well in conjunction with other angiogenesis inhibitors. Angiogenic inhibitors are known in the art and can be prepared by known methods. For example, angiogenic inhibitors include integrin inhibitory compounds such as alpha-V-beta-3 ($\alpha V \beta 3$). integrin inhibitory antibodies, cell adhesion proteins or functional fragments thereof which contain a cell adhesion binding sequence. Additional angiogenic inhibitors include, for example, angiostatin, functional fragments of angiostatin, endostatin, fibroblast growth factor (FGF) inhibitors, FGF receptor inhibitors, VEGF inhibitors, VEGF receptor inhibitors, vascular permeability factor (VPF) inhibitors, VPF receptor inhibitors, thrombospondin, platelet factor 4, interferon-alpha, interferon-gamma, interferon-inducible protein 10, interleukin 12, gro-beta, and the 16 kDa N-terminal fragment of prolactin, thalidomide, and other mechanisms for the inhibition of angiogenesis.

Thus, the methods can include the step of administering a compound or composition to an animal suffering from a condition associated with excessive angiogenesis. The methods can further include administering the instant compound or composition along with another anti-angiogenesis drug or along with other therapies for the condition be treated (e.g., with a chemotherapeutic or immunotherapeutic to treat cancer).

The compounds or compositions can be delivered in any disease and/or patient appropriate manner. Examples include, intravenous, oral, intramuscular, intraocular, intranasal, intraperatoneal, and the like.

The following references provide additional teaching regarding methods of using, administering and assaying for angiogenesis inhibition: Angiogenesis Protocols (Methods in Molecular Medicine) by J. Clifford Murray, Humana Press (Mar. 15, 2001) ISBN: 0896036987; Tumour Angiogenesis, by R. J. Bicknell, Claire E. Lewis, Napoleone Fe, Oxford University Press (Sep. 1, 1997) ISBN: 0198549377; and Angiogenesis in Health and Disease: Basic Mechanisms and Clinical Applications, by Gabor M. Rubanyi, Marcel Dekker (Nov. 1, 1999) ISBN: 0824781023. Each book is incorporated herein by reference in its entirety. In particular the protocols and methods are incorporated herein.

Example 63

Formulation to be Administered Orally or the Like

A mixture obtained by thoroughly blending 1 g of a compound obtained and purified by the method of the embodiment, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

Example 64

Propionate and Butyrate Feeding Studies

Feeding studies using [1-$^{13}$C] propionate and [U-$^{13}$C$_4$] butyrate were carried out. Salinosporamde A and analogs were purified from crude extracts obtained from both feeding studies, and the pure compounds were analyzed by LC-MS, $^1$H and $^{13}$C NMR.

General Fermentation Protocol

Revival into the first seed stage occurs by either thawing one (1×) NPS021184 and inoculating one (1×) sterile culture tube containing 11 mL sterile SD02 medium (8 g glucose, 6 g Hy Soy, 6 g Yeast Extract, 30 g Instant Ocean) with either all or 0.5 mL of the thawed culture (Method A) or thawing two (2×) NPS021184 and emptying their contents into one (1×) 500 mL Erlenmeyer flask containing 100 mL sterile SD02 medium (Method B). The first seed culture is then shaken at 250 rpm and 28° C. for 72 hours and then crossed into second seed. The second seed is crossed by taking 5 mL of the grown 1st seed culture and using it to inoculate one or multiple second seed flasks—500 mL Erlenmeyer flasks containing 100 mL sterile SD02 media. The second seed culture is allowed to grow for 48 hours under the same conditions as the first seed.

Roughly 48 hours after inoculation into the second seed, the cultures are crossed into production. The crossing is similar as when crossing to the second seed, however the production media flasks contain sterile SHY 10.4.4 media (10 g starch, 4 g Hy Soy, 46 yeast extract, 1 g calcium carbonate, 40 mg $Fe_3(SO_4)_3$, 40 mg KBr, 30 g Instant Ocean) instead of SD02.

At 47 hrs after inoculation into production, the biosynthetic substrate is added to the culture, and returned to the shaker for 1 hr. After 1 hr (at 48 hours after inoculation into the production flasks), 7 mL pre-treated sterile XAD-7 resin slurry is added to each flask of production culture. The cultures are then left undisturbed on the shaker (same shaking conditions) and harvested at various time points to determine productivity.

General Extraction Protocol 3.5 mL of the fermentation culture is mixed with equal volumes of EtOAc in an extraction tube. The mixture is shaken on the rotisserie shaker for 1 hr. 1 mL of the extract was removed and dried (under nitrogen or in vacuo) in an HPLC vial. The dried extract is resuspended with 320 μL DMSO and run on an HPLC.

Unlabeled Biosynthesis Studies

Preliminary studies were conducted to establish the concentrations of substrate tolerated by the microbe, and the concentrations at which production of analogs of interest would be optimally generated. Table 20 indicates concentrations of sodium propionate tested and Table 21 indicates the concentrations of sodium butyrate tested.

TABLE 20

The concentration effects of sodium propionate (3-carbon unit)
Sodium propionate concentration (wt %)

0.025% Sodium propionate
0.01% Sodium propionate
0.05% Sodium propionate
0.1% Sodium propionate
Control, no addition

TABLE 21

The concentration effects of sodium butyrate (4-carbon unit) and valeric acid (5-carbon unit)

| Condition | Amount added per 100 ml culture | Final concentration |
|---|---|---|
| CTL | — | No addition |
| 0.025% butyrate | 25 mg butyrate | 0.025% butyrate |
| 0.05% butyrate | 50 mg butyrate | 0.05% butyrate |
| 0.1% butyrate | 100 mg butyrate | 0.1% butyrate |
| 0.025% valerate | 0.5 mL stock | 0.025% valeric acid |
| 0.05% valerate | 1 mL stock | 0.05% valeric acid |
| 0.1% valerate | 2 mL stock | 0.1% valeric acid |

Table 22 indicates the concentrations of Salinosporamide A and various analogs produced by the indicated amounts of sodium propionate. Table 23 indicates the change in production of Salinosporamide A relative to the controls.

TABLE 22

Sodium propionate concentration effect on NPI-0052 and Analogs

| Propionate concentration | Max Titers (mg/L) | | | | |
|---|---|---|---|---|---|
| | II-16 | II-17 | II-26 | II-20 | aII-28 |
| 0% | 222.26 | 21.34 | 10.46 | 0.90 | 0.00 |
| 0.01% | 222.63 | 18.10 | 10.31 | 2.17 | 0.56 |
| 0.025% | 214.87 | 21.98 | 7.81 | 3.03 | 0.85 |
| 0.05% | 186.71 | 26.50 | 6.98 | 4.81 | 1.45 |
| 0.1% | 176.76 | 28.60 | 7.62 | 4.33 | 1.23 |

Note that all analog estimations are based on the relative ratios to the Salinosporamide A (II-16) production titer. Note also that these are all average values of each condition in duplicate.

TABLE 23

% Change in production of Salinosporamide A and analogs relative to the controls.

| Propionate concentration | % Inhibition (−) or % Increase (+) | | | | |
|---|---|---|---|---|---|
| | II-16 | II-17 | II-26 | II-20 | II-28 |
| 0 (Control) | — | — | — | — | — |
| 0.01% | +0.2 | −15.2 | −7.2 | +141.1 | +>460.0 |
| 0.025% | −3.3 | +3.0 | −29.7 | +236.7 | +>750.0 |
| 0.05% | −16.0 | +24.2 | −37.1 | +434.4 | +>1351.1 |
| 0.10% | −20.5 | +34.1 | −31.4 | +381.1 | +>1129.2 |

Note that because there was no detectable II-28 in the unfed (control) condition, the % increase values for II-28 were obtained by assuming II-28 is present in <0.1 mg/L.

There was a significant increase in the production of II-20 (>400% increase) and II-28 (>1300% increase) when propionate was added to the production culture. The production of II-20 and II-28 increased in general with increasing concentrations of propionate. The above findings support that propionate (a 3-carbon unit) is a direct biosynthetic precursor for II-20 and II-28. The best production of II-20 and II-28 occurred when propionate was fed to a final concentration of ~0.05% in the production culture. Production of II-17 generally increased with increasing concentrations of propionate, but the increase in II-17 is very minor at about 31%. Therefore, propionate is not a direct biosynthetic precursor for II-17. The increase in II-17 may be due to the increase in the intracellular four-carbon pool such as butyric acid pool that can be derived from propionate. Propionate inhibited the production of Salinosporamide A (20.5% inhibition at 0.1% propionate) and II-26 (37.1% inhibition at 0.05% propionate). This finding suggested that the three-carbon propionate competes with the chlorinated four-carbon unit into the "core" for the production of Salinosporamide A and II-26.

Figure 62:
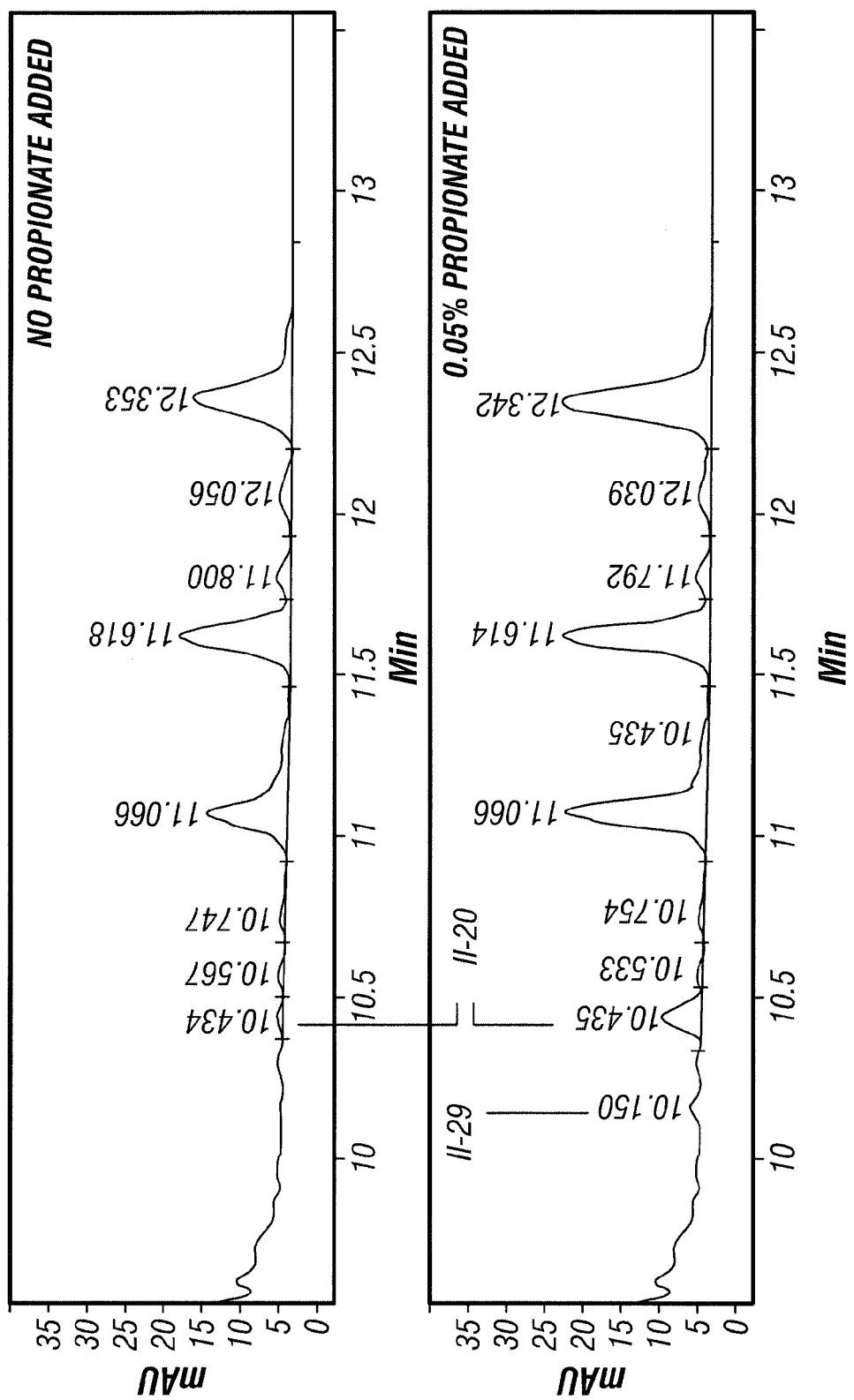
FIG. 62 depicts HPLC spectra comparing propionate fed and non-proprionate fed fermentation products.

FIG. 62 illustrates how propionate affected the production of compounds II-20 and II-28. When propionate was not added, levels of II-20 were barely detectable and II-29 was not detectable. The addition of propionate to a final concentration of 0.05% resulted in a dramatic increase in the production of II-20 and II-29. The range of propionate addition was thus established to be between 0.05% and 0.1% for optimal II-20 and II-29 production.

Table 24 indicates the concentrations of Salinosporamide A and various analogs produced by the indicated amounts of sodium butyrate as well as the change in production of Salinosporamide A relative to the controls.

TABLE 24

Sodium butyrate concentration effect

| Butyrate concentration | Max Titers (mg/L) | | | | % Increase (+) or % Inhibition (−) | | | |
|---|---|---|---|---|---|---|---|---|
| | II-16 | II-17 | II-26 | II-30 | II-16 | II-17 | II-26 | II-30 |
| 0% | 278.55 | 11.94 | 6.59 | 0.90 | — | — | — | — |
| 0.025% | 211.28 | 32.73 | 5.73 | 0.75 | −24.1 | 174.1 | −13.1 | −16.5 |
| 0.05% | 218.83 | 47.17 | 5.07 | 0.88 | −21.4 | 295.1 | −23.1 | −2.6 |
| 0.1% | 207.05 | 49.91 | 4.89 | 0.76 | −25.7 | 318.0 | −25.7 | −15.6 |

With the addition of butyrate, the production of II-17 increased dramatically by >300%, suggesting that butyrate (four carbon unit) is a direct biosynthetic precursor for II-17. Butyrate also suppressed the production of Salinosporamide A and II-26 by the similar extent of 25%. This finding indicated that the four carbon butyric acid competes with the chlorinated four-carbon unit into the "core" for the production of Salinosporamide A and II-26. Butyric acid also inhibited the production of II-30, which requires the incorporation of the 5-carbon unit such as valeric acid.

Figure 63:
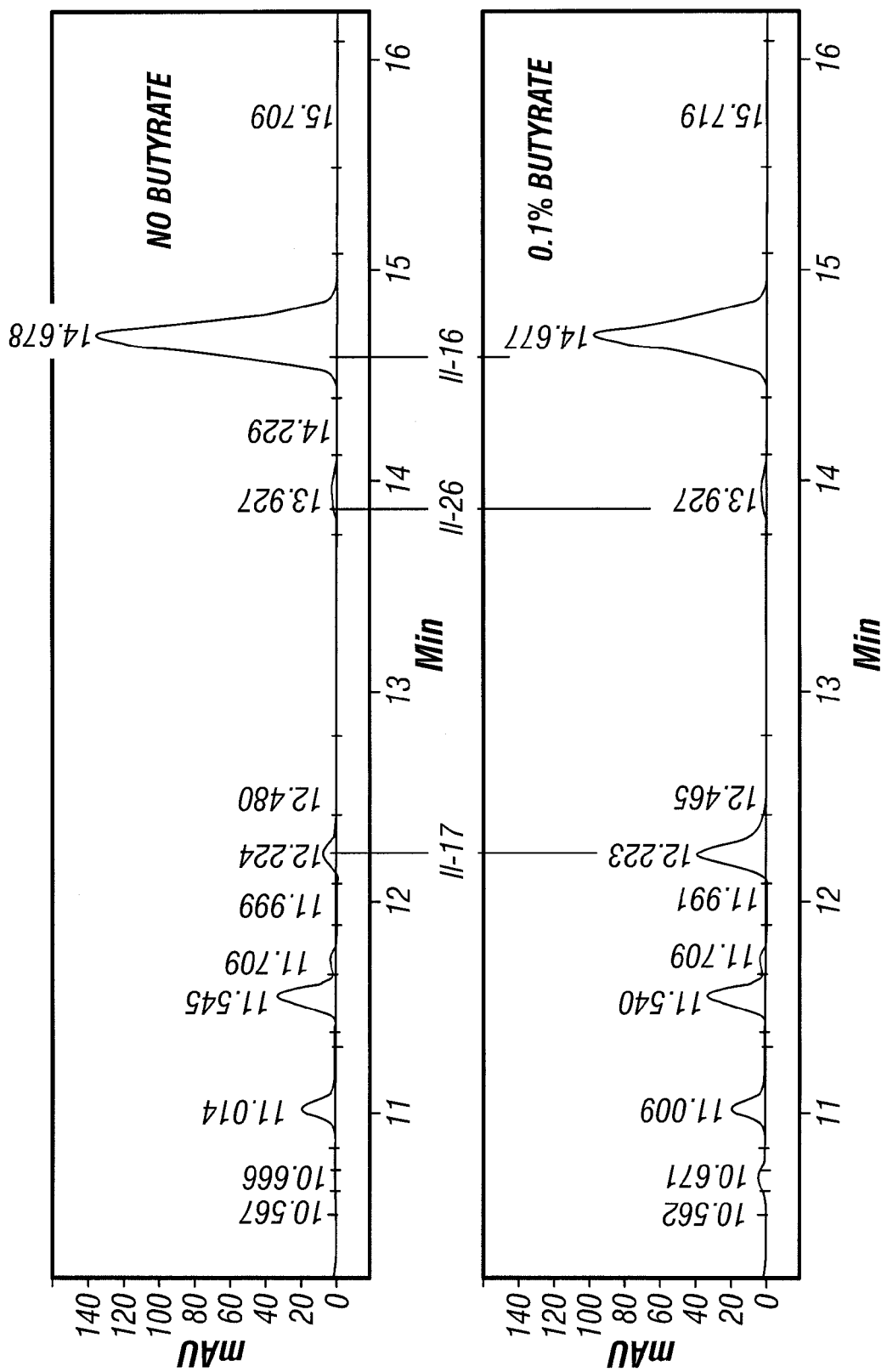
FIG. 63 depicts HPLC spectra comparing butyrate fed and non-butyrate fed fermentation products.

The increase in II-17 production is illustrated in FIG. 63. When no butyrate was added, the II-17 peak was only about one third to one half the size of when butyrate was added. Also note the suppression of the Salinosporamide A and II-26 peaks.

Table 25 indicates the concentrations of Salinosporamide A and various analogs produced by the indicated amounts of valeric acid as well as the change in production of Salinosporamide A relative to the controls.

similar to the chlorinated four carbon unit for the incorporation into II-16. Another possible explanation is the substrate specificity of the enzyme for the incorporation of different carbon units into the "core" can explain the different rates of incorporation.

Figure 64:
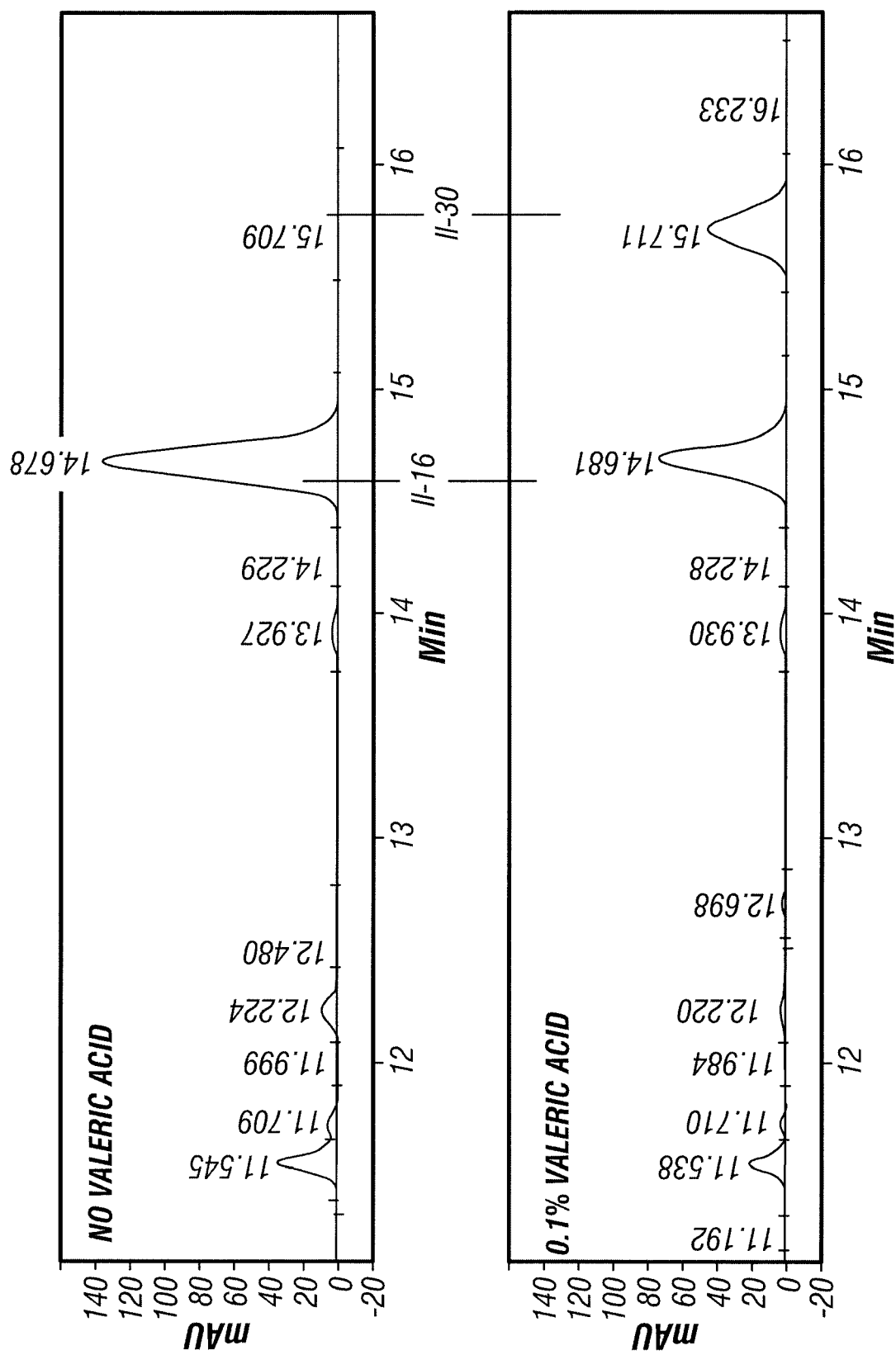
FIG. 64 depicts HPLC spectra comparing valeric acid fed and non-valeric acid fed fermentation products.

FIG. 64 illustrates the effect of valeric acid on the production of II-17. As with the case of propionate to II-20 and II-28, the addition of Valeric acid increased the II-30 peak from nearly undetectable levels to a major peak in the HPLC chromatogram. Again, II-16 was negatively affected by this addition.

Labeled Biosynthesis Studies

Once the feeding concentrations were established, labeled precursors were used in order to confirm (by mass spectrometry) the entrance of the suspected precursor into the biosynthetic pathway of the analog. Table 26 indicates the batches produced. Detailed protocols are described below.

TABLE 25

Valeric acid concentration effect

| Valeric acid concentration | Max Titers (mg/L) | | | | % Increase (+) or % Inhibition (−) | | | |
|---|---|---|---|---|---|---|---|---|
| | II-16 | II-17 | II-26 | II-30 | II-16 | II-17 | II-26 | II-30 |
| 0% | 278.55 | 11.94 | 6.59 | 0.90 | — | — | — | — |
| 0.025% | 206.00 | 8.52 | 5.96 | 48.93 | −26.1 | −28.6 | −9.6 | +5333.3 |
| 0.05% | 167.25 | 6.93 | 5.03 | 83.77 | −40.0 | −42.0 | −23.7 | +9227.2 |
| 0.1% | 156.88 | 6.27 | 4.59 | 109.21 | −43.7 | −47.5 | −30.4 | +12060 |

With increasing concentrations of valeric acid, the production of II-16, II-17, and II-26 decreased by 30-47%, while production of II-30 significantly increased by 12060%. This finding supported that the 5-carbon valeric acid is the direct biosynthetic precursors for II-30. The inhibition of production of II-16, II-17, and II-26 by the 5-carbon valeric acid also supported the postulation that valeric acid competes with the chlorinated four carbon unit and four carbon butyric acid unit for the formation of II-16, II-17, and II-26. Valeric acid demonstrated a much higher rate of incorporation into II-30 than that of butyrate into II-17 and propionate into II-20. Without being bound by any particular theory, propionate and butyrate may be common precursors for many other metabolites from both primary and secondary metabolic pathways inside the cell. Butyrate and propionate are diverted to other biosynthetic pathways from the II-16 biosynthetic pathway. Valeric acid may be more specific to the incorporation into II-30,

TABLE 26

Labeled biosynthesis studies

| Scale-up Condition | Precursor type | Final precursor concentration | Fermentation volume |
|---|---|---|---|
| Batch 1 | [1-$^{13}$C]propionate | 0.05% | 2 L |
| Batch 2 | [1,2-$^{13}$C$_2$]propionate | 0.025% | 1 L |
| Batch 3 | [1-$^{13}$C]propionate | 0.05% | 4 L |
| Batch 4 | [U-$^{13}$C$_4$]butyrate | 0.05% | 0.2 L |

Batch 1 Protocol

The General Fermentation Protocol was followed with 1st seed occurring as indicated by Method A. Second seed consisted of two (2×) second seed flasks, and production was in twenty (20×) production flasks. At 46 hours after inoculation into production, the labeled substrate was prepared by taking 1 g of [1-13C] propionate (Aldrich #493333) and dissolving it in de-ionized H2O to a final volume of 10 mL. Once dissolved, the solution was filter-sterilized with a 20 mL syringe and filtered into a clean sterile glass culture tube. At 47 hours after inoculation into production, 1 mL of this solution was added into each of the ten production flasks, and resin was added at 48 hrs. Two of the twenty flasks were selected for sampling, using the General Extraction protocol and sampled on Day 4 and Day 5 of production. On Day 5, the entire batch was extracted by filtering the 20 flasks through four layers of cheesecloth for the resins, and shaking the resins in a 2.8 L Fernbach flask with 2 L Ethyl Acetate for 1 hr at 250 rpm. The extract was then filtered through filter paper and dried in vacuo into a clean, tared, and labeled 20 mL scintillation vial.

Batch 2 Protocol

The General Fermentation Protocol was followed with $1^{st}$ seed occurring as indicated by Method A. Second seed consisted of one (1x) second seed flask, and production was in ten (10x) production flasks. At 46 hours after inoculation into production, the labeled substrate was prepared by taking 250 mg of [1,2-$^{13}C_2$] propionate (Aldrich #279455) and dissolving it in de-ionized $H_2O$ to a final volume of 20 mL. Once dissolved, the solution was filter-sterilized with a 20 mL syringe and filtered into a clean sterile glass culture tube. At 47 hours after inoculation into production, 1 mL of this solution was added into each of the twenty production flasks. Two of the ten flasks were selected for sampling, using the General Extraction protocol and sampled on Day 3 and Day 4 of production. On Day 4, 10 mL of each of the two flasks selected for sampling was placed into a clean sterile culture tube and returned to the shaker (this is used on Day 5 for sampling purposes.) Then, the two flasks along with the rest of the batch was extracted by filtering the 10 flasks through four layers of cheesecloth for the resins, and shaking the resins in a 2.8 L Fernbach flask with 1 L Ethyl Acetate for 1 hr at 250 rpm. The extract was then filtered through filter paper and dried in vacuo into a clean, tared, and labeled 20 mL scintillation vial.

Batch 3 Protocol

The General Fermentation Protocol was performed with $1^{st}$ seed occurring as indicated by Method B. Second seed consisted of four (4x) second seed flasks, and production was in forty (40x) production flasks. At 46 hours after inoculation into production, the labeled substrate was prepared by taking 2 g of [1-$^{13}C$] propionate (Aldrich #493333) and dissolving it in de-ionized $H_2O$ to a final volume of 20 mL. Once dissolved, the solution was filter-sterilized with a 20 mL syringe and filtered into a clean sterile glass culture tube. At 47 hours after inoculation into production, 0.5 mL of this solution was added into each of the forty production flasks, and resin was added at 48 hrs. Two of the forty flasks were selected for sampling, using the General Extraction protocol and sampled on Day 3 (in the morning and evening), and Day 4. On Day 4, the entire batch (EXCEPT for the two sampling flasks was extracted by filtering 2x (19 flasks through four layers of cheesecloth for the resins, and shaking the resins in a 2.8 L Fernbach flask with 2 L Ethyl Acetate) for 1 hr at 250 rpm. The extract was then filtered through filter paper and dried in vacuo into a clean, tared, and labeled 40 mL scintillation vial. The remaining two (2x) flasks were sampled on Day 5 of production using the General Extraction protocol.

Batch 4 Protocol

The General Extraction Protocol was followed with $1^{st}$ seed occurring as indicated by Method A. Second seed consisted of two (2x) second seed flasks, and production was in two (2x) production flasks. At 46 hours after inoculation into production, the labeled substrate was prepared by taking 100 mg of [U-$^{13}C_4$] butyrate (Aldrich #488380) and dissolving it in 2 mL de-ionized $H_2O$. Once dissolved, the solution was filter-sterilized with a 5 mL syringe and filter into a clean sterile glass culture tube. At 47 hours after inoculation into production, 1 mL of this solution was added into each of the two production flasks, and resin was added at 48 hrs. Both flasks were sampled, using the General Extraction protocol and sampled on Day 3, and Day 4. On Day 4, 10 mL of the culture was removed from each of the flasks and each placed in a clean sterile culture tube to sample at day 5. The remaining production culture was extracted by filtering the culture through four layers of cheesecloth. The resins were then placed in a clean 500 mL Erlenmeyer flask and shaken with 200 mL EtOAc for 1 hr at 250 rpm. After 1 hr, the extract was filtered through filter paper and dried in vacuo into a clean, tared, and labeled 20 mL scintillation vial. The remaining two (2x) tubes were sampled on Day 5 of production using the General Extraction protocol.

Results

The feeding studies using unlabeled metabolites suggested that propionate (3-carbon unit), butyrate (4-carbon unit) and valerate (5-carbon unit) are the presumptive precursors for II-20/II-28, II-17, and II-30, respectively. Since the above metabolites inhibited the production of II-16 and II-26, they are not the precursors for II-16 and II-26. These metabolites may act as competitive inhibitors by competing with the hypothetical precursor, a chlorinated 4-carbon unit, for incorporation into II-16 and II-26. In order to confirm the precursor role of propionate and butyrate, $^{13}C$-enriched propionate and butyrate were used in the feeding study. If propionate and butyrate are indeed the precursor for II-20 and II-17, respectively, the incorporation of the $^{13}C$-enriched propionate and butyrate into II-20 and II-17 can be determined by LC-MS and NMR analyses. LC-MS analysis can be used to determine the incorporation of precursor by the corresponding increase in mass of the metabolite due to the number of $^{13}C$-enriched carbons in the labeled-precursor. NMR analysis can be used to determine the actual carbon(s) in the metabolite that was/were derived from the labeled-precursor. Since $^{13}C$-enriched valerate is not available, the precursor role of valerate could not be validated in this study.

Table 27 summarizes the scale-up crudes from batches 1-4.

TABLE 27

Summary of Scale-up crudes

| Batch | Batch Size | Precursor Name | Conc. | Crude wt (mg) | Estimated Titer (mg/L) II-16 | II-20 | II-28 | Extract time |
|---|---|---|---|---|---|---|---|---|
| Batch 1 | 2 L | [1-$^{13}C$]Propionate | 0.05% | 505.38 | 219.32 | 1.99 | 0.44 | Day 5 |
| Batch 2 | 1 L | [1,2-$^{13}C_2$]Propionate | 0.025% | 252.83 | 243.42 | 3.75 | 0.74 | Day 4 |

TABLE 27-continued

Summary of Scale-up crudes

| Batch | | Precursor | | Crude | Estimated Titer (mg/L) | | | Extract |
| --- | --- | --- | --- | --- | --- | --- | --- | --- |
| | Size | Name | Conc. | wt (mg) | II-16 | II-20 | II-28 | time |
| Batch 3 | 4 L | [1-$^{13}$C]Propionate | 0.05% | 915.03 | 220.05 | 7.79 | 2.06 | Day 4 |
| Batch 4 | 0.2 L | [U-$^{13}$C$_4$]Butyrate | 0.05% | 46.00 | 156.22 | 66.50 | 3.74 | Day 4 |

The estimated titer was based on time point samples that were taken, and not the actual batch extract. Both II-20 and II-28 estimations are based on the relative ratios to the II-16 production titer.

Although Batch 1 and Batch 3 had the same final concentration of propionate, batch 1 was extracted at day 5, while Batch 3 was extracted on day 4, which may account for some of the differences seen, as II-20 titer decreased after day 5. While Batch 2 and Batch 3 were both extracted at day 4, Batch 2 had a final concentration of substrate that was about half that of Batch 3, which explains why the production of II-20 and II-28 in Batch 2 was about half that of Batch 3. The production of $^{13}$C enriched II-20 was significantly enhanced in each of these, and the LCMS data suggested that propionate is indeed a precursor to II-20.

Figure 65:
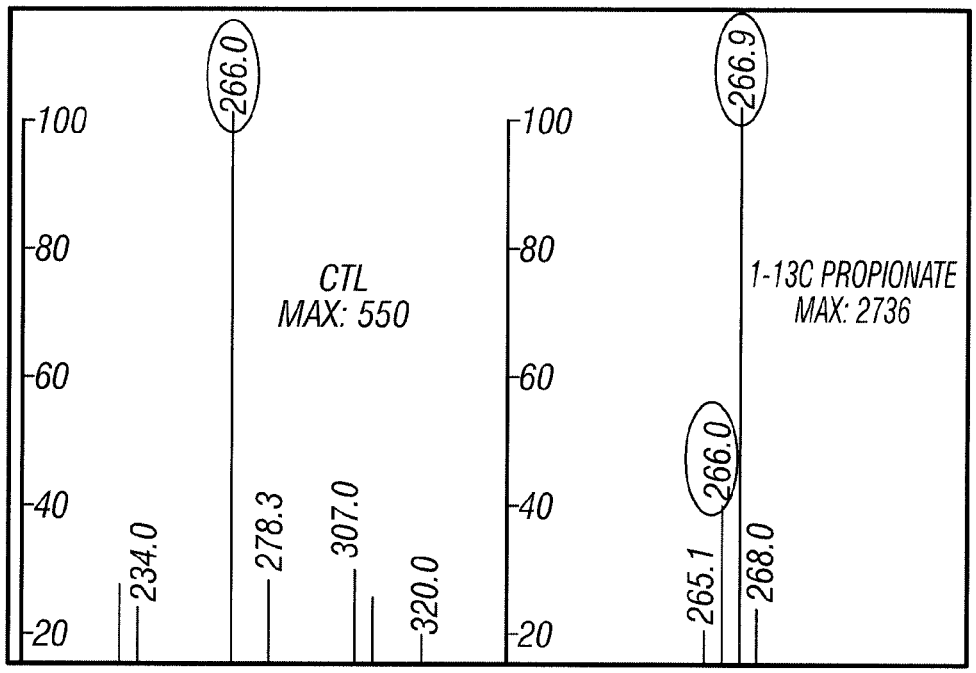
FIG. 65 depicts the mass spectrum of compound II-20 in a control condition versus that which has been enhanced by [1-$^{13}$C] propionate.

As depicted in FIG. 65, the molecular ion m/z 266.9 ([M+H+1]$^+$) was observed for II-20 from the [1-$^{13}$C]propionate-fed culture, in contrast to the molecular ion m/z 266.0 ([M+H]$^+$) observed for II-20 in the control culture. This corresponds to an increase in one mass unit (enrichment of one $^{13}$C). Also, the amount of $^{13}$C-labeled-II-20 present in the [1-$^{13}$C]propionate-fed culture was 5 times that of II-20 present in the control culture based on the signal intensity from the mass spectrum (2736 versus 550).

$^{13}$C is a naturally occurring isotope and represents ~1% natural abundance in the unlabelled metabolite. If the rate of incorporation of $^{13}$C-labeled precursor into the metabolite is high then there should be significant enrichment of the labeled carbon which can be detected LC-MS analysis. From the above LC-MS analysis (FIG. 65), the molecular ion of II-20 from the [1-$^{13}$C]propionate-fed culture is one mass unit higher than the molecular ion of II-20 from the control culture, supporting the incorporation of [1-$^{13}$C]propionate into II-20. The amount of $^{13}$C-labeled-II-20 present in the [1-$^{13}$C]propionate-fed culture was 5 times that of II-20 present in the control culture based on the signal intensity from the mass spectrum (2736 versus 550). II-28 results were similar to II-20 in the LCMS spectra (data not shown). However, it was noted that production of II-28 is much lower than that of II-20, despite the encouraging enhancement effects of propionate feeding.

Figure 66:
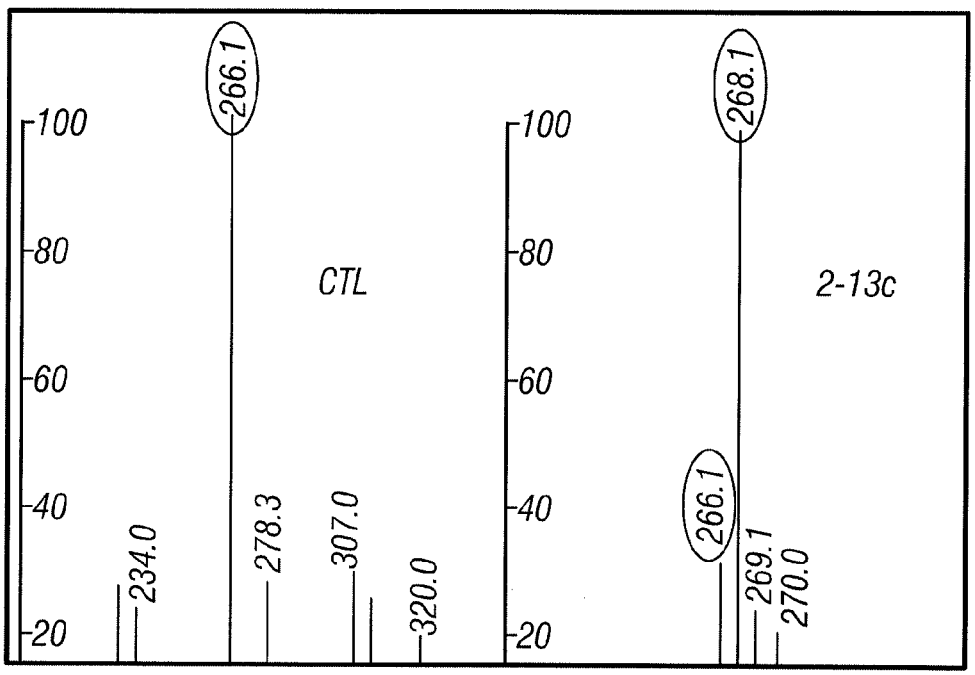
FIG. 66 depicts the mass spectrum of compound II-20 in a control condition versus that which has been enhanced by [1,2-$^{13}$C$_2$] propionate.

As depicted in FIG. 66, the molecular ion m/z 268.1 ([M+H+2]$^+$) was observed for II-20 from the [1,2-$^{13}$C$_2$] propionate-fed culture, in contrast to the molecular ion m/z 266.1 ([M+H]$^+$ observed for the control. This corresponds to an increase in two mass units (enrichment of two $^{13}$C). Also, the amount of $^{13}$C-labeled-II-20 presents in the [1,2-$^{13}$C$_2$] propionate-fed culture was 4-5 times that of II-20 present in the control culture based on the signal intensity from the mass spectrum.

From the above LC-MS analysis (FIG. 66), the molecular ion of II-20 from the [1,2-$^{13}$C$_2$] propionate-fed culture has two mass unit higher than the molecular ion of II-20 from the control culture, supporting the incorporation of [1, 2-$^{13}$C$_2$] propionate into II-20.

Figure 67:
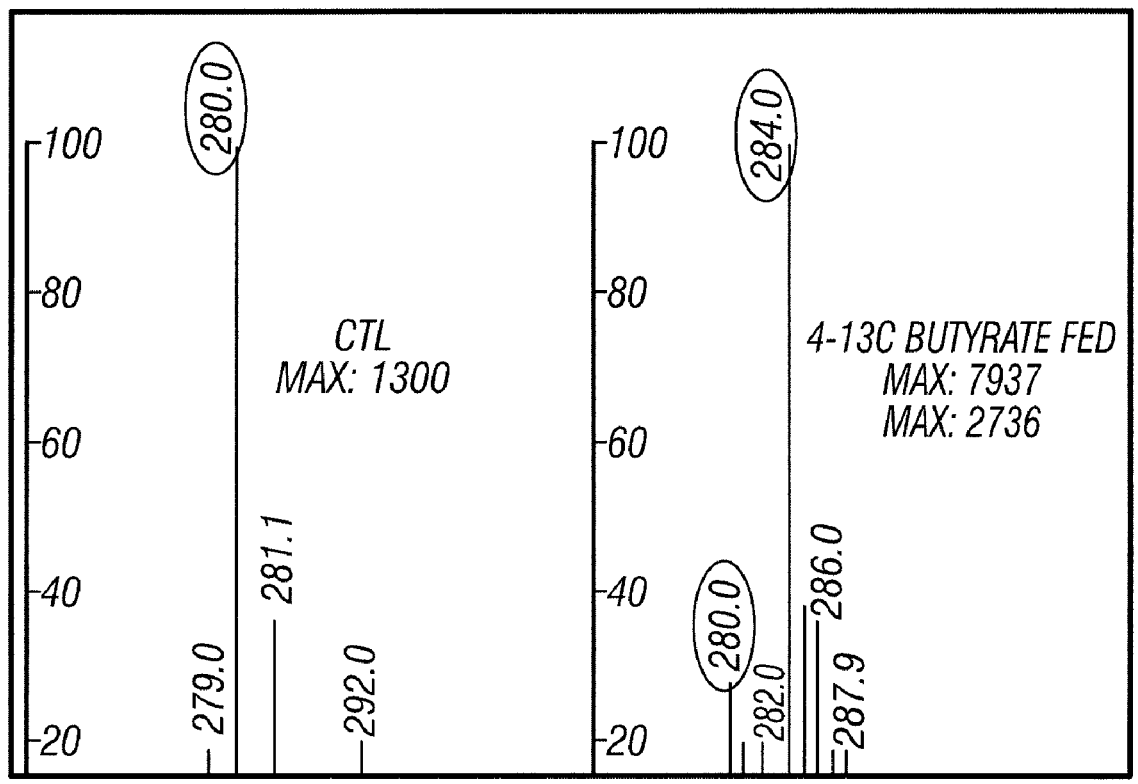
FIG. 67 depicts the mass spectrum of compound II-17 in a control condition versus that which has been enhanced by [U-$^{13}$C$_4$] butyrate.

As depicted in FIG. 67, the molecular ion m/z 284.0 ([M+H+4]$^+$) was observed for II-17 from the [U-$^{13}$C$_4$]butyrate-fed culture, in contrast to the molecular ion m/z 280.0 ([M+H]$^+$) observed for II-17 in the control. This corresponds to an increase in 4 mass units (enrichment of four $^{13}$C). Also, the amount of $^{13}$C-labeled-II-17 presents in the [U-13C$_4$] butyrate-fed culture was 6.1 times that of II-17 present in the control culture based on the signal intensity from the mass spectrum (7937 versus 1300).

From the above LC-MS analysis (FIG. 67), the molecular ion of II-17 from the [U-$^{13}$C$_4$] butyrate-fed culture was four mass units higher than the molecular ion of II-17 from the control culture, supporting the incorporation of [U-$^{13}$C$_4$]butyrate into II-17. The amount of $^{13}$C-labeled-II-17 present in the [U-$^{13}$C$_4$] butyrate-fed culture was 6.1 times that of II-17 present in the control culture based on the signal from the mass spectrum (7937 versus 1300). Note how two molecular ions were observed at m/z 282 [M+H+2]$^+$ and m/z 286 [M+H+6]$^+$ for II-17 in the [U-$^{13}$C$_4$]butyrate-fed culture. These ions may correspond to the enrichment of the two carbons at the C-3 ring junction and C-14 methyl moiety as [U-$^{13}$C$_4$] butyrate can be broken down into [1,2-$^{13}$C$_2$]acetates and then be incorporated into the NPI-0047 molecule with (m/z 286 [M+H+6]$^+$) or without incorporation of [U-$^{13}$C$_4$] butyrate (m/z 282 [M+H+2]$^+$).

Purification—[1-$^{13}$C] Propionate Feeding Study

Crude extract obtained from [1-$^{13}$C] propionate feeding studies (batch 3) was purified by HPLC using a Gilson HPLC equipped with a Gilson 215 fraction collector, and an evaporative light scattering detector (ELSD; Sedere) to monitor the purification process. The extract (915 mg) was dissolved in acetone to a final concentration of 40 mg/mL, filtered through a 0.45 micron syringe filter, and purified by HPLC using a normal phase silica column (Phenomenex Luna Si 10u, 100A; 250×21.2 mm id; 900 µL (36 mg) per injection). The mobile phase elution profile was 24% EtOAc/Hex for 27 minutes, 24% EtOAc/Hex to 100% EtOAc in 1 minute, followed by 100% EtOAc for 4 minutes at a flow rate of 25 mL/min. Thirty-second fractions were collected between 10 and 39 minutes. Compound 24C and II-26 co-eluted as a single peak at 12 minutes followed by II-16, which eluted from 14-19 minutes. II-17 eluted at 31 minutes as a pure compound while II-20 and II-28 co-eluted at 32 minutes during the 100% EtOAc portion of the run. The method was repeated until the entire 915 mg of crude extract was processed.

The sample containing a mixture of II-26 and II-24C generated from the process described above was further separated by reversed-phase HPLC using a Gilson HPLC equipped as described above and an Agilent PDA detector to monitor the separation. The sample was dissolved in 1 mL of acetonitrile, and 250 µL was loaded onto a reversed phase HPLC column (Eclipse XDB-C18, 21 mm i.d.×15 cm). The solvent gradient increased linearly from 15% acetonitrile/85% water to 100% acetonitrile over 23 minutes at a flow rate of 14.5 mL/min. The solvent composition was held at 100% acetonitrile for 3 minutes before returning to the starting solvent mixture. II-26 eluted at 13.5 minutes while II-24C eluted at 15.5 minutes under these conditions. To minimize hydrolysis of the β-lactone ring, which occurs during exposure to the aqueous mobile phase, samples were evaporated under reduced pressure on a rotary evaporator at room temperature immediately after being fractionated.

Figure 68:
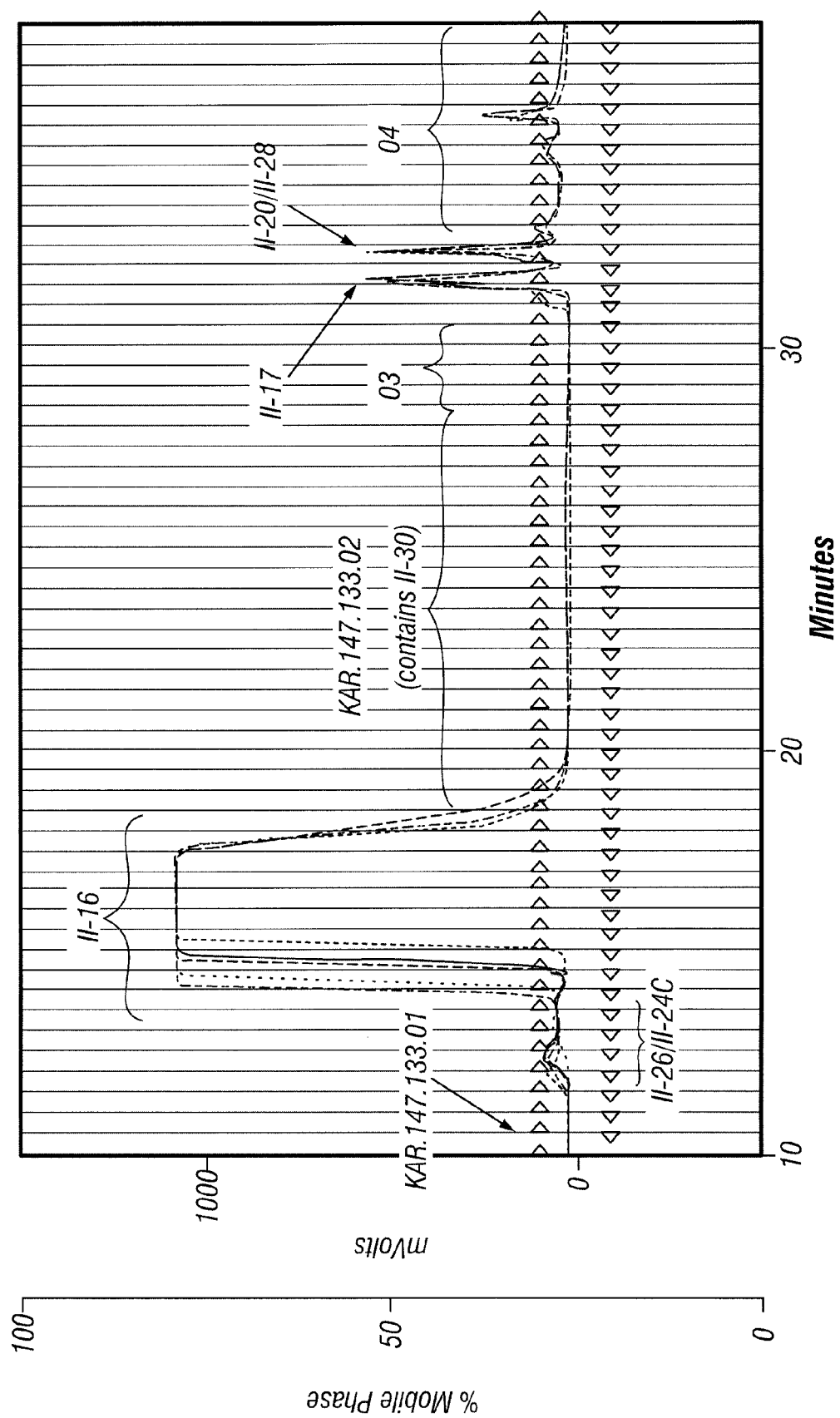
FIG. 68 depicts a chromatogram for the fractionation of compounds from proprionate-fed strains.

In order to separate II-28 from II-20, a normal-phase gradient method was developed. Sample containing both compounds was dissolved in acetone to a concentration of approximately 9 mg/mL, and loaded onto a normal-phase HPLC column (Phenomenex Luna Si 10u, 100A; 250×21.2 mm id) at 350 µL per injection. A 20 minute linear gradient from 60% Hex/40% EtOAc to 100% EtOAc at a flow rate of 25 mL/min was used to separate compounds II-28 and II-20, which eluted after 10 and 11 minutes, respectively. Remaining fractions from the initial normal phase purification were pooled and labeled KAR.147.144.01 through 04 (FIG. 68).

Sample KAR.147.144.02 contained approximately 17% II-30 based on LC-MS analysis. The sample (30 mg) was dissolved in acetone to a final concentration of 15 mg/mL and loaded onto a normal-phase HPLC column (Phenomenex Luna Si 10u, 100A; 250×21.2 mm id) at 250 µL per injection. A 27 minute linear gradient from 85% Hex/15% EtOAc to 100% EtOAc at a flow rate of 25 mL/min was used to purify Compound II-30, which eluted after 15 minutes.

Purification—[U-$^{13}$C$_4$] Butyrate Feeding Study

The crude extract (46 mg) from the [U-$^{13}$C$_4$] butyrate feeding study was generated as described above (batch 4) and purified using the same method and parameters as described above for the [1-$^{13}$C] propionate extract. One round of normal-phase HPLC resulted in pure II-16 and pure II-17.

Spectral Analysis of Compounds

Pure compounds were analyzed using an Agilent HP 1100 HPLC equipped with an Agilent PDA detector and an 1100 series MSD Agilent mass spectrometer. In order to determine where incorporation of labeled carbons was observed, $^1$H and $^{13}$C NMR spectra were collected using a 500 MHz Bruker Advance NMR spectrometer with a broad-band observe probe, except for the 2-D spectra collected for NPI-2080, in which an inverse probe equipped with x,y,z-gradients was used. All NMR data were acquired at 300 K in DMSO-d$_6$.

Results are summarized in Table 28 for both [1-$^{13}$C] propionate and [U-$^{13}$C$_4$] butyrate feeding studies. The following structures were obtained for the [1-$^{13}$C] propionate labeled compounds with the $^{13}$C-labeled carbon denoted with an asterisk. From the available data, it was not possible to determine whether the propionate incorporated into II-30 extends from C-12 to C-2 and C-1 or from C-12 to C-13 and C-16.

II-20

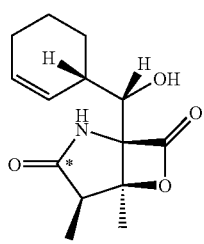

II-28

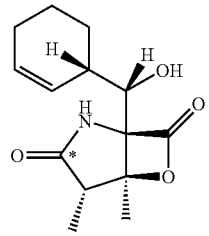

II-24C

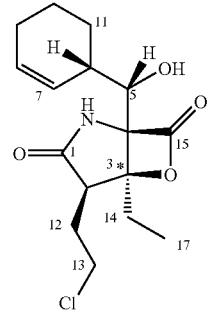

II-30

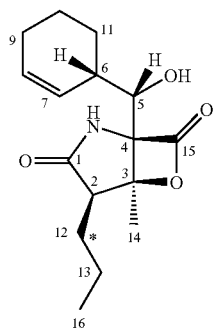

The following structures were obtained for the [U-$^{13}$C$_4$] butyrate labeled compounds. The $^{13}$C-labeled carbons are denoted with asterisks.

II-16

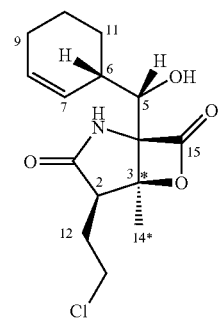

II-17

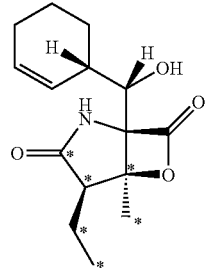

TABLE 28

Summary of Compounds Analyzed in Feeding Studies

| Feeding Study | Compound ID | Carbon(s) Labeled | Diagnostic Ion(s) Observed in LC-MS |
|---|---|---|---|
| [1-$^{13}$C] propionate | II-17 | None | m/z 280 [M + H]$^+$ |
| [1-$^{13}$C] propionate | II-16 | None | m/z 314 [M + H]$^+$ |
| [1-$^{13}$C] propionate | II-26 | None | m/z 314 [M + H]$^+$ |
| [1-$^{13}$C] propionate | II-20 | C-1 | m/z 267 [M + H + 1]$^+$ |
| [1-$^{13}$C] propionate | II-28 | C-1 | m/z 267 [M + H + 1]$^+$ |
| [1-$^{13}$C] propionate | II-24C | C-3 | m/z 329 [M + H + 1]$^+$ |
| [1-$^{13}$C] propionate | II-30 | C-12 | m/z 295 [M + H + 1]$^+$ |
| [U-$^{13}$C$_4$] butyrate | II-17 | C-1, C-2, C-12, C-13 and C-1, C-2, C-12, C-13, C-3, C-14 | m/z 284 [M + H + 4]$^+$ m/z 284 [M + H + 6]$^+$ |
| [U-$^{13}$C$_4$] butyrate | II-16 | C-3, C-14 | m/z 314 [M + H ]$^+$ & m/z 316 [M + H + 2]$^{+b}$ |

Figure 69:
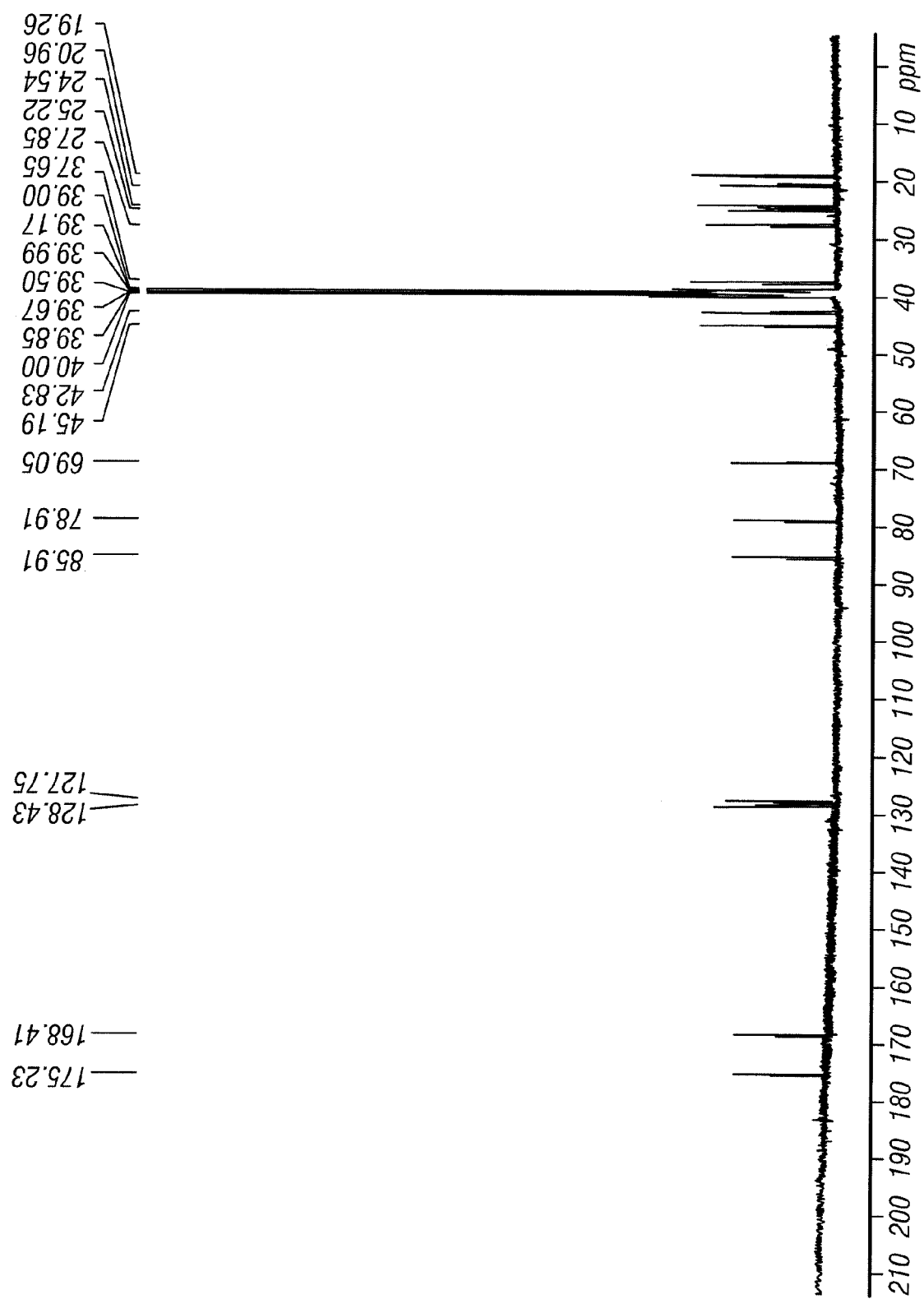
FIG. 69 is a $^{13}$C NMR (DMSO-$d_6$) spectrum of compound II-16 from a [$^{13}$C$_1$] propionate feeding study.
Figure 70:
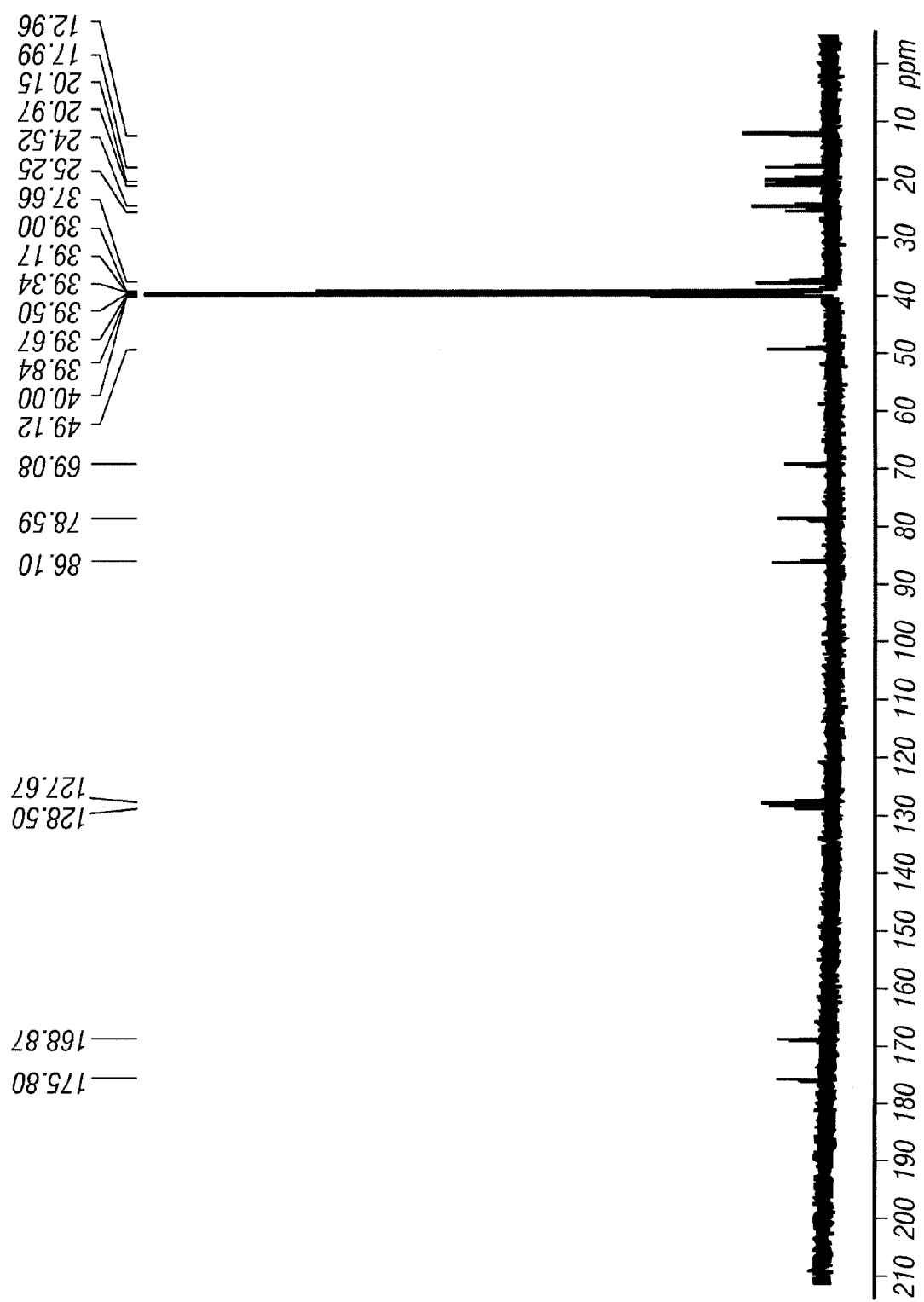
FIG. 70 is a $^{13}$C NMR (DMSO-$d_6$) spectrum of compound II-17 from a [$^{13}$C$_1$] propionate feeding study.
Figure 71:
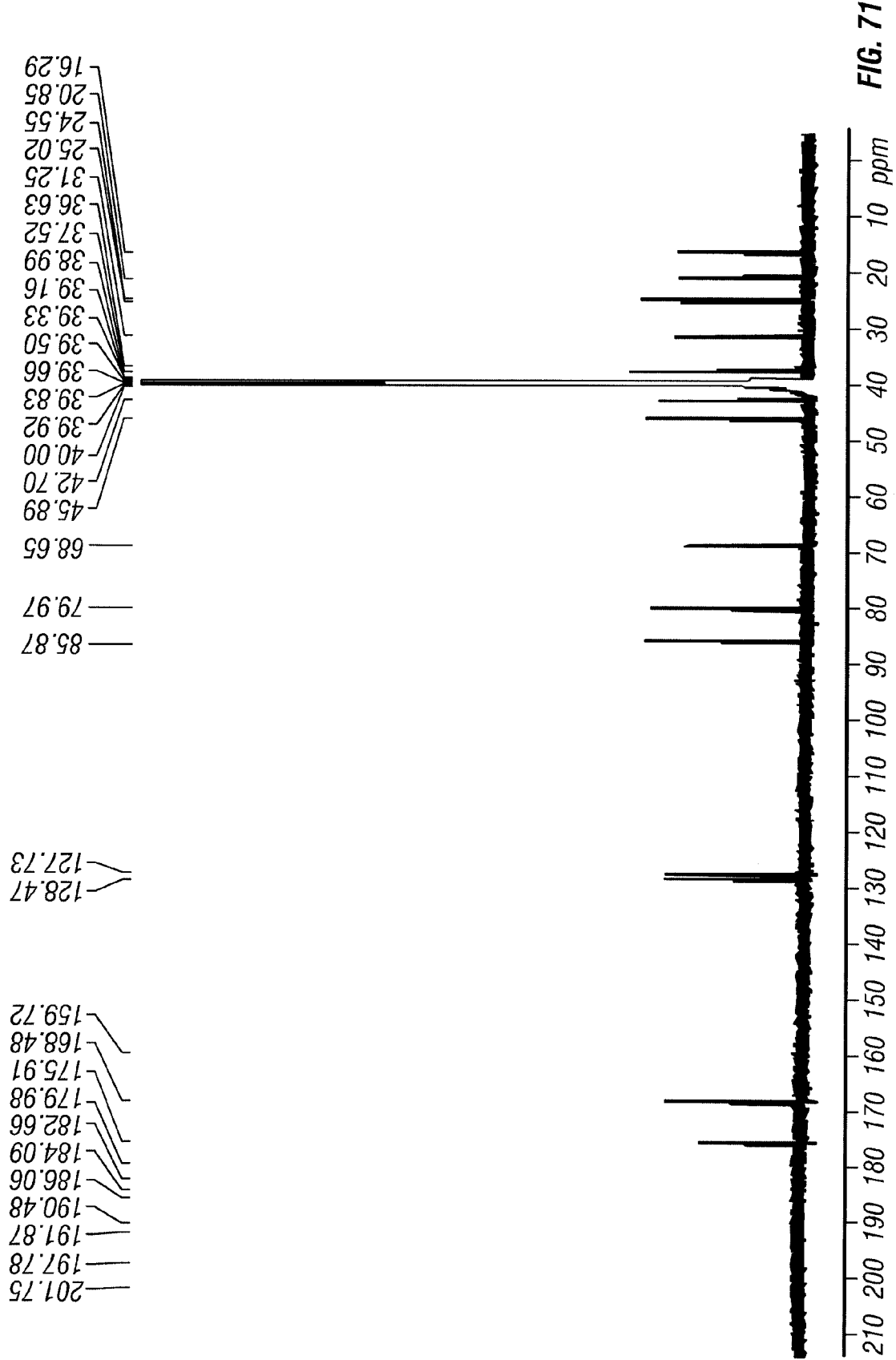
FIG. 71 is a $^{13}$C NMR (DMSO-$d_6$) spectrum of compound II-26 from a [$^{13}$C$_1$] propionate feeding study.
Figure 72:
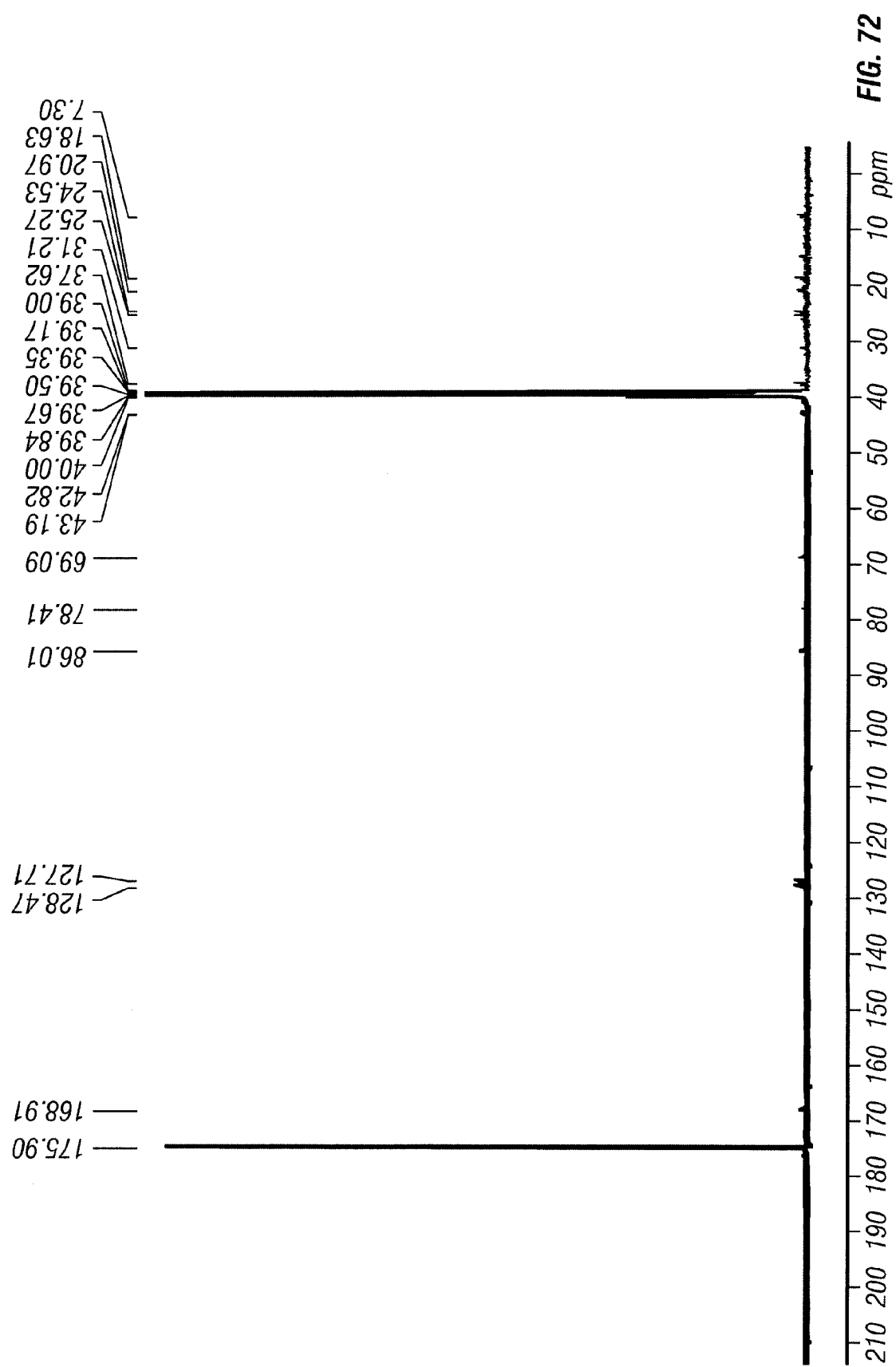
FIG. 72 is a $^{13}$C NMR (DMSO-$d_6$) spectrum of compound II-20 from a [$^{13}$C$_1$] propionate feeding study.
Figure 73:
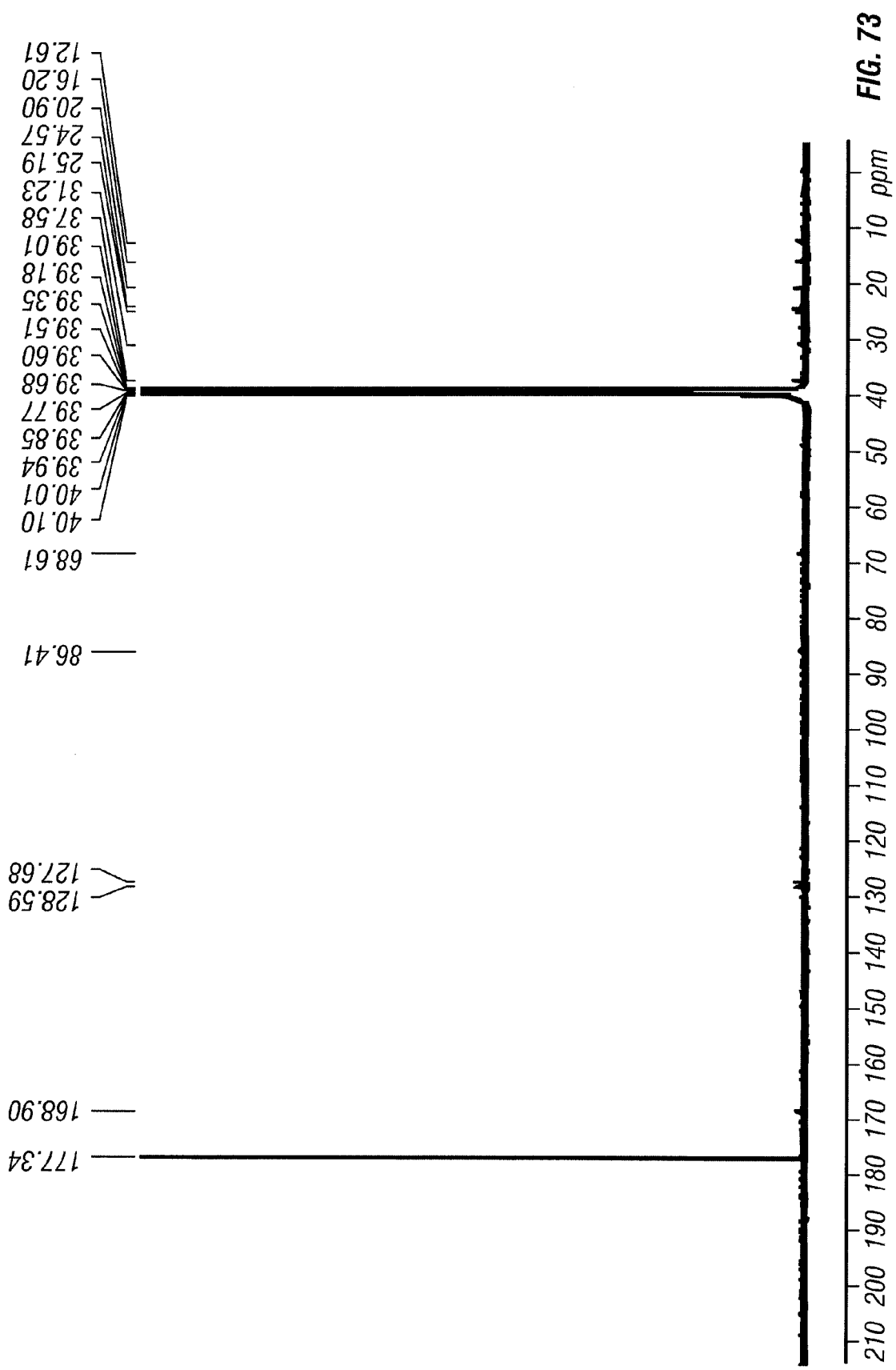
FIG. 73 is a $^{13}$C NMR (DMSO-$d_6$) spectrum of compound II-28 from a [$^{13}$C$_1$] propionate feeding study.
Figure 74:
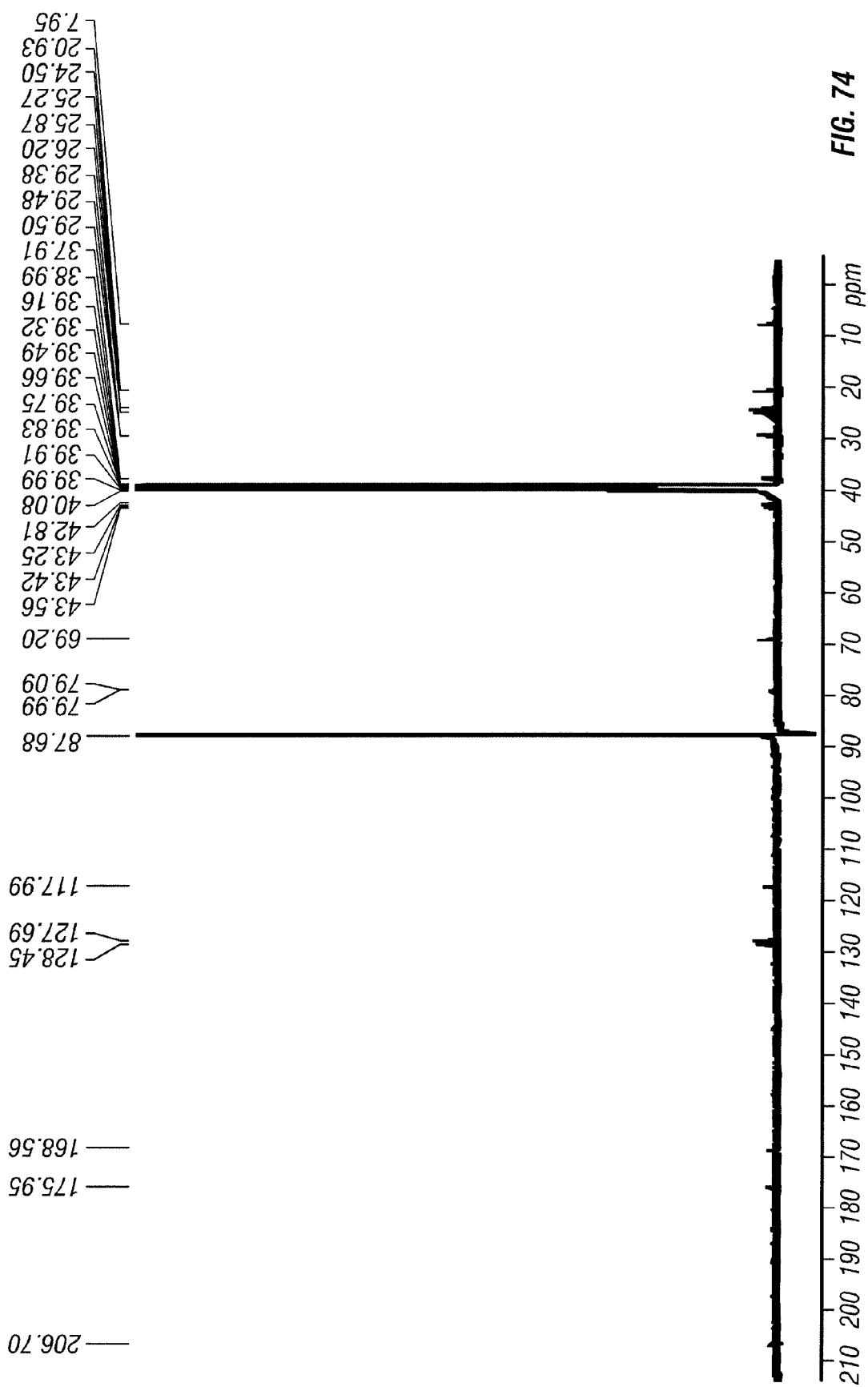
FIG. 74 is a $^{13}$C NMR (DMSO-$d_6$) spectrum of compound II-24C from a [$^{13}$C$_1$] propionate feeding study.
Figure 75:
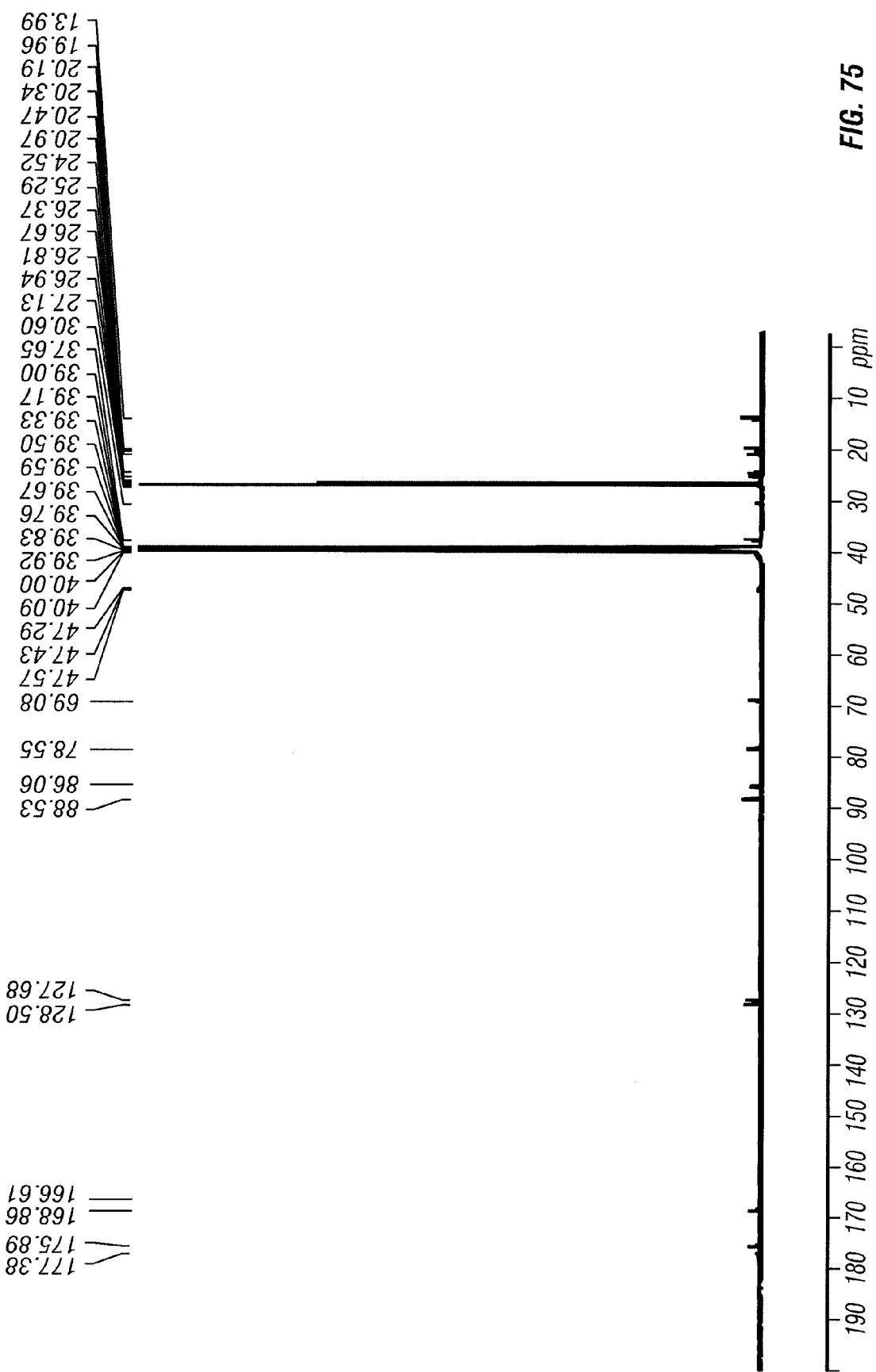
FIG. 75 is a $^{13}$C NMR (DMSO-$d_6$) spectrum of compound II-30 from a [$^{13}$C$_1$] propionate feeding study.

$^b$m/z 316 was more intense than expected from chlorine isotope of unlabeled species For the [1-$^{13}$C] propionate feeding study, II-16, II-17, and II-26 had no $^{13}$C incorporation based on $^{13}$C NMR (FIGS. 69-71). This was consistent with the LC-MS data, in which the parent ion [M+H]$^+$ of the unlabeled species was observed for each of the three compounds. In contrast, $^{13}$C NMR indicated that both II-20 and II-28 had [1-$^{13}$C] propionate incorporation with the $^{13}$C label at C-1, while II-24C was labeled at C-3 (FIGS. 72-74); these findings were consistent with the observation of [M+H+1]$^+$ ions by LC-MS for these compounds. For II-30, a major ion was observed at m/z 295 ([M+H+1]$^+$) in the LC-MS data, indicating that [1-$^{13}$C] propionate was incorporated within the molecule, and the $^{13}$C NMR spectrum confirmed that C-12 was $^{13}$C labeled (FIG. 75). An extraneous peak at $\delta_c$ 88.5 was observed; however, after analysis of HSQC and HMBC spectral data, this signal was interpreted to arise from a low-lying impurity that was $^{13}$C labeled at a quaternary carbon with a chemical shift similar to that of C-3. This was initially apparent from the HMBC spectrum, which showed correlations from protons at chemical shifts that were unique (i.e., did not arise) from II-30. These proton correlations to $\delta_c$ 88.5 suggested that the carbon in question is associated with a minor quantity of a compound that bears an ethyl side chain at both the C-2 and C-3 positions having the following structure and representing a hybrid of II-17 and II-24C:

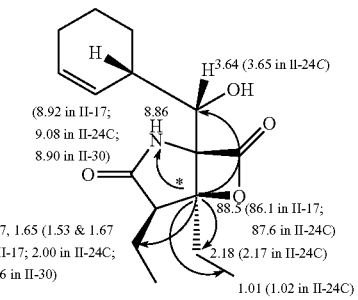

↷ Observed HMBC correlation

Comparison of $^1$H and $^{13}$C chemical shifts in this compound with those of II-17 and II-24C strongly supports this hypothesis.

Figure 76:
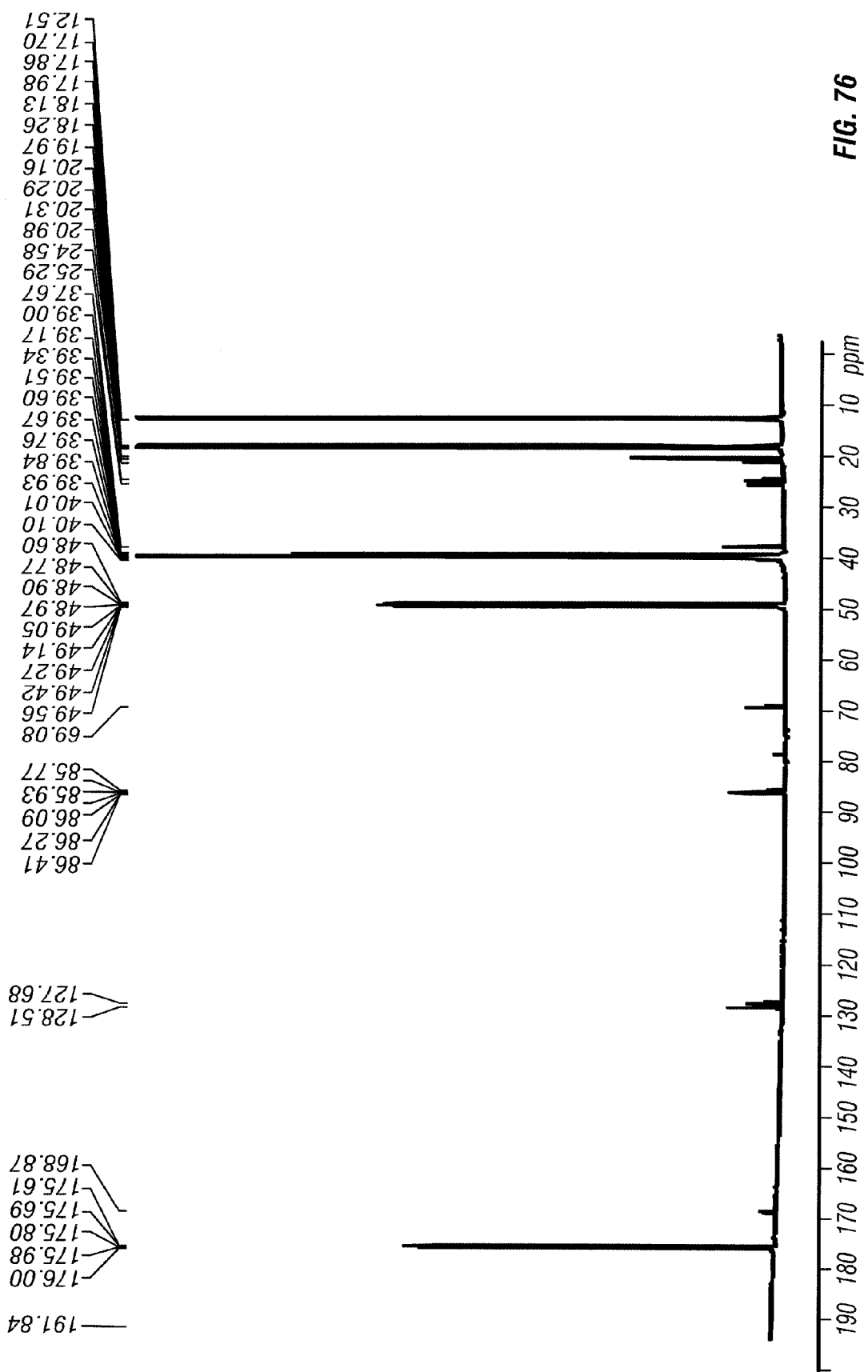
FIG. 76 is a $^{13}$C NMR (DMSO-$d_6$) spectrum of compound II-17 from a [U-$^{13}$C$_4$] buytrate feeding study.
Figure 77:
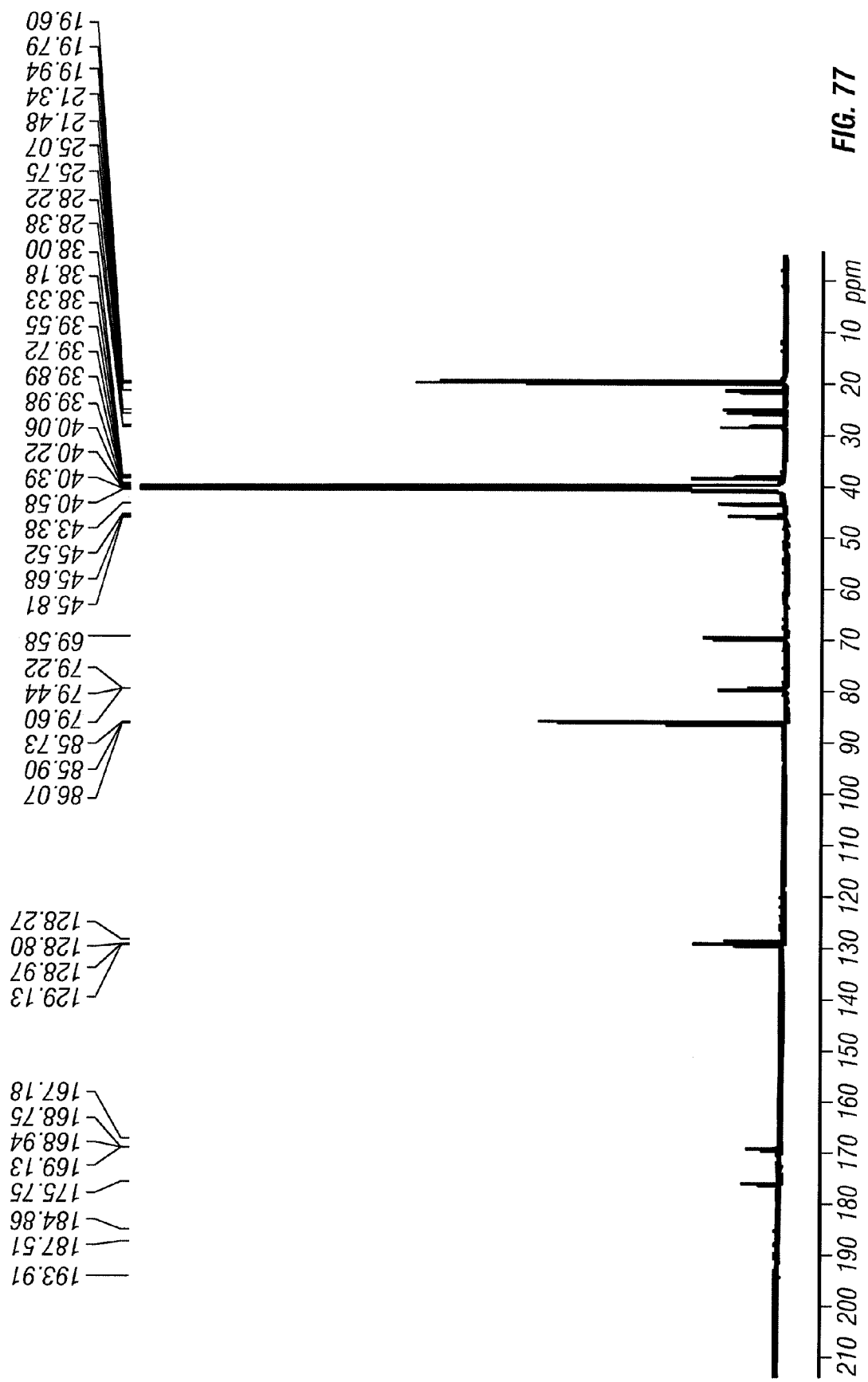
FIG. 77 is a $^{13}$C NMR (DMSO-$d_6$) spectrum of compound II-16 from a [U-$^{13}$C$_4$] buytrate feeding study.

For the [U-$^{13}$C$_4$] butyrate feeding study, preliminary LC-MS data indicated that the major ion for II-17 was m/z 284 ([M+H+4]$^+$), suggesting that [U-$^{13}$C$_4$] butyrate was incorporated. This was confirmed by $^{13}$C NMR, in which C-1, C-2, C-12, C-13 were all $^{13}$C-labeled (FIG. 76). In addition, C-3 and C-14 carbon resonances were slightly amplified in the $^{13}$C NMR spectrum, indicating partial incorporation of acetate at the C-3 ring junction; an ion at m/z 286 ([M+H+6]$^+$) was also detected, consistent with the presence of a species with both butyrate and acetate incorporation. II-16 purified from the same extract was $^{13}$C labeled at C-3 and C-14, which is also consistent with acetate incorporation at the ring juncture (FIG. 77). The doubly $^{13}$C-labeled species gave rise to an increase in the intensity of the ion at m/z 316 ([M+H+2]$^+$), which is coincident with the $^{37}$Cl isotope of the unlabeled parent. Although [U-$^{13}$C$_2$] labeled acetate was not directly fed into the fermentation, it is commonly seen as an artifact of [U-13C$_4$] butyrate.

CONCLUSIONS

Feeding propionate (3-carbon unit) to the fermentation significantly increased the production of II-20 by 434.4% and II-28 by 1351.1%. The most effective feeding concentration of propionate for enhancement of II-20 and II-28 is 0.05%-0.1%. This finding supports the claims that propionate is the biosynthetic precursor of II-20 and II-28, and adding biosynthetic precursor can enhance the production of the corresponding analogs.

Propionate inhibited the production of II-16 by 20.5% and II-26 by 37.1%. This suggested that II-16, II-26, II-20, and II-28 have a common biosynthetic precursor and propionate competes with other straight chain carbon units to this common precursor for the production of II-20 and II-28, thereby, lowering the production of II-16 and II-26.

[$^{13}$C]Propionate incorporated efficiently into II-20 and II-28 based on LC-MS analysis confirming that propionate is the biosynthetic precursor of II-20 and II-28.

[$^{13}$C]Propionate did not incorporate into II-16 and II-17 based on LC-MS analysis. This confirmed that propionate is not a biosynthetic precursor of II-16 and II-17. Therefore, the biosynthesis of II-20 and II-28 is different from II-16 and II-17.

Feeding butyrate (4-carbon unit) to the fermentation significantly increased the production of II-17 by 318%. The most effective feeding concentration of butyrate for enhancement of II-17 is around 0.1%. This finding supports the claims that butyrate is the biosynthetic precursor of II-17, and adding biosynthetic precursor can enhance the production of the corresponding analogs.

Butyrate inhibited the production of II-16 and II-26 by 25.7%. This suggested that II-17, II-16, and II-26 have a common biosynthetic precursor and butyrate competes with other straight chain carbon units to this common precursor for the production of II-17, thereby, lowering the production of II-16 and II-26.

[$^{13}$C]Butyrate incorporates very efficiently into II-17 as a whole unit based on LC-MS analysis confirming that butyrate is the biosynthetic precursor of II-17.

[$^{13}$C]Butyrate did not incorporate into II-16 as a whole unit indicating that the biosynthesis of II-17 is different from II-16. This may provide a method for inhibiting the production of II-17 while leaving the biosynthesis of II-16 intact. Removing the production of II-17 without affecting the production of II-16 would enhance the downstream purification process, increasing the yield of II-17).

Feeding valerate (5-carbon unit) to the fermentation significantly increased the production of II-30 by 12060%. The most effective feeding concentration of valerate for enhancement of II-30 is around 0.1%. This finding supports the claims that valerate is the biosynthetic precursor of II-30, and adding biosynthetic precursor can enhance the production of the corresponding analogs.

Valerate inhibited the production of II-16, II-26, and II-17 by 43.7%, 30.4% and 47.5%, respectively. This suggested that II-16, II-26, II-17, and II-30 have a common biosynthetic precursor and valerate competes with other straight chain carbon units for incorporation into this common precursor producing II-30, thereby, lowering the production of II-16, II-26, and II-17.

$^{13}$C NMR analysis definitively revealed that $^{13}$C was incorporated into C-1 of II-20 and II-28, as well as C-3 of II-24C. This pattern may be interpreted to suggest that the propionate unit is a biosynthetic precursor for these three analogs, comprising the contiguous chain C-1, C-2, C-12 in II-20 and II-28, and C-3, C-14, C-17 in II-24C. $^{13}$C incorporation was also observed at C-12 of II-30; although, from the available data, it can not be determined whether the propionate chain comprises C-1, C-2, C-12 or C-12, C-13, C-16. However, based on the assumption of the head-to-tail condensation of the acetate units, it is most likely that propionate incorporated into C-12, C-13 and C-16 in II-30.

For the butyrate studies, $^{13}$C incorporation into C-3 and C-14 of II-16 and II-17 suggests acetate (derived from butyrate) as the source of these contiguous carbons, while $^{13}$C incorporation into C-1, C-2, C-12 and C-13 of II-17 suggests butyrate as a source of these four contiguous carbons of this analog. These results were consistent with initial LC-MS of crude extract fed with [U-13C$_4$] butyrate and with the LC-MS data obtained on the purified compound. The lack of $^{13}$C incorporation into C-1, C-2, C-12, C-13 of II-16 suggests a unique pathway for introduction of this side chain as opposed to halogenation of II-17.

The examples described above are set forth solely to assist in the understanding of the embodiments. Thus, those skilled in the art will appreciate that the methods may provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications can be made to the embodiments disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably can be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed can be resorted to by those skilled in the art, and that such modifications and variations are considered to be falling within the scope of the embodiments of the invention.

What is claimed is:
1. A method of producing a first compound of Formula I,

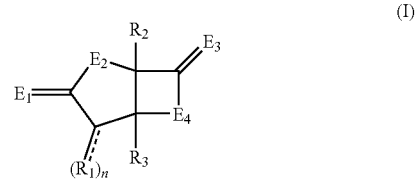

wherein the dashed lines represent a single or a double bond, wherein $R_1$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl, where n is equal to 1 or 2, and if n is equal to 2, then $R_1$ can be the same or different;

wherein $R_2$ is selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl;

wherein $R_3$ is selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl;

wherein each of $E_1$, $E_2$, $E_3$ and $E_4$ is a substituted or unsubstituted heteroatom;

the method comprising culturing a strain of *Salinospora* in a saline medium using a feedstock that is deficient in or has an excess of one or more of proprionate, butyrate, or valerate compared to levels of proprionate, butyrate, and valerate found in a medium comprising starch, Hy soy, and yeast in a ratio of 10 g to 4 g to 4 g such that the relative yield of the first compound in comparison to the yield of a second compound of Formula I is substantially different than the relative yield of the first compound in comparison to the yield of the second compound obtained when the strain is cultured in a medium comprising starch, Hy soy, and yeast in a ratio of 10 g to 4 g to 4 g.

2. The method of claim 1, wherein the first compound has the structure of Formula II:

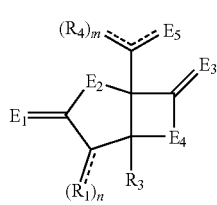

(II)

wherein each $R_4$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl, where m is equal to 1 or 2, and if m is equal to 2, then $R_4$ can be the same or different; and wherein $E_5$ is a substituted or unsubstituted heteroatom.

3. The method of claim 1, wherein the first compound has the structure of Formula III:

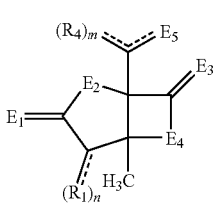

(III)

wherein each $R_4$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl, where m is equal to 1 or 2, and if m is equal to 2, then $R_4$ can be the same or different; and wherein $E_5$ is a substituted or unsubstituted heteroatom.

4. The method of claim 1, wherein the first compound has the structure of Formula IV:

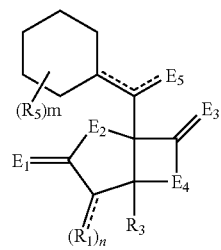

(IV)

wherein $R_5$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl, where m is equal to 0, 1, 2, 3, 4, 5, 6, 7, 8, 9, 10, or 11, and if m is greater than 1, then $R_5$ can be the same or different; and wherein $E_5$ is a substituted or unsubstituted heteroatom.

5. The method of claim 1, wherein the first compound has the structure of Formula V:

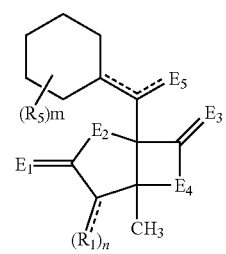

(V)

wherein $R_5$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, and halogenated alkyl including polyhalogenated alkyl, where m is equal to 0, 1, 2, 3, 4, 5, 6, 7, 8, 9, 10, or 11, and if m is greater than 1, then $R_5$ can be the same or different; and wherein $E_5$ is a substituted or unsubstituted heteroatom.

6. The method of claim 1, wherein the first compound is the compound of Formula II-16:

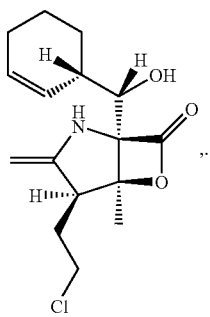

II-16

7. The method of claim 1, wherein the other second compound is the compound of Formula II-17:

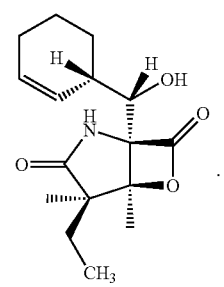

II-17

8. The method of claim 1, wherein said feedstock is deficient in one or more reagent selected from proprionate, butyrate, and valerate.

9. The method of claim 8, wherein the reagent is proprionate.

10. The method of claim 8, wherein the reagent is butyrate.

11. The method of claim 8, wherein the reagent is valerate.

12. The method of claim 1, wherein said feedstock comprises an excess of one or more reagent selected from proprionate, butyrate, and valerate.

13. The method of claim 12, wherein the reagent is proprionate.

14. The method of claim 12, wherein the reagent is butyrate.

15. The method of claim 12, wherein the reagent is valerate.

16. The method of claim 1, wherein said feedstock is deficient in butyrate,
wherein the first compound is the compound of Formula II-16:

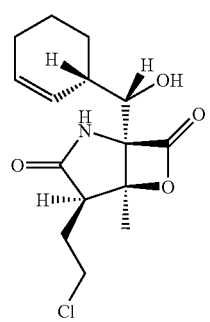

II-16 and wherein the second compound is the compound of Formula II-17:

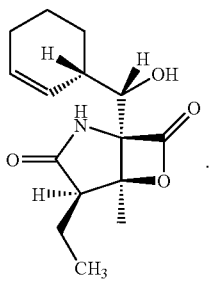

II-17

17. The method of claim 1, wherein said feedstock comprises an excess of propionate,
wherein the first compound is the compound of Formula II-20 or the compound of Formula II-29:

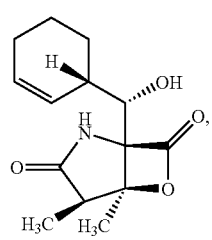

(II-20)

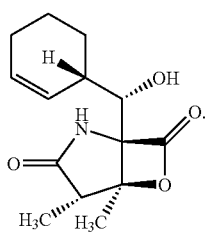

(II-28)

18. The method of claim 1, wherein said feedstock comprises an excess of valerate,
wherein the first compound is the compound of Formula II-30:

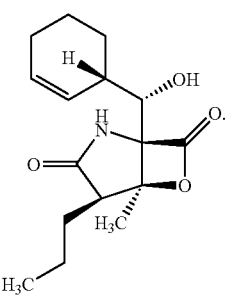

(II-30)

* * * * *

UNITED STATES PATENT AND TRADEMARK OFFICE
CERTIFICATE OF CORRECTION

| | | |
|---|---|---|
| PATENT NO. | : 7,572,606 B1 | |
| APPLICATION NO. | : 11/517899 | |
| DATED | : August 11, 2009 | |
| INVENTOR(S) | : Kin Sing Lam et al. | |

Figure 3:
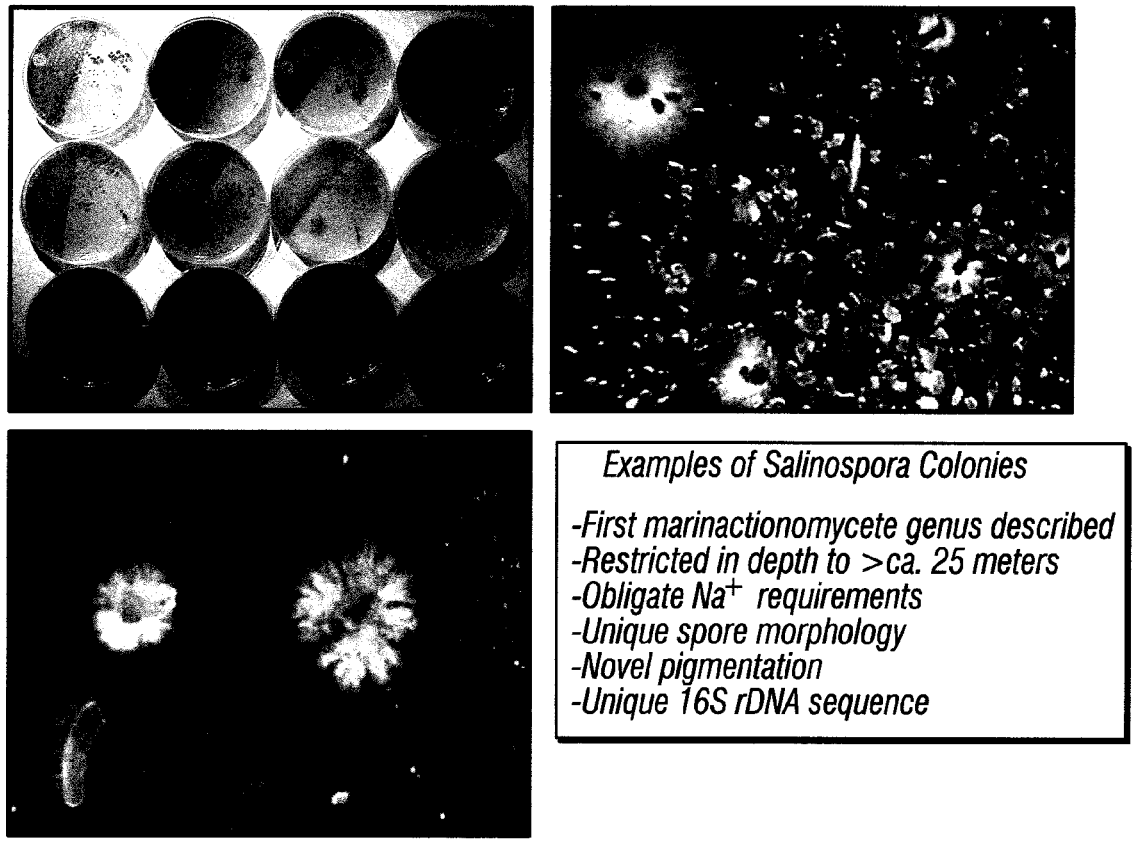
FIG. 3 shows colonies of *Salinospora*.

It is certified that error appears in the above-identified patent and that said Letters Patent is hereby corrected as shown below:

At sheet 3 of 52 (FIG. 3), line 2, delete "marinactionomycete" and insert --marineactinomycete--.

Figure 4:
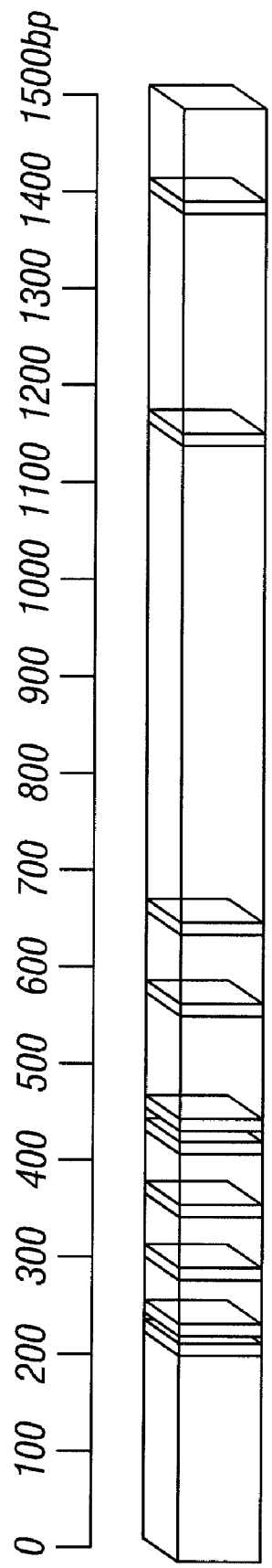
FIG. 4 shows the typical 16S rDNA sequence of the *Salinospora*. Bars represent characteristic signature nucleotides of the *Salinospora* that separate them from their nearest relatives.

At sheet 4 of 52 (FIG. 4), line 3, delete "nucelotides" and insert --nucleotides--.

At sheet 4 of 52 (FIG. 4), line 4, delete "seperate" and insert --separate--.

At sheet 7 of 52 (FIG. 10), line 2, After "8.0" please delete "9.0" and insert --7.0--.

At sheet 8 of 52 (FIG. 12), line 2, After "8.0" please delete "9.0" and insert --7.0--.

At sheet 9 of 52 (FIG. 14), line 2, After "8.0" please delete "9.0" and insert --7.0--.

At sheet 14 of 52 (FIG. 24), line 2, After "8.0" please delete "9.0" and insert --7.0--.

At column 3, line 1, delete "mitocycin" and insert --mitomycin--.

At column 4, line 64, delete "(NF-?B)" and insert --(NF-$_\kappa$B)--.

At column 6, line 31, delete "(NF-?B)" and insert --(NF-$_\kappa$B)--.

At column 10, line 3-12

Delete " 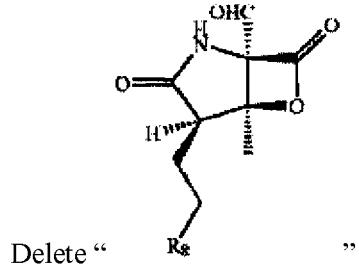 "

Signed and Sealed this
Twentieth Day of December, 2011

David J. Kappos
*Director of the United States Patent and Trademark Office*

CERTIFICATE OF CORRECTION (continued)
U.S. Pat. No. 7,572,606 B1

And insert -- 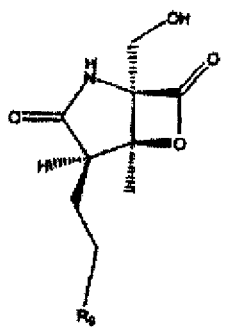 --.

At column 13, line 26-27, delete "cyclohexenecarbaldehyde" and insert --cyclohexanecarbaldehyde--.

At column 19, line 1, delete "E5" and insert --$E_5$--.

At column 19, line 52, delete "Formula 11-10" and insert --Formula II-10--.

At column 21, line 20,

Below " 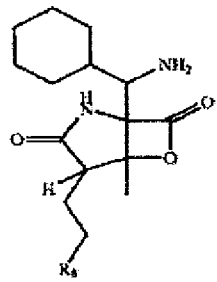 "

Insert --Formula II-12--.

At column 31, line 10-20,

Delete " 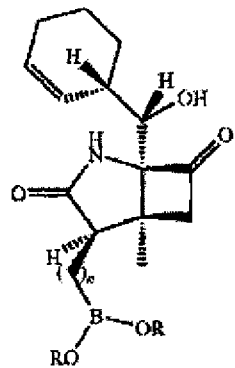 "

CERTIFICATE OF CORRECTION (continued)
U.S. Pat. No. 7,572,606 B1

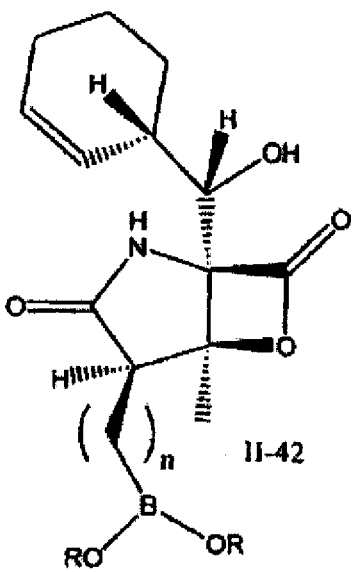

And insert -- --.

At column 52, line 41, delete "(NF-?B)" and insert --(NF-$_\kappa$B)--.

At column 52, line 43, delete "I?B" and insert --I$_\kappa$B--.

At column 52, line 44, delete "I?B" and insert --I$_\kappa$B--.

At column 52, line 46, delete "I?B, NF-?B" and insert --I$_\kappa$B, NF-$_\kappa$B--.

At column 52, line 49, delete "NF-?B" and insert --NF-$_\kappa$B--.

At column 52, line 61, delete "I?B" and insert --I$_\kappa$B--.

At column 55, line 50, delete "Opthalmologica," and insert --Ophthalmologica,--.

At column 62, line 46, delete "gouadotropin" and insert --gonadotropin--.

At column 62, line 49, delete "Cytoxin," and insert --Cytoxan--.

At column 62, line 49, delete "Toxotere," and insert --Taxotere,--.

At column 62, line 51-52, delete "Vincreistine," and insert --Vincristine,--.

At column 62, line 53, delete "Caminomycin," and insert --Carminomycin,--.

At column 63, line 14, delete "alkylosing" and insert --ankylosing--.

At column 63, line 21, delete "Telangiestasia." and insert --Telangiectasia.--.

At column 67, line 27, delete "(I))):" and insert --(I):--.

At column 67, line 51, delete "1H" and insert --$^1$H--.

At column 67, line 57, delete "1H" and insert --$^1$H--.

At column 71, line 44, delete "II-4; R = Br" and insert --II-4:R = Br--.

At column 71, line 63, delete "$\lambda_{man}$ 225 (sh) rim." and insert --$\lambda_{max}$ 225 (sh) nm.--.

At column 72, line 36, delete "I-18" and insert --II-18--.

At column 74, line 6, delete "1H" and insert --$^1$H--.

At column 74, line 12, delete "1H" and insert --$^1$H--.

At column 74, line 35, after "groups" insert --.--.

CERTIFICATE OF CORRECTION (continued)
U.S. Pat. No. 7,572,606 B1

At column 76, line 43, after "(FIG. 21)" insert --.--.

At column 77, line 48 delete "1H" and insert --$^1$H--.

At column 78, line 2, delete "1H" and insert --$^1$H--.

At column 80, line 21, Before "250" delete "max" and insert --$\lambda_{max}$--.

At column 85, line 11, delete "triethylaminde." and insert --triethylamine.--.

At column 87, line 22-35

Delete " 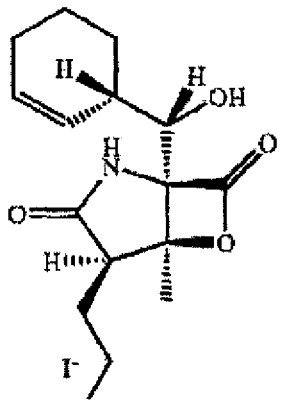 "

And insert -- 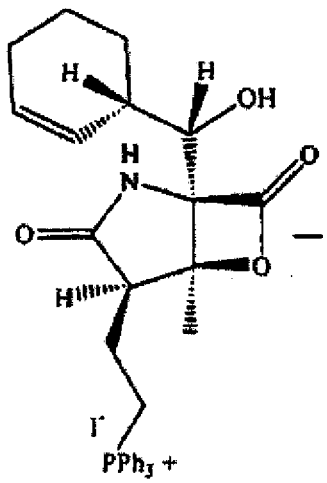 --.

At column 89, line 9, delete "(M+H)$^+$&" and insert --(M+H)$^+$ &--.

At column 94, line 26-35

Delete " 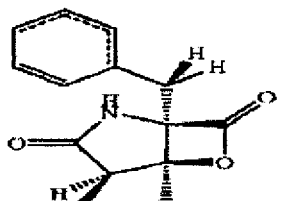 "

And insert -- 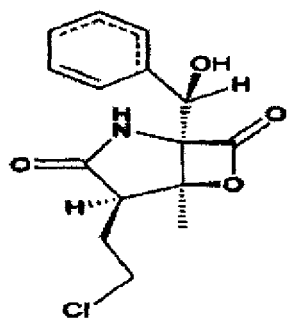 --.
At column 94, line 36-45
Delete " 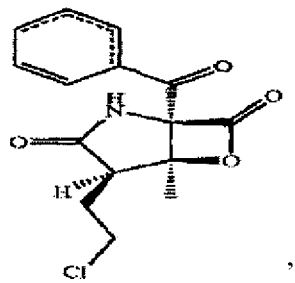 "
And insert -- 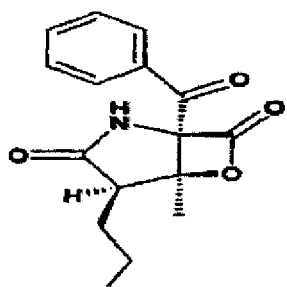 --.
At column 95-96, line 30-40,
Delete " 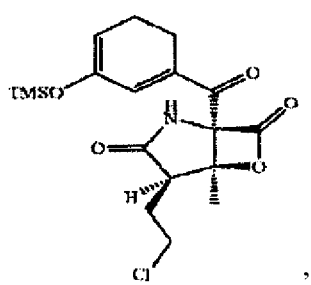 "
And insert -- 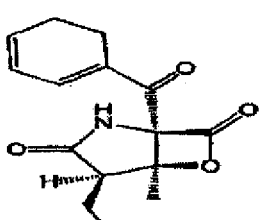 --.

CERTIFICATE OF CORRECTION (continued)
U.S. Pat. No. 7,572,606 B1

At column 98, line 7,

After " 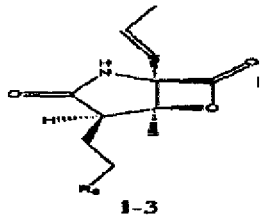 "

Delete "Pd/C, H2" and insert --Pd/C, $H_2$--.

At column 102, line 15,

Below " 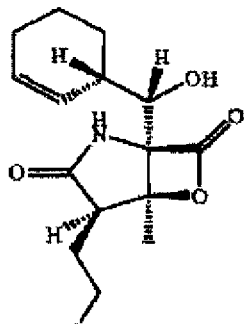 "

Insert --Formula II-16--.

At column 102, line 32-44,

Delete " 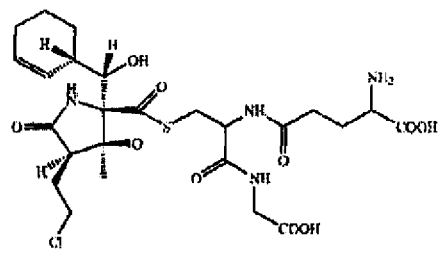 "

And insert -- 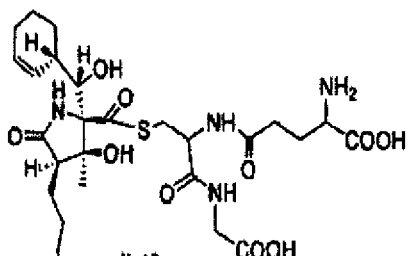 --.

At column 102, line 52-64,
Delete " 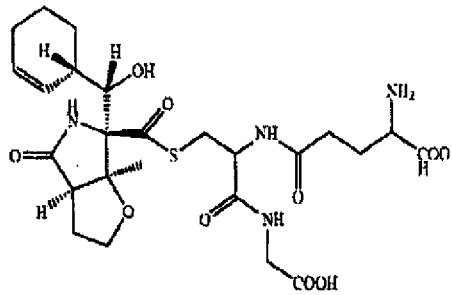 "
And insert -- 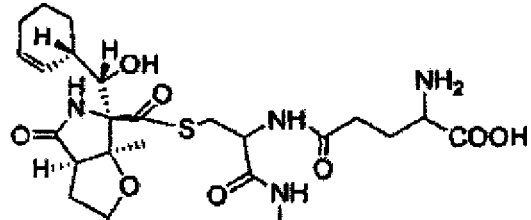 --.
At column 103, line 28, After "(M+Na)⁺" insert --.--.
At column 103, line 44,
Below " 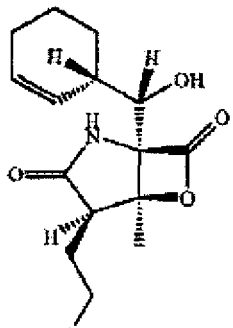 "
Insert --II-16--.
At column 103, line 55-65,
Delete " 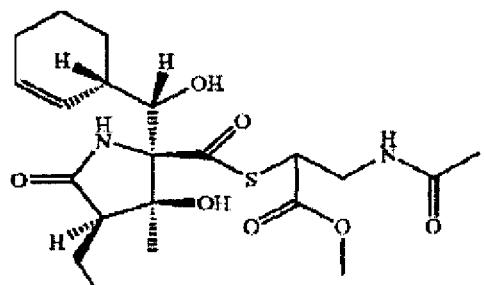 "

And insert -- 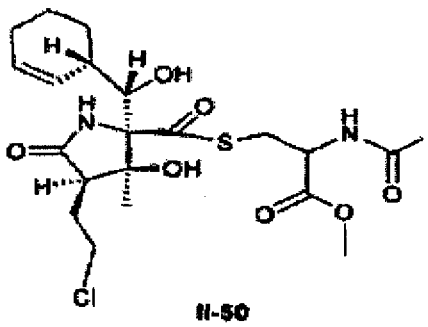 --.

At column 104, line 3-11,

Delete " 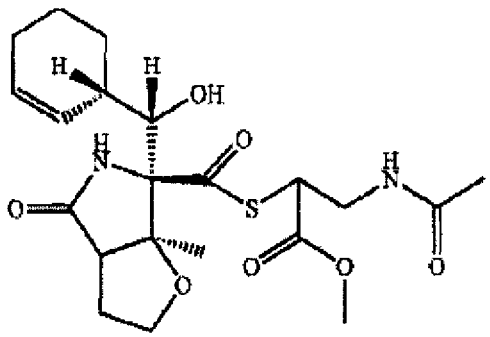 "

And insert -- 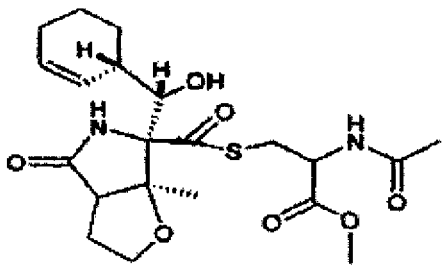 --.

At column 107, line 26, delete "0.2 µM." and insert --0.2 pM.--.

At column 108, line 33, delete "pH7.3," and insert --pH 7.3,--.

At column 118, line 32, delete "EC50" and insert --$EC_{50}$--.

At column 122, line 30, delete "$\mu_{em}$" and insert --$\lambda_{em}$--.

At column 123, line 47, delete "myloma" and insert --myeloma--.

At column 126, line 48, delete "(Calbochem" and insert --(Calbiochem--.

At column 127, line 38, delete "protealytic" and insert --proteolytic--.

At column 139, line 22, delete "Mg++, Ca++" and insert --$Mg^{++}$, $Ca^{++}$--.

At column 141, line 6, delete "cytotoxity" and insert --cytotoxicity--.

At column 143, line 52, delete "Webber" and insert --Weber--.

At column 146, line 17, delete "intraperatoneal," and insert --intraperitoneal,--.

At column 146, line 52, delete "Salinosporamde" and insert --Salinosporamide--.

At column 148, line 53, delete ""core"" and insert --"core"--.

At column 149, line 22, delete ""core"" and insert --"core"--.

At column 151, line 2, delete "H2O" and insert --$H_2O$--.

At column 154, line 16, delete "[U-13C4]" and insert --[U-$^{13}C_4$]--.

At column 158, line 21, delete "[U-13C4]" and insert --[U-$^{13}C_4$]--.

At column 159, line 35, delete "[U-13C4]" and insert --[U-$^{13}C_4$]--.

At column 163, line 3-15

In Claim 6, delete " 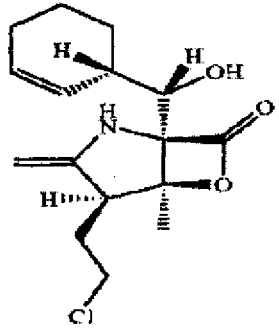 "

And insert -- 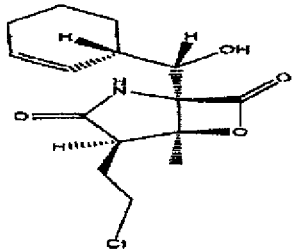 --.

At column 163, line 17, In claim 7, before "second" delete "other".

At column 163, line 20-30,

In Claim 7, delete " 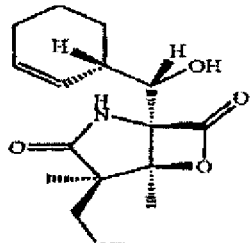 "

And insert -- 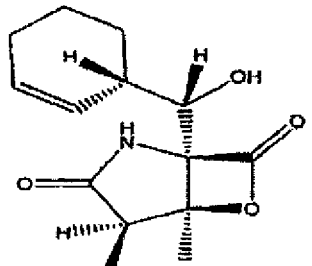 --.